US012799120B2

(12) United States Patent
Bollong et al.

(10) Patent No.: US 12,799,120 B2
(45) Date of Patent: Nov. 17, 2026

(54) SMALL MOLECULE REGULATORS OF ALVEOLAR TYPE 2 CELL PROLIFERATION FOR THE TREATMENT OF PULMONARY DISEASES

(71) Applicant: THE SCRIPPS RESEARCH INSTITUTE, La Jolla, CA (US)

(72) Inventors: Michael J. Bollong, San Diego, CA (US); Peter G. Schultz, La Jolla, CA (US); Sida Shao, San Diego, CA (US); Arnab Chatterjee, San Diego, CA (US); Jian Jeffrey Chen, San Diego, CA (US); Nan Zhang, San Mateo, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 380 days.

(21) Appl. No.: 18/261,889

(22) PCT Filed: Jan. 20, 2022

(86) PCT No.: PCT/US2022/070259

§ 371 (c)(1),
(2) Date: Jul. 18, 2023

(87) PCT Pub. No.: WO2022/159955

PCT Pub. Date: Jul. 28, 2022

(65) Prior Publication Data

US 2024/0174675 A1 May 30, 2024

Related U.S. Application Data

(60) Provisional application No. 63/139,956, filed on Jan. 21, 2021.

(51) Int. Cl.

| | |
|---|---|
| ***C07D 487/04*** | (2006.01) |
| ***A61P 11/00*** | (2006.01) |
| ***C07D 207/16*** | (2006.01) |
| ***C07D 209/52*** | (2006.01) |
| ***C07D 403/12*** | (2006.01) |
| ***C07D 473/06*** | (2006.01) |

(52) U.S. Cl.

CPC ............ *C07D 487/04* (2013.01); *A61P 11/00* (2018.01); *C07D 207/16* (2013.01); *C07D 209/52* (2013.01); *C07D 403/12* (2013.01); *C07D 473/06* (2013.01)

(58) Field of Classification Search

CPC .. C07D 487/04; C07D 207/16; C07D 209/52; C07D 403/12; C07D 473/06; A61P 11/00

USPC .......................................................... 514/249

See application file for complete search history.

(56) References Cited

U.S. PATENT DOCUMENTS

| | | | | |
|---|---|---|---|---|
| 2012/0010211 A1 | 1/2012 | Yuan et al. | | |
| 2012/0065209 A1* | 3/2012 | Tang | A61P 5/48 | 514/249 |

FOREIGN PATENT DOCUMENTS

| | | | |
|---|---|---|---|
| CN | 103087067 A | 5/2013 | |
| CN | 103896923 A | 7/2014 | |
| CN | 107303390 A | 10/2017 | |
| EP | 2230241 A1 | 9/2010 | |
| EP | 2404921 A1 | 1/2012 | |
| EP | 2230241 B1 | 11/2014 | |
| EP | 3305787 A1 | 4/2018 | |
| WO | 2000034241 A1 | 6/2000 | |
| WO | 2005012249 A2 | 2/2005 | |
| WO | 2006012441 A1 | 2/2006 | |
| WO | 2006090244 A1 | 8/2006 | |

OTHER PUBLICATIONS

Meyerholz, et al., "Dipeptidyl Peptidase 4 Distribution in the Human Respiratory Tract Implications for the Middle East Respiratory Syndrome", The American Journal of Pathology 186 (1), 79-86 (2016).

Patent Cooperation Treaty, International Search Report and Written Opinion for PCT/US2022/070259, 15 pages, dated Jun. 14, 2022.

Villhauer, et al., "1-[[(3-hydroxy-1-adamantyl)amino]acetyl]-2-cyano-(S)-pyrrolidine: a potent, selective, and orally bioavailable dipeptidyl peptidase IV inhibitor with antihyperglycemic properties", Journal of Medicinal Chemistry 46 (13), 2774-2789 (2003).

File Registry, RN 875315-30-3, 1 page (2006).

Liu, et al., "Vildagliptin, a CD26/DPP4 inhibitor, ameliorates bleomycin-induced pulmonary fibrosis via regulating the extracellular matrix", International Immunopharmacology 87, 106774, 9 pages (2020).

Smelcerovic, et al., "DPP-4 Inhibitors in the Prevention/Treatment of Pulmonary Fibrosis, Heart and Kidney Injury Caused by COVID-19—A Therapeutic Approach of Choice in Type 2 Diabetic Patients?", Frontiers in Pharmacology 11, 1185, 1-4 (2020).

* cited by examiner

*Primary Examiner* — Kristin A Vajda

(74) *Attorney, Agent, or Firm* — VIKSNINS HARRIS PADYS MALEN LLP

(57) ABSTRACT

The present disclosure relates to compounds, and to their pharmaceutical compositions, that inhibit dipeptidyl peptidase IV (DPP4). The compounds selectively promote the proliferation of alveolar type 2 cells (AEC2s) and are useful in therapeutic methods of treating diseases whose etiology, for example, derives from epithelial degeneration and maladaptive remodeling, such as pulmonary diseases like idiopathic pulmonary fibrosis (IPF), acute respiratory distress syndrome (ARDS), and infant respiratory distress syndromes (IRDS).

21 Claims, 10 Drawing Sheets

Fig. 5A
Cycling AEC2
Quiescent AEC2
AEC2→AEC1
AEC1

Fig. 5B
Log2 Max Count
proliferation gene set
9.0
3.0

SMALL MOLECULE REGULATORS OF ALVEOLAR TYPE 2 CELL PROLIFERATION FOR THE TREATMENT OF PULMONARY DISEASES

This application claims the benefit of priority to U.S. Provisional Patent Application No. 63/139,956, filed on Jan. 21, 2021, which application is incorporated in its entirety as if fully set forth herein.

BACKGROUND

Pharmacological stimulation of lower airway repair has significant potential for treating a variety of conditions in which alveolar destruction and maladaptive remodeling are causative of disease. The alveolus, the primary unit of mammalian gas exchange, is composed of two epithelial cell types: large squamous alveolar type 1 cells (AEC1s), which provide surface area for gas exchange, and cuboidal alveolar type 2 cells (AEC2s), which secrete surfactant.[1] In addition, AEC2s have been identified as the primary progenitor cell type responsible for repopulating the alveolar epithelium.[2] AEC2s clonally proliferate over adulthood, asymmetrically dividing to give rise to AEC1s and AEC2s.[2] It has been additionally demonstrated that idiopathic pulmonary fibrosis (IPF) is caused by exhaustion of the stem cell capacity of AEC2s.[3] Diminished AEC2 proliferation results in denuded alveolar basement membranes, which ultimately promotes colonization of the lower airway by hyperplastic upper airway-derived epithelial cells and extracellular matrix-secreting myofibroblasts.[3] Additionally, it has been demonstrated that restoring AEC2 proliferation through treatment with exogenous factors (IL-6 or hyaluronic acid) inhibits disease severity in mouse models of IPF.[4] In addition to IPF, acute respiratory distress syndrome (ARDS)—the acute loss of alveolar epithelial barrier function—is caused by damage to and insufficient reparative growth by AEC2 cells.[5]

SUMMARY

The present disclosure provides, in various embodiments, a compound that is useful, for example, in promoting specific proliferation of AEC2s relative to other cell types in the lung. The compound in some embodiments is of formula (I) or pharmaceutically acceptable salt thereof.

(I)

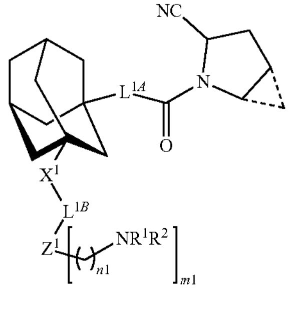

In formula (I), each --- represents a single bond that, when optionally present, form a fused cyclopropyl ring.

$L^{1A}$ is —$NHCH_2$— or —$CH(NH_2)$—.

$X^1$ is selected from —O—, —S—, —S(O)—, $S(O)_2$—, and —NH—. $L^{1B}$ is a $C_2$-$C_{12}$-alkyl wherein one or more —$CH_2$— are optionally and independently replaced by a moiety selected from —O—, —C(O)—, and —NH—. $Z^1$ is selected from H, $C_6$-$C_{10}$-aryl, and 5- to 10-membered heteroaryl (wherein 1-4 heteroaryl members are independently selected from N, O, and S).

Subscript m1 is an integer that is 0 when $Z^1$ is H, and is 1 when $Z^1$ is other than H. Subscript n1 is an integer selected from 0, 1, 2, and 3.

$R^1$ is selected from H, $C_1$-$C_{10}$-alkyl, and —$C_1$-$C_{10}$-alkyl-($C_6$-$C_{10}$-aryl), and is optionally substituted with one to six —OH. $R^2$ is $C_1$-$C_{10}$-alkyl substituted with one to six —OH.

Alternatively, per additional embodiments, the compound is formula (II) or a pharmaceutically acceptable salt thereof:

(II)

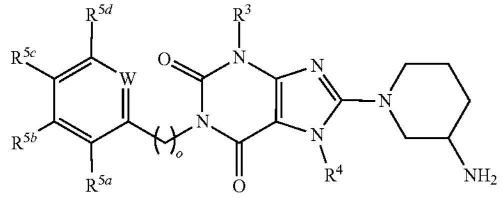

In formula (II), W is CH or N.

Subscript o is an integer selected from 1, 2, and 3.

$R^3$ is selected from $C_1$-$C_6$-alkyl, $C_1$-$C_6$-hydroxyalkyl, and —$(CH_2CH_2O)_xH$ (wherein x is an integer selected from 1, 2, 3, 4, and 5). $R^4$ is $C_2$-$C_8$-alkynyl.

$R^{5a}$, $R^{5b}$, $R^{5c}$, and $R^{5d}$ are independently selected from H, $C_1$-$C_6$-alkyl, halo, —$NR^AR^B$ (wherein $R^A$ and $R^B$ are independently selected from H and $C_1$-$C_{10}$-alkyl), —C(O)OH, —$B(OH)_2$, —$C(O)NR^AR^B$, —$C(O)OR^A$, and —C(O)-$L^2$-$Z^2$[$(CH_2)_{n2}$—$NR^6R^7$]$_{m2}$. $L^2$ is a $C_2$-$C_{12}$-alkyl wherein one or more —$CH_2$— are optionally and independently replaced by a moiety selected from —O—, —C(O)—, and —NH—. $Z^2$ is selected from H, $C_6$-$C_{10}$-aryl, and 5- to 10-membered heteroaryl (wherein 1-4 heteroaryl members are independently selected from N, O, and S). At least one of $R^{5a}$, $R^{5b}$, $R^{5c}$, and $R^{5d}$ is other than H.

$R^6$ is selected from H, $C_1$-$C_{10}$-alkyl, and —$C_1$-$C_{10}$-alkyl-($C_6$-$C_{10}$-aryl), and is optionally substituted with one to six —OH. $R^7$ is $C_1$-$C_{10}$-alkyl substituted with one to six —OH.

Subscripts m2 is an integer that is 0 when $Z^1$ is H, and is 1 when $Z^1$ is other than H. Subscript n2 is an integer selected from 0, 1, 2, and 3.

Further, when W is CH, then $R^{5a}$ and $R^{5d}$ are not selected from —C(O)OH, —C(O)OMe, and —C(O)OEt.

Alternatively, per additional embodiments, the compound is of formula (III) or a pharmaceutically acceptable salt thereof:

(III)

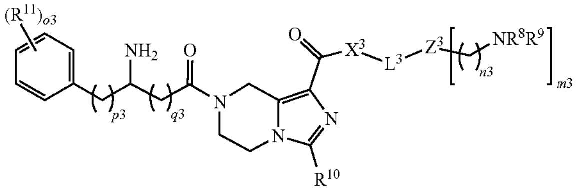

In formula (III), $X^3$ is —O— or —NH—. $L^3$ is a bond or $C_2$-$C_{12}$-alkyl wherein one or more —$CH_2$— are optionally and independently replaced by a moiety selected from —O—, —C(O)—, and —NH—. $Z^3$ is selected from H, —$N_3$, $C_6$-$C_{10}$-aryl, 5- to 10-membered heteroaryl (wherein 1-4 heteroaryl members are independently selected from N, O, and S), and (3- to 14-membered heterocycloalkyl (wherein 1-4 ring members are independently selected from N, O, and S). Heteroaryl and heterocycloalkyl are optionally substituted with 1 to 6 substituents selected from the group consisting of halo, $NO_2$, OH, CN, and $C_1$-$C_6$-haloalkyl.

Subscript m3 is an integer that is 0 when $Z^3$ is H or —$N_3$, and is 1 when Z is other than H or —$N_3$. Subscript n3 is an integer selected from 0, 1, 2, and 3.

$R^8$ is selected from H, $C_1$-$C_{10}$-alkyl or —$C_1$-$C_6$-alkyl-($C_6$-$C_{10}$-aryl), and is optionally substituted with one to six —OH. $R^9$ is $C_1$-$C_{10}$-alkyl substituted with one to six —OH. $R^{10}$ is $C_1$-$C_6$-haloalkyl. Each $R^9$ is independently selected from H, $C_1$-$C_6$-alkyl, and halo.

Subscript o3 is an integer selected from 0, 1, 2, and 3. Subscript p3 is an integer selected from 0, 1, 2, and 3. Subscript q3 is an integer selected from 0, 1, 2, and 3.

The compound of the present disclosure does not include any of the following compounds:

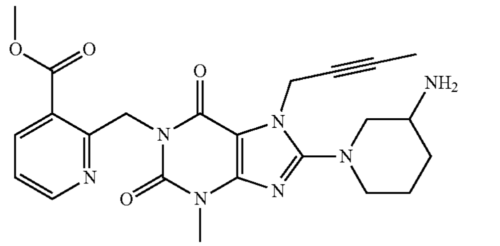

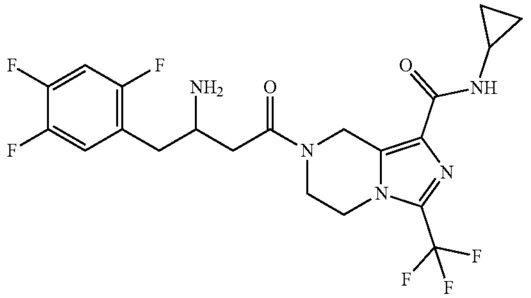

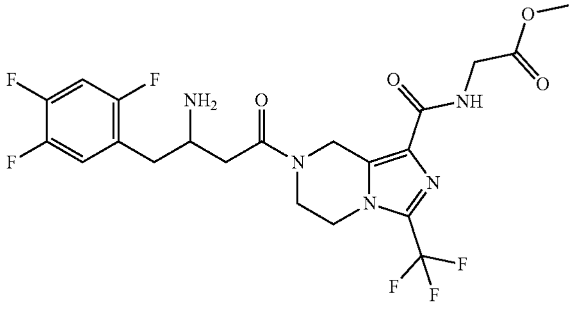

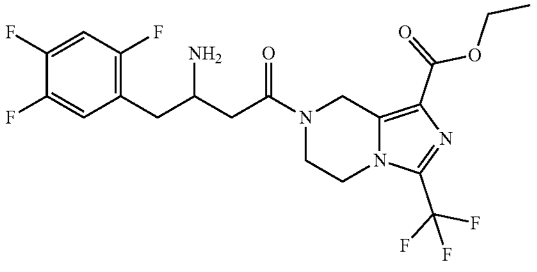

-continued

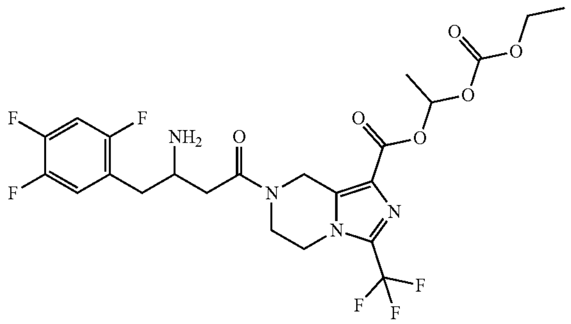

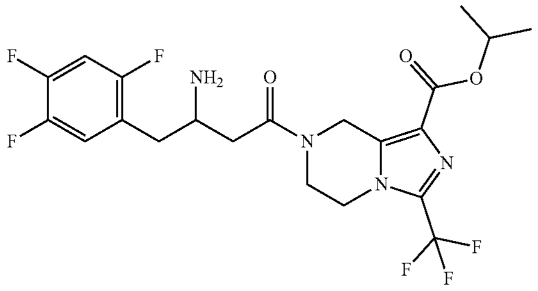

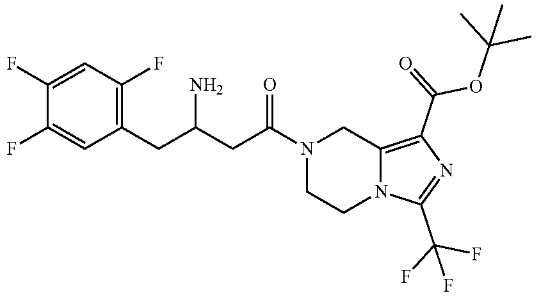

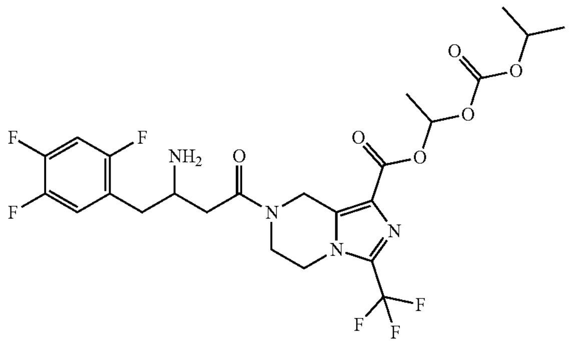

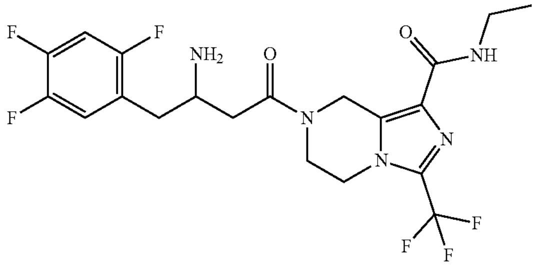

-continued

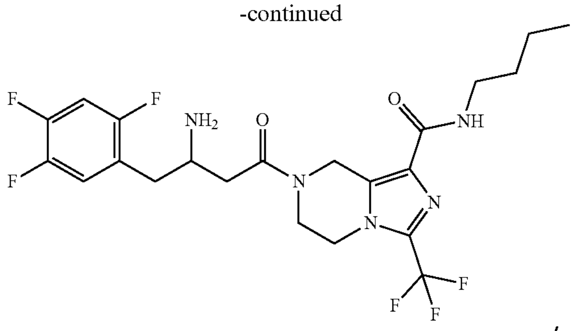

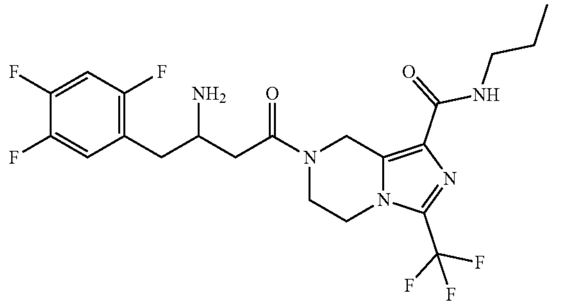

In another embodiment, the present disclosure provides a pharmaceutical composition comprising a compound or pharmaceutically acceptable salt thereof as described herein.

The present disclosure also provides, in an embodiment, a method for selectively increasing the proliferation of cuboidal alveolar type 2 (AEC2) cells in a subject in need thereof, or for restoring diminished proliferation of AEC2 cells in a subject in need thereof. The method comprises administering to the subject a compound or pharmaceutically acceptable salt thereof as described herein.

In an embodiment, the present disclosure provides a method for inhibiting dipeptidyl peptidase IV (DPP4) in a subject in need thereof. The method comprises administering to the subject a compound or pharmaceutically acceptable salt thereof as described herein.

Another embodiment of the present disclosure is a method for treating a pulmonary disease in a subject suffering therefrom. The method comprises administering to the subject a compound or pharmaceutically acceptable salt thereof as described herein.

Also provided in various embodiments is a compound or pharmaceutically acceptable salt thereof as described herein for use in selectively increasing the proliferation of cuboidal alveolar type 2 (AEC2) cells in a subject in need thereof, or for restoring diminished proliferation of AEC2 cells in a subject in need thereof.

In additional embodiments, the present disclosure provides a compound or pharmaceutically acceptable salt thereof as described herein for use in inhibiting dipeptidyl peptidase IV (DPP4) in a subject in need thereof.

In still additional embodiments, the present disclosure provides a compound or pharmaceutically acceptable salt thereof as described herein for use in treating a pulmonary disease in a subject suffering therefrom.

DETAILED DESCRIPTION

Figure 1:
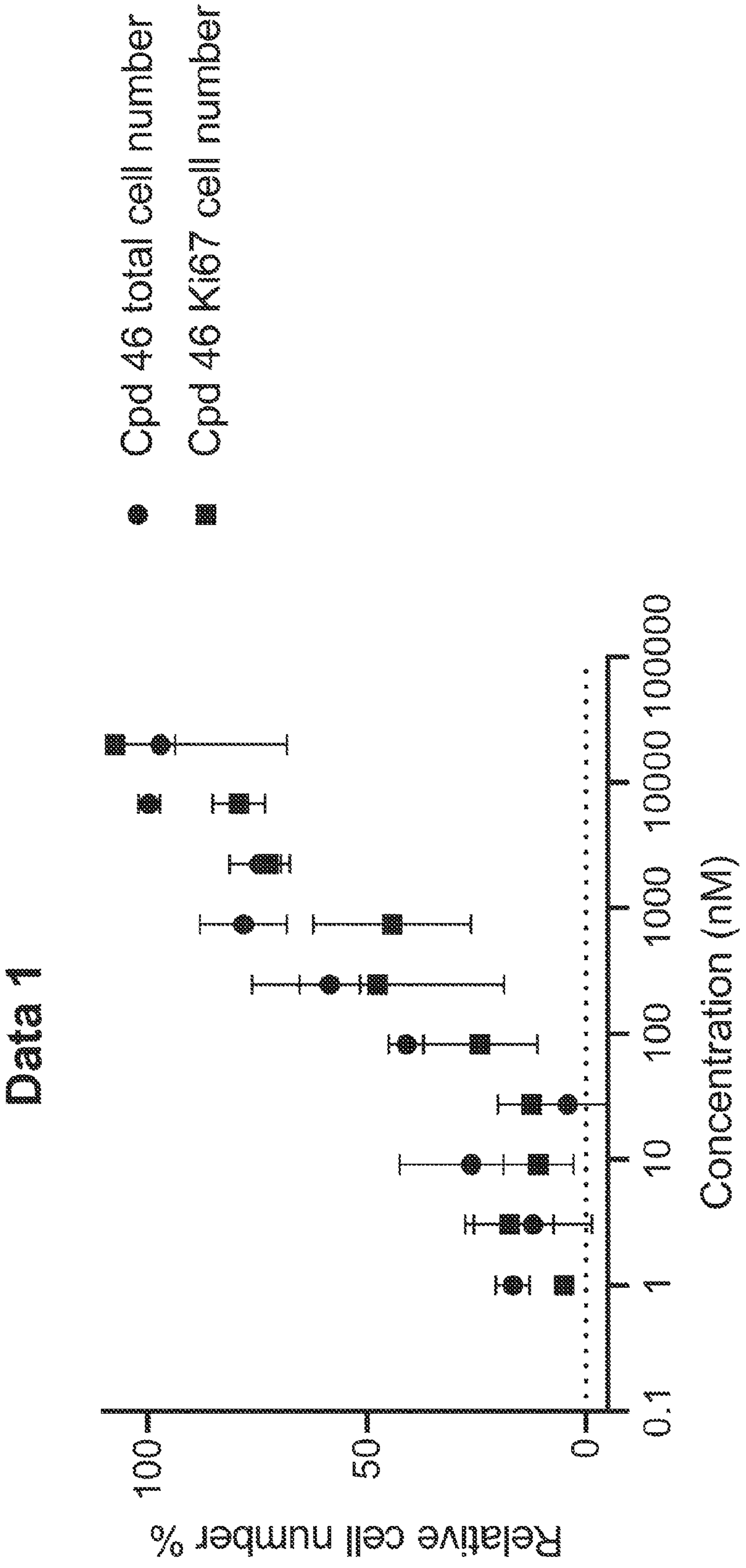
FIG. 1. AEC2 proliferation-concentration curve for Compound 46.

The present disclosure satisfies a long-felt need for drug-like compounds that stimulate reparative proliferation of pulmonary stem- and progenitor-cell populations. Compounds of the present disclosure promote specific proliferation of AEC2s relative to other cell types in the lung (e.g., pulmonary fibroblasts) and thereby exhibit disease-modifying efficacy in a number of lower airway diseases. Furthermore, the compounds are useful as inhibitors of dipeptidyl peptidase IV (DPP4).

Definitions

"Alkyl" refers to straight or branched chain hydrocarbyl including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, $—CH(CH_3)_2$, $—CH(CH_3)(CH_2CH_3)$, $—CH(CH_2CH_3)_2$, $—C(CH_3)_3$, $—C(CH_2CH_3)_3$, $—CH_2CH(CH)_2$, $—CH_2CH(CH_3)(CH_2CH_3)$, $—CH_2CH(CH_2CH_3)_2$, $—CH_2C(CH_3)_3$, $—CH_2C(CH_2CH_3)_3$, $—CH(CH_3)CH(CH_3)(CH_2CH_3)$, $—CH_2CH_2CH(CH_3)_2$, $—CH_2CH_2CH(CH_3)(CH_2CH_3)$, $—CH_2CH_2CH(CH_2CH_3)$ z, $—CH_2CH_2C(CH_3)_3$, $—CH_2CH_2C(CH_2CH_3)_3$, $—CH(CH_3)CH_2CH(CH_3)_2$, $—CH(CH_3)CH(CH_3)CH(CH_3)_2$, and the like. Thus, alkyl groups include primary alkyl groups, secondary alkyl groups, and tertiary alkyl groups. An alkyl group can be unsubstituted or optionally substituted with one or more substituents as described herein.

The term "haloalkyl" is an alkyl as defined herein that is substituted with 1, 2, 3, 4, 5, or 6 halo. An illustrative haloalkyl is $—CF_3$.

Each of the terms "halogen," "halide," and "halo" refers to —F or fluoro, —Cl or chloro, —Br or bromo, or —I or iodo.

"Alkyne or "alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein.

"Aryl" when used alone or as part of another term means an optionally fused carbocyclic aromatic group having the number of carbon atoms designated or if no number is designated, up to 14 carbon atoms, such as a $C_6$-$C_{14}$-aryl or $C_6$-$C_{10}$-aryl. Illustrative aryl groups are phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]). An exemplary aryl is phenyl. "Aryl" can be optionally fused with a cycloalkyl ring, as herein defined. An aryl group can be unsubstituted or optionally substituted with one or more substituents as described herein.

The term "heteroatom" refers to N, O, and S. Compounds of the present disclosure that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A heteroaryl group can be unsubstituted or optionally substituted with one or more substituents as described herein.

"Heterocycloalkyl" is a saturated or partially unsaturated non-aromatic monocyclic, bicyclic, tricyclic or polycyclic ring system, optionally spiro-fused, that has from 3 to 14, such as 3 to 6, atoms in which 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A heterocycloalkyl group can be unsubstituted or optionally substituted with one or more substituents as described herein.

The term "nitrile" or "cyano" can be used interchangeably and refer to a —CN group which is bound to a carbon atom of a heteroaryl ring, aryl ring and a heterocycloalkyl ring.

The term "oxo" refers to a ═O atom bound to an atom that is part of a saturated or unsaturated moiety. Thus, the ═O atom can be bound to a carbon, sulfur, or nitrogen atom that is part of a cyclic or acyclic moiety.

A "hydroxyl" or "hydroxy" refers to an —OH group.

The substituent —$CO_2H$ may be replaced with bioisosteric replacements such as:

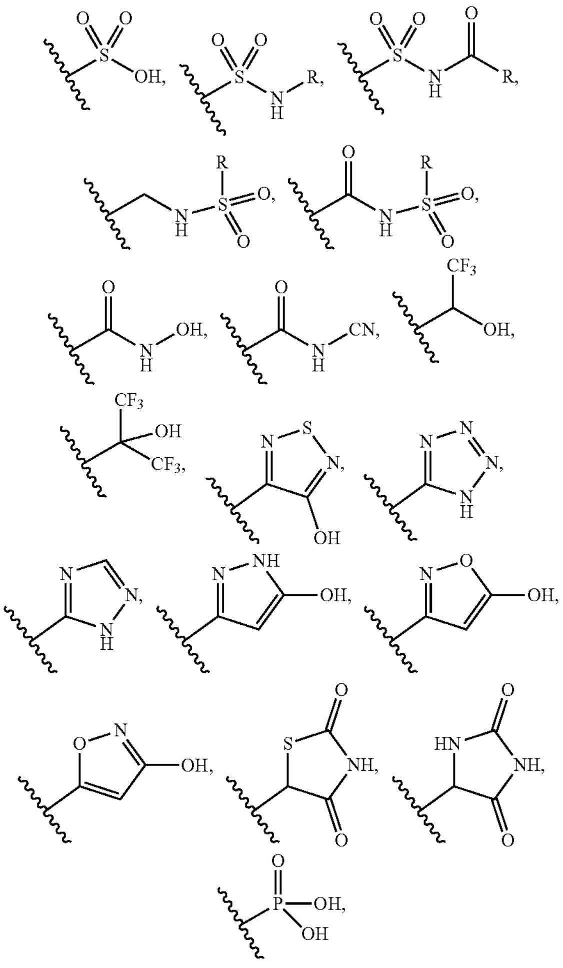

and the like, wherein R has the same definition as $R^A$ as defined herein. See, e.g., The Practice of Medicinal Chemistry (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified to the contrary, the term "compound" is inclusive in that it encompasses a compound or a pharmaceutically acceptable salt, stereoisomer, and/or tautomer thereof. Thus, for instance, a compound of the present disclosure includes a pharmaceutically acceptable salt of a tautomer of the compound.

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this example, the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or is synergistic with another therapeutic agent.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult. In the present disclosure, the terms "patient" and "subject" are used interchangeably.

"Inhibitor" means a compound which prevents or reduces the expression, catalytic activity, and/or localization (i.e., local concentration) of DPP4.

Compounds

As described generally above, the present disclosure provides a compound of formula (I) or pharmaceutically acceptable salt thereof:

(I)

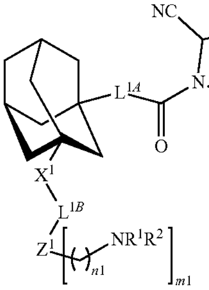

In formula (I), each — represents a single bond that, when optionally present, form a fused cyclopropyl ring.

$L^{1A}$ is —$NHCH_2$— or —$CH(NH_2)$—.

$X^1$ is selected from —O—, —S—, —S(O)—, $S(O)_2$—, and —NH—. $L^{1B}$ is a $C_2$-$C_{12}$-alkyl wherein one or more —$CH_2$— are optionally and independently replaced by a moiety selected from —O—, —C(O)—, and —NH—. $Z^1$ is selected from H, $C_6$-$C_{10}$-aryl, and 5- to 10-membered heteroaryl (wherein 1-4 heteroaryl members are independently selected from N, O, and S).

Subscript m1 is an integer that is 0 when $Z^1$ is H, and is 1 when $Z^1$ is other than H. Subscript n1 is an integer selected from 0, 1, 2, and 3.

$R^1$ is selected from H, $C_1$-$C_{10}$-alkyl, and —$C_1$-$C_{10}$-alkyl-($C_6$-$C_{10}$-aryl), and is optionally substituted with one to six —OH.

$R^2$ is $C_1$-$C_{10}$-alkyl substituted with one to six —OH. In various embodiments, $R^2$ is substituted with 1, 2, 3, 4, 5, or 6 —OH. An illustrative $R^2$ is shown below with one example of several of its diastereomers:

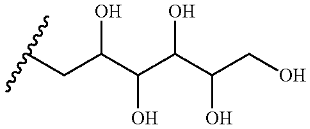

and

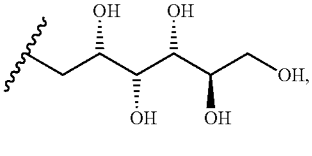

respectively.

In various embodiments, $L^{1A}$ is —$NHCH_2$. In other embodiments, $L^{1A}$ is —$CH(NH_2)$—.

In some embodiments, $X^1$ is O.

In additional embodiments, $Z^1$ is H. In other embodiments, $Z^1$ is $C_6$-$C_{10}$-aryl or 5- to 10-membered heteroaryl (wherein 1-4 heteroaryl members are independently selected from N, O, and S). An example of $C_6$-$C_{10}$-aryl is phenyl, per one embodiment. An example of heteroaryl is triazolyl, per another embodiment.

In various embodiments, optionally in combination with any other embodiment herein described, n1 is 1 or 2.

In additional embodiments, optionally in combination with any other embodiment herein described, $R^1$ is $C_1$-$C_{10}$-alkyl optionally substituted with one to six —OH. For example, in an illustrative embodiment, $R^1$ is $C_1$-$C_6$-alkyl.

In still additional embodiments, optionally in combination with any other embodiment herein described, $R^2$ is $C_2$-$C_6$-alkyl substituted with one to five —OH, or $R^2$ is $C_2$-$C_6$-alkyl substituted with three to five —OH. In an exemplary embodiment, $R^2$ is:

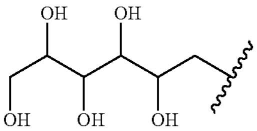

.

Further embodiments provide for a compound of formula (I) wherein:

$Z^1$ is $C_6$-$C_{10}$-aryl or 5- to 10-membered heteroaryl (wherein 1-4 heteroaryl members are independently selected from N, O, and S);

n1 is 1 or 2;

$R^1$ is $C_1$-$C_{10}$-alkyl; and $R^2$ is $R^2$ is $C_2$-$C_6$-alkyl substituted with one to five —OH.

In some embodiments, the optional single bonds represented by "—" are absent. In other embodiments, they are present so as to form a fused cyclopropyl ring. These embodiments are illustrated by the following structures:

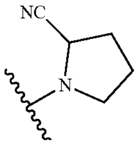

and

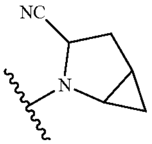

, respectively.

As described herein, the moiety $L^{1B}$ is a $C_2$-$C_{12}$-alkyl in which one or more —$CH_2$— groups are optionally and independently replaced by —O—, C(O)—, and —NH—. In some embodiments, 1, 2, 3, 4, or 5 —$CH_2$— groups are replaced. It should be understood, in accordance with chemical principles, that replacement forms only stable compounds, such as when replacement occurs at adjacent —$CH_2$— groups. Examples of $L^{1B}$ include the following:

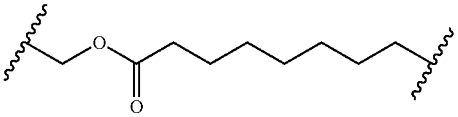

,

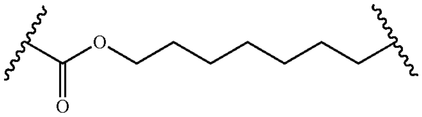

,

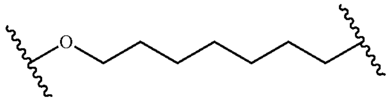

,

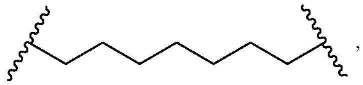

,

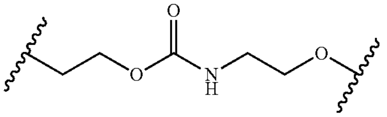

,

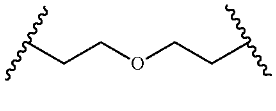

,

-continued

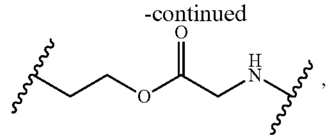

, and

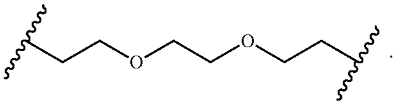

.

In other embodiments, the compound is of formula (II) or a pharmaceutically acceptable salt thereof:

(II)

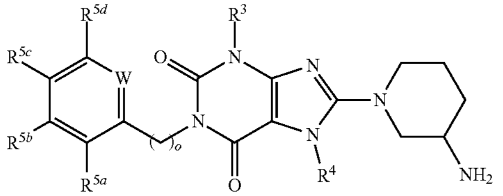

In formula (II), W is CH or N.

Subscript o is an integer selected from 1, 2, and 3.

$R^3$ is selected from $C_1$-$C_6$-alkyl, $C_1$-$C_6$-hydroxyalkyl, and —$(CH_2CH_2O)_xH$ (wherein x is an integer selected from 1, 2, 3, 4, and 5). $R^4$ is $C_2$-$C_8$-alkynyl.

$R^{5a}$, $R^{5b}$, $R^{5c}$, and $R^{5d}$ are independently selected from H, $C_1$-$C_6$-alkyl, halo, —$NR^AR^B$ (wherein $R^A$ and $R^B$ are independently selected from H and $C_6$-$C_{10}$-alkyl), —C(O)OH, —$B(OH)_2$, —$C(O)NR^AR^B$, —$C(O)OR^A$, and —C(O)-$L^2$-$Z^2$—$[(CH_2)_{n2}—NR^6R^7]_{m2}$. $L^2$ is a $C_2$-$C_{12}$-alkyl wherein one or more —$CH_2$— are optionally and independently replaced by a moiety selected from —O—, —C(O)—, and —NH—. $Z^2$ is selected from H, $C_9$-$C_{10}$-aryl, and 5- to 10-membered heteroaryl (wherein 1-4 heteroaryl members are independently selected from N, O, and S). At least one of $R^{5a}$, $R^{5b}$, $R^{5c}$, and $R^{5d}$ is other than H.

In addition, when W is CH, then $R^{5a}$ and $R^{5d}$ are not selected from —C(O)OH, —C(O)OMe, and —C(O)OEt.

$R^6$ is selected from H, $C_1$-$C_{10}$-alkyl, and —$C_1$-$C_{10}$-alkyl-($C_6$-$C_{10}$-aryl), and is optionally substituted with one to six —OH. $R^7$ is $C_1$-$C_{10}$-alkyl substituted with one to six —OH. In various embodiments, $R^7$ is substituted with 1, 2, 3, 4, 5, or 6 —OH. An illustrative $R^7$ is shown below with one example of several of its diastereomers:

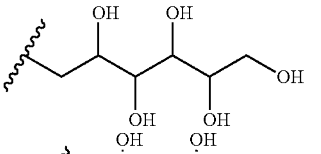

and

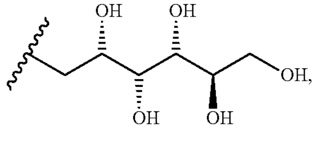

, respectively.

Subscripts m2 is an integer that is 0 when $Z^1$ is H, and is 1 when $Z^1$ is other than H. Subscript n2 is an integer selected from 0, 1, 2, and 3.

In embodiments, W is CH. In other embodiments, W is N.

In various embodiments, one, two, or three of $R^{5a}$, $R^{5b}$, $R^{5c}$, and $R^{5d}$ is H. In some embodiments, each of $R^{5b}$ and $R^{5d}$ is H. In other embodiments, $R^{5c}$ is halo, such as chloro. In still other embodiments, $R^{5a}$ is —C(O)OH or —C(O)$OR^A$. In further embodiments, $R^{5a}$ is —C(O)-$L^2$-$Z^2$—$[(CH_2)_{n2}—NR^6R^7]_{m2}$. All these embodiments and their combinations are contemplated.

In connection with embodiments wherein one of $R^{5a}$, $R^{5b}$, $R^{5c}$, and $R^{5d}$, such as $R^{5a}$, is —C(O)-$L^2$-$Z^2$—$[(CH_2)_{n2}—NR^6R^7]_{m2}$, an additional embodiment provides for $Z^2$ as phenyl or triazolyl. In exemplary embodiments, $Z^2$ is triazolyl.

In additional embodiments, optionally in combination with any other embodiment herein described, n2 is 1 or 2.

In still further embodiments, optionally in combination with any other embodiment herein described, $R^6$ is $C_1$-$C_{10}$-alkyl optionally substituted with one to six —OH. In an embodiment, $R^6$ is $C_1$-$C_6$-alkyl.

In additional embodiments, optionally in combination with any other embodiment herein described, $R^7$ is $C_2$-$C_6$-alkyl substituted with one to five —OH or three to five —OH. For example, in illustrative embodiments $R^7$ is:

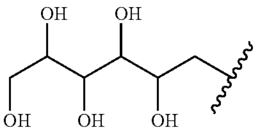

.

In still further embodiments, the present disclosure provides a compound of formula (II) wherein:

one of $R^{5a}$, $R^{5b}$, $R^{5c}$, and $R^{5d}$ is —C(O)-$L^2$-$Z^2$—$[(CH_2)_{n2}—NR^6R^7]_{m2}$;

$Z^2$ is $C_6$-$C_{10}$-aryl or 5- to 10-membered heteroaryl (wherein 1-4 heteroaryl members are independently selected from N, O, and S);

n2 is 1 or 2;

$R^6$ is $C_1$-$C_{10}$-alkyl; and $R^7$ is $C_2$-$C_6$-alkyl substituted with one to five —OH.

As described herein, in various embodiments, the moiety $L^2$ is a $C_2$-$C_{12}$-alkyl in which one or more —$CH_2$— groups are optionally and independently replaced by —O—, C(O)—, and —NH—. In some embodiments, 1, 2, 3, 4, or 5 —$CH_2$— groups are replaced. It should be understood, in accordance with chemical principles, that replacement forms only stable compounds, such as when replacement occurs at adjacent —$CH_2$— groups. Examples of $L^2$ include the following:

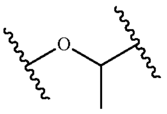

,

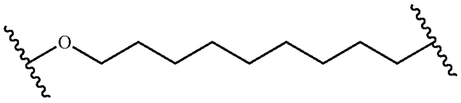

,

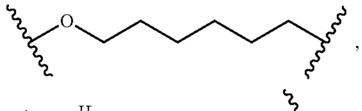

,

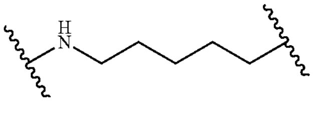

,

-continued

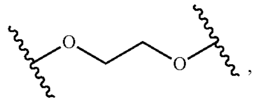

,

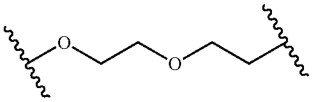

, and

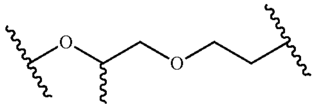

.

In various embodiments, o is 1 or 2. In a specific embodiment, o is 1.

Optionally in combination with any other embodiment are various embodiments in which $Z^2$ is $C_6$-$C_{10}$-aryl or 5- to 10-membered heteroaryl (wherein 1-4 heteroaryl members are independently selected from N, O, and S). In an embodiment, $Z^2$ is $C_6$-$C_{10}$-aryl, such as phenyl.

In additional embodiments, the compound is of formula (III) or a pharmaceutically acceptable salt thereof:

(III)

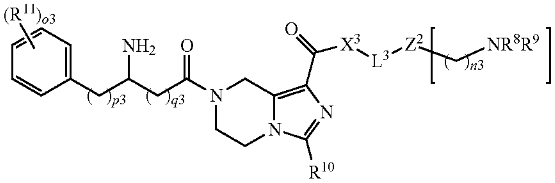

In formula (III), $X^3$ is —O— or —NH—. $L^3$ is a bond or $C_2$-$C_{12}$-alkyl wherein one or more —$CH_2$— are optionally and independently replaced by a moiety selected from —O—, —C(O)—, and —NH—. $Z^3$ is selected from H, —$N_3$, $C_6$-$C_{10}$-aryl, 5- to 10-membered heteroaryl (wherein 1-4 heteroaryl members are independently selected from N, O, and S), and (3- to 14-membered heterocycloalkyl (wherein 1-4 ring members are independently selected from N, O, and S). Heteroaryl and heterocycloalkyl are optionally substituted with 1 to 6 substituents selected from the group consisting of halo, $NO_2$, OH, CN, and $C_1$-$C_6$-haloalkyl.

Subscript m3 is an integer that is 0 when $Z^3$ is H or —$N_3$, and is 1 when $Z^3$ is other than H or —$N_3$. Subscript n3 is an integer selected from 0, 1, 2, and 3.

$R^8$ is selected from H, $C_1$-$C_{10}$-alkyl or —$C_1$-$C_{10}$-alkyl-($C_6$-$C_{10}$-aryl), and is optionally substituted with one to six —OH. $R^9$ is $C_1$-$C_{10}$-alkyl substituted with one to six —OH. $R^{10}$ is $C_1$-$C_6$-haloalkyl. Each $R^{11}$ is independently selected from H, $C_1$-$C_6$-alkyl, and halo.

Subscript o3 is an integer selected from 0, 1, 2, and 3. Subscript p3 is an integer selected from 0, 1, 2, and 3. Subscript q3 is an integer selected from 0, 1, 2, and 3.

In some embodiments, $X^3$ is 0. In other embodiments, $X^3$ is —NH—.

As described herein, the moiety $L^3$ is a $C_2$-$C_{12}$-alkyl in which one or more —$CH_2$-groups are optionally and independently replaced by —O—, C(O)—, and —NH—. In some embodiments, moiety $L^3$ is a $C_5$-$C_{12}$-alkyl, $C_5$-$C_{10}$-alkyl, $C_7$-$C_{12}$-alkyl, $C_8$-$C_{12}$-alkyl, or $C_9$-$C_{12}$-alkyl. In some embodiments, optionally in combination with any embodiment described herein, 1, 2, 3, 4, or 5 —$CH_2$— groups are replaced. It should be understood, in accordance with chemical principles, that replacement forms only stable compounds, such as when replacement occurs at adjacent —$CH_2$— groups. Examples of $L^3$ include the following:

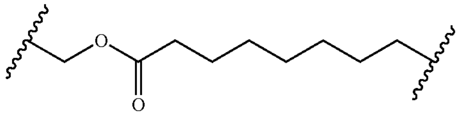

,

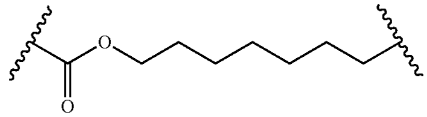

,

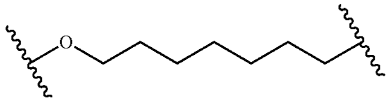

,

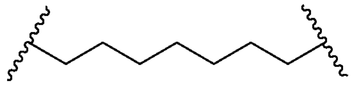

,

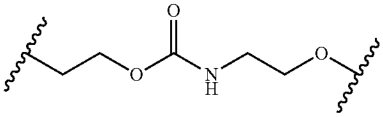

,

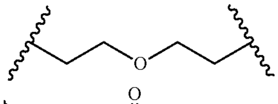

,

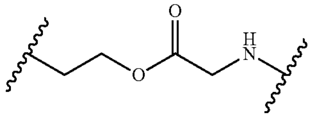

, and

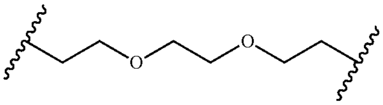

.

In various embodiments, $Z^3$ is —$N_3$. Accordingly, in these embodiments, m3 is 0.

In other embodiments, $Z^3$ is $C_6$-$C_{10}$-aryl or 5- to 10-membered heteroaryl (wherein 1-4 heteroaryl members are independently selected from N, O, and S). An illustrative $Z^3$ is phenyl or triazolyl.

In some embodiments, optionally in combination with any other embodiment herein described, n3 is 1 or 2.

In further embodiments, optionally in combination with any other embodiment herein described, $R^8$ is $C_1$-$C_{10}$-alkyl optionally substituted with one to six —OH. In an illustrative embodiment, $R^8$ is $C_1$-$C_6$-alkyl.

In additional embodiments, optionally in combination with any other embodiment herein described, $R^9$ is $C_2$-$C_6$-alkyl substituted with one to five —OH, such as three to five —OH. In an exemplary embodiment, $R^9$ is:

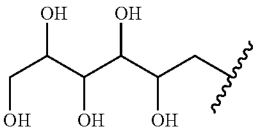

.

The present disclosure provides in embodiments a compound of formula (III) wherein:

$Z^3$ is $C_6$-$C_{10}$-aryl or 5- to 10-membered heteroaryl (wherein 1-4 heteroaryl members are independently selected from N, O, and S);

n3 is 1 or 2;
$R^8$ is $C_1$-$C_{10}$-alkyl; and
$R^9$ is $C_2$-$C_6$-alkyl substituted with one to five —OH.
It should be understood that, notwithstanding the general definitions described herein, the compound does not include any of the following compounds:
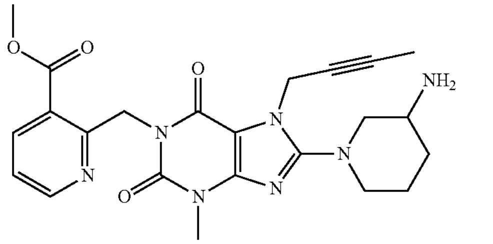
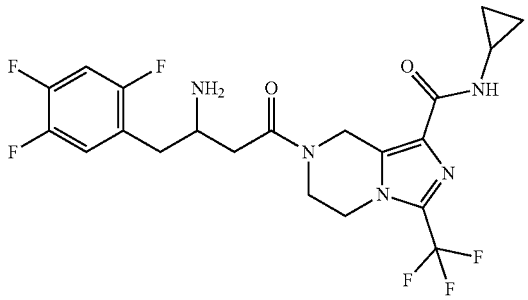
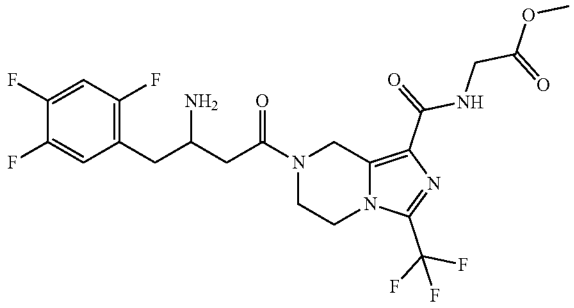
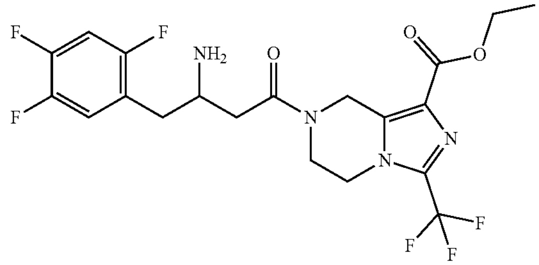
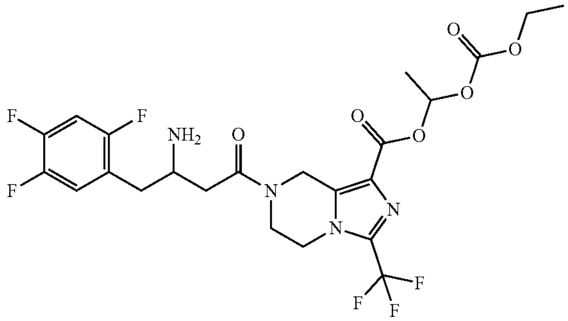
-continued
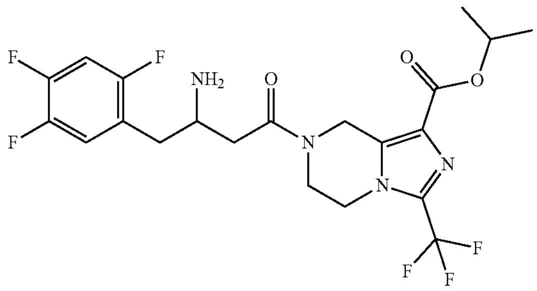
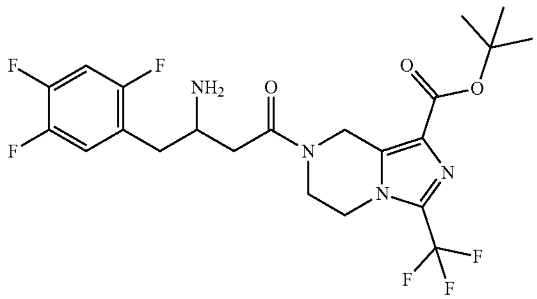
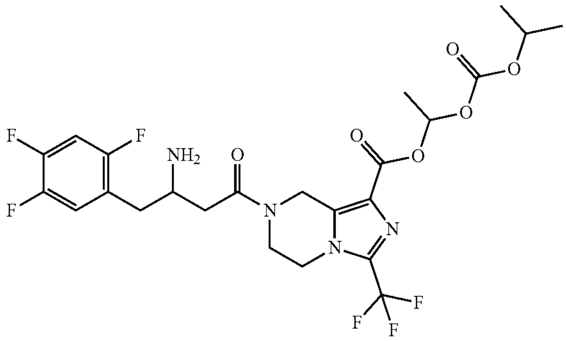
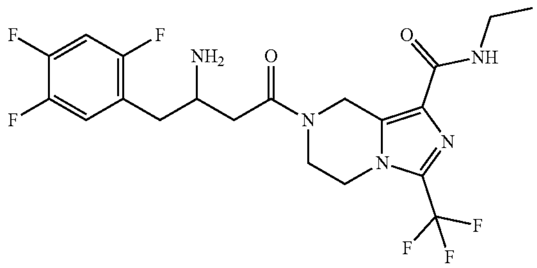
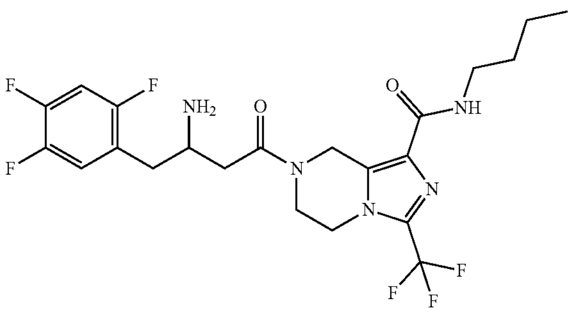

-continued
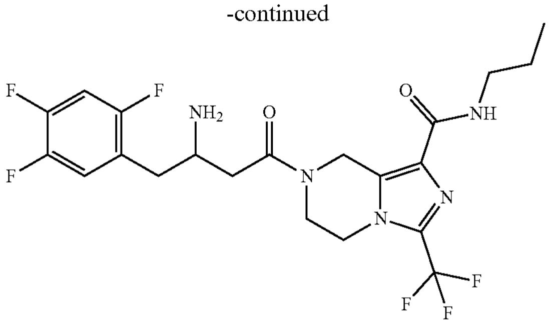
The present disclosure provides, in still additional embodiments, specific compounds or their pharmaceutically acceptable salts as set forth in Tables 1-4 below.
TABLE 1
| Examples of Formula (1) Compounds | |
|---|---|
| 24 | 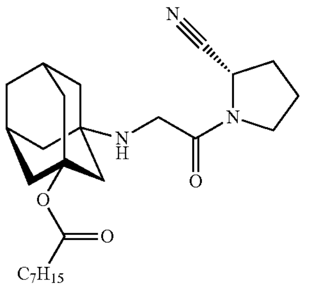 |
| 4 | 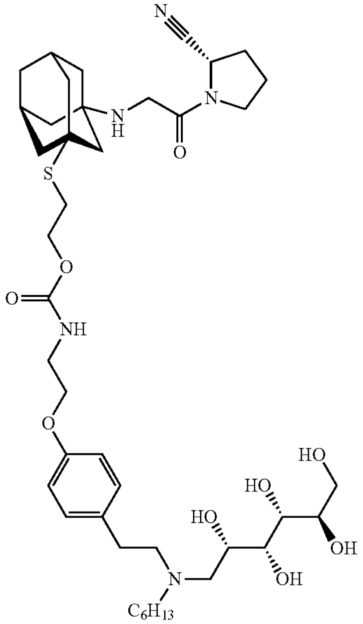 |

TABLE 1-continued
| Examples of Formula (1) Compounds | |
|---|---|
| 7 | 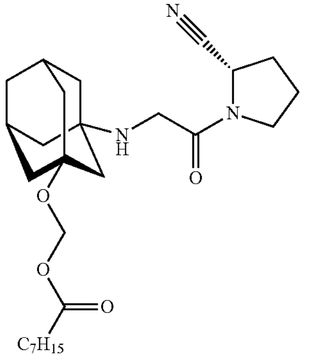 |
| 15 | 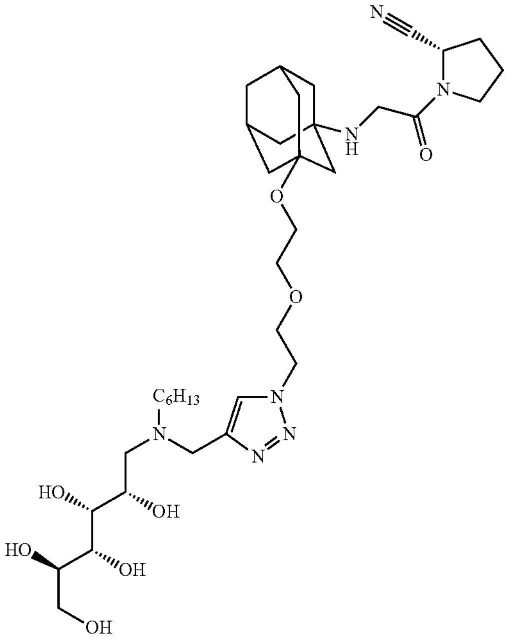 |
| 1 | 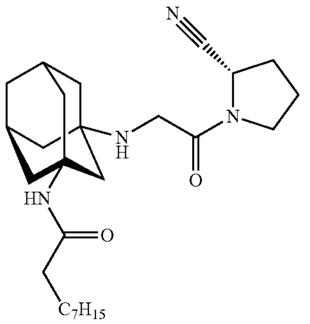 |

TABLE 1-continued
| Examples of Formula (1) Compounds | |
|---|---|
| 10 | 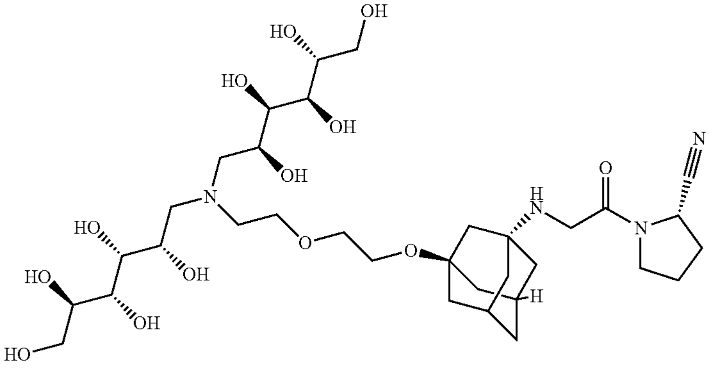 [SMILES: N#C[C@@H]1CCCN1C(=O)CN[C@]12CC3CC(C1)C[C@@](OCCOCCN(C[C@H](O)[C@@H](O)[C@H](O)[C@H](O)CO)C[C@H](O)[C@@H](O)[C@H](O)[C@H](O)CO)(C3)C2] |
| 6 | 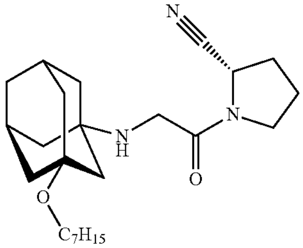 |
| 17 | 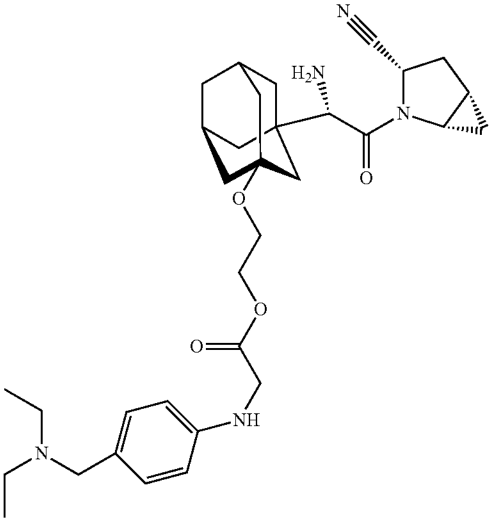 |
| 2 | 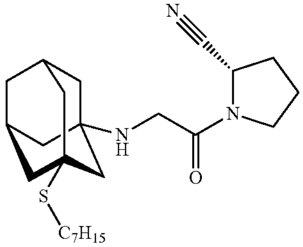 |

TABLE 1-continued
| Examples of Formula (1) Compounds | |
|---|---|
| 18 | 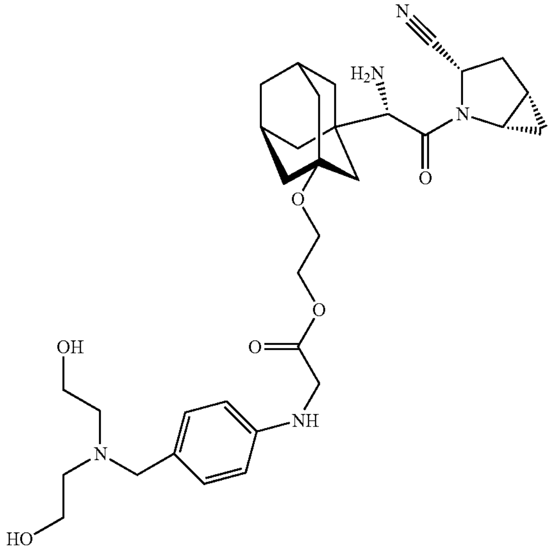 |
| 5 | 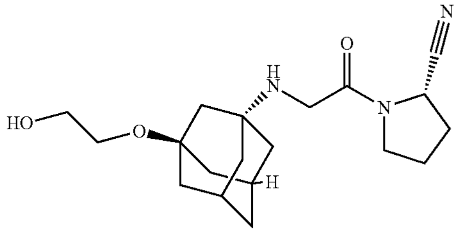 [SMILES: N#C[C@@H]1CCCN1C(=O)CN[C@]12CC3CC(C1)C[C@@](OCCO)(C3)C2] |
| 19 | 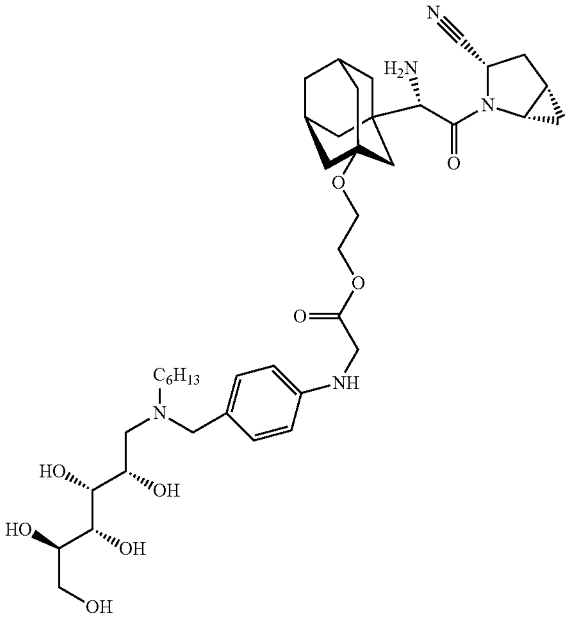 |

TABLE 1-continued
| Examples of Formula (1) Compounds | |
|---|---|
| 3 | 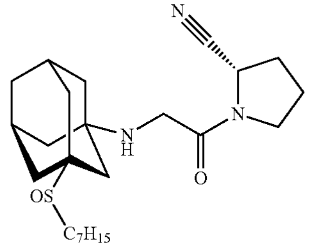 |
| 20 | 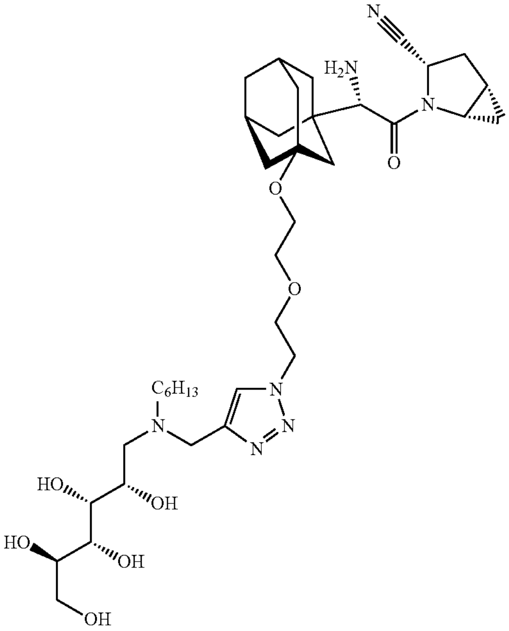 |
| 11 | 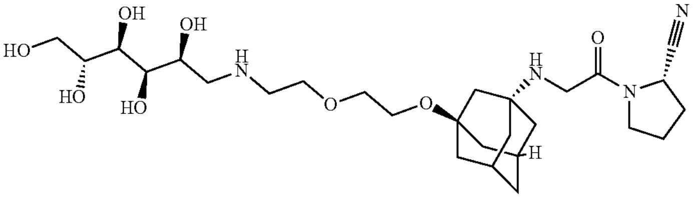 [SMILES: N#C[C@@H]1CCCN1C(=O)CN[C@]12CC3CC(C1)C[C@@](OCCOCCNC[C@H](O)[C@@H](O)[C@H](O)[C@H](O)CO)(C3)C2] |
| 8 | 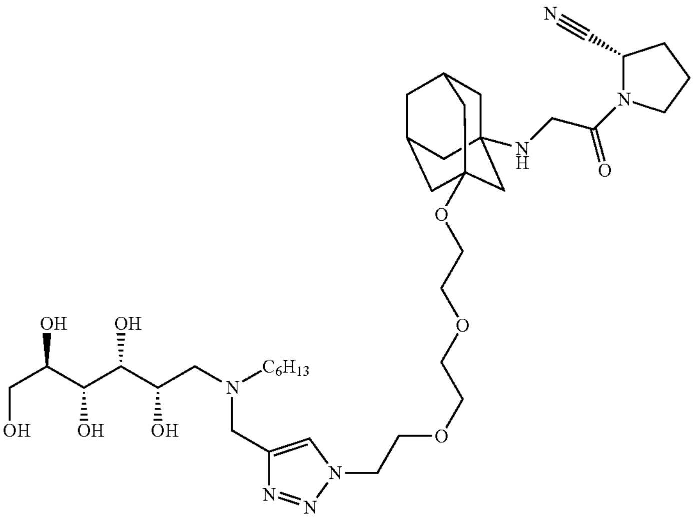 |

TABLE 1-continued
| Examples of Formula (1) Compounds |
|---|
| 13 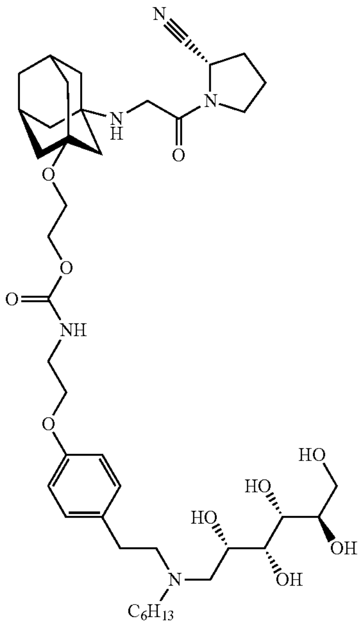 |
| 21 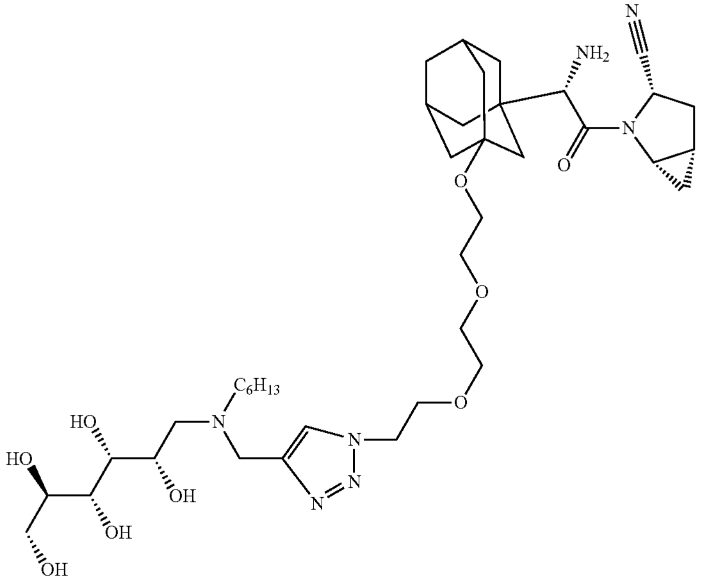 |

TABLE 1-continued
| Examples of Formula (1) Compounds | |
| --- | --- |
| 12 | 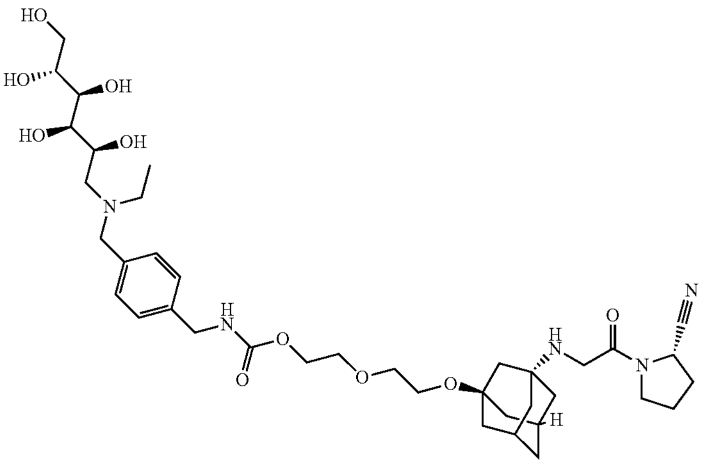 [SMILES: CCN(Cc1ccc(CNC(=O)OCCOCCO[C@]23CC4CC(C[C@](NCC(=O)N5CCC[C@H]5C#N)(C4)C2)C3)cc1)C[C@H](O)[C@@H](O)[C@H](O)[C@H](O)CO] |
| 14 | 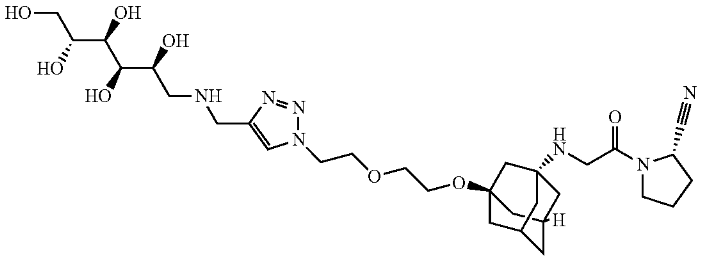 [SMILES: N#C[C@@H]1CCCN1C(=O)CN[C@]12CC3CC(C1)C[C@@](OCCOCCn1cc(CNC[C@H](O)[C@@H](O)[C@H](O)[C@H](O)CO)nn1)(C3)C2] |
| 16 | 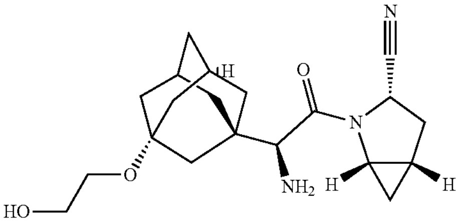 [SMILES: N#C[C@@H]1C[C@@H]2C[C@@H]2N1C(=O)[C@@H](N)[C@]12CC3C[C@H](C[C@](OCCO)(C3)C1)C2] |
| 9 | 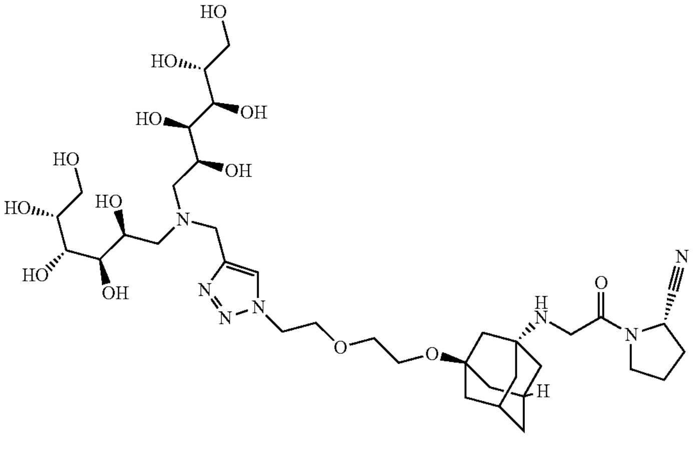 [SMILES: N#C[C@@H]1CCCN1C(=O)CN[C@]12CC3CC(C1)C[C@@](OCCOCCn1cc(CN(C[C@H](O)[C@@H](O)[C@H](O)[C@H](O)CO)C[C@H](O)[C@@H](O)[C@H](O)[C@H](O)CO)nn1)(C3)C2] |

TABLE 1-continued
| Examples of Formula (1) Compounds | |
|---|---|
| 22 | 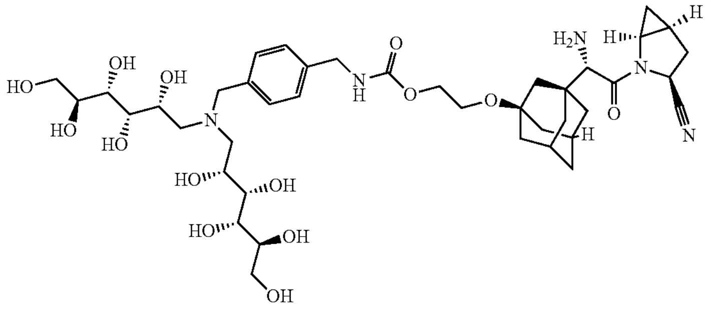 [SMILES: N#C[C@@H]1C[C@@H]2C[C@@H]2N1C(=O)[C@@H](N)[C@]12CC3CC(C[C@](OCCOC(=O)NCc4ccc(CN(C[C@@H](O)[C@H](O)[C@@H](O)[C@@H](O)CO)C[C@@H](O)[C@H](O)[C@@H](O)[C@@H](O)CO)cc4)(C3)C1)C2] |
| 23 | 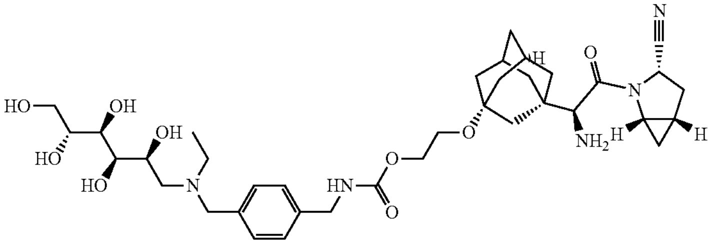 [SMILES: CCN(Cc1ccc(CNC(=O)OCCO[C@]23CC4C[C@H](C2)C[C@@]([C@H](N)C(=O)N2[C@H](C#N)C[C@@H]5C[C@@H]52)(C4)C3)cc1)C[C@H](O)[C@@H](O)[C@H](O)[C@H](O)CO] |
TABLE 2
| Examples of Formula (II) Compounds | |
|---|---|
| 37 | 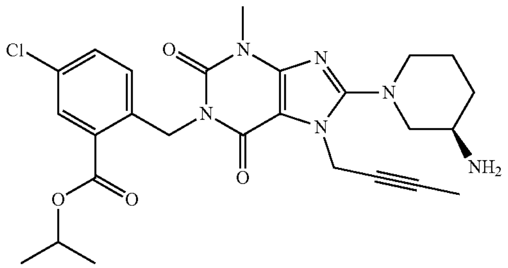 [SMILES: CC#CCn1c(N2CCC[C@@H](N)C2)nc2c1c(=O)n(Cc1ccc(Cl)cc1C(=O)OC(C)C)c(=O)n2C] |
| 33 | 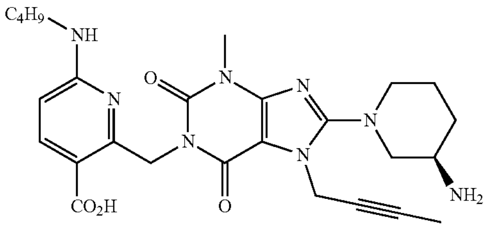 |
| 39 | 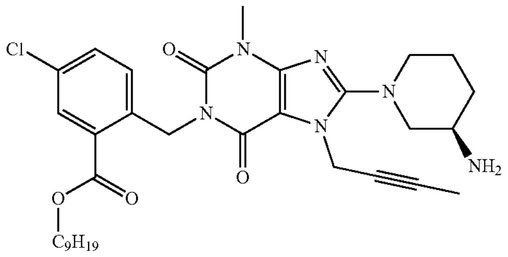 |

TABLE 2-continued
| Examples of Formula (II) Compounds | |
|---|---|
| 38 | 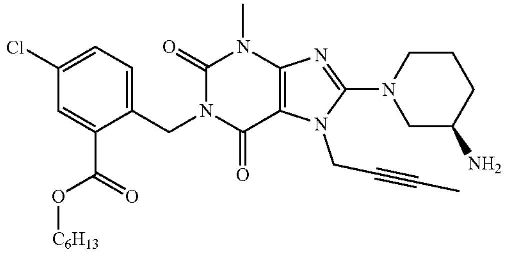 |
| 41 | 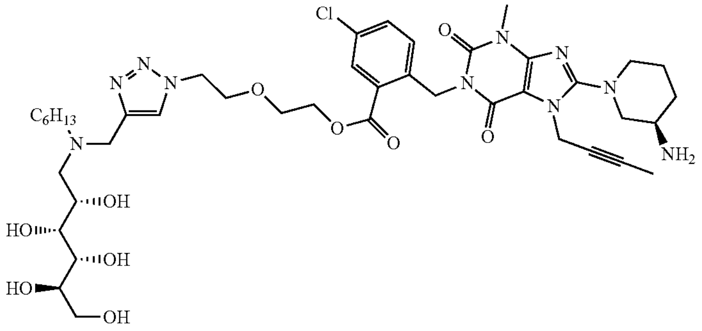 |
| 36 | 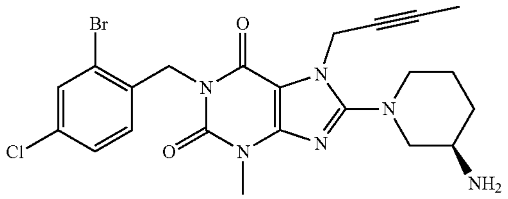 [SMILES: CC#CCn1c(N2CCC[C@@H](N)C2)nc2c1c(=O)n(Cc1ccc(Cl)cc1Br)c(=O)n2C] |
| 30 | 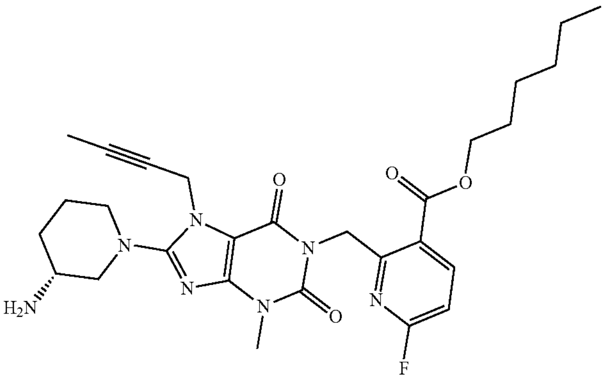 [SMILES: CC#CCn1c(N2CCC[C@@H](N)C2)nc2c1c(=O)n(Cc1nc(F)ccc1C(=O)OCCCCCC)c(=O)n2C] |
| 40 | 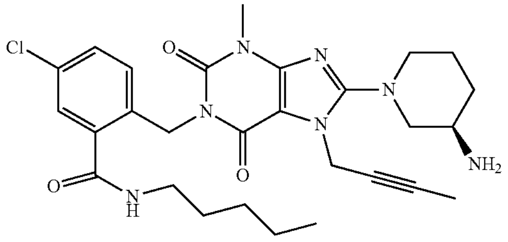 [SMILES: CC#CCn1c(N2CCC[C@@H](N)C2)nc2c1c(=O)n(Cc1ccc(Cl)cc1C(=O)NCCCCC)c(=O)n2C] |

TABLE 2-continued
| Examples of Formula (II) Compounds | |
|---|---|
| 28 | 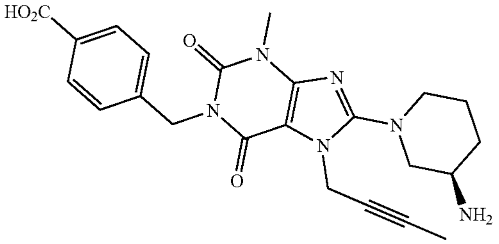 [SMILES: CC#CCn1c(N2CCC[C@@H](N)C2)nc2c1c(=O)n(Cc1ccc(C(=O)O)cc1)c(=O)n2C] |
| 27 | 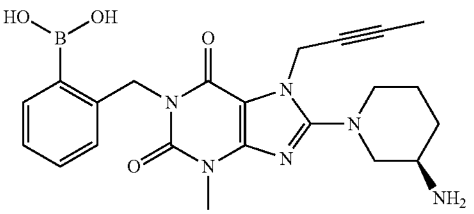 [SMILES: CC#CCn1c(N2CCC[C@@H](N)C2)nc2c1c(=O)n(Cc1ccccc1B(O)O)c(=O)n2C] |
| 31 | 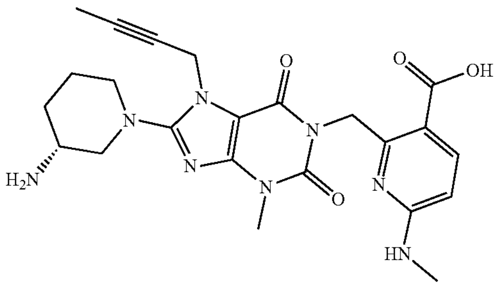 [SMILES: CC#CCn1c(N2CCC[C@@H](N)C2)nc2c1c(=O)n(Cc1nc(NC)ccc1C(=O)O)c(=O)n2C] |
| 29 | 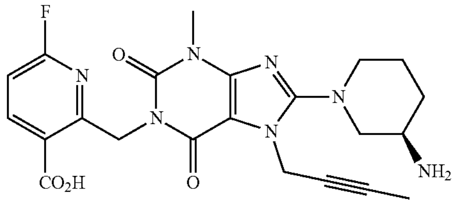 [SMILES: CC#CCn1c(N2CCC[C@@H](N)C2)nc2c1c(=O)n(Cc1nc(F)ccc1C(=O)O)c(=O)n2C] |
| 34 | 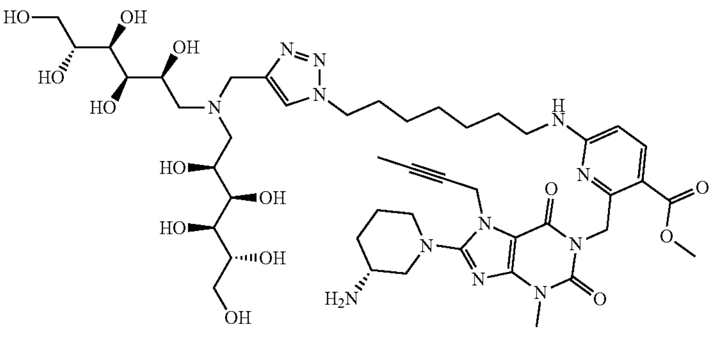 [SMILES: CC#CCn1c(N2CCC[C@@H](N)C2)nc2c1c(=O)n(Cc1nc(NCCCCCCCn3cc(CN(C[C@H](O)[C@@H](O)[C@H](O)[C@H](O)CO)C[C@H](O)[C@@H](O)[C@H](O)[C@H](O)CO)nn3)ccc1C(=O)OC)c(=O)n2C] |

TABLE 2-continued
| Examples of Formula (II) Compounds | |
|---|---|
| 32 | 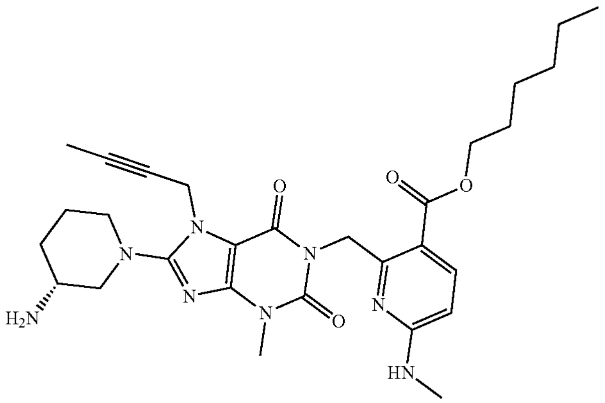 [SMILES: CC#CCn1c(N2CCC[C@@H](N)C2)nc2c1c(=O)n(Cc1nc(NC)ccc1C(=O)OCCCCCC)c(=O)n2C] |
| 35 | 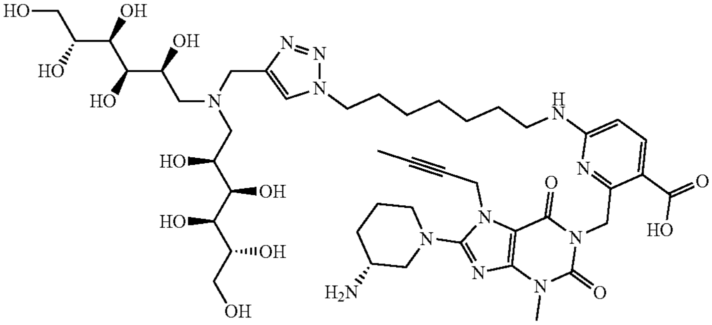 [SMILES: CC#CCn1c(N2CCC[C@@H](N)C2)nc2c1c(=O)n(Cc1nc(NCCCCCCCn3cc(CN(C[C@H](O)[C@@H](O)[C@H](O)[C@H](O)CO)C[C@H](O)[C@@H](O)[C@H](O)[C@H](O)CO)nn3)ccc1C(=O)O)c(=O)n2C] |
TABLE 3
| Examples of Formula (III) Compounds | |
|---|---|
| 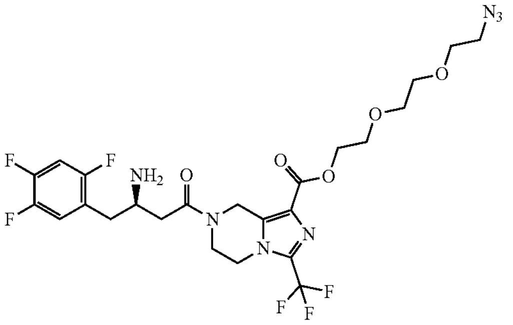 [SMILES: [N-]=[N+]=NCCOCCOCCOC(=O)c1nc(C(F)(F)F)n2c1CN(C(=O)C[C@H](N)Cc1cc(F)c(F)cc1F)CC2] | 42 |
| 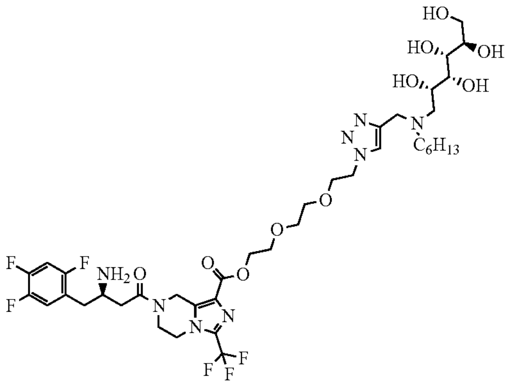 | 46 |
TABLE 3-continued
| Examples of Formula (III) Compounds | |
|---|---|
| 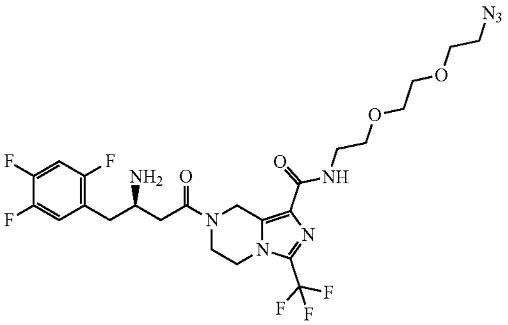 [SMILES: [N-]=[N+]=NCCOCCOCCNC(=O)c1nc(C(F)(F)F)n2c1CN(C(=O)C[C@H](N)Cc1cc(F)c(F)cc1F)CC2] | 43 |
| 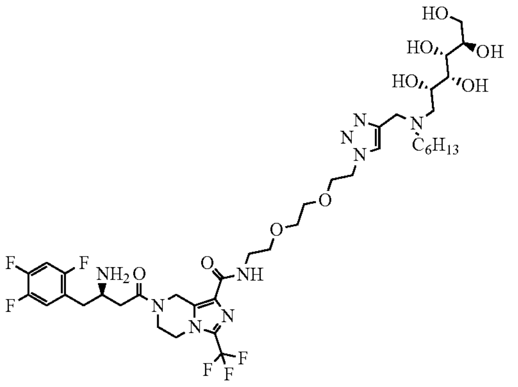 | 47 |

TABLE 3-continued
| Examples of Formula (III) Compounds | |
|---|---|
| 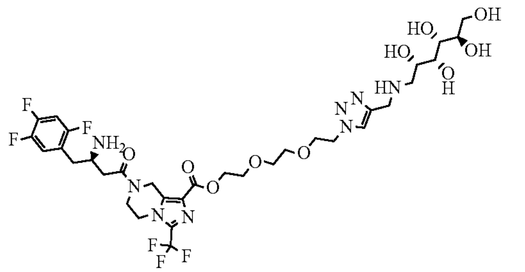 [SMILES: N[C@@H](CC(=O)N1CCn2c(C(F)(F)F)nc(C(=O)OCCOCCOCCn3cc(CNC[C@H](O)[C@@H](O)[C@H](O)[C@H](O)CO)nn3)c2C1)Cc1cc(F)c(F)cc1F] | 44 |
| 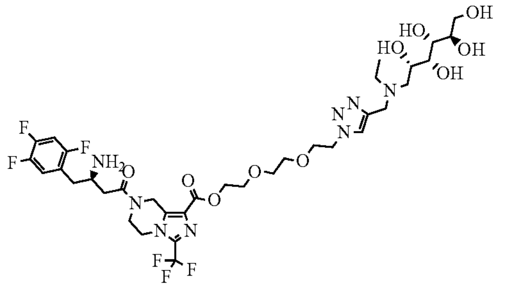 [SMILES: CCN(Cc1cn(CCOCCOCCOC(=O)c2nc(C(F)(F)F)n3c2CN(C(=O)C[C@H](N)Cc2cc(F)c(F)cc2F)CC3)nn1)C[C@H](O)[C@@H](O)[C@H](O)[C@H](O)CO] | 45 |
| 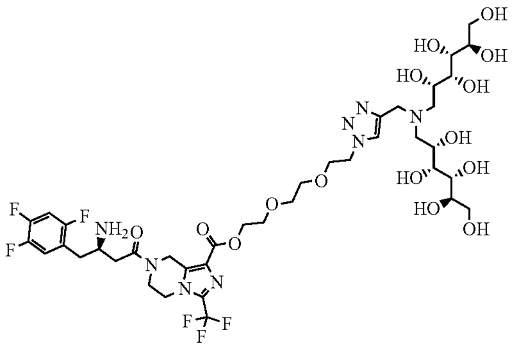 [SMILES: N[C@@H](CC(=O)N1CCn2c(C(F)(F)F)nc(C(=O)OCCOCCOCCn3cc(CN(C[C@H](O)[C@@H](O)[C@H](O)[C@H](O)CO)C[C@H](O)[C@@H](O)[C@H](O)[C@H](O)CO)nn3)c2C1)Cc1cc(F)c(F)cc1F] | 48 |
| 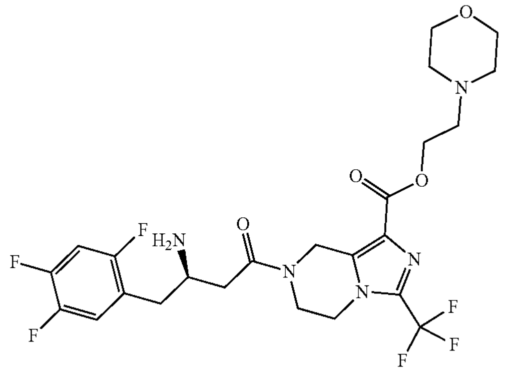 [SMILES: N[C@@H](CC(=O)N1CCn2c(C(F)(F)F)nc(C(=O)OCCN3CCOCC3)c2C1)Cc1cc(F)c(F)cc1F] | 49 |
| 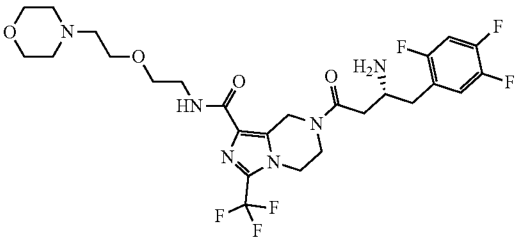 [SMILES: N[C@@H](CC(=O)N1CCn2c(C(F)(F)F)nc(C(=O)NCCOCCN3CCOCC3)c2C1)Cc1cc(F)c(F)cc1F] | 50 |
TABLE 3-continued
| Examples of Formula (III) Compounds | |
|---|---|
| 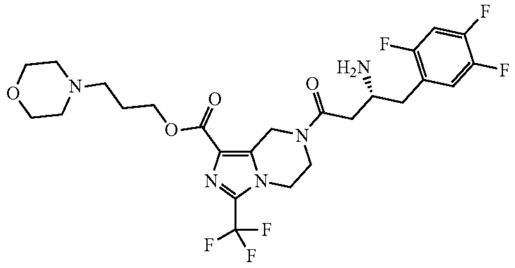 [SMILES: N[C@@H](CC(=O)N1CCn2c(C(F)(F)F)nc(C(=O)OCCCN3CCOCC3)c2C1)Cc1cc(F)c(F)cc1F] | 51 |
| 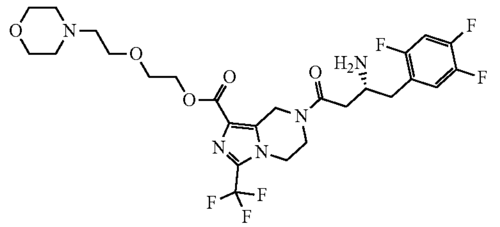 [SMILES: N[C@@H](CC(=O)N1CCn2c(C(F)(F)F)nc(C(=O)OCCOCCN3CCOCC3)c2C1)Cc1cc(F)c(F)cc1F] | 52 |
| 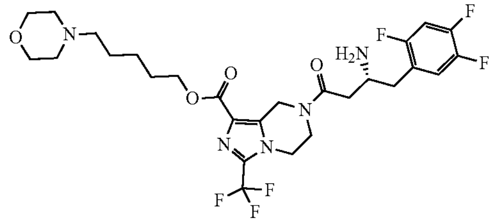 [SMILES: N[C@@H](CC(=O)N1CCn2c(C(F)(F)F)nc(C(=O)OCCCCCN3CCOCC3)c2C1)Cc1cc(F)c(F)cc1F] | 53 |
| 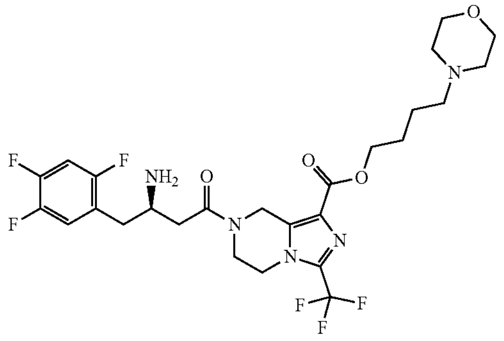 [SMILES: N[C@@H](CC(=O)N1CCn2c(C(F)(F)F)nc(C(=O)OCCCCN3CCOCC3)c2C1)Cc1cc(F)c(F)cc1F] | 54 |
| 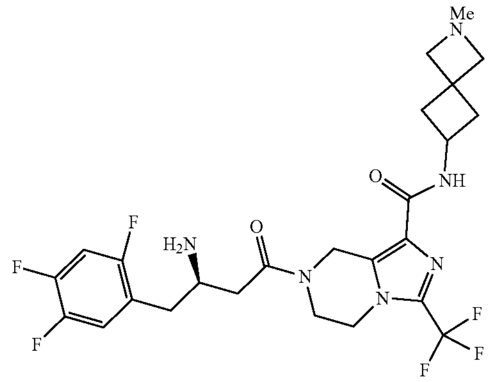 [SMILES: CN1CC2(CC(NC(=O)c3nc(C(F)(F)F)n4c3CN(C(=O)C[C@H](N)Cc3cc(F)c(F)cc3F)CC4)C2)C1] | 55 |
Pharmaceutical Compositions
The disclosure also provides a pharmaceutical composition comprising a therapeutically effective amount of one or more compounds as described herein, or a pharmaceutically acceptable salt, stereoisomer, and/or tautomer thereof in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in any table disclosed herein or a pharmaceutically acceptable salt, stereoisomer, and/or tautomer thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound or a pharmaceutically acceptable salt, stereoisomer, and/or tautomer thereof that is administered is governed by such considerations, and is the minimum amount necessary to regenerate AEC2 cell proliferation, or to inhibit DPP4, or both. Such amount may be below the amount that is toxic to normal cells, or the subject as a whole. Generally, the initial therapeutically effective amount of a compound (or a pharmaceutically acceptable salt, stereoisomer, or tautomer thereof) of the present disclosure that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 0.1 mg to about 1000 mg of a compound (or a pharmaceutically acceptable salt, stereoisomer, or tautomer thereof) of the present disclosure. In another embodiment, such dosage forms contain from about 50 mg to about 500 mg of a compound (or a pharmaceutically acceptable salt, stereoisomer, or tautomer thereof) of the present disclosure. In yet another embodiment, such dosage forms contain from about 25 mg to about 200 mg of a compound (or a pharmaceutically acceptable salt, stereoisomer, or tautomer thereof) of the present disclosure. In still another embodiment, such dosage forms contain from about 10 mg to about 100 mg of a compound (or a pharmaceutically acceptable salt, stereoisomer, or tautomer thereof) of the present disclosure. In a further embodiment, such dosage forms contain from about 5 mg to about 50 mg of a compound (or a pharmaceutically acceptable salt, stereoisomer, or tautomer thereof) of the present disclosure. In any of the foregoing embodiments the dosage form can be administered once a day or twice per day.

The compositions of the present disclosure can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, hard or soft capsules, syrups or elixirs.

In another aspect, also encompassed are pharmaceutical compositions suitable for single unit dosages that comprise a compound of the disclosure or its pharmaceutically acceptable stereoisomer, salt, or tautomer and a pharmaceutically acceptable carrier.

The compositions of the present disclosure that are suitable for oral use may be prepared according to any method known to the art for the manufacture of pharmaceutical compositions. For instance, liquid formulations of the compounds of the present disclosure contain one or more agents selected from the group consisting of sweetening agents, flavoring agents, coloring agents and preserving agents in order to provide pharmaceutically palatable preparations of the compound.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration. These compositions can be prepared by mixing the compounds with a suitable non-irritating excipient which is solid at ordinary temperatures but liquid at the rectal temperature and will therefore melt in the rectum to release the compound. Such materials are cocoa butter and polyethylene glycols.

Compositions for parenteral administrations are administered in a sterile medium. Depending on the vehicle used and concentration the concentration of the compounds in the formulation, the parenteral formulation can either be a suspension or a solution containing dissolved compound. Adjuvants such as local anesthetics, preservatives and buffering agents can also be added to parenteral compositions.

Methods

Compounds of the present disclosure are useful as inhibitors of DPP4. They are further useful in selectively promoting the proliferation AEC2 cells, without affecting myofibroblast activation or proliferation, which is undesirable in most disease contexts. The compounds, in various embodiments, promote alveolar repair as therapy for diseases whose etiology derives from epithelial degeneration and maladaptive remodeling. Exemplary indications include but are not limited to idiopathic pulmonary fibrosis (IPF), acute respiratory distress syndromes (ARDS), and infant respiratory distress syndromes (IRDS).

An advantage of the compounds of the present disclosure is their ability to modulate the regenerative capacity of AEC2 cells. Against this property are drugs approved for IPF, for example, that inhibit the activation and proliferation of pulmonary fibroblasts and myofibroblasts, which are the source of scar tissue production in the diseased lung. In contrast, the compounds of the present disclosure promote repair of the alveolus by directly targeting the source of disease in IPF: this is the ineffective self-renewal of damaged AEC2 cells. Therefore, AEC2-targeting compounds of the presenting disclosure offer additional disease modifying efficacy as a single agent or as combination therapy with an approved IPF drug (e.g., Pirfenidone).

The present disclosure, in various embodiments, thus provides a method for selectively increasing the proliferation of cuboidal alveolar type 2 (AEC2) cells in a subject in need thereof, or for restoring diminished proliferation of AEC2 cells in a subject in need thereof. The method comprises administering to the subject a compound or pharmaceutically acceptable salt as disclosed herein.

Also provided in another embodiment is a method for inhibiting dipeptidyl peptidase IV (DPP4) in a subject in need thereof. The method comprises administering to the subject a compound or pharmaceutically acceptable salt as disclosed herein.

The present disclosure provides, in various embodiments, a method for treating a subject suffering from a disease or condition whose etiology derives from epithelial degeneration, maladaptive remodeling, and/or ineffective self-renewal of damaged AEC2 cells. In some embodiments, the disease is a pulmonary disease or lung condition. In additional embodiments, the disease or condition includes those selected from Idiopathic pulmonary fibrosis (IPF), Acute respiratory distress syndrome (ARDS), Chronic Obstructive Pulmonary Disease (COPD), Emphysema, Silicosis, Asbestosis, Pneumoconiosis, Aluminosis, Bauxite fibrosis, Berylliosis, Siderosis, Stannosis, Pulmonary Talcosis, Labrador lung (mixed dust Pneumoconiosis), Sarcoidosis, Hypersensitivity pneumonitis (HP)/extrinsic allergic alveolitis (EAA), Chronic Bronchitis, Desquamative interstitial pneumonia (DIP), Respiratory bronchiolitis interstitial lung disease (RBILD), Acute interstitial pneumonia (AIP), Nonspecific interstitial pneumonia (NSIP), Cryptogenic organizing pneumonia (COP=idiopathic BOOP), Secondary organizing pneumonia (BOOP), Lymphoid interstitial pneumonia (LIP), Idiopathic interstitial pneumonia: unspecified, Hypereosinophilic lung diseases, Tuberculosis (TB), Pulmonary Edema, Interstitial Lung Disease, Bronchopulmonary Dysplasia (BPD), Coronavirus, COVID-19, Cryptogenic Organizing Pneumonia (COP), Cystic Fibrosis (CF), E-cigarette or Vaping Use-Associated Lung Injury (EVALI), Hantavirus Pulmonary Syndrome (HPS), Histoplasmosis, Influenza, Legionnaires' Disease, MAC Lung Disease, Alpha-1 Antitrypsin Deficiency, Aspergillosis, Lymphangioleiomyomatosis (LAM), Middle Eastern Respiratory Syndrome (MERS), Nontuberculous Mycobacterial Lung Disease (N™), Lung cancer, Pulmonary Embolism, Goodpasture syndrome, idiopathic pulmonary hemosiderosis, alveolar hemorrhage syndrome of undetermined origin, alveolar hemorrhage syndrome of determined origin, Sporadic pulmonary lymphangioleiomyomatosis (S-LAM), Pulmonary lymphangioleiomyomatosis in tuberous sclerosis (TSC-LAM), Alveolar proteinosis, Pulmonary amyloidosis, Primary pulmonary lymphoma, Primary ciliary dyskinesia (without or with situs inversus), Rare cause of hypersensitivity pneumonitis (all causes other than farmer's lung disease and pigeon breeder's lung disease), Pulmonary arteriovenous malformations in hereditary hemorrhagic telangiectasia (HHT), interstitial lung disease in systemic sclerosis, interstitial lung disease in rheumatoid arthritis, interstitial lung disease in idiopathic inflammatory myopathies (polymyositis, dermatomyositis, anti-synthetase syndrome), interstitial lung disease in Sjögren syndrome, interstitial lung disease in mixed connective tissue disease (MCTD), interstitial lung disease in overlap syndromes, interstitial lung disease in undifferentiated connective tissue disease, and Bronchiolitis obliterans (in non-transplanted patients).

In other embodiments, the disease is chosen from inflammatory diseases, and other diseases and disorders. The disease or disorder includes those selected from Infectious colitis, Ulcerative colitis, Crohn's disease, Ischemic colitis, Radiation colitis, Peptic ulcer, Intestinal cancer, Intestinal obstruction, Rheumatoid arthritis, Psoriatic arthritis, Hashimoto thyroiditis, Systemic lupus erythematosus, Multiple Sclerosis, Graves' Disease, Type 1 Diabetes Mellitus, Psoriasis, Ankylosing spondylitis, Scleroderma, Myositis, Gout, Antiphospholipid Antibody Syndrome (APS), Vasculitis, Dilated cardiomyopathy, Hypertrophic cardiomyopathy, Restrictive cardiomyopathy, Left-sided heart failure, Right-sided heart failure, Systolic heart failure, Diastolic heart failure (heart failure with preserved ejection fraction), Atrial Septal Defect, Atrioventricular Septal Defect, Coarctation of the Aorta, Double-outlet Right Ventricle, d-Transposition of the Great Arteries, Ebstein Anomaly, Hypoplastic Left Heart Syndrome, Interrupted Aortic Arch, Pulmonary Atresia, Single Ventricle, Tetralogy of Fallot, Total Anomalous Pulmonary Venous Return, Tricuspid Atresia, Truncus Arteriosus, Ventricular Septal Defect, Polycystic kidney disease, Diabetes Insipidus, Goodpasture's Disease, IgA Vasculitis, IgA Nephropathy, Lupus Nephritis, Adult Nephrotic Syndrome, Childhood Nephrotic Syndrome, Hemolytic Uremic Syndrome, Medullary Sponge Kidney, Kidney dysplasia, Renal artery stenosis, Renovascular hypertension, Renal tubular acidosis, Alport syndrome, Wenger's granulomatosis, Alagille syndrome, Cystinosis, Fabry disease, Focal segmental glomerulosclerosis (FSGS), Glomerulonephritis, aHUS (atypical hemolytic uremic syndrome), Hemolytic uremic syndrome (HUS), Henoch-Schönlein purpura, IgA nephropathy (Berger's disease), Interstitial nephritis, Minimal change disease, Nephrotic syndrome, Thrombotic thrombocytopenic purpura (TTP), Granulomatosis with polyangiitis (GPA), Eczema, Psoriasis, Cellulitis, Impetigo, Atopic dermatitis, Epidermolysis Bullosa, Lichen Sclerosis, Ichthyosis, Vitiligo, Acral peeling skin syndrome, Blau syndrome, Primary cutaneous amyloidosis, Cutaneous abscess, Pressure Ulcers, Blepharitis, Furunculosis, Full or partial thickness burns, Capillaritis, Cellulitis, Corneal Abrasion, Corneal Erosion, Xerosis, Lichen Planus, Lichen Simplex Chronicus, Venous Ulcer (Stasis Ulcer), Adult Still's disease, Agammaglobulinemia, Alopecia areata, Autoimmune angioedema, Autoimmune dysautonomia, Autoimmune encephalomyelitis, Autoimmune hepatitis, Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Bullous pemphigoid, Celiac disease, Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Coxsackie myocarditis, CREST syndrome, Dermatitis herpetiformis, Dermatomyositis, Devic's disease (neuromyelitis optica), Discoid lupus, Eosinophilic esophagitis (EoE), Eosinophilic fasciitis, Erythema nodosum, Essential mixed cryoglobulinemia, Giant cell arteritis (temporal arteritis), Giant cell myocarditis, Granulomatosis with Polyangiitis, Guillain-Barre syndrome, Hashimoto's thyroiditis, Henoch-Schonlein purpura (HSP), Herpes gestationis or pemphigoid gestationis (PG), Hypogammaglobulinemia, IgG4-related sclerosing disease, Immune thrombocytopenic purpura (ITP), Inclusion body myositis (IBM), Lambert-Eaton syndrome, Leukocytoclastic vasculitis, Linear IgA disease (LAD), Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Primary biliary cirrhosis, Primary sclerosing cholangitis, Progesterone dermatitis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Thyroid eye disease (TED), Alagille Syndrome, Alcohol-Related Liver Disease, Autoimmune Hepatitis, Biliary Atresia, Cirrhosis, Lysosomal Acid Lipase Deficiency (LAL-D), Liver Cysts, Liver Cancer, Newborn Jaundice, Non-Alcoholic Fatty Liver Disease, Non-Alcoholic Steatohepatitis, Primary Biliary Cholangitis (PBC), Progressive Familial Intrahepatic Cholestasis (PFIC), Osteoporosis, Paget's Disease, Osteonecrosis, Osteoarthritis, Low Bone Density, Gout, Fibrous Dysplasia, Marfan Syndrome, and Osteogenesis Imperfecta.

Numbered references in the preceding sections are as follows:

[1] Hogan, B. L., Barkauskas, C. E., Chapman, H. A., Epstein, J. A., Jain, R., Hsia, C. C., Niklason, L., Calle, E., Le, A., Randell, S. H., Rock, J., Snitow, M., Krummel, M., Stripp,

[1] B. R., Vu, T., White, E. S., Whitsett, J. A., and Morrisey, E. E. (2014) Repair and regeneration of the respiratory system: complexity, plasticity, and mechanisms of lung stem cell function, *Cell Stem Cell* 15, 123-138.

[2] Barkauskas, C. E., Cronce, M. J., Rackley, C. R., Bowie, E. J., Keene, D. R, Stripp, B. R., Randell, S. H., Noble, P. W., and Hogan, B. L. (2013) Type 2 alveolar cells are stem cells in adult lung, *J Clin Invest* 123, 3025-3036.

[3] Noble, P. W., Barkauskas, C. E., and Jiang, D. (2012) Pulmonary fibrosis: patterns and perpetrators, *J Clin Invest* 122, 2756-2762.

[4] Liang, J., Zhang, Y., Xie, T., Liu, N., Chen, H., Geng, Y., Kurkciyan, A., Mena, J. M., Stripp, B. R, Jiang, D., and Noble, P. W. (2016) Hyaluronan and TLR4 promote surfactant-protein-C-positive alveolar progenitor cell renewal and prevent severe pulmonary fibrosis in mice, *Nat Med* 22, 1285-1293.

[5] Thompson, B. T., Chambers, R. C., and Liu, K. D. (2017) Acute Respiratory Distress Syndrome, *N Engl J Med* 377, 1904-1905.

[6] Janes, J., Young, M. E., Chen, E., Rogers, N. H., Burgstaller-Muehlbacher, S., Hughes, L. D., Love, M. S., Hull, M. V., Kuhen, K. L., Woods, A. K., Joseph, S. B., Petrassi, H. M., McNamara, C. W., Tremblay, M. S., Su, A. I., Schultz, P. G., and Chatterjee, A. K. (2018) The ReFRAME library as a comprehensive drug repurposing library and its application to the treatment of cryptosporidiosis, *Proc Natl Acad Sci USA* 115, 10750-10755.

[7] Xu, J., Wang, J., He, M., Han, H., Xie, W., Wang, H., and Kong, H. (2018) Dipeptidyl peptidase IV (DPP-4) inhibition alleviates pulmonary arterial remodeling in experimental pulmonary hypertension, *Lab Invest* 98, 1333-1346.

[8] Kawasaki, T., Chen, W., Htwe, Y. M., Tatsumi, K., and Dudek, S. M. (2018) DPP4 inhibition by sitagliptin attenuates LPS-induced lung injury in mice, *Am J Physiol Lung Cell Mol Physiol.*

[9] Stone, M. L., Sharma, A. K., Zhao, Y., Charles, E. J., Huerter, M. E., Johnston, W. F., Kron, I. L., Lynch, K. R., and Laubach, V. E. (2015) Sphingosine-1-phosphate receptor 1 agonism attenuates lung ischemia-reperfusion injury, *Am J Physiol Lung Cell Mol Physiol* 308, L1245-1252.

[10] Diab, K. J., Adamowicz, J. J., Kamocki, K., Rush, N. I., Garrison, J., Gu, Y., Schweitzer, K. S., Skobeleva, A., Rajashekhar, G., Hubbard, W. C., Berdyshev, E. V., and Petrache, I. (2010) Stimulation of sphingosine 1-phosphate signaling as an alveolar cell survival strategy in emphysema, *Am J Respir Crit Care Med* 181, 344-352.

Additional embodiments of the present disclosure are set forth in the following non-limiting examples. All compounds of the present disclosure are made by procedures analogous to those illustrated below.

EXAMPLES

Intermediate Compounds

Synthesis of (2R,3R,4R,5S)-6-(hexyl(prop-2-yn-1-yl)amino)hexane-1,2,3,4,5-pentaol (Int-1)

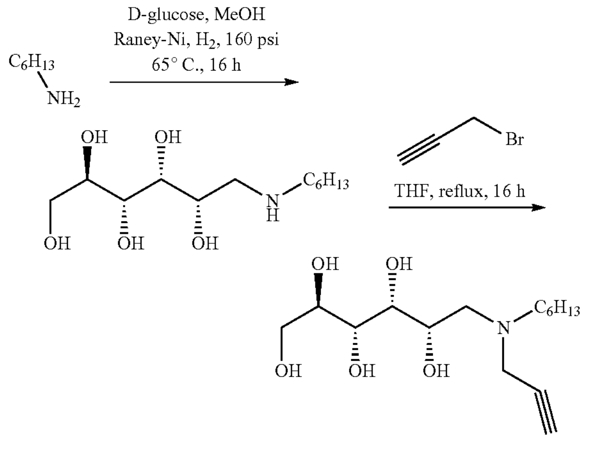

Int-1

Step 1. (2R,3R,4R,5S)-6-(hexylamino)hexane-1,2,3,4,5-pentaol

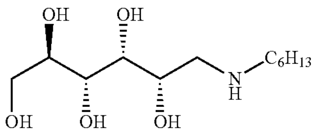

To a stirred solution of hexan-1-amine (2.0 g, 19.76 mmol) and D-glucose (3.56 g, 19.76 mmol) in methanol (20 mL) was added Raney-Ni (1.2 g) at room temperature. The reaction mixture was heated at 65° C. under $H_2$ gas pressure (160 psi) for 16 h. After consumption of the starting materials, the reaction mixture was filtered through celite bed. The filtrate was concentrated under reduced pressure to afford 4.5 g of (2R,3R,4R,5S)-6-(hexylamino)hexane-1,2,3,4,5-pentaol as an off-white solid. [TLC system: MeOH:DCM (1:9); $R_f$ value: 0.2].

Step 2. (2R,3R,4R,5S)-6-(hexyl(prop-2-yn-1-yl)amino)hexane-1,2,3,4,5-pentaol (Int-1)

Int-1

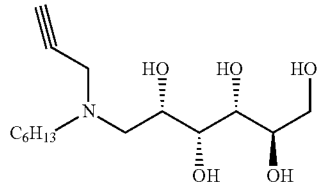

To a stirred solution of (2R,3R,4R,5S)-6-(hexylamino)hexane-1,2,3,4,5-pentaol (1.0 g, 3.77 mmol) in THF (15 mL) was added 3-bromoprop-1-yne (80% solution in toluene, 0.84 mL, 5.65 mmol) and the reaction mixture was stirred at 80° C. for 16 h. After consumption of the starting materials, the reaction mixture was filtered and the filtrate was concentrated under reduced pressure to afford 0.5 g of (2R,3R,4R,5S)-6-(hexyl(prop-2-yn-1-yl)amino)hexane-1,2,3,4,5-pentaol as yellow colour gum. [TLC system: MeOH:DCM (1:9); $R_f$ value: 0.3].

(1R,3S,5S)-3-((tert-butoxycarbonyl)(2-((S)-2-cyanopyrrolidin-1-yl)-2-oxoethyl)amino)adamantan-1-yl Methanesulfonate (Int-2)

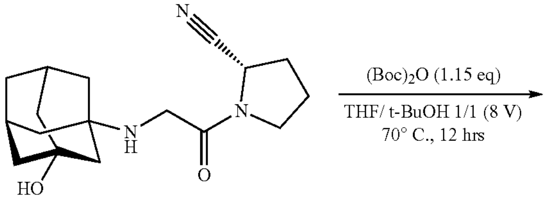

-continued

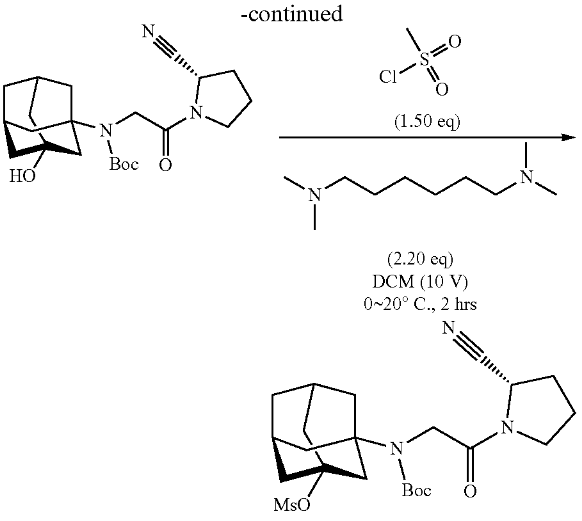

Int-2

Step 1. Tert-butyl (2-((S)-2-cyanopyrrolidin-1-yl)-2-oxoethyl)((1S,3R,5S)-3-hydroxyadamantan-1-yl) carbamate

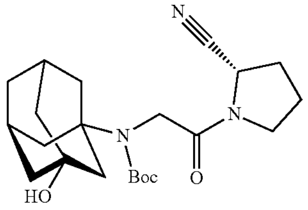

A mixture of (2S)-1-(((1S,3R,5S)-3-hydroxyadamantan-1-yl)glycyl)pyrrolidine-2-carbonitrile (200 g, 659 mmol, 1.00 eq) and $(Boc)_2O$ (165 g, 758 mmol, 1.15 eq) in THF (400 mL) and t-BuOH (400 mL) was degassed and purged with $N_2$ for 3 times, and then the mixture was stirred at 70° C. for 12 hrs under $N_2$ atmosphere. The solution was concentrated under reduced pressure, and MTBE (200 mL) was added. The mixture was filtered to give tert-butyl (2-((S)-2-cyanopyrrolidin-1-yl)-2-oxoethyl)((1 S,3R,5S)-3-hydroxyadamantan-1-yl)carbamate (239 g, 592 mmol, 89.8% yield, 99.7% purity) as a white solid. TLC system: PE:EA (0:1); $R_f$: 0.40.

Step 2. (1R,3S,5S)-3-((tert-butoxycarbonyl)(2-((S)-2-cyanopyrrolidin-1-yl)-2-oxoethyl)amino)adamantan-1-yl methanesulfonate (Int-2)

Int-2

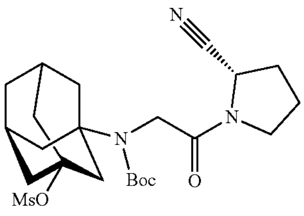

To a solution of compound tert-butyl (2-((S)-2-cyanopyrrolidin-1-yl)-2-oxoethyl)((1S,3R,5S)-3-hydroxyadamantan-1-yl)carbamate (230 g, 570 mmol, 1.00 eq) and N,N,N',N'-tetramethyl-1,6-hexanediamine (216 g, 1.25 mol, 2.20 eq) in DCM (2.30 L) and cooled to 0-10° C., methanesulfonyl chloride (97.9 g, 855 mmol, 1.50 eq) were added at 0-10° C. The reaction was stirred for 2 hrs at 15-20° C. The reaction mixture was quenched by adding ice water (1.00 L) at 0° C., and extracted with EA (2.00 L). The combined organic layers were washed with brine 1.00 L, dried over $Na_2SO_4$, filtered and concentrated under reduced pressure to give (1R,3S,5S)-3-((tert-butoxycarbonyl)(2-((S)-2-cyanopyrrolidin-1-yl)-2-oxoethyl)amino)adamantan-1-yl methanesulfonate (440 g, crude) as a light yellow oil. TLC system: PE:EA (10:1); $R_f$: 0.60).

Synthesis of tert-butyl ((1S,3R,5S)-3-(2-(2-azidoethoxy)ethoxy)adamantan-1-yl)(2-((S)-2-cyanopyrrolidin-1-yl)-2-oxoethyl)carbamate (Int-3)

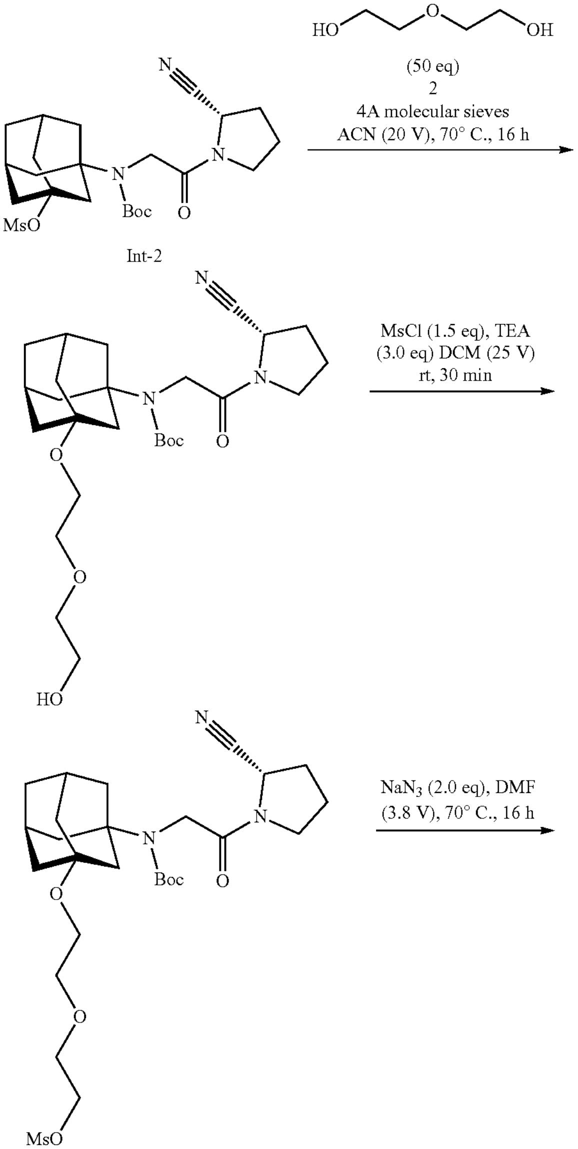

-continued

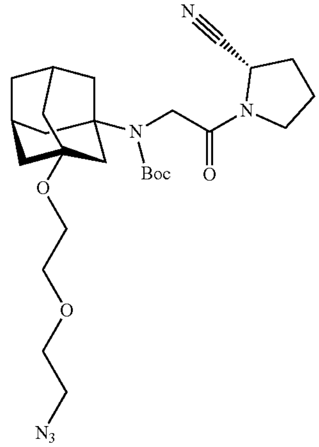

Int-3

Step 1. Tert-butyl (2-((S)-2-cyanopyrrolidin-1-yl)-2-oxoethyl)((1S,3R,5S)-3-(2-(2-hydroxyethoxy)ethoxy)adamantan-1-yl)carbamate

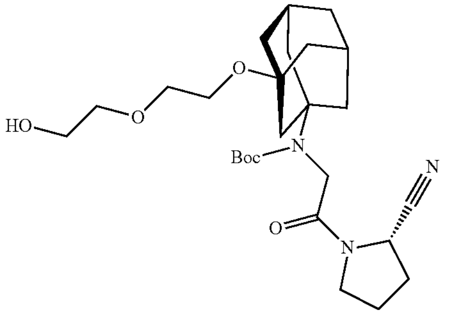

To a stirred solution of (1R,3S,5S)-3-((tert-butoxycarbonyl)(2-((S)-2-cyanopyrrolidin-1-yl)-2-oxoethyl)amino)adamantan-1-yl methanesulfonate (3.58 g, 7.43 mmol) and 2,2'-oxybis(ethan-1-ol) (35.2 mL, 371.67 mmol) in acetonitrile (10 mL) was added molecular sieves 4 Å (4 g) and the mixture was stirred at 70° C. for 16 h. After completion, the reaction mixture was diluted with water (500 mL) and resulting mixture was extracted with ethyl acetate (3×500 mL). The combined organic layer was dried over anhydrous sodium sulfate and evaporated to give crude product. The crude was then purified by silica gel column chromatography (230-400 mesh) using 3% methanol in dichloromethane to afford tert-butyl (2-((S)-2-cyanopyrrolidin-1-yl)-2-oxoethyl)((1 S,3R,5S)-3-(2-(2-hydroxyethoxy)ethoxy)adamantan-1-yl)carbamate (2.7 g) as a brown gum. TLC system: MeOH:DCM (1:9); $R_f$: 0.4.

Step 2. 2-(2-(((1R,3S,5S)-3-((tert-butoxycarbonyl)(2-((S)-2-cyanopyrrolidin-1-yl)-2-oxoethyl)amino)adamantan-1-yl)oxy)ethoxy)ethyl methanesulfonate

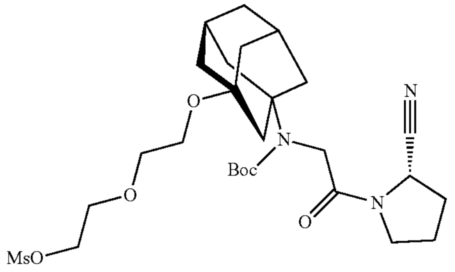

To a stirred solution of tert-butyl (2-((S)-2-cyanopyrrolidin-1-yl)-2-oxoethyl)((1S,3R,5S)-3-(2-(2-hydroxyethoxy)ethoxy)adamantan-1-yl)carbamate (2.7 g, 5.49 mmol) in dichloromethane (25 mL) was added triethylamine (1.67 g, 16.47 mmol) followed by methanesulfonyl chloride (1.26 g, 10.98 mmol) in dichloromethane (5 mL) at −10° C. The resultant mixture was stirred at −10° C. for 1 h. After completion, the reaction mixture was diluted with water (100 mL) and resulting mixture was extracted with dichloromethane (2×300 mL). The combined organic layer was dried over anhydrous sodium sulfate and evaporated to give 2-(2-(((1R,3S,5S)-3-((tert-butoxycarbonyl)(2-((S)-2-cyanopyrrolidin-1-yl)-2-oxoethyl)amino)adamantan-1-yl)oxy)ethoxy)ethyl methanesulfonate (3.1 g) as a pale yellow foamy solid. TLC system: MeOH:DCM (0.5:9.5); $R_f$: 0.4 (TLC was eluted 2 times).

Step 3. Tert-butyl ((1S,3R,5S)-3-(2-(2-azidoethoxy)ethoxy)adamantan-1-yl)(2-((S)-2-cyanopyrrolidin-1-yl)-2-oxoethyl)carbamate (Int-3)

Int-6

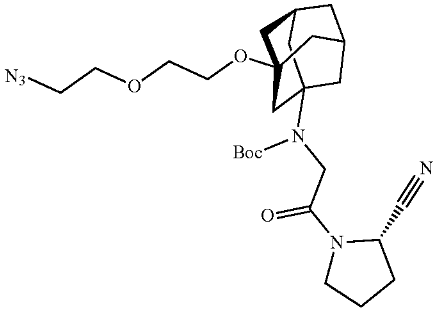

To a stirred solution of 2-(2-(((1R,3S,5S)-3-((tert-butoxycarbonyl)(2-((S)-2-cyanopyrrolidin-1-yl)-2-oxoethyl)amino)adamantan-1-yl)oxy)ethoxy)ethyl methanesulfonate (3.1 g, 5.44 mmol) in N,N-dimethylformamide (10 mL), sodium azide (0.71 g, 10.88 mmol) was added and the reaction mixture was stirred at 70° C. for 16 h. After completion, the reaction mixture was diluted with water (100 mL) and extracted with ethyl acetate (3×300 mL). The combined organic layer was dried over anhydrous sodium sulfate and evaporated to give tert-butyl ((1S,3R,5S)-3-(2-(2-azidoethoxy)ethoxy)adamantan-1-yl)(2-((S)-2-cyanopyrrolidin-1-yl)-2-oxoethyl)carbamate (2.5 g) as a yellow gum. TLC system: MeOH:DCM (0.5:9.5); $R_f$: 0.3 (TLC was eluted 2 times).

Synthesis of (2R,2'R,3R,3'R,4R,4'R,5S,5'S)-6,6'-(prop-2-yn-1-ylazanediyl)bis(hexane-1,2,3,4,5-pentaol) (Int-4)

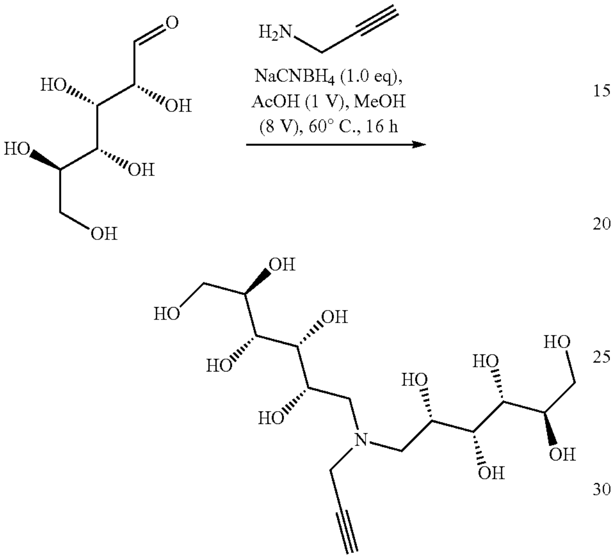

Int-4

To a mixture of (2R,3S,4R,5R)-2,3,4,5,6-pentahydroxyhexanal (2.0 g, 11.08 mmol), prop-2-yn-1-amine (0.3 g, 5.54 mmol) and acetic acid (2.0 mL) in methanol (16 mL) was added sodium cyanoborohydride (0.7 g, 11.08 mmol). The reaction mixture was stirred at 60° C. for 16 h. After completion (reaction monitored by LCMS), the reaction mixture was evaporated and the residue was washed with methanol (2×20 mL), diethyl ether (2×20 mL) and dried to afford (2R,2'R,3R,3'R,4R,4'R,5S,5'S)-6,6'-(prop-2-yn-1-ylazanediyl)bis(hexane-1,2,3,4,5-pentaol) (1.3 g) as an off-white solid.

Synthesis of tert-butyl ((1S,3R,5S)-3-(2-(2-aminoethoxy)ethoxy)adamantan-1-yl)(2-((S)-2-cyanopyrrolidin-1-yl)-2-oxoethyl)carbamate (Int-5)

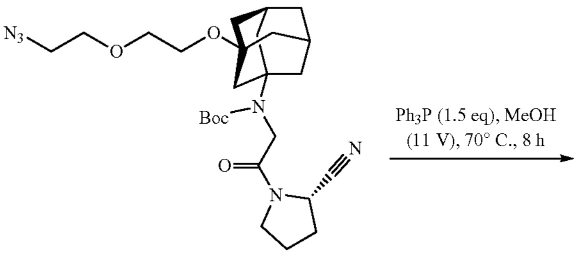

Int-3

-continued

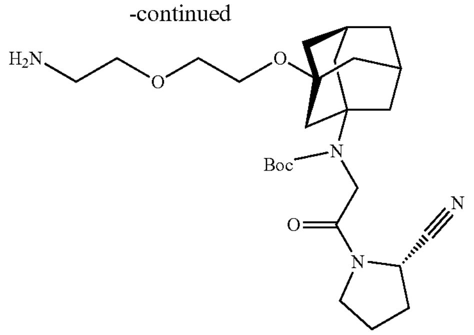

Int-5

To the stirred solution of tert-butyl ((1S,3R,5S)-3-(2-(2-azidoethoxy)ethoxy)adamantan-1-yl)(2-((S)-2-cyanopyrrolidin-1-yl)-2-oxoethyl)carbamate (1.0 g, 1.94 mmol) in methanol (10 mL), triphenylphosphine (0.76 g, 2.9 mmol) was added and the reaction mixture was stirred at 70° C. for 16 h. After completion of reaction, the reaction mixture was evaporated, residue was purified by silica gel column chromatography (basified by triethylamine) using 6% methanol in dichloromethane to afford tert-butyl ((1S,3R,5S)-3-(2-(2-aminoethoxy)ethoxy)adamantan-1-yl)(2-((S)-2-cyanopyrrolidin-1-yl)-2-oxoethyl)carbamate (0.28 g) as pale yellow solid. TLC system: MeOH:DCM (1:9); $R_f$: 0.2.

Synthesis of tert-butyl (2-((S)-2-cyanopyrrolidin-1-yl)-2-oxoethyl)((1S,3R,5S)-3-(2-(2-hydroxyethoxy)ethoxy)adamantan-1-yl)carbamate (Int-6)

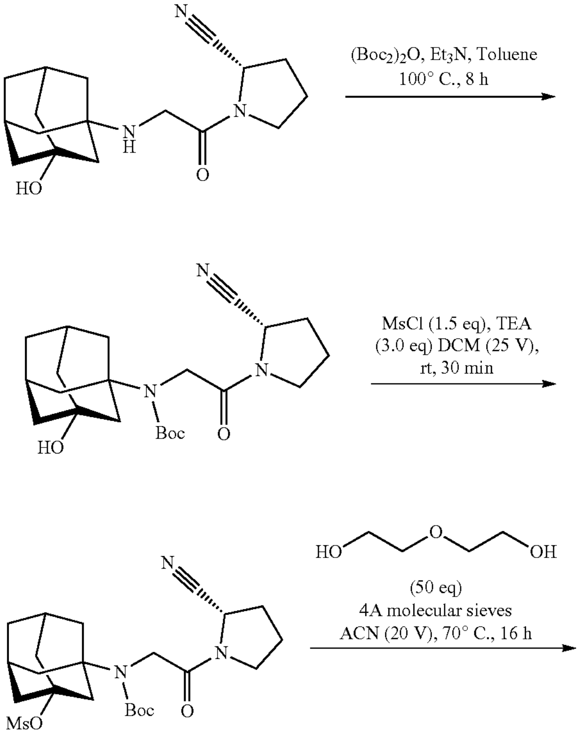

-continued

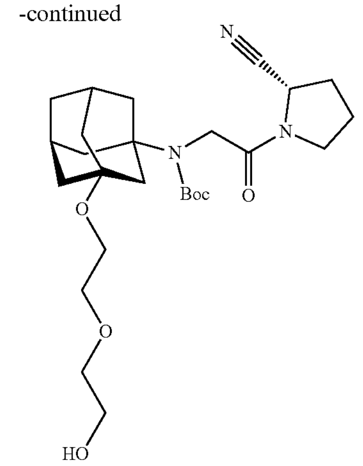

Int-6

Step 1. Tert-butyl (2-((S)-2-cyanopyrrolidin-1-yl)-2-oxoethyl)((S,3R,5S)-3-hydroxyadamantan-1-yl)carbamate

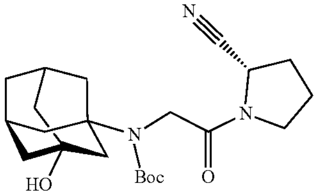

To a stirred suspension of (2S)-1-(((1S,3R,5S)-3-hydroxyadamantan-1-yl)glycyl)pyrrolidine-2-carbonitrile (15 g, 49.44 mmol) in toluene (150 mL) were added triethylamine (13.78 mL, 98.88 mmol) and di-tert-butyl dicarbonate (17.0 mL, 74.16 mmol) and the reaction mixture was stirred at 100° C. for 16 h. After completion, the reaction mixture was evaporated to give crude residue, which was then purified by silica gel (230-400 mesh) column chromatography using 3% methanol in dichloromethane to afford tert-butyl (2-((S)-2-cyanopyrrolidin-1-yl)-2-oxoethyl)((1S,3R,5S)-3-hydroxyadamantan-1-yl)carbamate (17.0 g) as an off-white solid. TLC system: MeOH:DCM (0.5:9.5); $R_f$: 0.2 (TLC was eluted 2 times).

Step 2. (1R,3S,5S)-3-((tert-butoxycarbonyl)(2-((S)-2-cyanopyrrolidin-1-yl)-2-oxoethyl)amino)adamantan-1-yl methanesulfonate

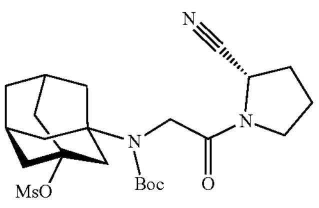

To a stirred solution of tert-butyl (2-((S)-2-cyanopyrrolidin-1-yl)-2-oxoethyl)((1S,3R,5S)-3-hydroxyadamantan-1-yl)carbamate (0.5 g, 1.24 mmol) in dichloromethane (10 mL) was added triethylamine (0.38 g, 3.72 mmol) followed by methanesulfonyl chloride (0.21 g, 1.86 mmol) in dichloromethane (2.5 mL) at −10° C. The reaction mixture was stirred at −10° C. for 30 min. After completion, the reaction mixture was diluted with water (10 mL) and resulting mixture was extracted with dichloromethane (2×30 mL). The combined organic layer was dried over anhydrous sodium sulfate and evaporated to give (1R,3S,5S)-3-((tert-butoxycarbonyl)(2-((S)-2-cyanopyrrolidin-1-yl)-2-oxoethyl)amino)adamantan-1-yl methanesulfonate (0.59 g) as a pale yellow foamy solid. TLC system: MeOH:DCM (0.5:9.5); $R_f$: 0.3 (TLC was eluted 2 times).

Step 3. Tert-butyl (2-((S)-2-cyanopyrrolidin-1-yl)-2-oxoethyl)((1S,3R,5S)-3-(2-(2-hydroxyethoxy)ethoxy)adamantan-1-yl)carbamate (Int-6)

Int-6

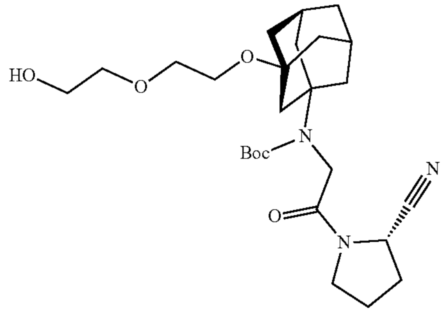

To a stirred solution of (1R,3S,5S)-3-((tert-butoxycarbonyl)(2-((S)-2-cyanopyrrolidin-1-yl)-2-oxoethyl)amino)adamantan-1-yl methanesulfonate (3.58 g, 7.43 mmol) and 2,2'-oxybis(ethan-1-ol) (35.2 mL, 371.67 mmol) in acetonitrile (10 mL) was added molecular sieves 4 Å (4 g) and the mixture was stirred at 70° C. for 16 h. After completion, the reaction mixture was diluted with water (500 mL) and resulting mixture was extracted with ethyl acetate (3×500 mL). The combined organic layer was dried over anhydrous sodium sulphate and evaporated to give crude product. The crude was then purified by silica gel column chromatography (230400 mesh) using 3% methanol in dichloromethane to afford tert-butyl (2-((S)-2-cyanopyrrolidin-1-yl)-2-oxoethyl)((1S,3R,5S)-3-(2-(2-hydroxyethoxy)ethoxy)adamantan-1-yl)carbamate (2.7 g) as a brown gum. TLC system: MeOH:DCM (1:9); $R_f$: 0.4.

Synthesis of (2R,3R,4R,5S)-6-((4-(2-aminoethoxy)phenethyl)(hexyl)amino)hexane-1,2,3,4,5-pentaol (Int-7)

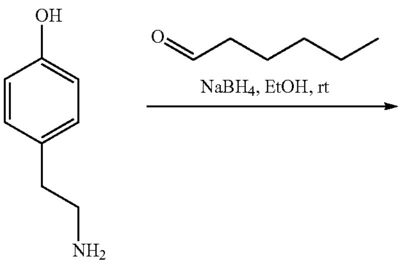

-continued
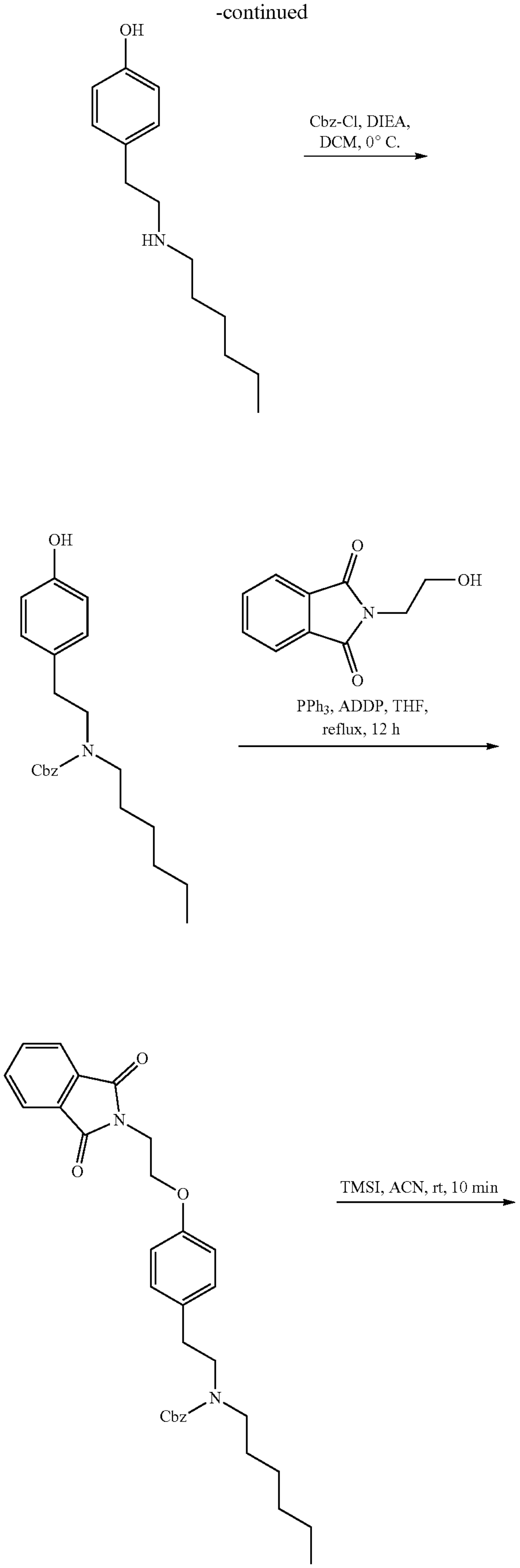
-continued
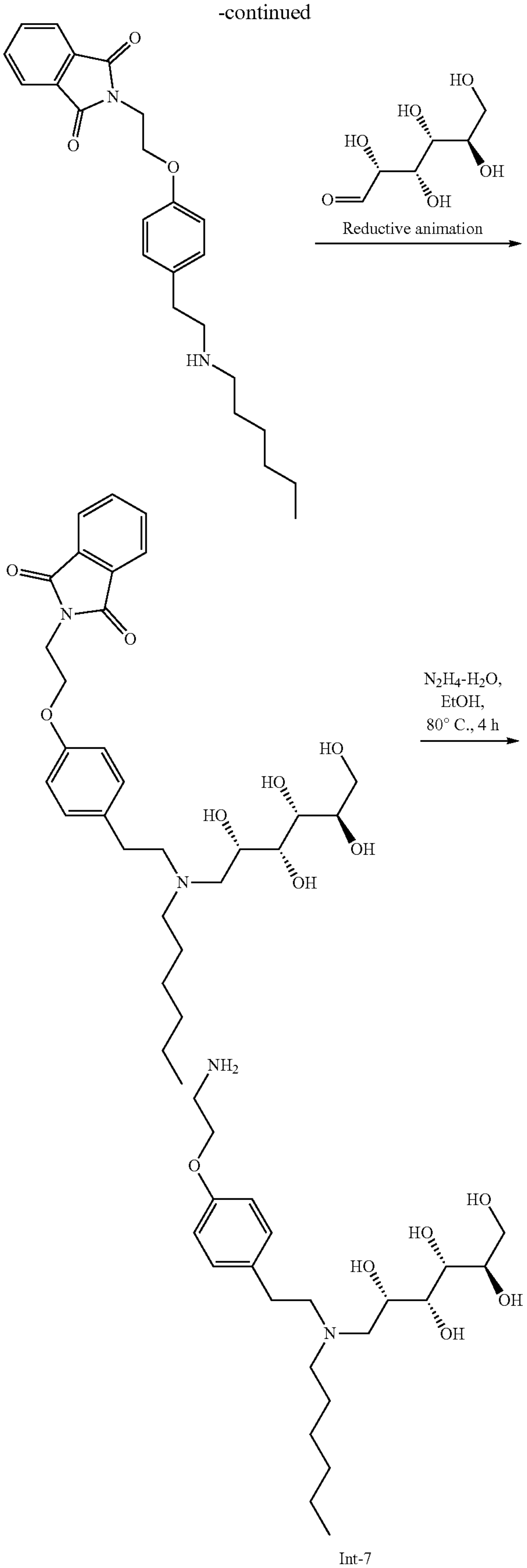
Int-7

Step 1. 4-(2-(hexylamino)ethyl)phenol

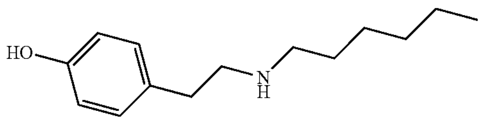 [SMILES: CCCCCCNCCc1ccc(O)cc1]

To a solution of 4-(2-aminoethyl)phenol (15 g, 109 mmol) and hexanal (10 g, 100 mmol) in EtOH (100 mL) was added AcOH (1 drop). The reaction mixture was stirred at 25° C. for 12 hrs. Then $NaBH_4$ (2 g, 54 mmol) was added, and the reaction mixture was stirred at 25° C. for 1 h. The reaction mixture was concentrated under pressure at 40° C. The residue was diluted with water and extracted with EtOAc (200 mL×2). The organic layers were washed with brine (50 mL), then dried over anhydrous $Na_2SO_4$. After filtration, the filtrate was concentrated under vacuum to give crude product. The crude product was purified via Flash column chromatography, eluting with ($CH_2Cl_2$/MeOH, from 0% to 10%) to give 4-(2-(hexylamino)ethyl)phenol (6 g, 24% yield) as a yellow oil. ES MS M/Z=222 (M+1).

Step 2. Benzyl hexyl(4-hydroxyphenethyl)carbamate

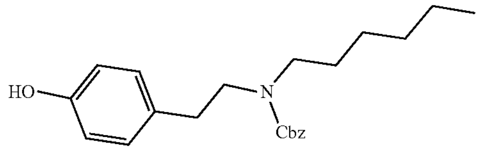 [SMILES: CCCCCCN(CCc1ccc(O)cc1)C(=O)OCc1ccccc1]

To a solution of 4-[2-(hexylamino)ethyl]phenol (6.2 g, 28 mmol) and DIEA (5.41 g, 42 mmol) in DCM (100 mL) was added a solution of CbzCl (4.29 g, 25 mmol) in DCM (10 mL) at 0° C. The reaction mixture was stirred at 0° C. for 1 h. Then the mixture was diluted with $H_2O$ (100 mL) and extracted with DCM (100 mL×2). The DCM phase was dried over $Na_2SO_4$ and concentrated. The residue was purified via Flash column chromatography, eluting with (PE/EtOAc, from 5% to 20%) to give benzyl hexyl(4-hydroxyphenethyl)carbamate (7.63 g, 76% yield) as a yellow oil. ES MS M/Z=356 (M+1).

Step 3. Benzyl (4-(2-(1,3-dioxoisoindolin-2-yl)ethoxy)phenethyl)(hexyl)carbamate

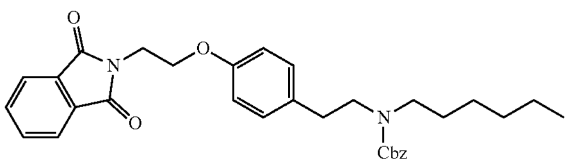 [SMILES: CCCCCCN(CCc1ccc(OCCN2C(=O)c3ccccc3C2=O)cc1)C(=O)OCc1ccccc1]

To a mixture of benzyl hexyl(4-hydroxyphenethyl)carbamate (8.63 g, 24.3 mmol), 2-(2-hydroxyethyl)isoindole-1,3-dione (4.64 g, 24.3 mmol), $PPh_3$ (12.73 g, 48.6 mol) in THF (50 mL) was added a solution of ADDP (12.24 g, 48.6 mmol) in THF (30 mL) at 25° C. under $N_2$ atmosphere. The reaction mixture was stirred at 70° C. under $N_2$ atmosphere for 12 hrs. The reaction mixture was concentrated under pressure at 40° C. The residue was purified via Flash column chromatography, eluting with (PE/EtOAc, from 10% to 50%) to give benzyl (4-(2-(1,3-dioxoisoindolin-2-yl)ethoxy)phenethyl)hexyl)carbamate (10.4 g, 81% yield) as a yellow oil. ES MS M/Z=529 (M+1).

Step 4. 2-(2-(4-(2-(hexylamino)ethyl)phenoxy)ethyl)isoindoline-1,3-dione

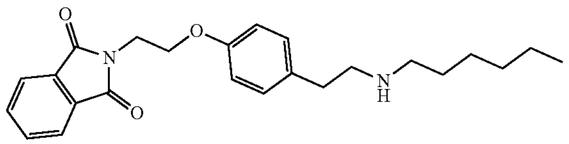 [SMILES: CCCCCCNCCc1ccc(OCCN2C(=O)c3ccccc3C2=O)cc1]

To a solution of benzyl (4-(2-(1,3-dioxoisoindolin-2-yl)ethoxy)phenethyl)hexyl)carbamate (4.86 g, 9.20 mmol) in MeCN (10 mL) was added TMSI (5 g, 35.7 mmol). The reaction mixture was stirred at 25° C. for 10 min. The reaction mixture was concentrated under pressure at 40° C. The residue was purified via Flash column chromatography and eluting with ($CH_2Cl_2$/MeOH, from 5% to 10%) to give 2-(2-(4-(2-(hexylamino)ethyl)phenoxy)ethyl)isoindoline-1,3-dione (2.56 g, 70% yield) as a yellow solid. ES MS M/Z=395 (M+1).

Step 5. 2-(2-(4-(2-(hexyl((2S,3R,4R,5R)-2,3,4,5,6-pentahydroxyhexyl)amino)ethyl)phenoxy)ethyl)isoindoline-1,3-dione

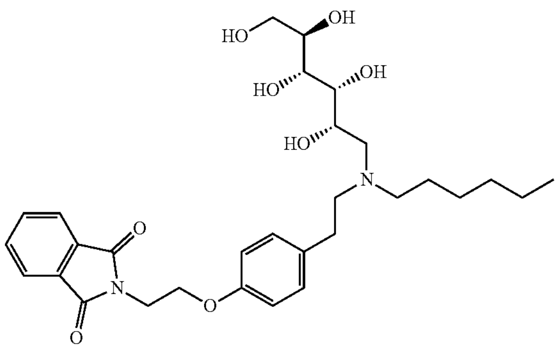 [SMILES: CCCCCCN(CCc1ccc(OCCN2C(=O)c3ccccc3C2=O)cc1)C[C@H](O)[C@@H](O)[C@H](O)[C@H](O)CO]

To a solution of 2-(2-(4-(2-(hexylamino)ethyl)phenoxy)ethyl)isoindoline-1,3-dione (2.92 g, 7.41 mmol) and (2R,3S,4R,5R)-2,3,4,5,6-pentahydroxyhexanal (4.00 g, 22.23 mmol) in MeOH (20 mL) was added AcOH (10 drops). The reaction mixture was stirred at 25° C. for 1 h. Then $NaBH_3CN$ (1.86 g, 29.64 mmol) was added, and the reaction mixture was stirred at 50° C. for 12 hrs. To the reaction mixture was added (2R,3S,4R,5R)-2,3,4,5,6-pentahydroxyhexanal (1.33 g, 14.82 mmol) every 12 hrs until 2-(2-(4-(2-(hexylamino)ethyl)phenoxy)ethyl)isoindoline-1,3-dione was disappeared (total about 4 equivalent of (2R,3S,4R,5R)-2,3,4,5,6-pentahydroxyhexanal was added into the reaction mixture, total reaction time was about 3 days). The reaction mixture was concentrated under pressure at 40° C. The residue was purified via Flash column chromatography and eluted with (DCM/MeOH, from 5% to 10%) to give impure 2-(2-(4-(2-(hexyl((2S,3R,4R,5R)-2,3,4,5,6-pentahydroxyhexyl)amino)ethyl)phenoxy)ethyl)isoindoline-1,3-dione (4 g, 87% yield) as a colorless oil. ES MS M/Z=559 (M+1).

Step 6. (2R,3R,4R,5S)-6-((4-(2-aminoethoxy)phenethyl)(hexyl)amino)hexane-1,2,3,4,5-pentaol (Int-7)

Int-7

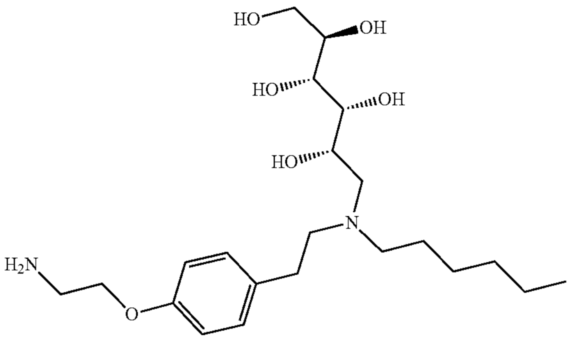

To a solution of 2-(2-(4-(2-(hexyl((2S,3R,4R,5R)-2,3,4,5,6-pentahydroxyhexyl)amino)ethyl)phenoxy)ethyl) isoindoline-1,3-dione (3.5 g, 6.27 mmol) in EtOH (20 mL) was added Hydrazine hydrate (10 mL). The reaction mixture was stirred at 80° C. for 4 hrs. The reaction mixture was concentrated under pressure at 40° C. The residue was purified via Flash column chromatography and eluted with (MeOH/DCM, from 20% to 50%) and give (2R,3R,4R,5S)-6-((4-(2-aminoethoxy)phenethyl)(hexyl)amino)hexane-1,2,3,4,5-pentaol (2.5 g, 93% yield) as a colorless oil. ES MS M/Z=429 (M+1).

Synthesis of (2R,3R,4R,5S)-6-(prop-2-yn-1-ylamino)hexane-1,2,3,4,5-pentaol (Int-8)

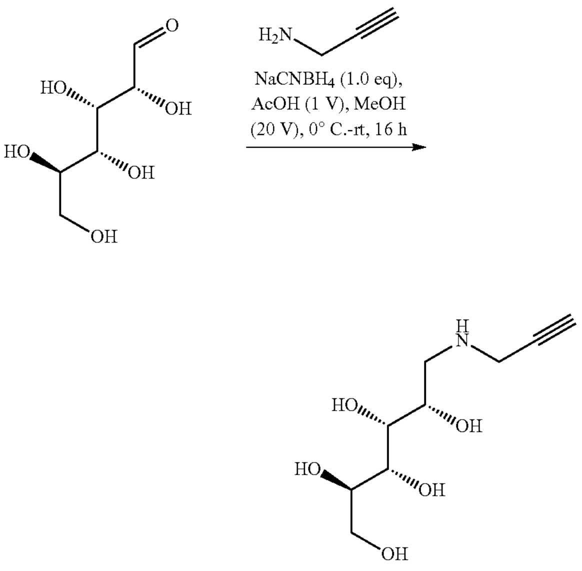

Int-8

To a mixture of (2R,3S,4R,5R)-2,3,4,5,6-pentahydroxyhexanal (1.0 g, 5.54 mmol), prop-2-yn-1-amine (0.61 g, 11.08 mmol) and acetic acid (1.0 mL) in methanol (20 mL) was added sodium cyanoborohydride (0.35 g, 5.54 mmol) at 0° C. The reaction mixture was stirred at room temperature for 16 h. After completion (reaction monitored by LCMS), the reaction mixture was evaporated and residue was washed with diethyl ether (2×20 mL) and dried to afford (2R,3R,4R,5S)-6-(prop-2-yn-1-ylamino)hexane-1,2,3,4,5-pentaol (1.0 g, crude) as an off-white solid.

Synthesis of tert-butyl ((1S)-2-((1S,3S,5S)-3-cyano-2-azabicyclo[3.1.0]hexan-2-yl)-1-((1S,3R,5S)-3-(2-hydroxyethoxy)adamantan-1-yl)-2-oxoethyl)carbamate (Int-9)

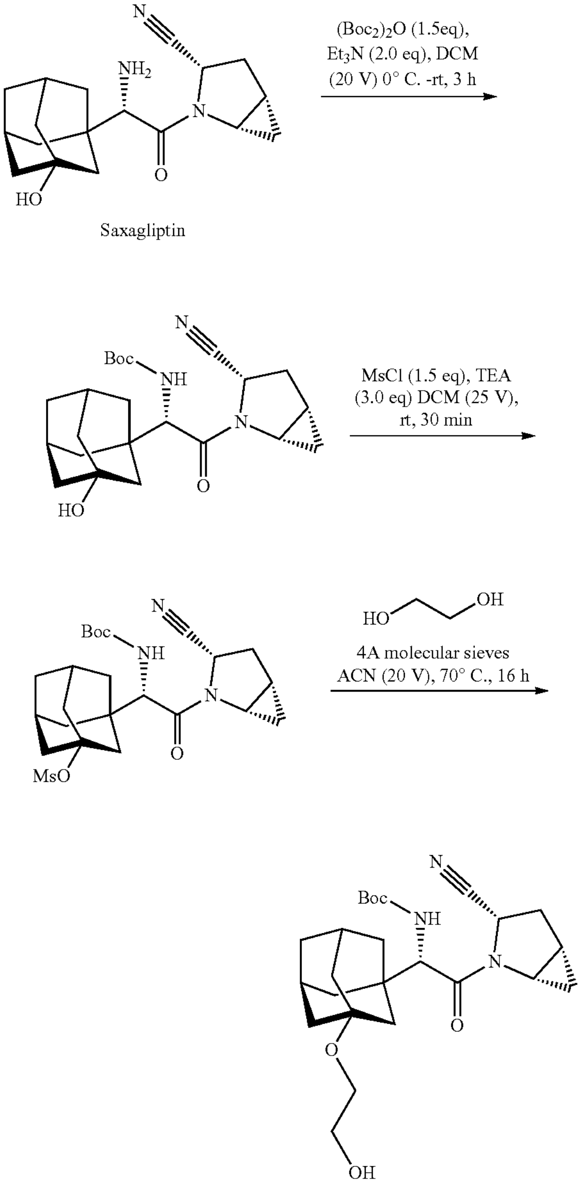

Int-9

Step 1. Tert-butyl ((1S)-2-((1S,3S,5S)-3-cyano-2-azabicyclo[3.1.0]hexan-2-yl)-1-((1S,3R,5S)-3-hydroxyadamantan-1-yl)-2-oxoethyl)carbamate

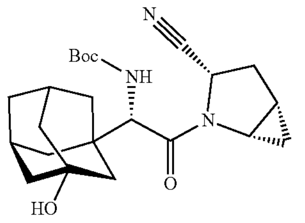

To a stirred suspension of (1S,3S,5S)-2-((2S)-2-amino-2-((1S,3R,5S)-3-hydroxyadamantan-1-yl)acetyl)-2-azabicyclo[3.1.0]hexane-3-carbonitrile (2 g, 6.34 mmol) in dichloromethane (40 mL) was added triethylamine (1.8 mL, 12.68 mmol) followed by di-tert-butyl dicarbonate (2.2 mL, 9.51 mmol) at 0° C. and the reaction mixture was stirred at room temperature for 3 h. After completion, the reaction mixture was evaporated to give crude residue, which was then purified by silica gel (230-400 mesh) column chromatography using 3% methanol in dichloromethane to afford tert-butyl ((1S)-2-((1S,3S,5S)-3-cyano-2-azabicyclo[3.1.0]hexan-2-yl)-1-((1S,3R,5S)-3-hydroxyadamantan-1-yl)-2-oxoethyl)carbamate (2.5 g) as an off-white solid. TLC system: MeOH:DCM (0.5:9.5); $R_f$: 0.4.

Step 2. (1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl methanesulfonate

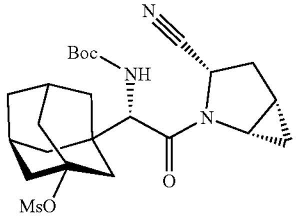

To a stirred solution of tert-butyl ((1S)-2-((1S,3S,5S)-3-cyano-2-azabicyclo[3.1.0]hexan-2-yl)-1-((1S,3R,5S)-3-hydroxyadamantan-1-yl)-2-oxoethyl)carbamate (2.5 g, 6.02 mmol) in dichloromethane (50 mL) was added triethylamine (2.5 mL, 18.06 mmol) followed by methanesulfonyl chloride (1.03 g, 9.03 mmol) in dichloromethane (2.5 mL) at −10° C. and the mixture was stirred for 30 min. After completion, water (50 mL) was added to the reaction mixture and extracted with dichloromethane (2×100 mL). The combined organic layer was dried over anhydrous sodium sulfate and evaporated to give (1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl methanesulfonate (3.2 g) crude as a white foamy solid. TLC system: 100% EtOAc; $R_f$: 0.4.

Step 3. Tert-butyl ((1S)-2-((1S,3S,5S)-3-cyano-2-azabicyclo[3.1.0]hexan-2-yl)-1-((1S,3R,5S)-3-(2-hydroxyethoxy)adamantan-1-yl)-2-oxoethyl)carbamate (Int-9)

Int-9

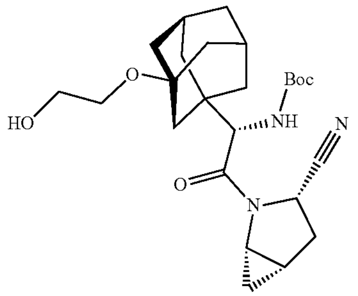

To a stirred solution of (1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl methanesulfonate (3.2 g, 6.48 mmol) and ethane-1,2-diol (18.2 mL, 324.13 mmol) in acetonitrile (30 mL) was added molecular sieves 4 Å (3.5 g), the resultant mixture was stirred at 70° C. for 16 h. After completion, the reaction mixture was concentrated and the crude was filtered through Buchner funnel, diluted with water (100 mL) and extracted with ethyl acetate (3×100 mL). The combined organic layer was dried over anhydrous sodium sulfate and evaporated to afford tert-butyl ((1 S)-2-((1S,3S,5S)-3-cyano-2-azabicyclo[3.1.0]hexan-2-yl)-1-((1S,3R,5S)-3-(2-hydroxyethoxy)adamantan-1-yl)-2-oxoethyl)carbamate (2.0 g) crude as an off-white foamy solid. TLC system: 100% EtOAc, $R_f$: 0.3.

tert-butyl ((1S)-2-((1S,3S,5S)-3-cyano-2-azabicyclo[3.1.0]hexan-2-yl)-1-((1S,3R,5S)-3-(2-(2-hydroxyethoxy)ethoxy)adamantan-1-yl)-2-oxoethyl)carbamate (Int-9B) was prepared according to the same route.

Synthesis of (2R,3R,4R,5S)-6-((4-(aminomethyl)benzyl)(hexyl)amino)hexane-1,2,3,4,5-pentaol (Int-10)

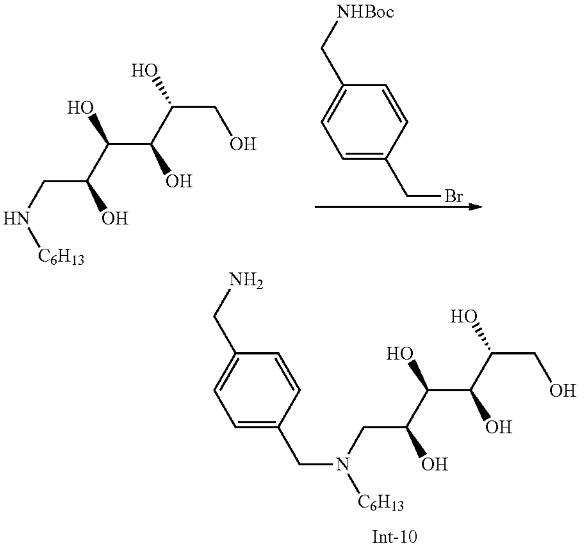

Int-10

To a suspension of N-hexyl-D-glucamine (840 mg, 1.05 eq) and potassium carbonate (594 mg, 1.5 eq) in methanol (8 mL), tert-butyl 4-(bromomethyl)benzylcarbamate (820 mg, 1.0 eq) was added portion wise at 0° C. After 4 hours of stirring at room temperature, the reaction mixture was filtered via a pad of Celite with dichloromethane. The filtrate was then washed by water can concentrated in vacuo to provide the crude product as a yellow oil which was used for the next step without further purification. The above crude (700 mg) was dissolved with 4 M HCl in dioxane (4.5 mL) and methanol (0.5 mL) at 0° C. After stirring at room temperature for 3 hours, the volatiles were removed under reduced pressure to afford a white powder of (2R,3R,4R,5S)-6-((4-(aminomethyl)benzyl)(hexyl)amino)hexane-1,2,3,4,5-pentaol hydrochloride which was used for next step without further purification.

Synthesis of 1-azido-2-(2-(2-bromoethoxy)ethoxy)ethane (Int-11)

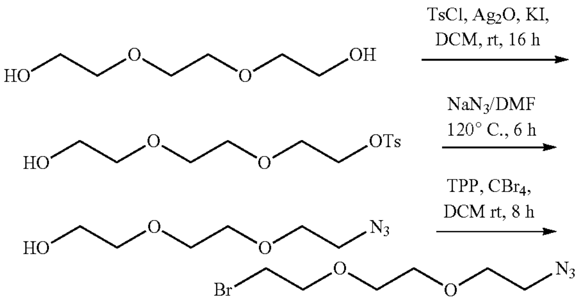

Int-11

Step 1. 2-(2-(2-hydroxyethoxy)ethoxy)ethyl 4-methylbenzenesulfonate

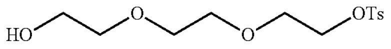 [SMILES: Cc1ccc(S(=O)(=O)OCCOCCOCCO)cc1]

To a stirred solution of compound 2,2'-(ethane-1,2-diylbis(oxy))bis(ethan-1-ol) (15 g, 99.88 mmol) in DCM (150 mL) was added silver oxide (27.7 g, 119.85 mmol) followed by potassium iodide (1.6 g, 9.98 mmol) under nitrogen atm at rt. The resultant reaction mixture was stirred at rt for 10 min. p-TsCl (19 g, 99.88 mmol) was added and the resultant reaction mixture was stirred at rt for 16 h. The progress of the reaction was monitored by TLC. After completion of starting material, reaction mixture was concentrated under reduced pressure to get crude compound. The crude compound was purified by column chromatography using silica gel (230-400 mesh) eluting with 10% EtOAC-petether to get 11 g of compound 5 as a colorless liquid. [TLC system: EtOAC:petether (2:8); $R_f$ value: 0.5].

Step 2. 2-(2-(2-azidoethoxy)ethoxy)ethan-1-ol

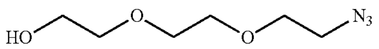 [SMILES: [N-]=[N+]=NCCOCCOCCO]

To a stirred solution of compound 2-(2-(2-hydroxyethoxy)ethoxy)ethyl 4-methylbenzenesulfonate (11 g, 36.14 mmol) in DMF (200 mL) was added sodium azide (4.7 g, 72.28 mmol) at rt. The resultant reaction mixture was heated at 120° C. for 6 h. The progress of the reaction was monitored by TLC. After completion of starting material, reaction mixture was concentrated under reduced pressure to get crude compound. The crude compound was dissolved in diethyl ether (150 mL) and the solid precipitate was removed by filtration through celite pad. The filtrate was collected and concentrated under reduced pressure to get crude compound. The crude compound was purified by column chromatography using silica gel (230-400 mesh) eluting with 10% EtOAC-petether to get 5 g of compound 6 as an off-white solid. [TLC system: EtOAC:petether (3:7); $R_f$ value: 0.3].

Step 3. 1-azido-2-(2-(2-bromoethoxy)ethoxy)ethane (Int-11)

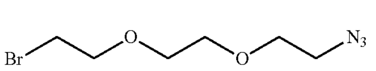

Int-11

To a stirred solution of $CBr_4$ (4.1 g, 12.56 mmol) in DCM (40 mL) was added $Ph_3P$ (3.3 g, 12.56 mmol). Reaction mixture was cooled to 0° C., compound 2-(2-(2-azidoethoxy)ethoxy)ethan-1-ol (2 g, 11.42 mmol) was diluted with DCM (15 mL) and added to reaction mixture slowly drop wise. The reaction mixture was stirred at rt for 8 h. After completion of starting material, the reaction mixture was quenched with water (20 mL) and extracted with DCM (2×50 mL). The combined organic layer was concentrated under reduced pressure to get crude compound. The crude compound was purified by column chromatography using silica gel (230-400 mesh) eluting with 15% EtOAC-petether to get 1.2 g of Int-11 as a colour less liquid. [TLC system: EtOAC:petether (1:1); $R_f$ value: 0.7].

Synthesis of tert-butyl (R)-(1-(7-(but-2-yn-1-yl)-3-methyl-2,6-dioxo-2,3,6,7-tetrahydro-1H-purin-8-yl)piperidin-3-yl)carbamate (Int-13)

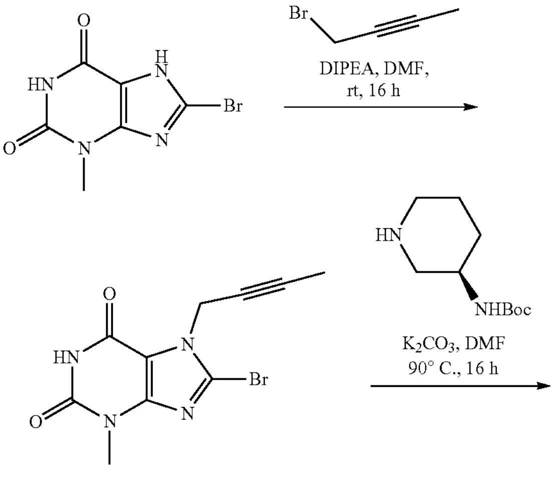

-continued

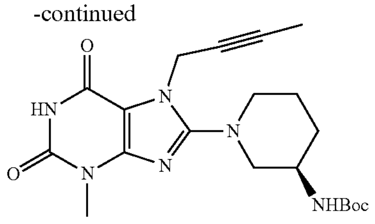

Int-13

Step 1. 8-bromo-7-(but-2-yn-1-yl)-3-methyl-3,7-dihydro-1H-purine-2,6-dione

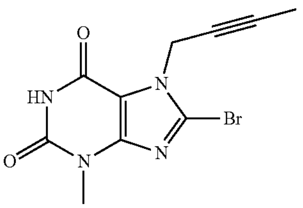 [SMILES: CC#CCn1c(Br)nc2c1c(=O)[nH]c(=O)n2C]

To a stirred solution of compound 8-bromo-3-methyl-3,7-dihydro-1H-purine-2,6-dione (10.0 g, 40.81 mmol) in DMF (100 mL) was added DIPEA (7.13 mL, 40.81 mmol) and 1-bromobut-2-yne (5.43 g, 40.81 mmol) portion wise at room temperature. The reaction mixture was stirred at room temperature for 16 h. After completion of starting material, the reaction mixture was quenched with cold water and the precipitated solid was filtered off, dried under vacuum to get 9.3 g of compound 8-bromo-7-(but-2-yn-1-yl)-3-methyl-3,7-dihydro-1H-purine-2,6-dione as an off-white solid. [TLC system: MeOH:DCM (1:9); $R_f$ value: 0.7].

Step 2. Tert-butyl (R)-(1-(7-(but-2-yn-1-yl)-3-methyl-2,6-dioxo-2,3,6,7-tetrahydro-1H-purin-8-yl) piperidin-3-yl)carbamate (Int-13)

Int-13

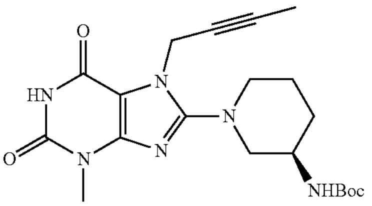

To a stirred solution of 8-bromo-7-(but-2-yn-1-yl)-3-methyl-3,7-dihydro-1H-purine-2,6-dione (4.5 g, 15.15 mmol) in DMF (45 mL) were added tert-butyl (R)-piperidin-3-ylcarbamate (3.33 g, 16.66 mmol) and K2CO3 (6.28 g, 45.45 mmol) and the reaction mixture was stirred at 90° C. for 16 h. After completion of starting material, the reaction mixture was quenched with cold water and the precipitated solid was filtered off, dried under vacuum to get 5.0 g of tert-butyl (R)-(1-(7-(but-2-yn-1-yl)-3-methyl-2,6-dioxo-2,3,6,7-tetrahydro-1H-purin-8-yl)piperidin-3-yl)carbamate as an off-white solid. [TLC system: EtOAc:pet-ether (1:1); Rf value: 0.3].

Synthesis of methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl) methyl)-6-fluoronicotinate (Int-14)

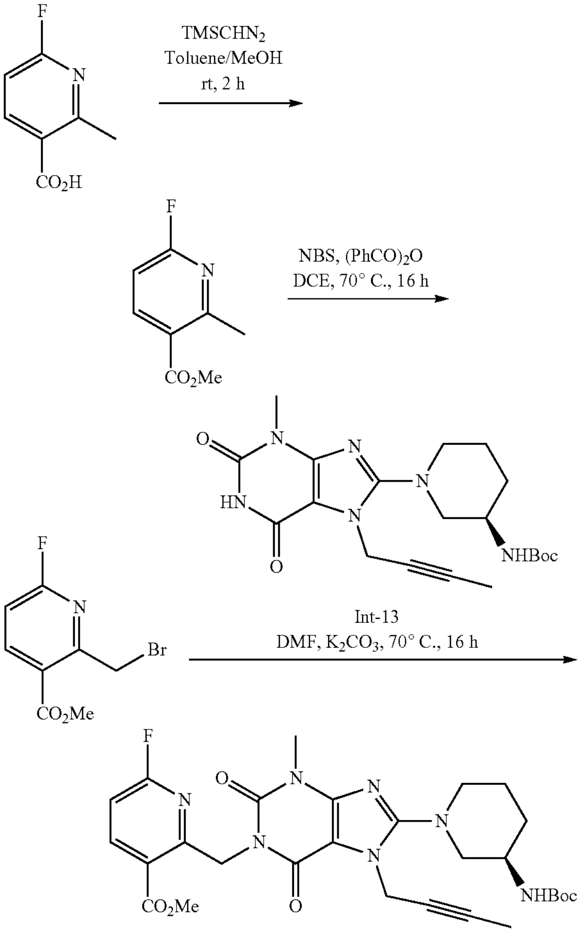

Int-14

Step 1. Methyl 6-fluoro-2-methylnicotinate

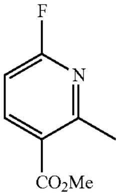

To a stirred solution of 6-fluoro-2-methylnicotinic acid (3.0 g, 19.34 mmol) in THF (36 mL) and methanol (9 mL) at 0° C. was added TMS diazomethane solution 2 M in toluene (12.57 mL, 25.14 mmol) and the reaction mixture was allowed to warm to room temperature over 2 h. After completion of the reaction, volatiles were removed under reduced pressure to get the crude compound. The crude compound was purified by column chromatography (using silica gel 100-200 mesh, 0-10% EtOAc in pet-ether as an eluent) to afford 1.6 g of compound methyl 6-fluoro-2-methylnicotinate as colorless liquid product. [TLC system: EtOAc:pet-ether (3:7); $R_f$ value: 0.8].

Step 2. Methyl 2-(bromomethyl)-6-fluoronicotinate

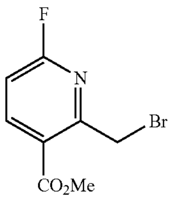 [SMILES: COC(=O)c1ccc(F)nc1CBr]

To a stirred solution of methyl 6-fluoro-2-methylnicotinate methyl 6-fluoro-2-methylnicotinate (1.6 g, 9.46 mmol) in 1,2-dichloroethane (16 mL), were added N-Bromosuccinimide (1.68 g, 9.46 mmol) followed by catalytic benzoyl peroxide (0.11 g, 0.47 mmol) portion wise. The reaction mixture was stirred at 70° C. for 16 h. After completion of the starting material, solvent was evaporated under reduced pressure, quenched with water (100 mL) and extracted the compound with dichloromethane (100 mL*2). The combined organic layer were washed with brine solution (50 mL), dried over anhydrous sodium sulfate, concentrated under reduced pressure to get the crude compound. The crude compound was purified by column chromatography (using silica gel 230-400 mesh, 0-4% EtOAc in pet-ether as an eluent) to afford 1.2 g of compound methyl 2-(bromomethyl)-6-fluoronicotinate as colorless liquid product. [TLC system: EtOAc:pet-ether (1:9); $R_f$ value: 0.7].

Step 3. Methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinate (Int-14)

Int-14

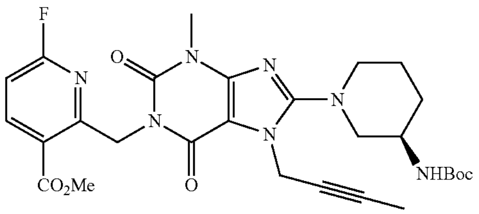

To a stirred solution of methyl 2-(bromomethyl)-6-fluoronicotinate methyl 2-(bromomethyl)-6-fluoronicotinate (0.6 g, 2.42 mmol) in DMF (6 mL), were added compound tert-butyl (R)-(1-(7-(but-2-yn-1-yl)-3-methyl-2,6-dioxo-2,3,6,7-tetrahydro-1H-purin-8-yl)piperidin-3-yl)carbamate (1.01 g, 2.42 mmol) and $K_2CO_3$ (0.33 g, 2.42 mmol) and the reaction mixture was stirred at 70° C. for 16 h. After completion of starting material, the reaction mixture was quenched with cold water and the precipitated solid was filtered off, dried under vacuum to get 1 g of compound methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinate as an off-white solid. [TLC system: EtOAc:pet-ether (1:1); $R_f$ value: 0.4].

Synthesis of (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-(methylamino)nicotinic acid (Int-15)

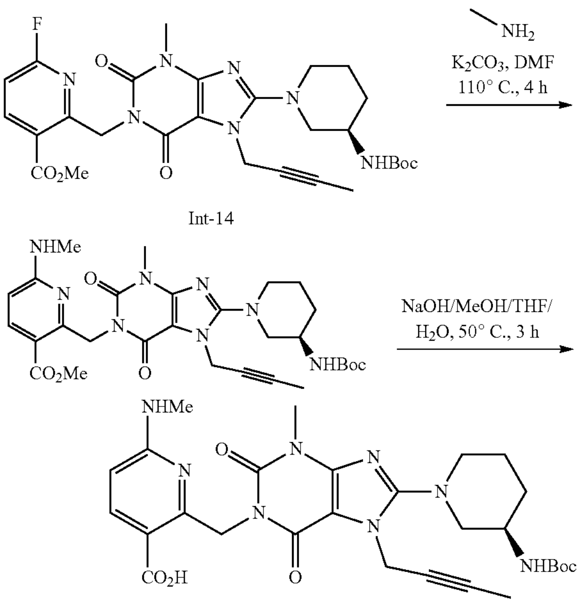

Int-15

Sep 1. Methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-(methylamino)nicotinate

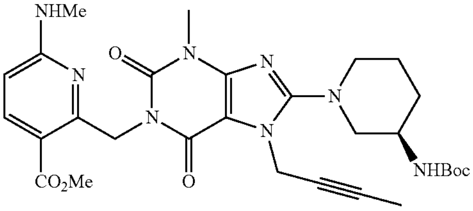 [SMILES: CC#CCn1c(N2CCC[C@@H](NC(=O)OC(C)(C)C)C2)nc2c1c(=O)n(Cc1nc(NC)ccc1C(=O)OC)c(=O)n2C]

To a stirred solution of compound methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinate (1.1 g, 1.88 mmol) in DMF (11 mL) was added $K_2CO_3$ (0.39 g, 2.82 mmol) followed by compound methanamine (1.1 mL, 2.26 mmol) and the reaction mixture was stirred at rt for 4 h. After completion of starting material (TLC monitoring), the reaction mixture was quenched with cold water and the precipitated solid was filtered off, dried under vacuum to get 0.82 g of compound methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-(methylamino)nicotinate as an off-white solid. [TLC system: EtOAc:Pet ether (1:9); $R_f$ value: 0.3].

Step 2 (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-(methylamino)nicotinic acid (Int-15)

Int-15

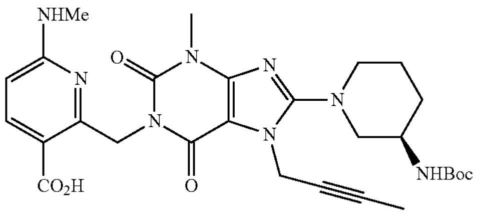

To a stirred solution of compound methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-(methylamino)nicotinate (0.6 g, 1.01 mmol) in MeOH (3 mL), THF (3 mL) and water (1 mL) was added NaOH (0.081 g, 2.02 mmol) at 0° C. The reaction mixture was stirred at 50° C. for 3 h. After completion of starting material (TLC monitoring), the reaction mixture was concentrated under reduced pressure to get crude compound. The crude compound was diluted with water, acidified with 1N HCl. The precipitated solid was filtered off and dried under vacuum to afford 0. g of compound as an off-white solid. [TLC system: MeOH:DCM (1:9); $R_f$ value: 0.1].

Synthesis of 7-azidoheptan-1-amine (Int-16)

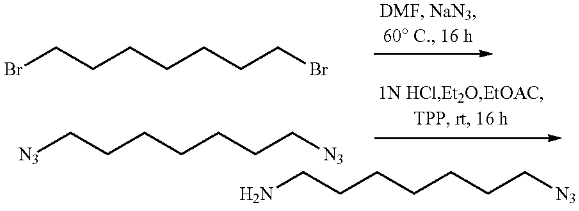

Int-16

Step 1. 1,7-diazidoheptane

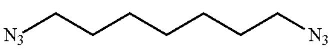

To the solution of compound 1,7-dibromoheptane (10 g, 38.76 mmol) in DMF (100 mL) was added $NaN_3$ (5.04 g, 77.52 mmol) portion wise at room temperature. The reaction mixture was stirred at 60° C. for 16 h. After completion of the reaction (TLC monitoring). The reaction mixture was diluted with water (300 mL) and extracted with EtOAc (2×100 mL). The combined organic layer was dried over anhydrous sodium sulfate and evaporated to get crude. The obtained crude was purified by silica gel (100-200 mesh) column chromatography using 3% EtOAc in pet-ether to afford 1,7-diazidoheptane (6.5 g) as colorless oil compound. [TLC system: EtOAc:pet-ether (1:9); R value: 0.8].

Step 2. 7-azidoheptan-1-amine (Int-16)

Int-16

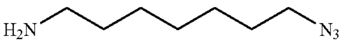

To the solution of compound 1,7-diazidoheptane (6.5 g, 35.67 mmol) in 1N HCl (100 mL) was added EtOAc (32.5 mL) and $Et_2O$ (32.5 mL) followed by TPP (4.68 g, 17.84 mmol) and the reaction mixture was stirred at rt for 16 h. After completion of the reaction (TLC monitoring), the reaction mixture was diluted with water (200 mL) and washed with $Et_2O$ (200 mL). The aqueous layer was basified with saturated $NaHCO_3$ and extracted with EtOAc (2×300 mL). The combined organic layer was dried over anhydrous sodium sulfate and evaporated to afford 7-azidoheptan-1-amine (2.5 g) as colorless oil compound. [TLC system: MeOH:DCM (1:9); $R_f$ value: 0.1].

Synthesis of (1R,1'R,2S,2'S)-3,3'-(prop-2-yn-1-ylazanediyl)bis(1-((4R,5R)-5-hydroxy-2-phenyl-1,3-dioxan-4-yl)propane-1,2-diol) (Int-17)

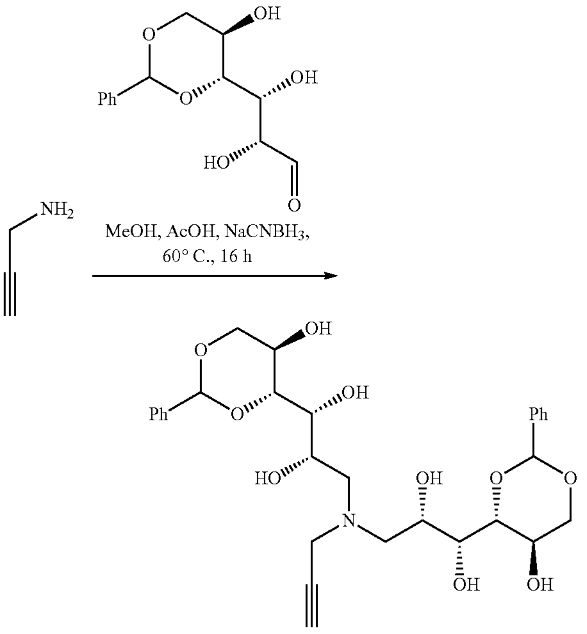

Int-17

To the solution of compound prop-2-yn-1-amine (0.2 g, 1.81 mmol) and (2R,3R)-2,3-dihydroxy-3-((4R,5R)-5-hydroxy-2-phenyl-1,3-dioxan-4-yl)propanal (0.97 g 3.62 mmol) in MeOH (20 mL) and was added AcOH (0.1 mL) and the reaction mixture was stirred at 60° C. for 1 h. The reaction mixture was allowed to come to rt and then added $NaCNBH_3$ (0.68 g 10.86 mmol) at portion wise at 0° C. The reaction mixture was stirred at 60° C. for 16 h. After completion of the reaction (TLC monitoring), the reaction mixture was concentrated under reduced pressure to get a crude mass. The crude compound washed with $Et_2O$ (50 mL) and dried under vacuo to afford compound (1R,1'R,2S,2'S)-3,3'-(prop-2-yn-1-ylazanediyl)bis(1-((4R,5R)-5-hydroxy-2-phenyl-1,3-dioxan-4-yl)propane-1,2-diol) (0.9 g) as off-white solid. [TLC system: MeOH:DCM (1:9); $R_f$ value: 0.1].

Synthesis of methyl 6-((7-(4-((bis((2S,3R)-2,3-dihydroxy-3-((4R,5R)-5-hydroxy-2-phenyl-1,3-dioxan-4-yl)propyl)amino)methyl)-1H-1,2,3-triazol-1-yl)heptyl)amino)-2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)nicotinate (Int-18)
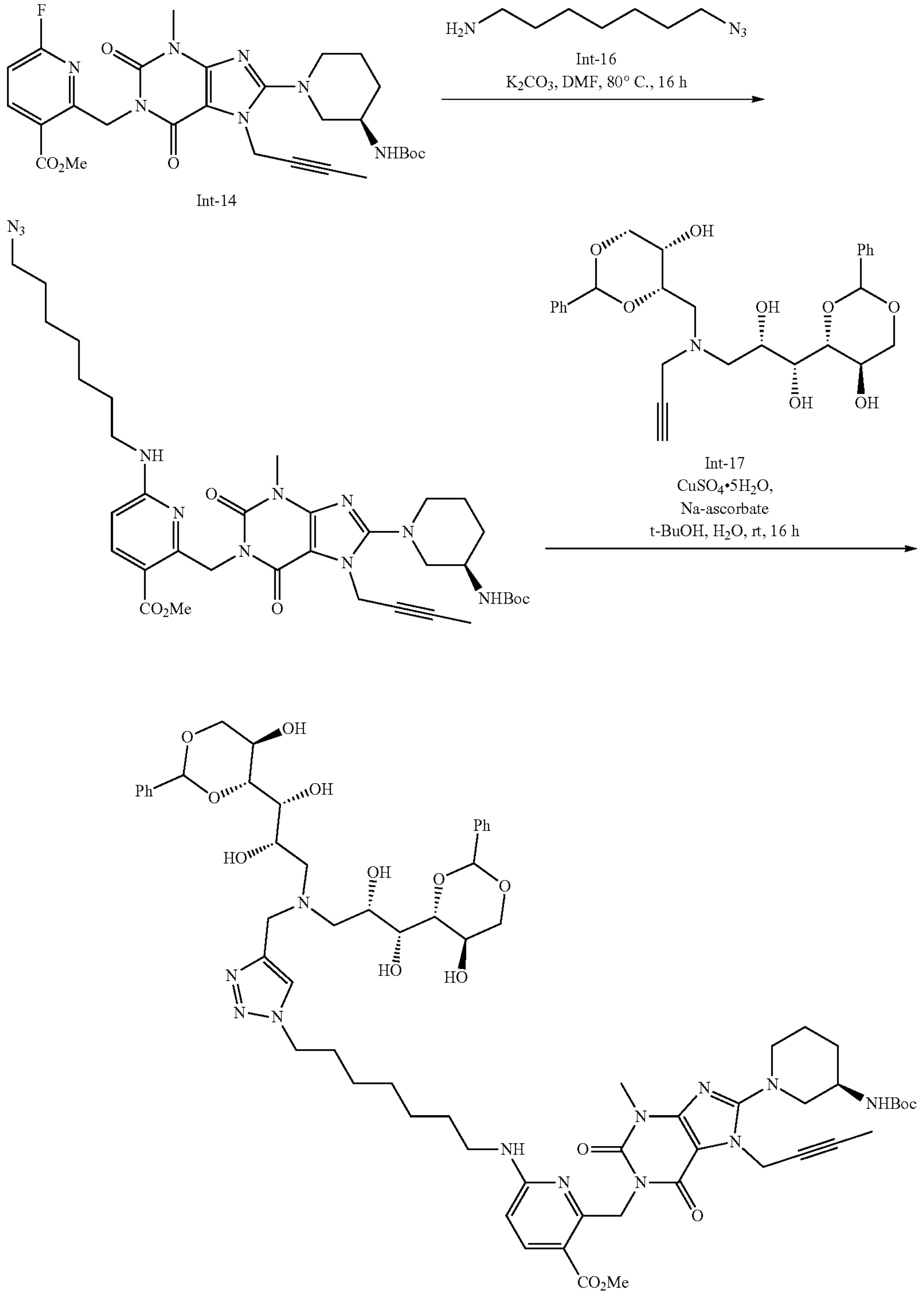
Int-18

Step 1. Methyl (R)-6-((7-azidoheptyl)amino)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)nicotinate

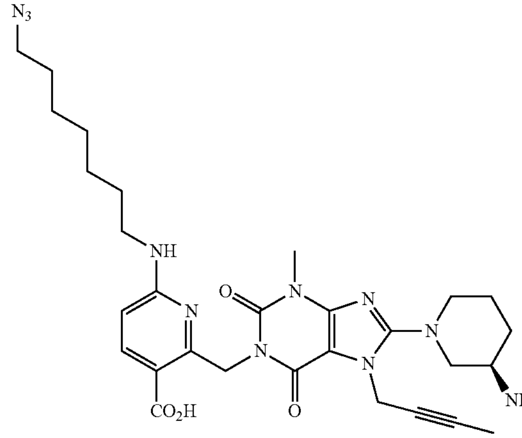

To the of solution of compound methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinate (3.5 g, 6.00 mmol) in DMF (30 mL) was added compound 3 (1.41 g, 9.00 mmol) and $K_2CO_3$ (1.24 g, 9.00 mmol) and the reaction mixture was stirred at 80° C. for 16 h. After completion of the reaction (TLC monitoring), the reaction mixture was diluted with water (100 mL) and extracted with EtOAc (2×100 mL). The combined organic layer was dried over anhydrous sodium sulfate and evaporated to get crude. The obtained crude was purified by silica gel (100-200 mesh) column chromatography using 30% EtOAc in pet-ether to afford methyl (R)-6-((7-azidoheptyl)amino)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)nicotinate (2.8 g) as off-white solid. [TLC system: EtOAc:pet-ether (1:1); $R_f$ value: 0.5].

Step 2. Methyl 6-((7-(4-((bis((2S,3R)-2,3-dihydroxy-3-((4R,5R)-5-hydroxy-2-phenyl-1,3-dioxan-4-yl)propyl)amino)methyl)-1H-1,2,3-triazol-1-yl)heptyl)amino)-2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)nicotinate (Int-18)

Int-18

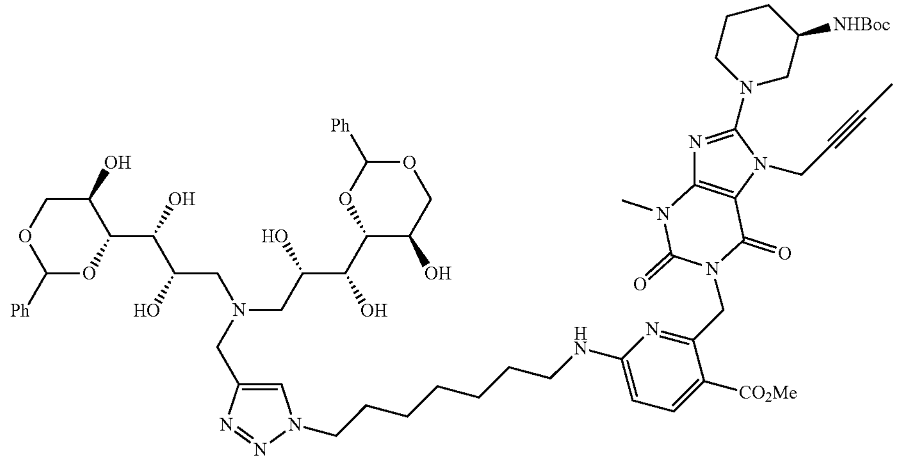

To the solution of compound methyl (R)-6-((7-azidoheptyl)amino)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)nicotinate (0.5 g, 0.69 mmol) and (1R,1'R,2S,2'S)-3,3'-(prop-2-yn-1-ylazanediyl)bis(1-((4R,5R)-5-hydroxy-2-phenyl-1,3-dioxan-4-yl)propane-1,2-diol) (0.97 g 3.62 mmol) in t-BuOH (10 mL) and $H_2O$ (1 mL) and was added $CuSO4{\cdot}5H_2O$ (0.207 g, 0.83 mmol) and Na-ascorbate (0.204 g 1.03 mmol) and the reaction mixture was stirred at rt for 16 h. After completion of the reaction (TLC monitoring). The reaction mixture was concentrated under reduced pressure to get a crude mass. The crude compound was washed with $Et_2O$ (50 mL) and dried under vacuo to afford compound methyl 6-((7-(4-((bis((2S,3R)-2,3-dihydroxy-3-((4R,5R)-5-hydroxy-2-phenyl-1,3-dioxan-4-yl)propyl)amino)methyl)-1H-1,2,3-triazol-1-yl)heptyl)amino)-2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)nicotinate (0.9 g) as off-white solid. The crude compound was taken to the next step without further purification. [TLC system: MeOH:DCM (1:9); $R_f$ value: 0.1].

Synthesis of methyl 2-(bromomethyl)-5-chlorobenzoate (Int-19)

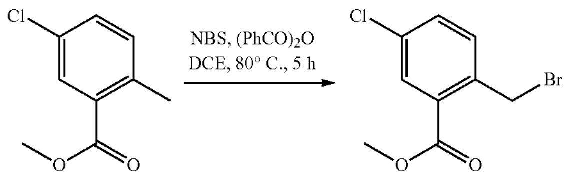

Int-19

To a stirred solution of methyl 5-chloro-2-methylbenzoate methyl 5-chloro-2-methylbenzoate (10.0 g, 54.16 mmol) in 1,2-dichloroethane (100 mL) were added N-bromosuccinimide (9.64 g, 54.16 mmol) and catalytic benzoyl peroxide (0.66 g, 2.71 mmol) portion wise. The reaction mixture was stirred at 80° C. for 5 h. After completion of the starting material the reaction mixture was evaporated under reduced pressure, quenched with water and extracted with ethyl acetate (3×100 mL). The organic layer was washed with brine solution (150 mL), dried over anhydrous sodium sulfate, concentrated under reduced pressure to get the crude compound. The crude compound was purified by column chromatography (using silica gel 230-400 mesh, 100% pet-ether as an eluent) to afford 8 g of compound methyl 2-(bromomethyl)-5-chlorobenzoate as colorless liquid. [TLC system: pet-ether; $R_f$ value: 0.7].

Synthesis of (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoic Acid (Int-20)

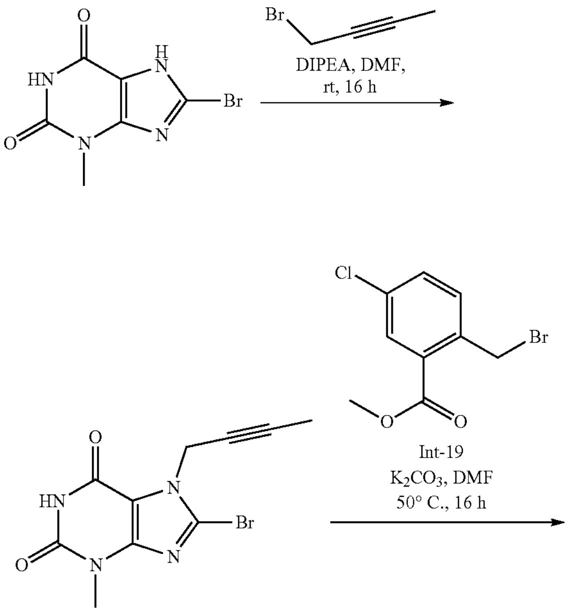

-continued

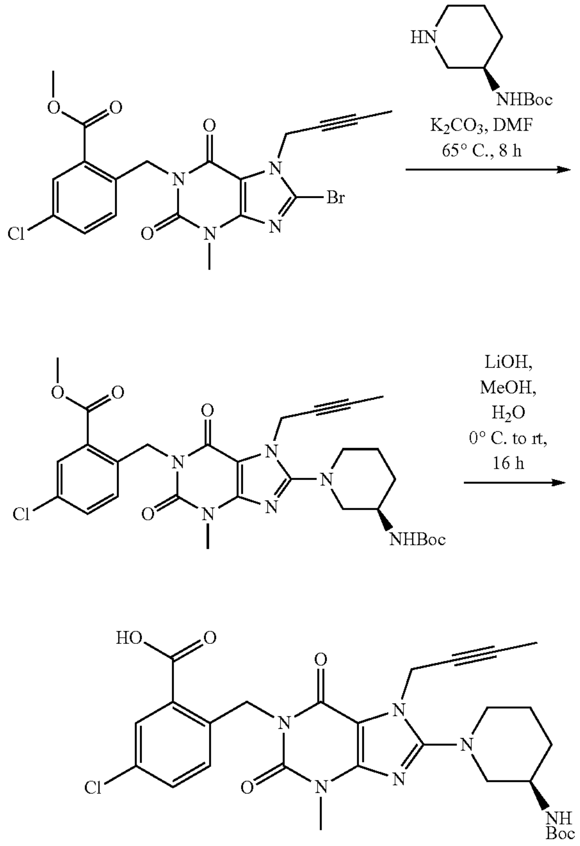

Int-20

Step 1. 8-bromo-7-(but-2-yn-1-yl)-3-methyl-3,7-dihydro-1H-purine-2,6-dione

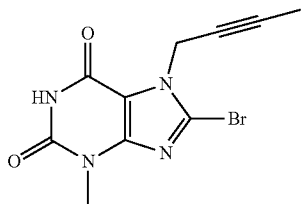 [SMILES: CC#CCn1c(Br)nc2c1c(=O)[nH]c(=O)n2C]

To a stirred solution of compound 8-bromo-3-methyl-3,7-dihydro-1H-purine-2,6-dione (10.0 g, 40.81 mmol) in DMF (100 mL) was added DIPEA (7.13 mL, 40.81 mmol) and 1-bromobut-2-yne (5.43 g, 40.81 mmol) portion wise at room temperature. The reaction mixture was stirred at room temperature for 16 h. After completion of starting material, the reaction mixture was quenched with cold water and the precipitated solid was filtered off, dried under vacuum to get 9.3 g of compound 8-bromo-7-(but-2-yn-1-yl)-3-methyl-3,7-dihydro-1H-purine-2,6-dione as an off-white solid. [TLC system: MeOH:DCM (1:9); $R_f$ value: 0.7].

Step 2. Methyl 2-((8-bromo-7-(but-2-yn-1-yl)-3-methyl-2,6-dioxo-2,3,6,7-tetrahydro-1H-purin-1-yl)methyl)-5-chlorobenzoate

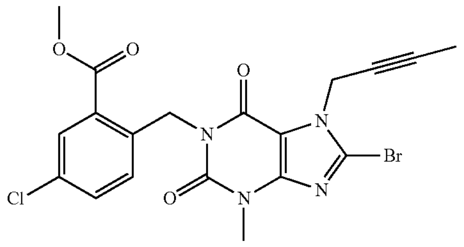 [SMILES: CC#CCn1c(Br)nc2c1c(=O)n(Cc1ccc(Cl)cc1C(=O)OC)c(=O)n2C]

To a stirred solution of compound 8-bromo-7-(but-2-yn-1-yl)-3-methyl-3,7-dihydro-1H-purine-2,6-dione (2.0 g, 6.73 mmol) in DMF (20 mL) were added compound methyl 2-(bromomethyl)-5-chlorobenzoate (1.77 g, 6.73 mmol) and $K_2CO_3$ (2.79 g, 20.19 mmol) and the reaction mixture was stirred at 50° C. for 16 h. After completion of starting material, the reaction mixture was quenched with cold water and the precipitated solid was filtered off, dried under vacuum to get 2.5 g of compound methyl 2-((8-bromo-7-(but-2-yn-1-yl)-3-methyl-2,6-dioxo-2,3,6,7-tetrahydro-1H-purin-1-yl)methyl)-5-chlorobenzoate as an off-white solid. [TLC system: EtOAc:pet-ether (1:1); $R_f$ value: 0.7].

Step 3. Ethyl methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate

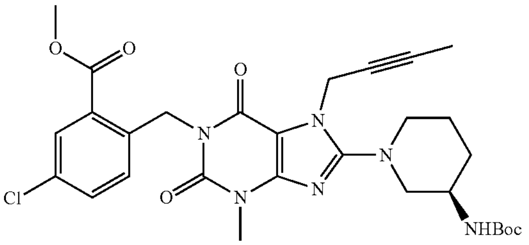 [SMILES: CC#CCn1c(N2CCC[C@@H](NC(=O)OC(C)(C)C)C2)nc2c1c(=O)n(Cc1ccc(Cl)cc1C(=O)OC)c(=O)n2C]

To a stirred solution of compound methyl 2-((8-bromo-7-(but-2-yn-1-yl)-3-methyl-2,6-dioxo-2,3,6,7-tetrahydro-1H-purin-1-yl)methyl)-5-chlorobenzoate (2.5 g, 5.21 mmol) in DMF (25 mL) were added compound tert-butyl (R)-piperidin-3-ylcarbamate (1.25 g, 6.25 mmol) and $K_2CO_3$ (2.16 g, 15.63 mmol) and the reaction mixture was stirred at 65° C. for 8 h. After completion of starting material, the reaction mixture was quenched with cold water and the precipitated solid was filtered off, dried under vacuum to get 2.0 g of compound ethyl methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate as an off-white solid. [TLC system: EtOAc:pet-ether (1:1); $R_f$ value: 0.3].

Step 4. (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoic Acid (Int-20)

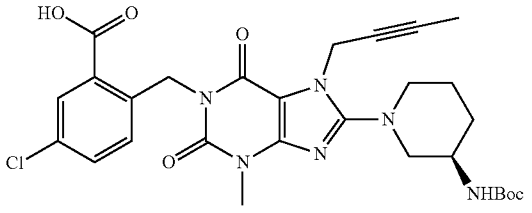

Int-20

To a stirred solution of compound ethyl methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate (0.5 g, 0.83 mmol) in MeOH (5 mL) and water (1 mL) was added $LiOH \cdot H_2O$ (0.11 g, 2.5 mmol) at 0° C. The reaction mixture was stirred at room temperature for 16 h. After completion of starting material, the reaction mixture was concentrated under reduced pressure to get crude compound. The crude compound was diluted with water, acidified with 1N HCL. The precipitated solid was filtered off and dried under vacuum to afford 0.4 g of compound (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoic acid as an off-white solid. [TLC system: MeOH:DCM (1:9); $R_f$ value: 0.3].

Synthesis of (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic Acid (Int-21)

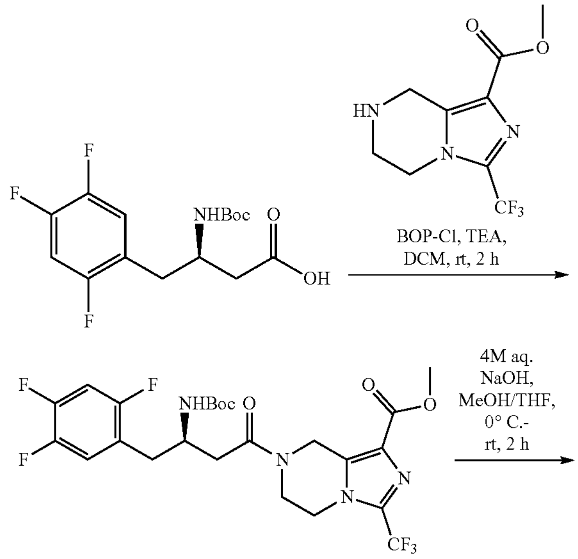

-continued

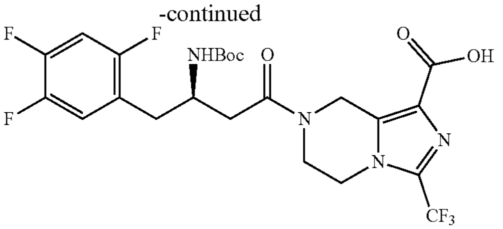

Int-21

Step 1. Methyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate

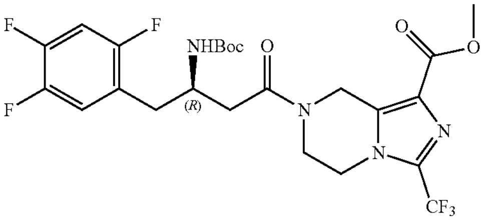

To the stirred suspension of compound (R)-3-((tert-butoxycarbonyl)amino)-4-(2,4,5-trifluorophenyl)butanoic acid (1.35 g, 4.05 mmol) in DCM (20 mL), was added $Et_3N$ (1.69 mL, 12.15 mmol) and BOP—Cl (1.54 g, 6.07 mmol) followed by compound methyl 3-(trifluoromethyl)-5,6,7,8-tetrahydroimidazo[1,5-a]pyrazine-1-carboxylate (1.0 g, 4.05 mmol). The reaction was stirred at RT for 16 h and the progress of reaction was monitored by TLC. After completion of reaction, reaction mixture was concentrated under reduced pressure to get crude compound. The crude compound was purified by column chromatography over silica gel (Davisil) (using 0-60% EtOAc in Pet Ether as an eluent) to afford 1.6 g of compound methyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate as white solid. [TLC system: EtOAc: Pet Ether (6:4); $R_f$-value: 0.5].

Step 2. (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid (Int-21)

Int-21

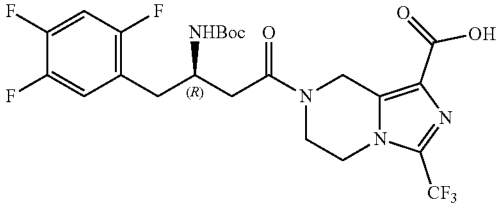

To a solution of compound methyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.5 g, 0.88 mmol) in MeOH (10 mL) and THF (10 mL) was added 4 M NaOH solution (2.7 mL, 5.5V) at 0° C. Then reaction was stirred at RT for 2 h. After completion of reaction, reaction mixture was concentrated and residue was acidified with 10% HCl up to pH–4 then reaction mixture was concentrated to get residue which was dried by co-evaporation with ACN and toluene to afford 0.450 g of compound (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid as off white solid.

Synthesis of 2-(2-(2-azidoethoxy)ethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (Int-22)

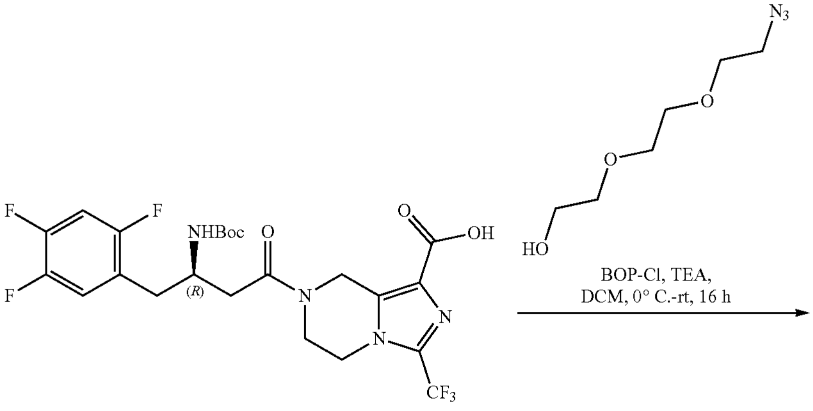

Int-21

-continued

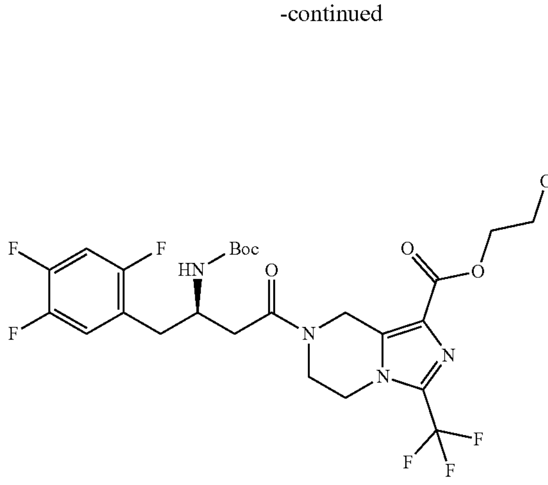

Int-22

To the stirred suspension of compound (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid (0.45 g, 0.81 mmol) in DCM (10 mL), was added $Et_3N$ (0.341 mL, 2.45 mmol) and BOP—Cl (0.312 g, 1.22 mmol) followed by compound 2-(2-(2-azidoethoxy)ethoxy)ethan-1-ol (0.214 g, 1.22 mmol). The reaction mixture was stirred at RT for 16 h. The progress of reaction was monitored by TLC. After completion of reaction, reaction mixture was concentrated to get crude compound which was purified by column chromatography over silica gel (Davisil) (using 0-60% EtOAc in Pet Ether as an eluent) to afford 0.4 g of compound 2-(2-(2-azidoethoxy)ethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate as colorless gum. [TLC system: EtOAc: Pet Ether (7:3); $R_f$ value: 0.7].

Synthesis of 2-(2-(2-azidoethoxy)ethoxy)ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (Int-23)

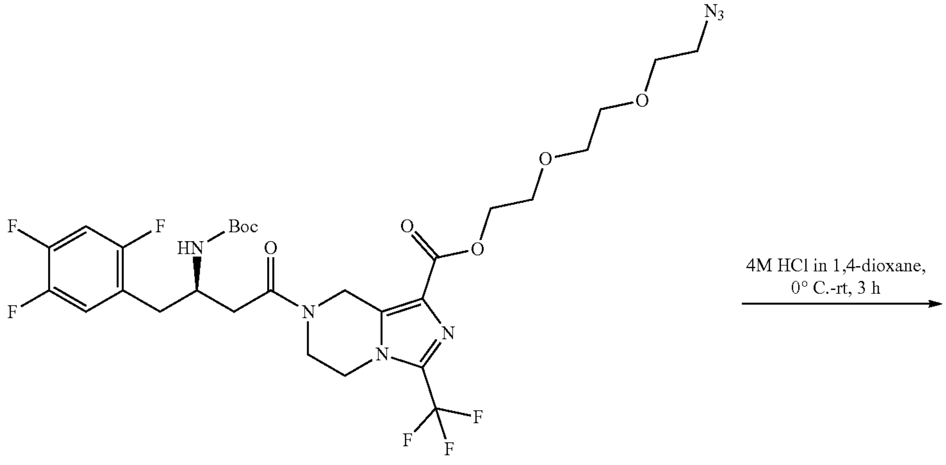

Int-22

-continued

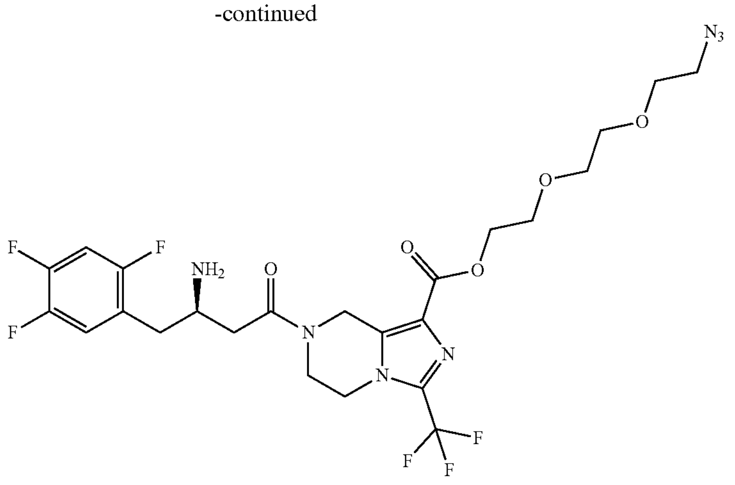

Int-23

To a stirred solution of 2-(2-(2-azidoethoxy)ethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.45 g, 0.64 mmol) in 1,4-dioxane (4.5 mL) was added 4 M HCl in 1,4-dioxane (1 mL) dropwise at 0° C. and the reaction mixture was stirred at room temperature for 2 h. After completion of starting material, the reaction mixture was concentrated under reduced pressure to get crude compound. The crude compound was purified by reverse phase preparative-HPLC to afford 0.1 g of compound Int-23 as an off-white solid[TLC system: EtOAc: Pet Ether (7:3); $R_f$ value: 0.2].

EXEMPLARY COMPOUNDS OF THE DISCLOSURE

Example 1. Synthesis of Heptyl(3-((2-((S)-2-cyanopyrrolidin-1-yl)-2-oxoethyl)amino)adamantan-1-yl) carbamate (1)

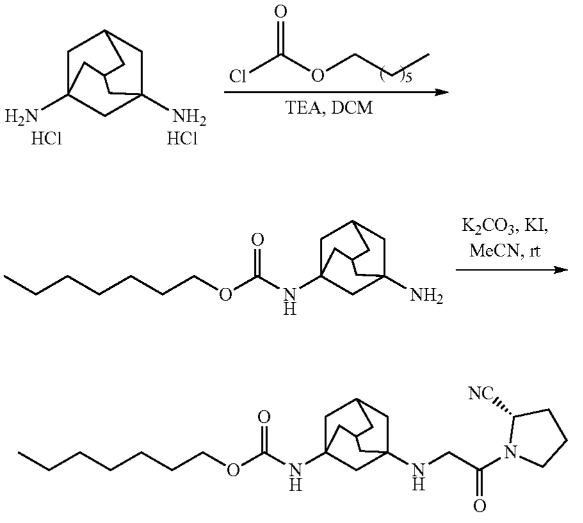

3

Step 1. Heptyl (3-aminoadamantan-1-yl)carbamate

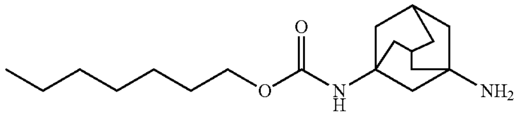 [SMILES: CCCCCCCOC(=O)NC12CC3CC(CC(N)(C3)C1)C2]

Adamantane-1,3-diamine dihydrochloride [500 mg, 2.09 mmol], heptyl chloroformate [336 mg, 1.88 mmol] and TEA [316 mg, 3.14 mmol] were added to DCM [15 mL]. The reaction mixture was stirred for 2 h at rt under $N_2$. The mixture was filtered and washed three times with DCM (5 mL). The filtrate was concentrated to afford methyl 6-chloro-4-methoxypyridazine-3-carboxylate (270 mg, 14% yield) as a white solid. ES MS M/Z=309 (M+1).

Step 2. Heptyl (3-((2-((S)-2-cyanopyrrolidin-1-yl)-2-oxoethyl)amino)adamantan-1-yl)carbamate (1)

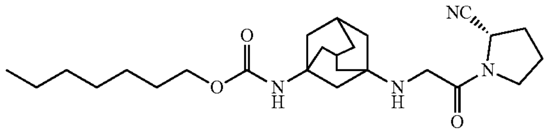 [SMILES: CCCCCCCOC(=O)NC12CC3CC(CC(NCC(=O)N4CCC[C@H]4C#N)(C3)C1)C2]

Heptyl N-(3-aminoadamantan-1-yl)carbamate [300 mg, 0.97 mmol], (2S)-1-(2-chloroacetyl)pyrrolidine-2-carbonitrile [150 mg, 0.87 mmol], $K_2CO_3$ [402 mg, 2.91 mmol] and potassium iodide [161 mg, 0.97 mmol] were added to MeCN [10 mL]. The reaction mixture was stirred for 2 h at rt. The mixture was concentrated and the residue was purified by column chromatography on silica gel, eluting with (DCM: MeOH=20:1) to give heptyl (3-((2-((S)-2-cyanopyrrolidin-1-yl)-2-oxoethyl)amino)adamantan-1-yl)carbamate (1, 160 mg, 90% yield) as a yellow oil. ES MS M/Z=445 (M+1). $^1H$ NMR (400 MHz, DMSO-$d_6$) 6.79 (s, 1H), 4.73 (dd, J=7.3, 3.8 Hz, 1H), 3.85 (t, J=6.4 Hz, 2H), 3.65-3.55 (m, 1H), 3.51-3.38 (m, 2H), 3.36 (d, J=7.3 Hz, 1H), 3.29 (s, 1H), 2.17-2.06 (m, 4H), 2.05-1.95 (m, 2H), 1.72 (d, J=17.5 Hz, 6H), 1.49 (d, J=12.8 Hz, 8H), 1.26 (s, 8H), 0.86 (t, J=6.9 Hz, 3H).

Example 2. Synthesis of (2S)-1-((3-(heptylthio) adamantan-1-yl)glycyl)pyrrolidine-2-carbonitrile (2)

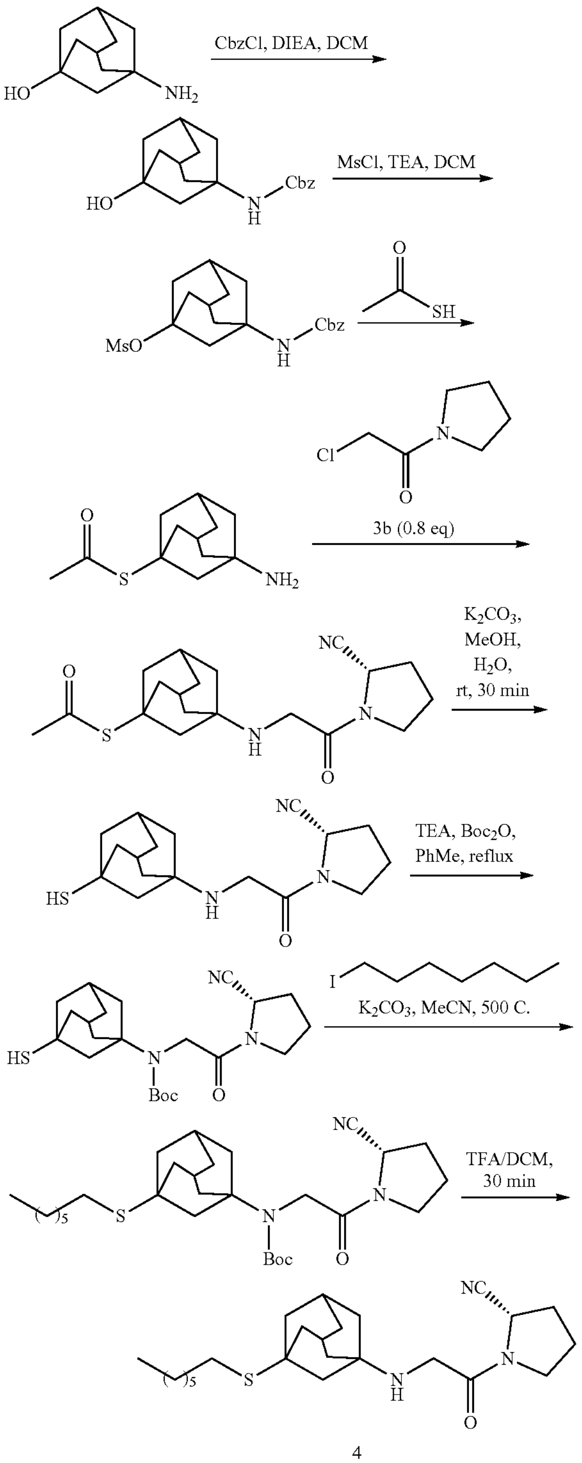

4

Step 1. Benzyl (3-hydroxyadamantan-1-yl)carbamate

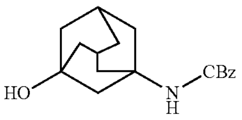

To a solution of 3-aminoadamantan-1-ol (5 g, 29.9 mmol) and DIEA (5.79 g, 44.9 mmol) in DCM (20 mL) was added a solution of CbzCl (5.08 g, 29.9 mmol) in DCM (20 mL) at 0° C. The reaction mixture was stirred at 25° C. for 1 h. The mixture was diluted with water and extracted with DCM (100 mL). The organic layers were dried over $Na_2SO_4$ and concentrated under pressure at 40° C. The residue was purified via Flash column chromatography, eluted with (MeOH/DCM, from 5% to 10%) to give benzyl (3-hydroxyadamantan-1-yl)carbamate (8.5 g, 94% yield) as a white solid. ES MS M/Z=302 (M+1).

Step 2. 3-(((benzyloxy)carbonyl)amino)adamantan-1-yl methanesulfonate

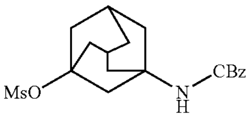

To a solution of benzyl (3-hydroxyadamantan-1-yl)carbamate (3.01 g, 10 mmol) and triethylamine (3 g, 30 mmol) in DCM (20 mL) was added a solution of methanesulfonyl chloride (1.71 g, 15 mmol) in DCM (2 mL) at 0° C. The reaction mixture was stirred at 0° C. for 1 h. The mixture was diluted with water and extracted with DCM (30 mL). The organic layers were dried over $Na_2SO_4$ and concentrated under pressure at 30° C. to give 3-(((benzyloxy)carbonyl)amino)adamantan-1-yl methanesulfonate (3.3 g, 87% yield) as a white solid, which was used to the next step without further purification. ES MS M/Z=402 (M+23).

Step 3. S-(3-aminoadamantan-1-yl) ethanethioate

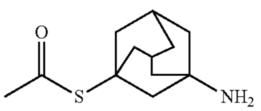

A solution of 3-(((benzyloxy)carbonyl)amino)adamantan-1-yl methanesulfonate (2.5 g, 6.59 mmol) in thiolacetic acid (15 mL) was stirred at 100° C. for 12 h. The reaction mixture was concentrated under pressure at 45° C. The residue was purified via Flash column chromatography, eluted with MeOH/DCM (from 5% to 10%) to give S-(3-aminoadamantan-1-yl) ethanethioate (1 g, 67% yield) as a yellow solid. ES MS M/Z=226 (M+1).

Step 4. S-(3-((2-((S)-2-cyanopyrrolidin-1-yl)-2-oxoethyl)amino)adamantan-1-yl) ethanethioate

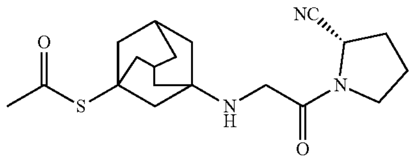 [SMILES: CC(=O)SC12CC3CC(CC(NCC(=O)N4CCC[C@H]4C#N)(C3)C1)C2]

To a mixture of S-(3-aminoadamantan-1-yl) ethanethioate (113 mg, 0.5 mmol), $K_2CO_3$ (207 mg, 1.5 mmol) and KI (8 mg, 0.05 mmol) in MeCN (5 mL) was added 2-chloro-1-(pyrrolidin-1-yl)ethan-1-one (58 mg, 0.4 mmol). The reaction mixture was stirred at 75° C. for 6 h. The reaction mixture was concentrated under pressure at 40° C. The residue was purified via Flash column chromatography, eluted with MeOH/DCM (from 5% to 10%) to give S-(3-((2-((S)-2-cyanopyrrolidin-1-yl)-2-oxoethyl)amino)adamantan-1-yl) ethanethioate (128 mg, 71% yield) as a yellow oil. ES MS M/Z=362 (M+1).

Step 5. (2S)-1-((3-mercaptoadamantan-1-yl)glycyl)pyrrolidine-2-carbonitrile

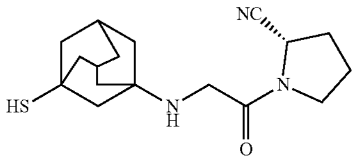 [SMILES: N#C[C@@H]1CCCN1C(=O)CNC12CC3CC(CC(S)(C3)C1)C2]

To a solution of S-(3-((2-((S)-2-cyanopyrrolidin-1-yl)-2-oxoethyl)amino)adamantan-1-yl) ethanethioate (1 g, 2.77 mmol) in MeOH/$H_2O$ (V/V=20:1, 10 mL) was added $K_2CO_3$ (1.14 g, 8.31 mmol). The reaction mixture was stirred at 25° C. for 30 min. The reaction mixture was dried over $Na_2SO_4$ and concentrated under pressure at 35° C. The residue was purified via Flash column chromatography, eluted with MeOH/DCM (from 10% to 20%) to give (2S)-1-((3-mercaptoadamantan-1-yl)glycyl)pyrrolidine-2-carbonitrile (300 mg, 33% yield) as a yellow oil. ES MS M/Z=320 (M+1)

Step 6. Tert-butyl (2-((S)-2-cyanopyrrolidin-1-yl)-2-oxoethyl)(3-mercaptoadamantan-1-yl)carbamate

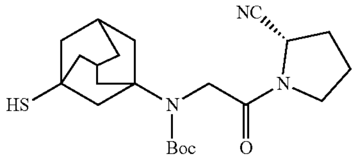 [SMILES: CC(C)(C)OC(=O)N(CC(=O)N1CCC[C@H]1C#N)C12CC3CC(CC(S)(C3)C1)C2]

A mixture of (2S)-1-((3-mercaptoadamantan-1-yl)glycyl)pyrrolidine-2-carbonitrile (400 mg, 1.25 mmol), $Boc_2O$ (545 mg, 2.5 mmol) and TEA (631 mg, 6.25 mmol) in toluene (10 mL) was stirred at reflux for 12 h. The mixture was concentrated. The residue was purified via Flash column chromatography, eluted with MeOH/DCM (from 5% to 10%) to give tert-butyl (2-((S)-2-cyanopyrrolidin-1-yl)-2-oxoethyl)(3-mercaptoadamantan-1-yl)carbamate (400 mg, 76% yield) as a colorless oil. ES MS M/Z=442 (M+23)

Step 7. Tert-butyl (2-((S)-2-cyanopyrrolidin-1-yl)-2-oxoethyl)(3-(heptylthio)adamantan-1-yl)carbamate

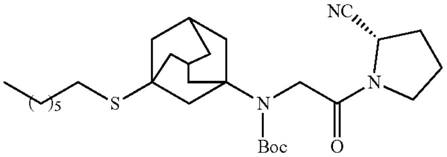

A mixture of tert-butyl (2-((S)-2-cyanopyrrolidin-1-yl)-2-oxoethyl)(3-mercaptoadamantan-1-yl)carbamate (170 mg, 0.40 mmol), 1-iodoheptane (138 mg, 0.61 mmol) and potassium carbonate (224 mg, 1.62 mmol) in MeCN (3 mL) was stirred at 50° C. for 15 hrs. The mixture was concentrated and the residue was purified by column chromatography on silica gel, eluting with (PE:EtOAc=2:1) to give tert-butyl (2-((S)-2-cyanopyrrolidin-1-yl)-2-oxoethyl)(3-(heptylthio)adamantan-1-yl)carbamate (50 mg, 27% yield) as a yellow solid. ES MS M/Z=540 (M+23).

Step 8. (2S)-1-((3-(heptylthio)adamantan-1-yl)glycyl)pyrrolidine-2-carbonitrile (2)

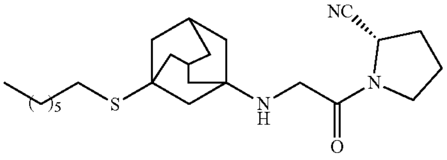

A solution of tert-butyl (2-((S)-2-cyanopyrrolidin-1-yl)-2-oxoethyl)(3-(heptylthio)adamantan-1-yl)carbamate (50 mg, 0.10 mmol) in TFA/DCM (V/V=1:3, 4 mL) was stirred at room temperature for 30 min. The mixture was concentrated and the residue was purified by Prep-HPLC (Gemini-C18 150×21.2 mm, 5 um, mobile phase: ACN—$H_2O$, gradient: 30~70%) to give (2S)-1-((3-(heptylthio)adamantan-1-yl)glycyl)pyrrolidine-2-carbonitrile (32 mg, 80% yield) as a white solid. ES MS M/Z=418 (M+1). $^1H$ NMR (400 MHz, $CD_3OD$) 8.40 (s, 1H), 4.81 (t, J=5.2 Hz, 1H), 3.99-3.87 (m, 2H), 3.74-3.68 (m, 1H), 3.56-3.49 (m, 1H), 2.56 (t, J=7.2 Hz, 2H), 2.35-2.24 (m, 4H), 2.23-2.14 (m, 2H), 2.01-1.94 (m, 2H), 1.92-1.78 (m, 8H), 1.73-1.65 (m, 2H), 1.57-1.50 (m, 2H), 1.43-1.36 (m, 2H), 1.35-1.24 (m, 6H), 0.90 (t, J=6.8 Hz, 3H).

Example 3. Synthesis of (2S)-1-(((1S,3R,5S)-3-(heptylsulfinyl)adamantan-1-yl)glycyl)pyrrolidine-2-carbonitrile (3)

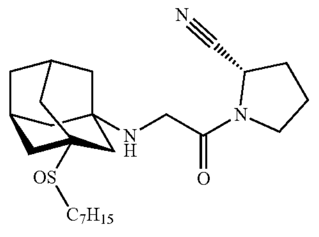

To a solution of tert-butyl (2-((S)-2-cyanopyrrolidin-1-yl)-2-oxoethyl)((1S,3R,5S)-3-(heptylthio)adamantan-1-yl) carbamate (20 mg, 0.03 mmol) in DCM (3 mL) under nitrogen atmosphere, was added dropwise 3-Chloroperbenzoic acid (10 mg, 0.05 mmol) at −40° C. The reaction mixture was stirred at −40° C. for 30 min. TFA (1 mL) was added slowly. The reaction mixture was stirred at room temperature for addition 30 min. The reaction mixture was concentrated under pressure. Then the crude product was purified via Genal-Prep-HPLC (Gemini-C18 150×21.2 mm, 5 um, mobile phase: ACN—$H_2O$, 0.1% FA, gradient: 5~50%) to give the product (2S)-1-((3-(heptylsulfinyl)adamantan-1-yl)glycyl)pyrrolidine-2-carbonitrile (6.5 mg, 38.90%) as a white solid. MS (ESI): mass calcd. for C24H39N3O2S 433.66, m/z found 433.8 [M+H]+. 1H NMR (400 MHz, CD3OD) 8.38 (s, 1H), 4.82-4.79 (m, 1H), 3.95-3.84 (m, 2H), 3.75-3.70 (m, 1H), 3.56-3.50 (m, 1H), 2.72-2.66 (m, 2H), 2.43 (s, 2H), 2.31-2.25 (m, 2H), 2.22-2.14 (m, 2H), 2.01-1.72 (m, 14H), 1.57-1.45 (m, 2H), 1.42-1.35 (m, 2H), 1.33-1.31 (m, 4H), 0.92-0.89 (m, 3H).

Example 4. Synthesis of 2-(((1R,3S,5S)-3-((2-((S)-2-cyanopyrrolidin-1-yl)-2-oxoethyl)amino)adamantan-1-yl)thio)ethyl (2-(4-(2-(hexyl((2S,3R,4R,5R)-2,3,4,5,6-pentahydroxyhexyl)amino)ethyl)phenoxy)ethyl)carbamate (4)

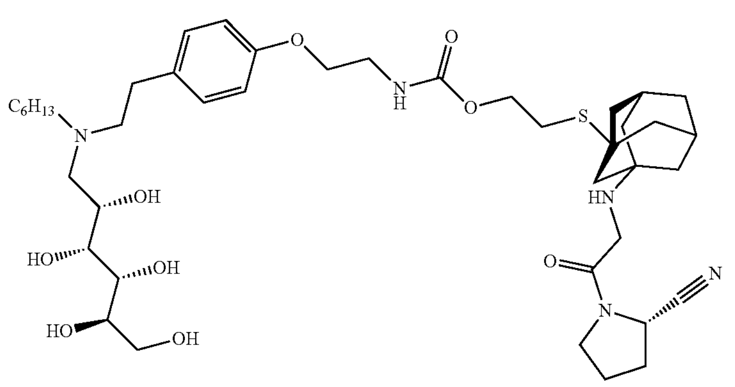

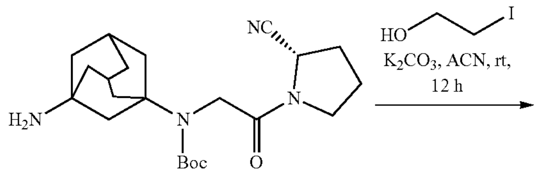

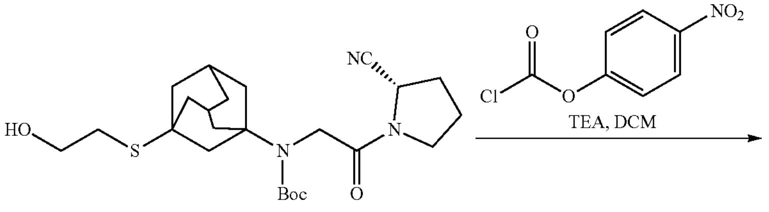

-continued

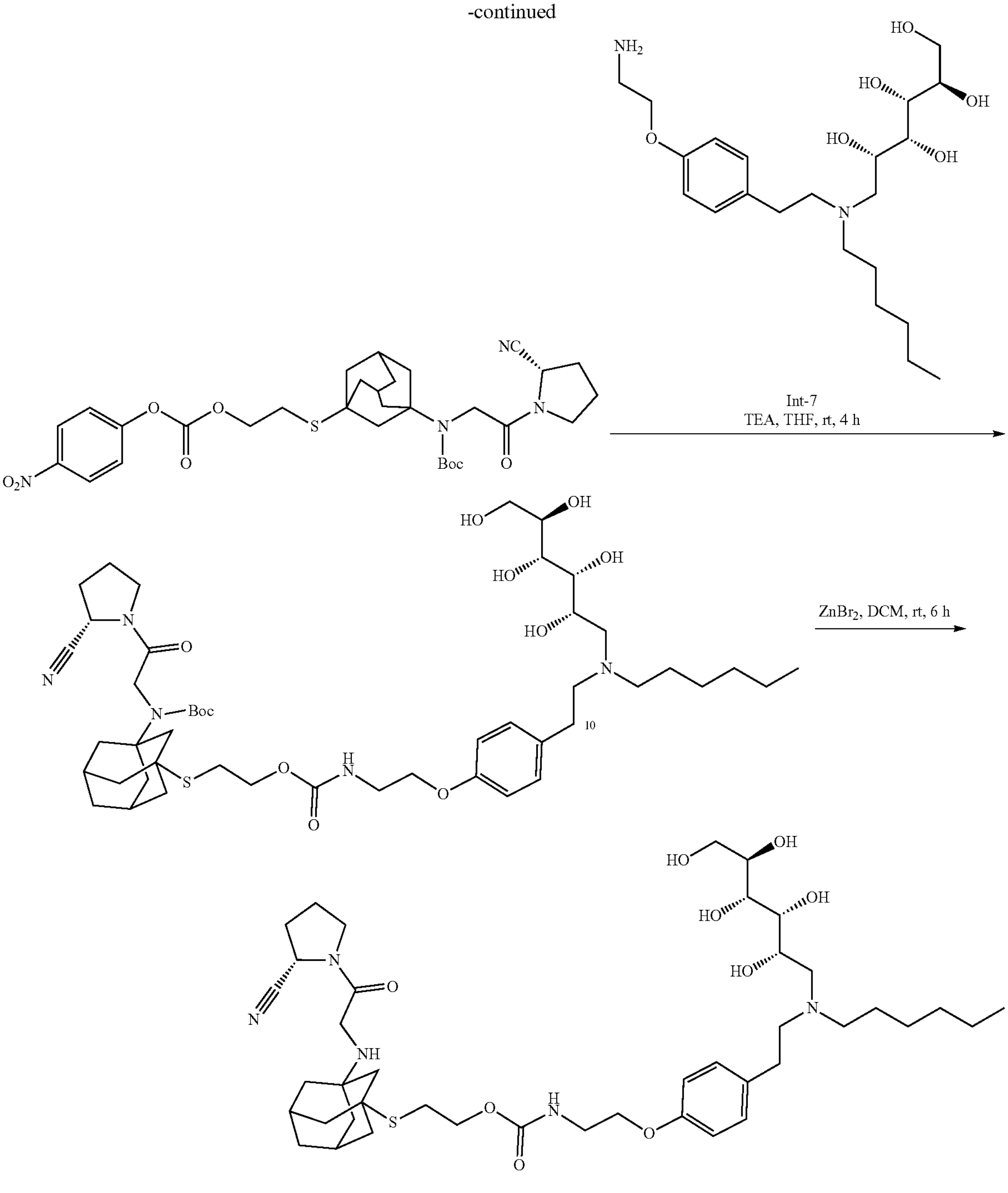

Step 1. tert-butyl (2-((S)-2-cyanopyrrolidin-1-yl)-2-oxoethyl)(3-((2-hydroxyethyl)thio)adamantan-1-yl) carbamate To a mixture of tert-butyl (2-((S)-2-cyanopyrrolidin-1-yl)-2-oxoethyl)(3-mercaptoadamantan-1-yl)carbamate (350 mg, 0.83 mmol) and $K_2CO_3$ (572 mg, 4.15 mmol) in MeCN (15 mL) was added 2-iodoethanol (1.42 g, 8.3 mmol). The reaction mixture was stirred at 25° C. for 12 h. The reaction mixture was concentrated under pressure. The residue was purified via Flash Chromatography and was eluted with $CH_2Cl_2$/MeOH (10:1) to give the product tert-butyl (2-((S)-2-cyanopyrrolidin-1-yl)-2-oxoethyl)(3-((2-hydroxyethyl) thio)adamantan-1-yl)carbamate (340 mg, 88%) as a yellow oil. MS (ESI): mass calcd. for $C_{24}H_{37}N_3O_4S$ 463.25, m/z found 486.2 $[M+Na]^+$.

Step 2. tert-butyl (2-((S)-2-cyanopyrrolidin-1-yl)-2-oxoethyl)(3-((2-(((4-nitrophenoxy)carbonyl)oxy) ethyl)thio) adamantan-1-yl)carbamate To a mixture of tert-butyl (2-((S)-2-cyanopyrrolidin-1-yl)-2-oxoethyl)(3-((2-hydroxyethyl)thio)adamantan-1-yl) carbamate (340 mg, 0.73 mmol) and $Et_3N$ (221 mg, 2.19 mmol) in DCM (20 mL) was added 4-nitrophenyl chloroformate (220 mg, 1.09 mmol). The reaction mixture was stirred at 25° C. for 3 hrs. $H_2O$ (20 mL) was added. The residue was extracted with DCM (30 mL). The DCM phase was concentrated to give tert-butyl (2-((S)-2-cyanopyrrolidin-1-yl)-2-oxoethyl)(3-((2-(((4-nitrophenoxy)carbonyl)oxy)ethyl)thio)adamantan-1-yl)carbamate (600 mg, crude) as a yellow oil, which was used to the next step without further purification. MS (ESI): mass calcd. for $C_{31}H_{40}N_4O_8S$ 628.26, m/z found 629.7 $[M+H]^+$.

Step 3. tert-butyl (2-((S)-2-cyanopyrrolidin-1-yl)-2-oxoethyl)((1S,3R,5S)-3-((2-(((2-(4-(2-(hexyl((2S,3R,4R,5R)-2,3,4,5,6-pentahydroxyhexyl)amino)ethyl)phenoxy)ethyl)carbamoyl)oxy)ethyl)thio)adamantan-1-yl)carbamate To a solution of (2R,3R,4R,5S)-6-((4-(2-aminoethoxy)phenethyl)(hexyl)amino)hexane-1,2,3,4,5-pentaol (410 mg, 0.95 mmol) in THF (15 mL) was added TEA (303 mg, 3 mmol), followed by a solution of tert-butyl (2-((S)-2-cyanopyrrolidin-1-yl)-2-oxoethyl)(3-((2-(((4-nitrophenoxy)carbonyl)oxy)ethyl)thio)adamantan-1-yl)carbamate (903 mg, 1.43 mmol) in THF (5 mL). The reaction mixture was stirred at 25° C. for 4 hrs. The reaction mixture was concentrated under pressure. The residue was purified via Flash Chromatography and was eluted with $CH_2Cl_2$/MeOH (5:1) to give the product tert-butyl (2-((S)-2-cyanopyrrolidin-1-yl)-2-oxoethyl)((1S,3R,5S)-3-((2-(((2-(4-(2-(hexyl((2S,3R,4R,5R)-2,3,4,5,6-pentahydroxyhexyl)amino)ethyl)phenoxy)ethyl)carbamoyl)oxy)ethyl)thio) adamantan-1-yl)carbamate (220 mg, 25%) as a yellow oil. MS (ESI): mass calcd. for $C_{47}H_{75}N_5O_{11}S$ 917.52, m/z found 918.4 $[M+H]^+$.

Step 4. 2-(((1R,3S,5S)-3-((2-((S)-2-cyanopyrrolidin-1-yl)-2-oxoethyl)amino)adamantan-1-yl)thio)ethyl (2-(4-(2-(hexyl((2S,3R,4R,5R)-2,3,4,5,6-pentahydroxyhexyl)amino)ethyl)phenoxy)ethyl)carbamate To a solution of tert-butyl (2-((S)-2-cyanopyrrolidin-1-yl)-2-oxoethyl)((1S,3R,5S)-3-((2-(((2-(4-(2-(hexyl((2S,3R,4R,5R)-2,3,4,5,6-pentahydroxyhexyl)amino)ethyl)phenoxy)ethyl)carbamoyl)oxy)ethyl)thio) adamantan-1-yl) carbamate (400 mg, 0.43 mmol) in DCM (15 mL) was added $ZnBr_2$ (1086 mg, 4.8 mmol). The reaction mixture was stirred at 25° C. for 8 hrs. The solution was filtered, the filtrate was concentrated and purified via Prep-TLC ($CH_2Cl_2$/MeOH)=(5:1) to give impure product, then the impure product was purified via Genal-Prep-HPLC (Gemini-C18 150×21.2 mm, 5 um, mobile phase: ACN—$H_2O$, 0.1% FA, gradient: 5-50%) to give the product 2-(((1R,3S,5S)-3-((2-((S)-2-cyanopyrrolidin-1-yl)-2-oxoethyl)amino)adamantan-1-yl)thio)ethyl (2-(4-(2-(hexyl((2S,3R,4R,5R)-2,3,4,5,6-pentahydroxyhexyl)amino)ethyl)phenoxy)ethyl)carbamate (V2209613) (20 mg, 5%) as a white solid. MS (ESI): mass calcd. for $C_{42}H_{67}N_5O_9S$ 817.47, m/z found 818.4 $[M+H]^+$. $^1H$ NMR (400 MHz, MeOD) δ 8.53 (s, 2H), 7.24 (d, J=8.1 Hz, 2H), 6.94 (d, J=8.2 Hz, 2H), 4.77-4.86 (m, 1H), 4.24-3.97 (m, 5H), 3.94-3.78 (m, 4H), 3.77-3.63 (m, 4H), 3.61-3.45 (m, 3H), 3.44-3.33 (m, 5H), 3.22-3.15 (m, 2H), 3.10-2.95 (m, 2H), 2.88-2.73 (m, 2H), 2.40-2.10 (m, 6H), 2.02-1.92 (m, 2H), 1.88-1.66 (m, 11H), 1.45-1.30 (m, 6H), 1.00-0.90 (m, 3H).

Example 5. Synthesis of_(2S)-1-(((1S,3R,5S)-3-(2-hydroxyethoxy)adamantan-1-yl)glycyl)pyrrolidine-2-carbonitrile (5)

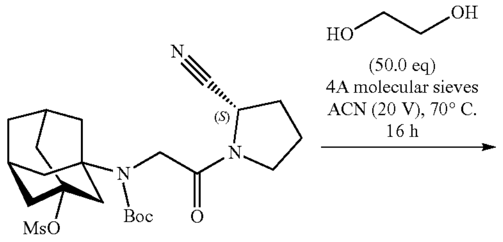

Int-2

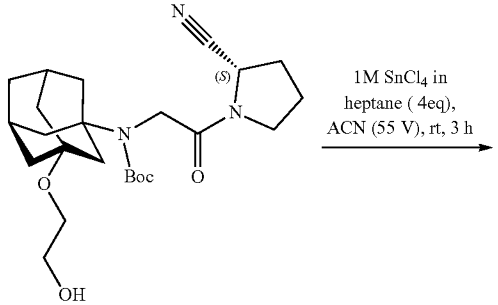

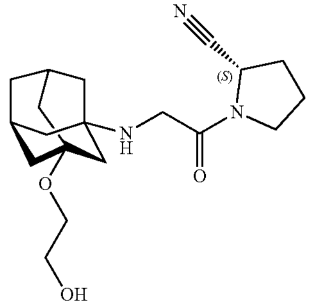

10

Step 1. Tert-butyl (2-((S)-2-cyanopyrrolidin-1-yl)-2-oxoethyl)((1S,3R,5S)-3-(2-hydroxyethoxy)adamantan-1-yl)carbamate

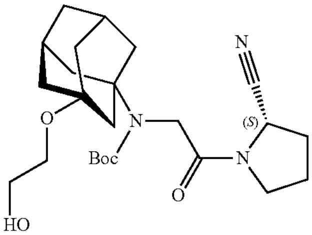

To a stirred solution of (1R,3S,5S)-3-((tert-butoxycarbonyl)(2-((S)-2-cyanopyrrolidin-1-yl)-2-oxoethyl)amino)adamantan-1-yl methanesulfonate (Int-2, 0.59 g, 1.22 mmol) and ethane-1,2-diol (3.8 g, 61.25 mmol) in acetonitrile (3.0 mL) was added molecular sieves 4 Å (2.0 g) and the resultant mixture was stirred at 70° C. for 16 h. After completion, the reaction mixture was diluted with water (50 mL) and extracted with ethyl acetate (3×50 mL). The combined organic layer was dried over anhydrous sodium sulfate and evaporated to give crude product. The crude was then purified by silica gel column chromatography using 3% methanol in dichloromethane and further purified by RP-HPLC using following conditions: column/dimensions: X-BRIDGE-C18 (19*250, 5 um), mobile phase A: 10 mM ammonium bicarbonate in water, Mobile phase B: ACN Gradient (Time/% B): 00/10, 3/10, 7/35, 20/75, 20.1/100, 22/100, 22.1/10, 24/10, flow rate: 17 ml/min. The desired fraction was evaporated to afford tert-butyl (2-((S)-2-cyanopyrrolidin-1-yl)-2-oxoethyl)((1S,3R,5S)-3-(2-hydroxyethoxy)adamantan-1-yl)carbamate (0.1 g) as an off-white solid. TLC system: MeOH: DCM (1:9); $R_f$: 0.4.

Step 2. (2S)-1-(((1S,3R,5S)-3-(2-hydroxyethoxy)adamantan-1-yl)glycyl)pyrrolidine-2-carbonitrile (5)

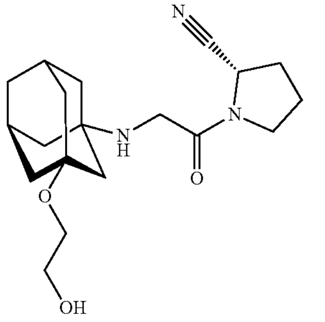

To a stirred suspension of tert-butyl (2-((S)-2-cyanopyrrolidin-1-yl)-2-oxoethyl)((1S,3R,5S)-3-(2-hydroxyethoxy)adamantan-1-yl)carbamate (0.09 g, 0.2 mmol) in acetonitrile (5 mL), 1 M tin(IV) chloride solution in heptane (0.8 mL, 0.8 mmol) was added and the mixture was stirred at room temperature for 3 h. After completion, the reaction mixture was evaporated, the residue was co-evaporated with methanol (10 mL) and washed with diethyl ether (2×5 mL) to give crude product. The crude product was then purified by C-18 column chromatography using 30% methanol in 10 mM ammonium bicarbonate in water. The desired fraction was lyophilized to afford (2S)-1-(((1S,3R,5S)-3-(2-hydroxyethoxy)adamantan-1-yl)glycyl)pyrrolidine-2-carbonitrile (0.055 g) as an off-white solid. TLC system: MeOH:DCM (0.5:9.5); $R_f$: 0.1. LCMS M/Z 348.37 (M+1) $^1$H NMR (400 MHz, DMSO-$d_6$) δ 4.74-4.72 (m, 1H), 4.46 (bs, 1H), 3.63-3.32 (m, 8H), 2.17-2.11 (m, 4H), 2.03-1.99 (m, 2H), 1.68 (t, J=6.0 Hz, 1H), 1.60-1.40 (m, 12H).

Example 7. Synthesis of ((3-((2-((S)-2-cyanopyrrolidin-1-yl)-2-oxoethyl)amino)adamantan-1-yl)oxy)methyl Octanoate (7)

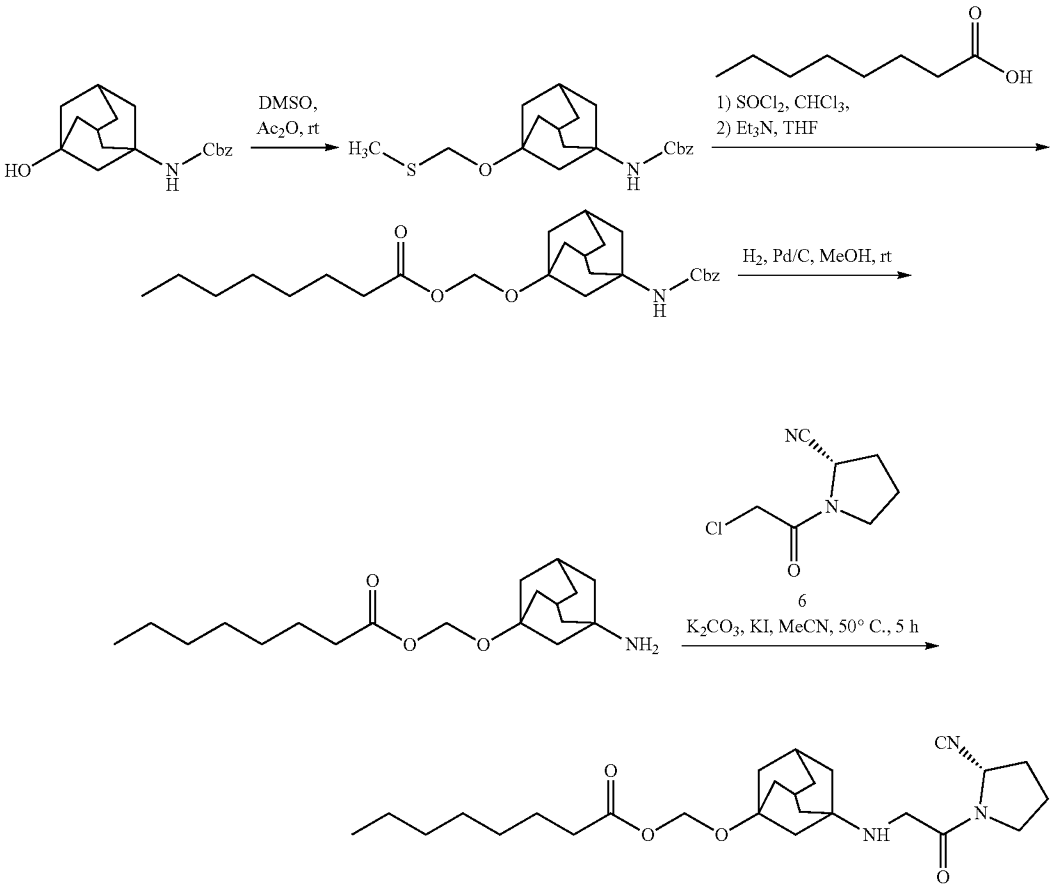

Step 1. Benzyl (3-((methylthio)methoxy)adamantan-1-yl)carbamate

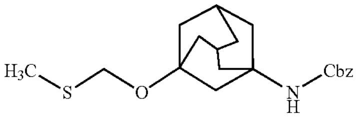 [SMILES: CSCOC12CC3CC(CC(NC(=O)OCc4ccccc4)(C3)C1)C2]

A mixture of benzyl (3-hydroxyadamantan-1-yl)carbamate (3 g, 9.97 mmol) and $Ac_2O$ (35.1 g, 29.9 mmol) in DMSO (30 mL) was stirred at room temperature overnight. The reaction mixture was diluted with EtOAc (100 mL) and washed with water (30 mL×3). The organic phase was dried over anhydrous $Na_2SO_4$, filtered, and concentrated under reduced pressure. The crude product was purified by column chromatography on silica gel, eluting with (PE/EtOAc=8/1) to give benzyl (3-((methylthio)methoxy) adamantan-1-yl) carbamate (2.6 g, 72.2% yield) as a pale yellow oil. ES MS M/Z=384 (M+23).

Step 2. ((3-(((benzyloxy)carbonyl)amino)adamantan-1-yl)oxy)methyl octanoate

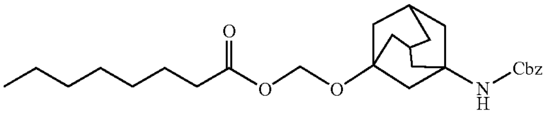 [SMILES: CCCCCCCC(=O)OCOC12CC3CC(CC(NC(=O)OCc4ccccc4)(C3)C1)C2]

To a solution of benzyl (3-((methylthio)methoxy) adamantan-1-yl)carbamate (2.5 g, 6.93 mmol) in $CDCl_3$ (20 mL) was added $SOCl_2$ (1.99 g, 13.86 mmol) at 0° C. slowly. The mixture was stirred at 0° C. for 30 min. The mixture was concentrated and dissolved in THF (20 mL). To the solution was added TEA (1.40 g, 13.86 mmol) and octanoic acid (1.99 g, 13.86 mmol). The reaction mixture was stirred at room temperature overnight. The mixture was diluted with EtOAc (50 mL) and washed with water (20 mL×2). The organic phase was dried over anhydrous $Na_2SO_4$, filtered, and concentrated under reduced pressure. The crude product was purified by column chromatography on silica gel, eluting with (PE/EtOAc=8/1) to give ((3-(((benzyloxy)carbonyl)amino)adamantan-1-yl)oxy)methyl octanoate (1.9 g, 60% yield) as a pale yellow oil. ES MS M/Z=480 (M+23).

Step 3. ((3-aminoadamantan-1-yl)oxy)methyl octanoate

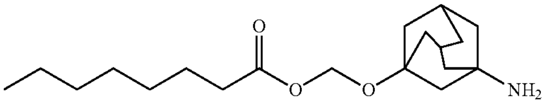 [SMILES: CCCCCCCC(=O)OCOC12CC3CC(CC(N)(C3)C1)C2]

To a solution of -(((benzyloxy)carbonyl)amino)adamantan-1-yl)oxy)methyl octanoate (1.7 g, 3.72 mmol) in MeOH (10 mL) was added Pd/C (500 mg). The reaction mixture was stirred at room temperature under $H_2$ atmosphere overnight. The mixture was filtered and the filtrate was evaporated under reduced pressure to give ((3-aminoadamantan-1-yl)oxy)methyl octanoate (1.1 g, 91.4% yield) as a colorless oil. ES MS M/Z=324 (M+1).

Step 4. ((3-((2-((S)-2-cyanopyrrolidin-1-yl)-2-oxoethyl)amino)adamantan-1-yl)oxy)methyl octanoate (7)

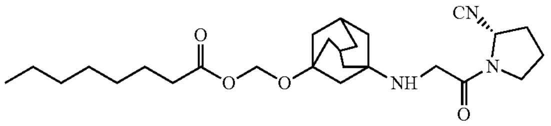

A mixture of ((3-aminoadamantan-1-yl)oxy)methyl octanoate (1 g, 3.1 mmol), (S)-1-(2-chloroacetyl) pyrrolidine-2-carbonitrile (533 mg, 3.1 mmol), potassium carbonate (513 mg, 3.72 mmol) and Potassium iodide (257 mg, 1.55 mmol) in Acetonitrile (15 mL) was stirred at 50° C. under $N_2$ atmosphere for 5 hrs. The mixture was diluted with EtOAc (30 mL) and washed with water (10 mL×2). The organic phase was dried over anhydrous $Na_2SO_4$, filtered, and concentrated under reduced pressure. The crude product was purified by column chromatography on silica gel, eluting with (PE/EtOAc=6/1) to give ((3-((2-((S)-2-cyanopyrrolidin-1-yl)-2-oxoethyl)amino)adamantan-1-yl)oxy)methyl octanoate (mCMP694) (400 mg, 28% yield) as a pale yellow oil. ES MS M/Z=460 (M+1). $^1H$ NMR (400 MHz, $CDCl_3$) 5.39 (s, 2H), 4.87-4.73 (m, 1H), 3.66-3.39 (m, 4H), 2.36-2.25 (m, 6H), 2.24-2.13 (m, 2H), 1.83 (s, 3H), 1.80-1.68 (m, 6H), 1.66-1.56 (m, 6H), 1.33-1.24 (m, 8H), 0.88 (t, J=7.2 Hz, 3H).

Example 8. Synthesis of (2S)-1-(((1S,3R,5S)-3-(2-(2-(2-(4-((hexyl((2S,3R,4R,5R)-2,3,4,5,6-pentahydroxyhexyl)amino)methyl)-1H-1,2,3-triazol-1-yl)ethoxy)ethoxy)ethoxy)adamantan-1-yl)glycyl)pyrrolidine-2-carbonitrile (8)

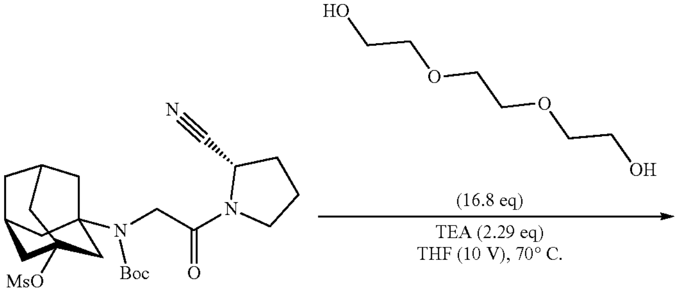

Int-2

-continued
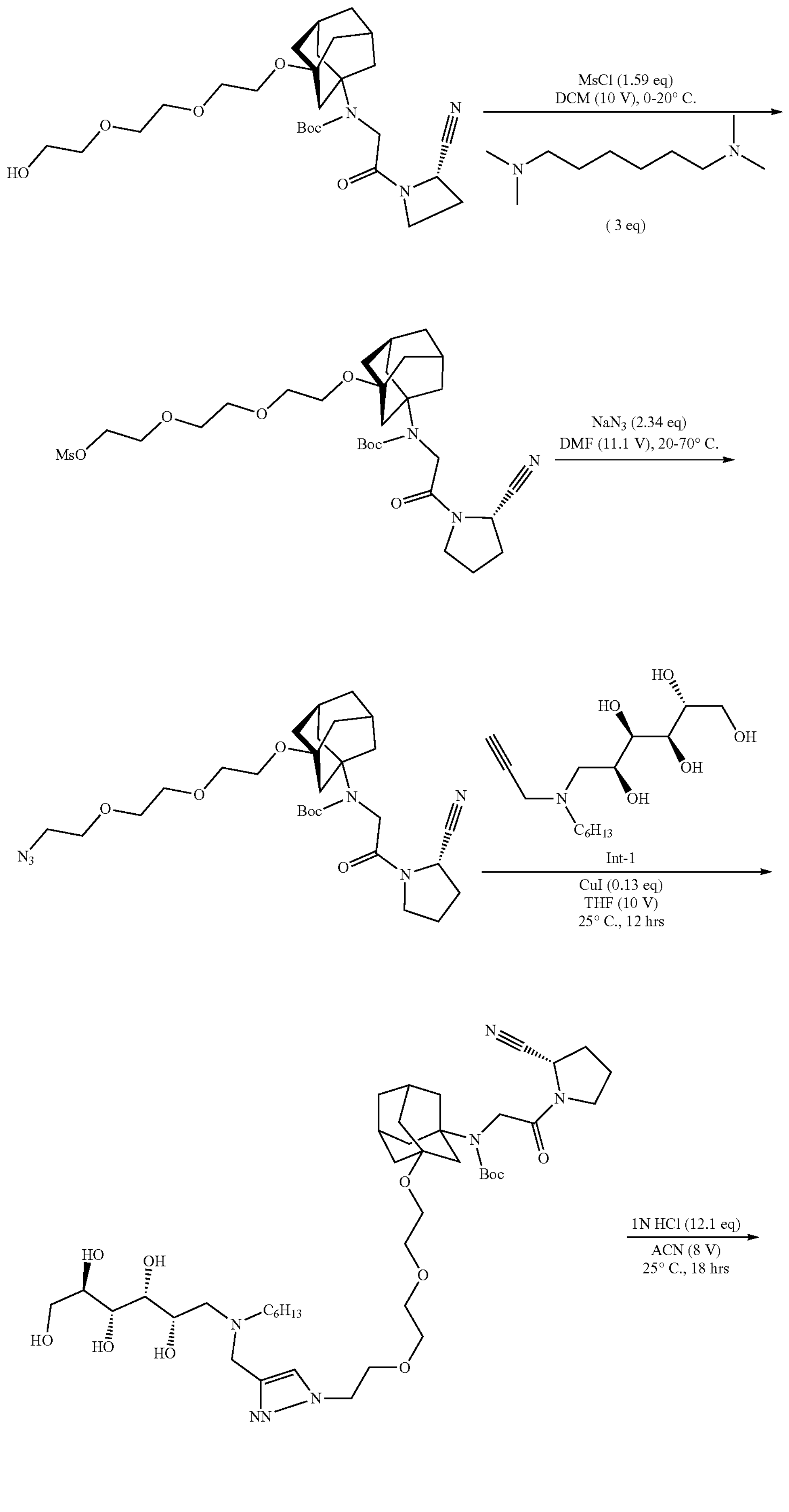

-continued

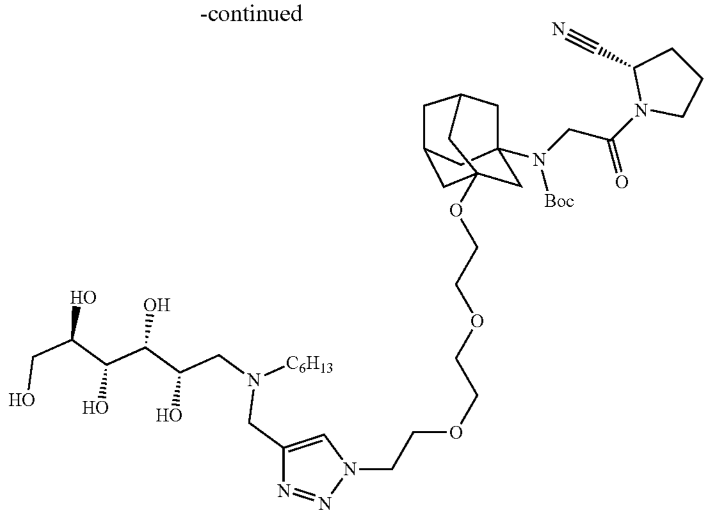

Step 1. Tert-butyl (2-((S)-2-cyanopyrrolidin-1-yl)-2-oxoethyl)((1S,3R,5S)-3-(2-(2-(2-hydroxyethoxy)ethoxy)ethoxy)adamantan-1-yl)carbamate

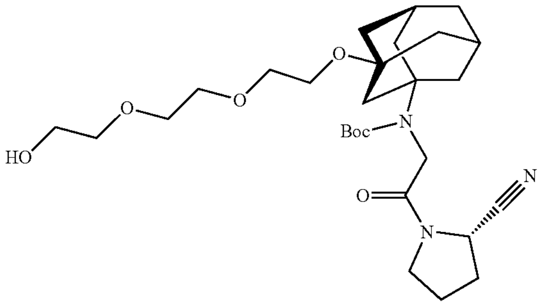

To a solution of compound (1R,3S,5S)-3-((tert-butoxycarbonyl)(2-((S)-2-cyanopyrrolidin-1-yl)-2-oxoethyl)amino)adamantan-1-yl methanesulfonate (137 g, 285 mmol, 1.00 eq) in THF (1.40 L), TEA (66.1 g, 653 mmol, 2.29 eq) and 2,2'-(ethane-1,2-diylbis(oxy))bis(ethan-1-ol) (722 g, 4.81 mol, 16.8 eq) were added. The reaction was heated to 70° C. for 48 hrs. The reaction mixture was diluted with $H_2O$ (2.00 L) and extracted with EA (2.00 L×2). The combined organic layers were washed with 5% aqueous solution of citric acid (2.00 L), then the combined organic layers were washed with saturated aqueous solution of $NaHCO_3$ (2.00 L), dried over $Na_2SO_4$, filtered and concentrated under reduced pressure <45° C. The residue was purified by column chromatography ($SiO_2$, PE/EA=1/1 to 0/1) to give compound tert-butyl (2-((S)-2-cyanopyrrolidin-1-yl)-2-oxoethyl)((1S,3R,5S)-3-(2-(2-(2-hydroxyethoxy)ethoxy)ethoxy)adamantan-1-yl)carbamate (175 g, 327 mmol, 57.4% yield, N/A purity) as a light yellow oil. TLC System: EA only; $R_f$: 0.15.

Step 2. 2-(2-(2-(((1R,3S,5S)-3-((tert-butoxycarbonyl)(2-((S)-2-cyanopyrrolidin-1-yl)-2-oxoethyl)amino)adamantan-1-yl)oxy)ethoxy)ethoxy)ethyl methanesulfonate

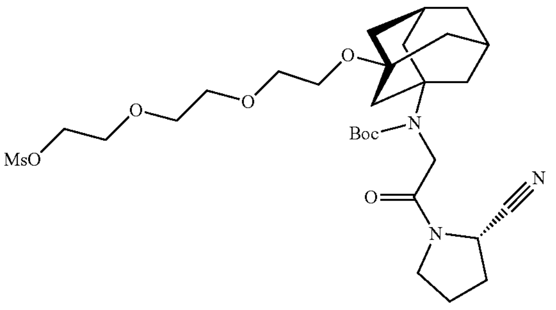

To a solution of compound tert-butyl (2-((S)-2-cyanopyrrolidin-1-yl)-2-oxoethyl)((1S,3R,5S)-3-(2-(2-(2-hydroxyethoxy)ethoxy)ethoxy)adamantan-1-yl)carbamate (162 g, 302 mmol, 1.00 eq) and N,N,N',N'-tetramethyl-1,6-hexanediamine (115 g, 667 mmol, 2.21 eq) in DCM (1600 mL), MsCl (54.9 g, 479 mmol, 37.1 mL, 1.59 eq) were added at 0-10° C. The reaction was stirred for 2 hrs at 0-10° C. The reaction mixture was quenched by addition of ice water (1.00 L) at 0° C., and then titrated with 5% aqueous solution of citric acid (2.00 L) until the pH=5~6, and extracted with EA (3.00 L). The combined organic layers were washed with $NaHCO_3$ (1.00 L), dried over $Na_2SO_4$, filtered and concentrated under reduced pressure to give compound 2-(2-(2-(((1R,3S,5S)-3-((tert-butoxycarbonyl)(2-((S)-2-cyanopyrrolidin-1-yl)-2-oxoethyl)amino)adamantan-1-yl)oxy)ethoxy)ethoxy)ethyl methanesulfonate (180 g, crude) as a light yellow oil. TLC system: EA; $R_f$: 0.30.

Step 3. tert-butyl ((1S,3R,5S)-3-(2-(2-(2-azidoethoxy)ethoxy)ethoxy)adamantan-1-yl)(2-((S)-2-cyanopyrrolidin-1-yl)-2-oxoethyl)carbamate

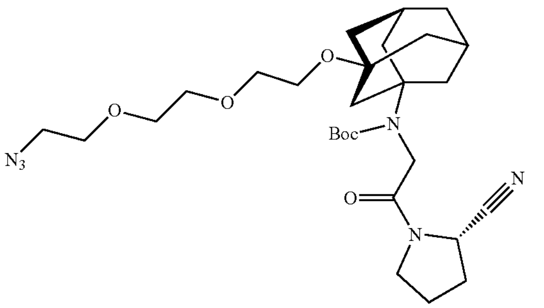

To a solution of compound 2-(2-(2-(((1R,3S,5S)-3-((tert-butoxycarbonyl)(2-((S)-2-cyanopyrrolidin-1-yl)-2-oxoethyl)amino)adamantan-1-yl)oxy)ethoxy)ethoxy)ethyl methanesulfonate (90.0 g, 146 mmol, 1.00 eq) in DMF (1.00 L) was added $NaN_3$ (22.3 g, 343 mmol, 2.34 eq) at 20~30° C. under $N_2$, then the mixture was stirred at 70° C. for 12 hrs. The reaction was added to saturated $Na_2CO_3$ aqueous solution (2.00 L), then extracted with EA 2.00 L. The combined organic layers were washed with brine 2.00 L, dried over $Na_2SO_4$, filtered and concentrated under reduced pressure to give compound tert-butyl ((1S,3R,5S)-3-(2-(2-(2-azidoethoxy)ethoxy)ethoxy)adamantan-1-yl)(2-((S)-2-cyanopyrrolidin-1-yl)-2-oxoethyl)carbamate (153 g, crude) as a light yellow oil. TLC system: EA; $R_f$: 0.30.

Step 4. Tert-butyl (2-((S)-2-cyanopyrrolidin-1-yl)-2-oxoethyl)((1S,3R,5S)-3-(2-(2-(2-(4-((hexyl((2S,3R,4R,5R)-2,3,4,5,6-pentahydroxyhexyl)amino)methyl)-1H-1,2,3-triazol-1-yl)ethoxy)ethoxy)ethoxy)adamantan-1-yl)carbamate

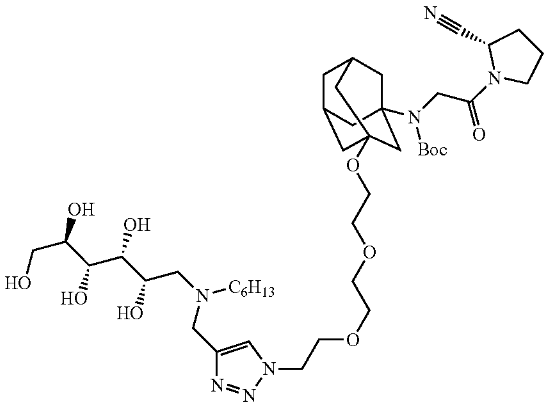

A mixture of compound tert-butyl ((1S,3R,5S)-3-(2-(2-(2-azidoethoxy)ethoxy)ethoxy)adamantan-1-yl)(2-((S)-2-cyanopyrrolidin-1-yl)-2-oxoethyl)carbamate (152 g, 271 mmol, 1.00 eq), (2R,3R,4R,5S)-6-(hexyl(prop-2-yn-1-yl)amino)hexane-1,2,3,4,5-pentaol (98.8 g, 325 mmol, 1.20 eq) and CuI (6.84 g, 35.9 mmol, 0.13 eq) in THF (1.52 L) was stirred 12 hrs at 25° C. The reaction mixture was diluted with $H_2O$ (2.00 L) and extracted with EA (2.00 L). The combined organic layers were washed with brine (1.00 L), dried over $Na_2SO_4$, filtered and concentrated under reduced pressure. The crude product was purified by reversed-phase HPLC (0.1% $NH_3 \cdot H_2O$) to give compound tert-butyl (2-((S)-2-cyanopyrrolidin-1-yl)-2-oxoethyl)((1S,3R,5S)-3-(2-(2-(2-(4-((hexyl((2S,3R,4R,5R)-2,3,4,5,6-pentahydroxyhexyl)amino)methyl)-1H-1,2,3-triazol-1-yl)ethoxy)ethoxy)ethoxy)adamantan-1-yl)carbamate (100 g, 115 mmol, 42.7% yield, 41.3% purity) as a yellow oil. TLC system: DCM: MeOH=5:1; $R_f$: 0.20.

Step 5. (2S)-1-(((1S,3R,5S)-3-(2-(2-(2-(4-((hexyl((2S,3R,4R,5R)-2,3,4,5,6-pentahydroxyhexyl)amino)methyl)-1H-1,2,3-triazol-1-yl)ethoxy)ethoxy)ethoxy)adamantan-1-yl)glycyl)pyrrolidine-2-carbonitrile (8)

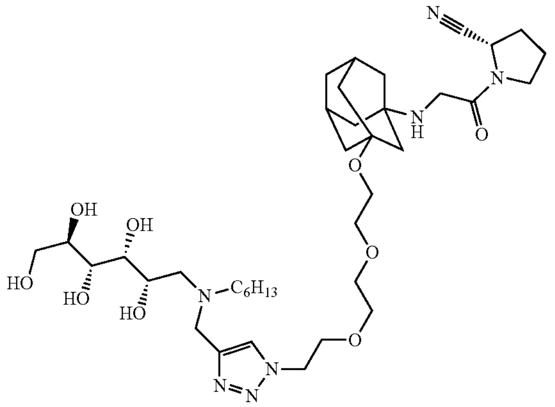

To a solution of compound tert-butyl (2-((S)-2-cyanopyrrolidin-1-yl)-2-oxoethyl)((1S,3R,5S)-3-(2-(2-(2-(4-((hexyl((2S,3R,4R,5R)-2,3,4,5,6-pentahydroxyhexyl)amino)methyl)-1H-1,2,3-triazol-1-yl)ethoxy)ethoxy)ethoxy)adamantan-1-yl)carbamate (40.0 g, 46.3 mmol, 1.00 eq) in ACN (320 mL) was added HCl (1 M, 560 mL, 12.1 eq) at 0° C. The reaction mixture was stirred at 25° C. for 18 hrs. The reaction mixture was extracted with DCM (1.00 L×2). The aqueous phase was adjusted to pH 9~10 by Sat. $NaHCO_3$ and $K_2CO_3$ and extracted with DCM (1.00 L×2). The combined organic phase was dried over $Na_2SO_4$, filtered and concentrated under reduced pressure to give 13 (24.5 g, 31.0 mmol, 66.9% yield, 96.7% purity) as a light yellow oil. LCMS M/Z M+1=764.7. $^1$H-NMR (400 MHz, $CDCl_3$) δ 7.73 (s, 1H), 4.92-4.70 (m, 1H), 4.52 (br t, J=4.5 Hz, 2H), 3.94-3.82 (m, 5H), 3.81-3.71 (m, 4H), 3.71-3.63 (m, 3H), 3.56 (br d, J=19.3 Hz, 9H), 3.47-3.33 (m, 3H), 2.77-2.58 (m, 2H), 2.53 (td, J=7.7, 12.7 Hz, 1H), 2.47-2.37 (m, 1H), 2.36-2.01 (m, 6H), 1.99 (s, 1H), 1.75-1.40 (m, 14H), 1.23 (br s, 6H), 0.84 (br t, J=6.7 Hz, 3H).

Similarly, Compound 15 was prepared from Int-1 and Int-5. Compounds 20 and 21 were prepared from saxagliptin according to the route for compound 8.

Example 9. Synthesis of (2S)-1-(((1S,3R,5S)-3-(2-(2-(4-((bis((2S,3R,4R,5R)-2,3,4,5,6-pentahydroxy-hexyl)amino)methyl-1H-1,2,3-triazol-1-yl)ethoxy)ethoxy)adamantan-1-yl)glycyl)pyrrolidine-2-carbonitrile (9)
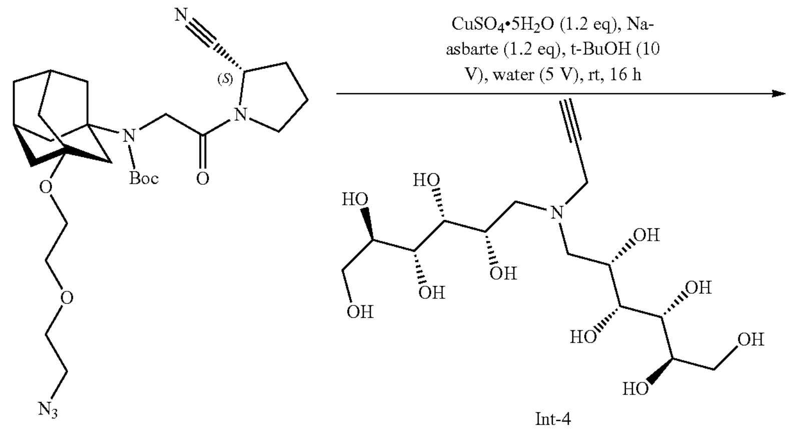
Int-3
Int-4
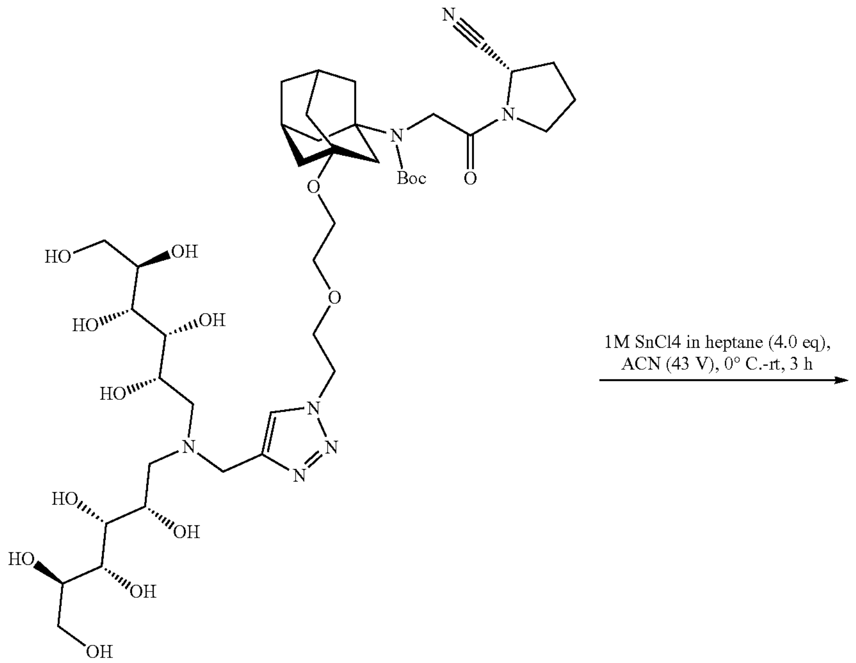

-continued

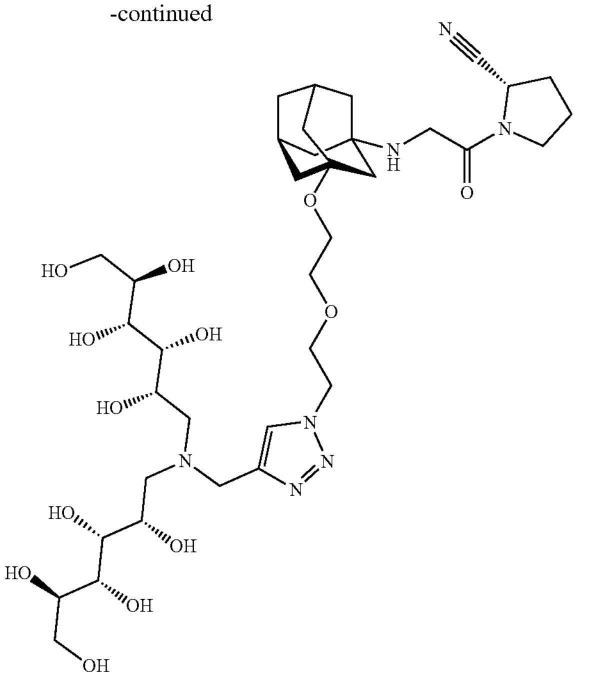

Step 1. Tert-butyl ((1S,3R,5S)-3-(2-(2-(4-((bis((2S,3R,4R,5R)-2,3,4,5,6-pentahydroxyhexyl)amino)methyl)-1H-1,2,3-triazol-1-yl)ethoxy)ethoxy)adamantan-1-yl)(2-((S)-2-cyanopyrrolidin-1-yl)-2-oxoethyl)carbamate

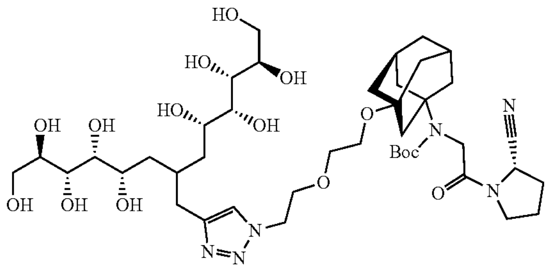

Mixture of tert-butyl ((1 S,3R,5S)-3-(2-(2-azidoethoxy)ethoxy) adamantan-1-yl)(2-((S)-2-cyanopyrrolidin-1-yl)-2-oxoethyl)carbamate (0.6 g, 1.16 mmol), (2R,2'R,3R,3'R,4R,4'R,5S,5'S)-6,6'-(prop-2-yn-1-ylazanediyl)bis(hexane-1,2,3,4,5-pentaol) (0.66 g, 1.74 mmol), copper sulfate pentahydrate (0.35 g, 1.39 mmol) and sodium ascorbate (0.34 g, 1.74 mmol) in tert-Butyl alcohol (10 mL) and water (2 mL) mixture was stirred at room temperature for 16 h. After completion (monitored by LCMS), the reaction mixture was filtered through celite and washed with methanol and water (1:1) (100 mL) and filtrate was evaporated to give crude product. The crude was then purified by reverse phase C18 column chromatography using 50% methanol in 0.1% formic acid in water. The desired product containing fractions were collected and evaporated to give tert-butyl ((1S,3R,5S)-3-(2-(2-(4-((bis((2S,3R,4R,5R)-2,3,4,5,6-pentahydroxyhexyl)amino)methyl)-1H-1,2,3-triazol-1-yl)ethoxy)ethoxy)adamantan-1-yl)(2-((S)-2-cyanopyrrolidin-1-yl)-2-oxoethyl)carbamate (0.46 g, 44%) as an off-white solid.

Step 2. (2S)-1-(((1S,3R,5S)-3-(2-(2-(4-((bis((2S,3R,4R,5R)-2,3,4,5,6-pentahydroxyhexyl)amino)methyl)-1H-1,2,3-triazol-1-yl)ethoxy)ethoxy)adamantan-1-yl)glycyl)pyrrolidine-2-carbonitrile (9)

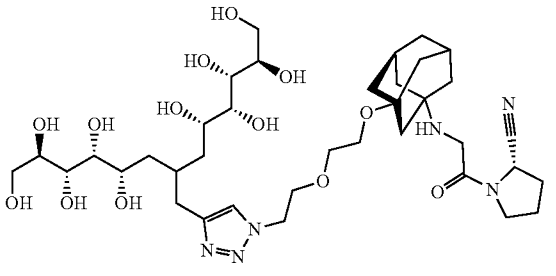

To a stirred suspension of tert-butyl ((1S,3R,5S)-3-(2-(2-(4-((bis((2S,3R,4R,5R)-2,3,4,5,6-pentahydroxyhexyl)amino)methyl)-1H-1,2,3-triazol-1-yl)ethoxy)ethoxy)adamantan-1-yl)(2-((S)-2-cyanopyrrolidin-1-yl)-2-oxoethyl)carbamate (0.35 g, 0.39 mmol) in acetonitrile (15 mL) was added 1 M tin(IV) chloride solution in heptane (1.55 mL, 1.55 mmol) and the reaction mixture was stirred at room temperature for 3 h. After completion (reaction monitored by LCMS), the reaction mixture was evaporated and the residue was co-evaporated with methanol (10 mL), washed with diethyl ether (2×5 mL) to give crude product. The crude was then purified by C-18 column chromatography using 30% methanol in 10 mM ammonium bicarbonate in water. The desired fraction was lyophilized to afford (2S)-1-(((1S,3R,5S)-3-(2-(2-(4-((bis((2S,3R,4R,5R)-2,3,4,5,6-pentahydroxyhexyl)amino)methyl)-1H-1,2,3-triazol-1-yl)ethoxy)ethoxy)adamantan-1-yl)glycyl)pyrrolidine-2-carbonitrile (0.076 g) as a pale yellow solid. LCMS M/Z 800.59 (M+1) $^1$H NMR (400 MHz, DMSO-$d_6$) δ 7.95 (s, 1H), 4.75-4.72 (m, 1H), 4.70-4.10 (m, 12H), 3.81-3.72 (m, 6H), 3.63-3.39 (m, 22H), 2.17-1.91 (m, 6H), 1.56-1.44 (m, 12H).

Example 10. Synthesis of (2S)-1-(((1S,3R,5S)-3-(2-(2-(bis((2S,3R,4R,5R)-2,3,4,5,6-pentahydroxyhexyl)amino)ethoxy)ethoxy)adamantan-1-yl)glycyl)pyrrolidine-2-carbonitrile (10)

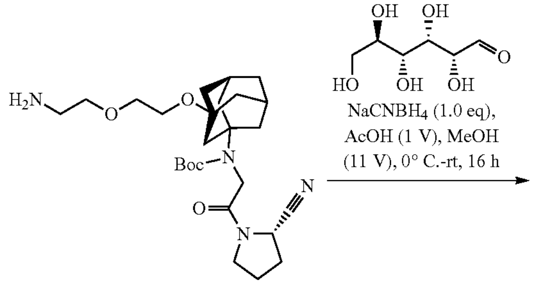

Int-5

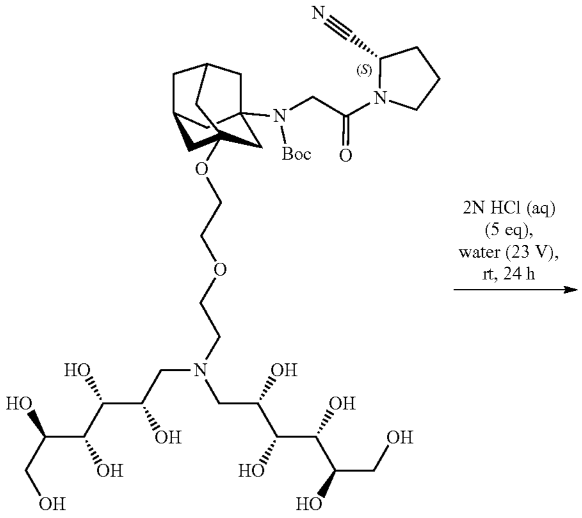

-continued

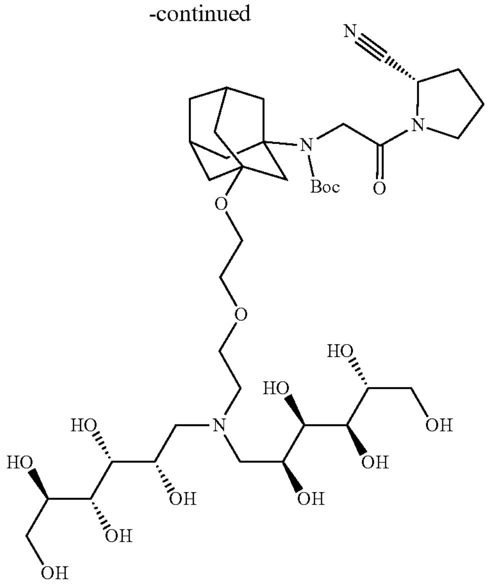

Step 1. Tert-butyl ((1S,3R,5S)-3-(2-(2-(bis((2S,3R,4R,5R)-2,3,4,5,6-pentahydroxyhexyl)amino)ethoxy)ethoxy)adamantan-1-yl)(2-((S)-2-cyanopyrrolidin-1-yl)-2-oxoethyl)carbamate

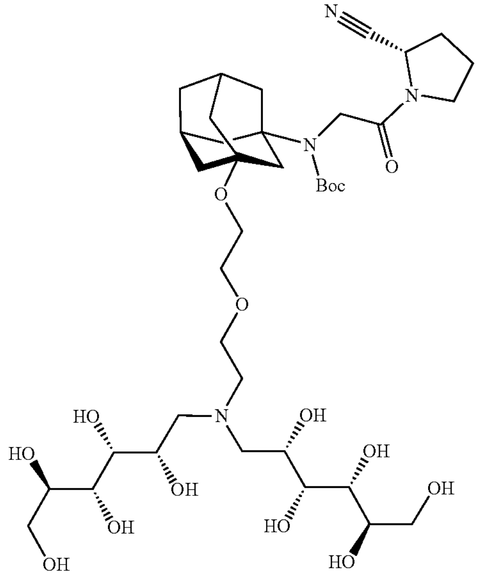

To a mixture of tert-butyl ((1S,3R,5S)-3-(2-(2-aminoethoxy)ethoxy)adamantan-1-yl)(2-((S)-2-cyanopyrrolidin-1-yl)-2-oxoethyl)carbamate (0.21 g, 0.43 mmol), (2R,3S,4R,5R)-2,3,4,5,6-pentahydroxyhexanal (0.19 g, 1.07 mmol) and acetic acid (1.0 mL) in methanol (10 mL) was added sodium cyanoborohydride (0.034 g, 0.52 mmol). The reaction mixture was stirred at 70° C. for 24 h. After completion of reaction (reaction monitored by LCMS), the reaction mixture was evaporated to get crude. The obtained crude was purified by reverse phase C18 column chromatography using 50% methanol in 0.1% formic acid in water. The desired product containing fractions were collected and evaporated to give tert-butyl ((1S,3R,5S)-3-(2-(2-(bis((2S,3R,4R,5R)-2,3,4,5,6-pentahydroxyhexyl)amino)ethoxy)ethoxy)adamantan-1-yl)(2-((S)-2-cyanopyrrolidin-1-yl)-2-oxoethyl)carbamate (0.28 g) as colorless gum.

Step 2. (2S)-1-(((1S,3R,5S)-3-(2-(2-(bis((2S,3R,4R,5R)-2,3,4,5,6-pentahydroxyhexyl)amino)ethoxy)ethoxy)adamantan-1-yl)glycyl)pyrrolidine-2-carbonitrile (10)

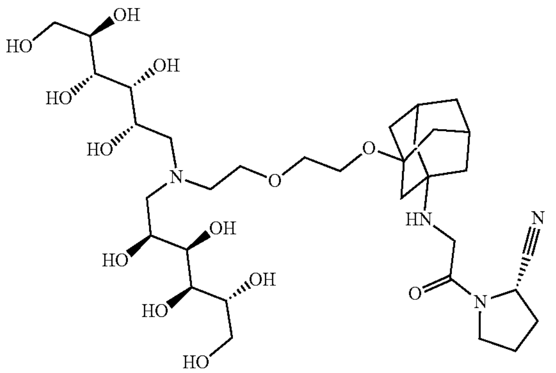 [SMILES: CC1CC2CC(C)(NCC(=O)N3CCC[C@H]3C#N)CC(OCCOCCN(C[C@H](O)[C@@H](O)[C@H](O)[C@H](O)CO)C[C@H](O)[C@@H](O)[C@H](O)[C@H](O)CO)(C1)C2]

To the stirred solution of tert-butyl ((1S,3R,5S)-3-(2-(2-(bis((2S,3R,4R,5R)-2,3,4,5,6-pentahydroxyhexyl)amino)ethoxy)ethoxy)adamantan-1-yl)(2-((S)-2-cyanopyrrolidin-1-yl)-2-oxoethyl)carbamate (0.22 g, 0.27 mmol) in water (5 mL), 2N aqueous hydrochloric acid was added and the reaction mixture was stirred at room temperature for 24 h. After completion of reaction (monitored by LCMS), the reaction mixture was purified by RP prep HPLC using following conditions: Column/dimensions: X-BRIDGE (19*150), 5 um, mobile phase A: 10 mM ammonium bicarbonate in water (aq), mobile phase B: ACN, Gradient (Time % B): 0/2, 3/2, 16/36, 16.1/100, 18/100, 18.1/2, 20/2, flow rate: 17 ml/min. The desired fraction was lyophilized to afford (2S)-1-(((1S,3R,5S)-3-(2-(2-(bis((2S,3R,4R,5R)-2,3,4,5,6-pentahydroxyhexyl)amino)ethoxy)ethoxy)adamantan-1-yl)glycyl)pyrrolidine-2-carbonitrile (0.14 g, 72.5%) as off-white solid. LCMS: M/Z 717.52 [M−1] $^{1}$H NMR (400 MHz, DMSO-$d_6$): δ 4.74-4.70 (m, 1H), 4.51-4.46 (m, 4H), 4.35-4.29 (m, 4H), 4.19 (d, J=6.4 Hz, 2H), 3.65-3.55 (m, 7H), 3.49-3.33 (m, 16H), 2.75-2.50 (m, 5H), 2.17-1.95 (m, 6H), 1.70 (bs, 1H), 1.59-1.45 (m, 12H).

Example 11. Synthesis of (2S)-1-(((1S,3R,5S)-3-(2-(2-(((2S,3R,4R,5R)-2,3,4,5,6-pentahydroxyhexyl)amino)ethoxy)ethoxy)adamantan-1-yl)glycyl)pyrrolidine-2-carbonitrile (11)

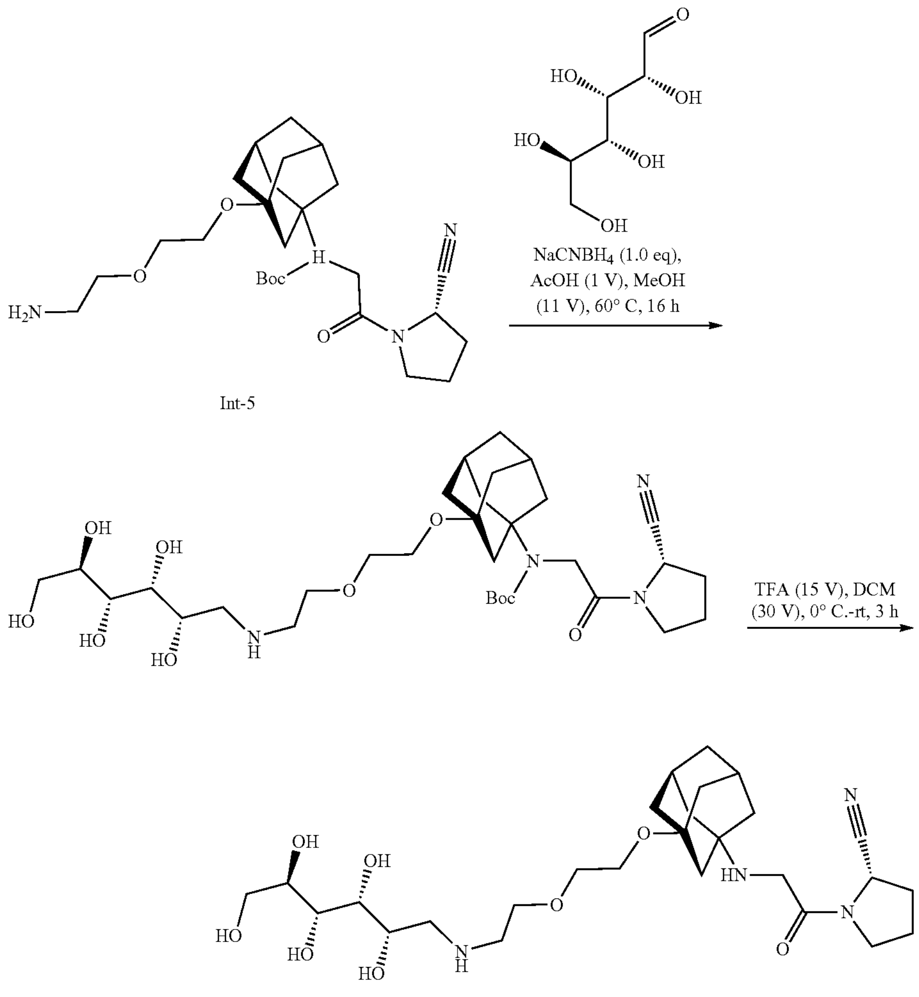

Int-5

Step 1. Tert-butyl (2-((S)-2-cyanopyrrolidin-1-yl)-2-oxoethyl)((1S,3R,5S)-3-(2-(2-(((2S,3R,4R,5R)-2,3,4,5,6-pentahydroxyhexyl)amino)ethoxy)ethoxy)adamantan-1-yl)carbamate

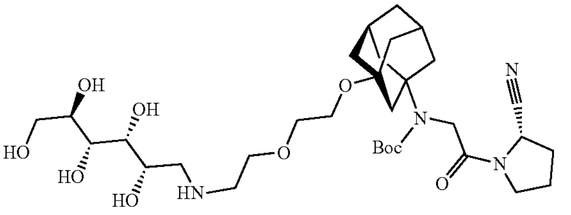

To a mixture of tert-butyl ((1S,3R,5S)-3-(2-(2-aminoethoxy)ethoxy)adamantan-1-yl)(2-((S)-2-cyanopyrrolidin-1-yl)-2-oxoethyl)carbamate (0.22 g, 0.45 mmol), (2R,3S,4R,5R)-2,3,4,5,6-pentahydroxyhexanal (0.081 g, 0.45 mmol) and acetic acid (1.0 mL) in methanol (50 mL) was added sodium cyanoborohydride (0.03 g, 0.45 mmol). The reaction mixture was stirred at 60° C. for 24 h. After completion (reaction monitored by LCMS), the mixture was evaporated under reduced pressure to give crude product. The crude was then purified by reverse phase preparative HPLC using following conditions. Column/dimensions: X-BRIDGE (19*150), 5 um, mobile phase A: 10 mM ammonium bicarbonate in water (aq), mobile phase B: ACN, gradient (Time/% B): 0/10, 1/10, 20/50, 20.10/95, 22.10/95, 22.20/10, 24/10 flow rate: 17 ml/min. The desired fractions were collected and lyophilized to afford tert-butyl (2-((S)-2-cyanopyrrolidin-1-yl)-2-oxoethyl)((1S,3R,5S)-3-(2-(2-(((2S,3R,4R,5R)-2,3,4,5,6-pentahydroxyhexyl)amino)ethoxy)ethoxy)adamantan-1-yl)carbamate (0.035 g) as an off-white solid.

Step 2. (2S)-1-(((1S,3R,5S)-3-(2-(2-(((2S,3R,4R,5R)-2,3,4,5,6-pentahydroxyhexyl)amino)ethoxy)ethoxy)adamantan-1-yl)glycyl)pyrrolidine-2-carbonitrile (11)

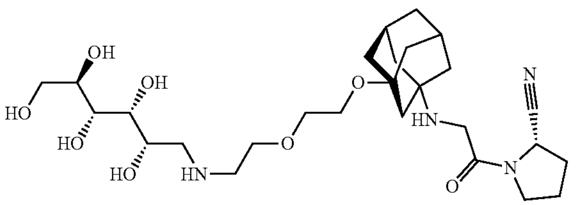

To the stirred suspension of tert-butyl (2-((S)-2-cyanopyrrolidin-1-yl)-2-oxoethyl)((1S,3R,5S)-3-(2-(2-(((2S,3R,4R,5R)-2,3,4,5,6-pentahydroxyhexyl)amino)ethoxy)ethoxy)adamantan-1-yl)carbamate (0.03 g, 0.046 mmol) in dichloromethane (1 mL), trifluoroacetic acid was added at 0° C. and the reaction mixture was stirred at room temperature for 1 h. After completion (monitored by LCMS), the reaction mixture was evaporated under reduced pressure to give crude product. The crude was then purified by reverse phase preparative HPLC using following conditions: Column/dimensions: X-BRIDGE (19*150), 5 um, mobile phase A: 10 mM ammonium bicarbonate in water (aq), mobile phase B: ACN, gradient (Time/% B): 0/10, 1/10, 11/45.20, 11.10/95, 13.10/95, 13.20/10, 15/10, flow rate: 17 ml/min. The desired fraction was lyophilized to afford (2S)-1-(((1S,3R,5S)-3-(2-(2-(((2S,3R,4R,5R)-2,3,4,5,6-pentahydroxyhexyl)amino)ethoxy)ethoxy)adamantan-1-yl)glycyl)pyrrolidine-2-carbonitrile (0.012 g, 47.2%) as an off-white solid. LCMS: M/Z 555.29 (M+1) $^1$H NMR (400 MHz, DMSO-$d_6$) δ 4.73-4.29 (m, 6H), 3.63-3.13 (m, 17H), 2.67-2.60 (m, 4H), 2.16-1.99 (m, 6H), 1.59-1.45 (m, 12H).

Example 12. Synthesis of 2-(2-(((1R,3S,5S)-3-((2-((S)-2-cyanopyrrolidin-1-yl)-2-oxoethyl)amino)adamantan-1-yl)oxy)ethoxy)ethyl (4-((ethyl((2S,3R,4R,5R)-2,3,4,5,6-pentahydroxyhexyl)amino)methyl)benzyl)carbamate (12)

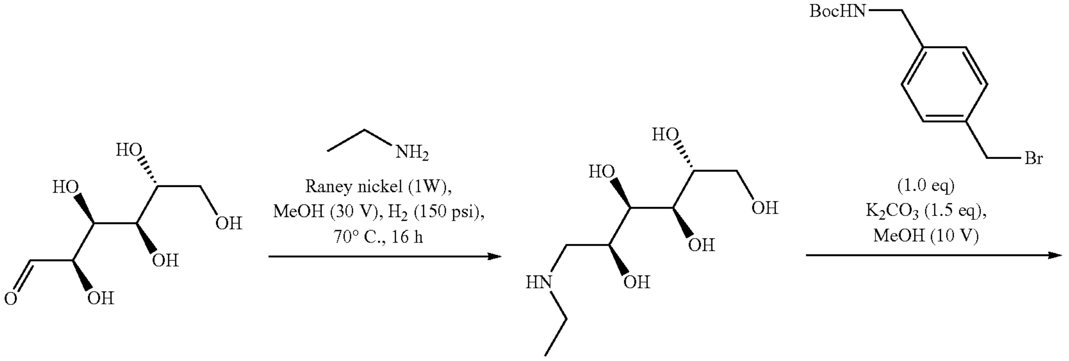

-continued
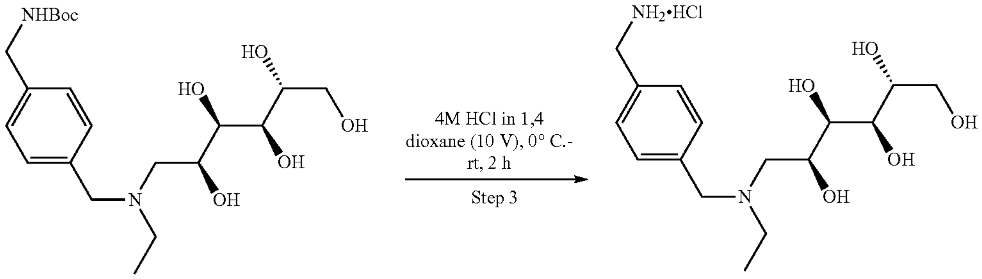
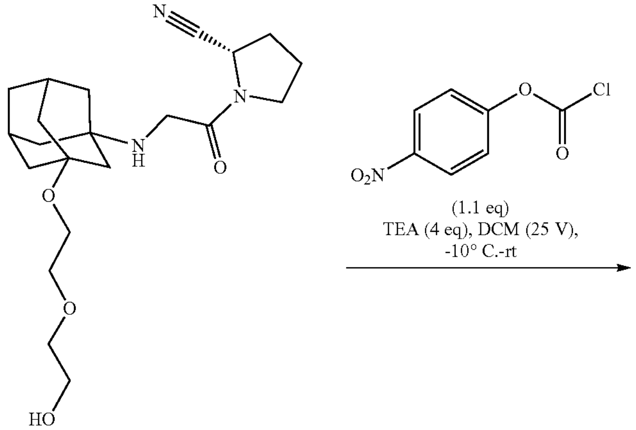
Int-6
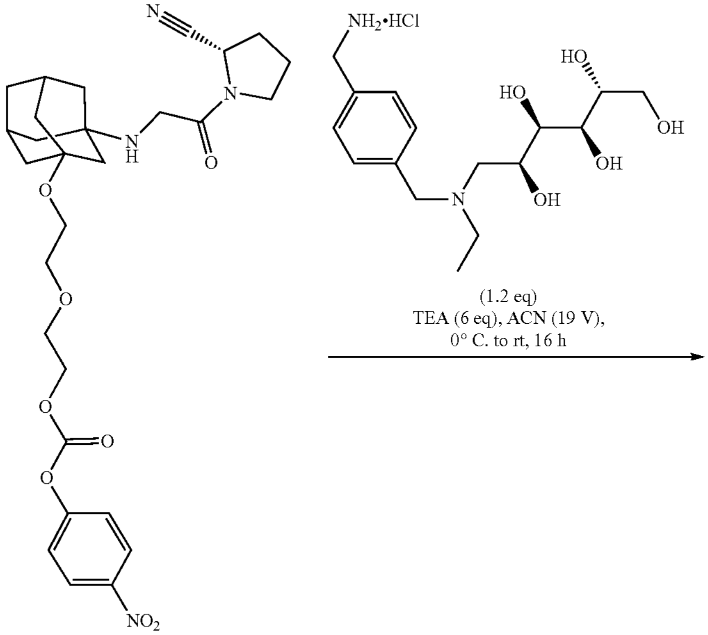

-continued

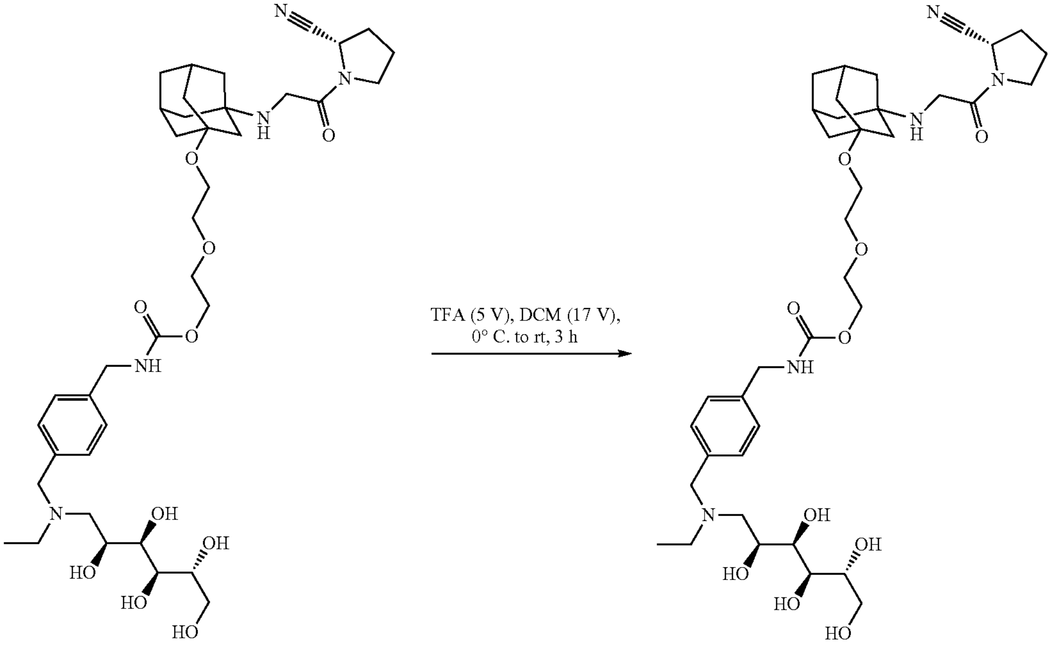 [SMILES: CCN(Cc1ccc(CNC(=O)OCCOCCOC23CC4CC(CC(NCC(=O)N5CCC[C@H]5C#N)(C4)C2)C3)cc1)C[C@H](O)[C@@H](O)[C@H](O)[C@H](O)CO ; CCN(Cc1ccc(CNC(=O)OCCOCCOC23CC4CC(CC(NCC(=O)N5CCC[C@H]5C#N)(C4)C2)C3)cc1)C[C@H](O)[C@@H](O)[C@H](O)[C@H](O)CO]

Step 1. (2R,3R,4R,5S)-6-(ethylamino)hexane-1,2,3,4,5-pentaol

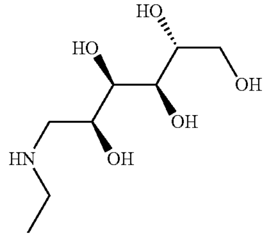

To the mixture of (2R,3S,4R,5R)-2,3,4,5,6-pentahydroxyhexanal (5 g, 2.77 mmol) and 2 M ethylamine in THF (20 mL, 41.6 mmol) in methanol (150 mL) was added raney nickel (5 g) and the reaction mixture was stirred at 70° C. for 16 h under 150 psi hydrogen gas. After completion (monitored by LCMS), the reaction mixture was filtered through a pad of celite and washed with methanol (50 mL). The filtrate was evaporated to give solid, which was triturated with diethyl ether (50 mL) and dried to afford (2R,3R 4R,5S)-6-(ethylamino)hexane-1,2,3,4,5-pentaol (5 g, 86%) as an off-white solid.

Step 2. Tert-butyl (4-((ethyl((2S,3R,4R,5R)-2,3,4,5,6-pentahydroxyhexyl)amino)methyl)benzyl)carbamate

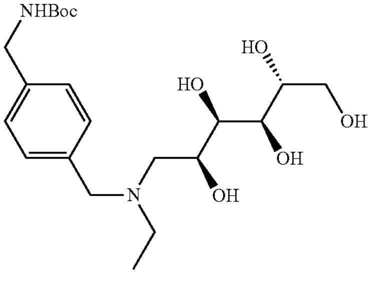 [SMILES: CCN(Cc1ccc(CNC(=O)OC(C)(C)C)cc1)C[C@H](O)[C@@H](O)[C@H](O)[C@H](O)CO]

To a solution of (2R,3R,4R,5S)-6-(ethylamino)hexane-1,2,3,4,5-pentaol (1.0 g, 4.78 mmol) in methanol (10 mL) was added potassium carbonate (0.99 g, 7.17 mmol) followed by tert-butyl (4-(bromomethyl)benzyl)carbamate (1.44 g, 4.78 mmol) portion wise at 0° C. and the mixture was stirred at room temperature for 16 h. After completion (monitored by LCMS), the reaction mixture was evaporated to give crude. The crude product was then purified by reverse phase C18 flash column chromatography using 18% of 0.1% formic acid in water and methanol as a mobile phase. The desired product containing fractions were collected and evaporated to give tert-butyl (4-((ethyl((2S,3R,4R,5R)-2,3,4,5,6-pentahydroxyhexyl)amino)methyl)benzyl)carbamate formate (1.3 g) as a colorless foamy solid.

Step 3. (2R,3R,4R,5S)-6-((4-(aminomethyl)benzyl)(ethyl)amino)hexane-1,2,3,4,5-pentaol hydrochloride

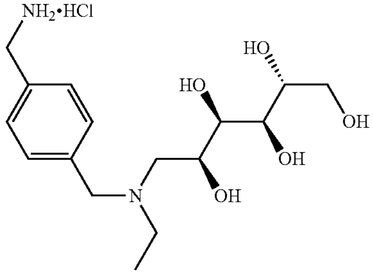

To a stirred solution of tert-butyl (4-((ethyl((2S,3R,4R,5R)-2,3,4,5,6-pentahydroxyhexyl)amino)methyl)benzyl)carbamate formate (0.25 g, 0.527 mmol) in methanol (2.5 mL) was added 4 M hydrochloric acid in 1.4 dioxane slowly at 0° C. and the resultant mixture was stirred at room temperature for 2 h. After completion (monitored by LCMS), the reaction mixture was evaporated to give (2R,3R,4R,5S)-6-((4-(aminomethyl)benzyl)(ethyl)amino)hexane-1,2,3,4,5-pentaol hydrochloride (0.19 g, crude) as a green semi solid.

Step 4. 2-(2-(((1R,3S,5S)-3-((2-((S)-2-cyanopyrrolidin-1-yl)-2-oxoethyl)amino)adamantan-1-yl)oxy)ethoxy)ethyl (4-nitrophenyl) carbonate

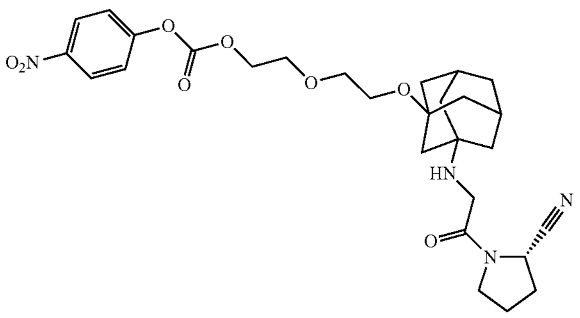 [SMILES: N#C[C@@H]1CCCN1C(=O)CNC12CC3CC(C1)CC(OCCOCCOC(=O)Oc1ccc([N+](=O)[O-])cc1)(C3)C2]

To a stirred solution of (2S)-1-(((1S,3R,5S)-3-(2-(2-hydroxyethoxy)ethoxy)adamantan-1-yl)glycyl)pyrrolidine-2-carbonitrile (0.2 g, 0.407 mmol) in dichloromethane (4 mL) was added triethylamine (0.164 g, 1.628 mmol) subsequently 4-nitrophenyl carbonochloridate (0.09 g, 0.447 mmol) in dichloromethane (1 mL) at −10° C. and the mixture was stirred at room temperature for 2 h. After completion, the reaction mixture was taken as such to next step.

Step 5. 2-(2-(((1R,3S,5S)-3-((2-((S)-2-cyanopyrrolidin-1-yl)-2-oxoethyl)amino)adamantan-1-yl)oxy)ethoxy)ethyl (4-((ethyl((2S,3R,4R,5R)-2,3,4,5,6-pentahydroxyhexyl)amino)methyl)benzyl)carbamate

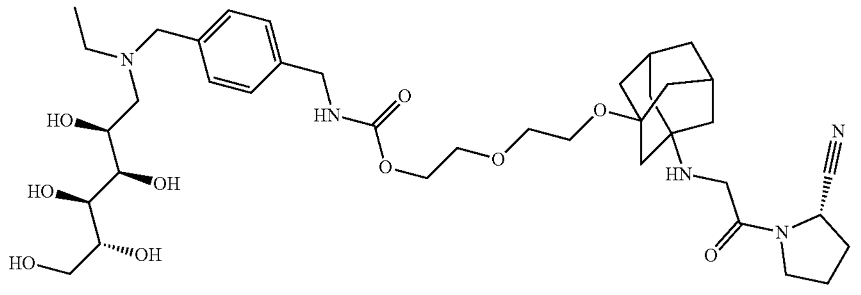 [SMILES: CCN(Cc1ccc(CNC(=O)OCCOCCOC23CC4CC(CC(NCC(=O)N5CCC[C@H]5C#N)(C4)C2)C3)cc1)C[C@H](O)[C@@H](O)[C@H](O)[C@H](O)CO]

To a stirred suspension of (2R,3R,4R,5S)-6-((4-(aminomethyl)benzyl)(ethyl)amino)hexane-1,2,3,4,5-pentaol hydrochloride (0.17 g, 0.47 mmol) in acetonitrile (5 mL) was added triethylamine (0.24 g, 2.34 mmol) followed by 2-(2-(((1R 3S,5S)-3-((2-((S)-2-cyanopyrrolidin-1-yl)-2-oxoethyl)amino)adamantan-1-yl)oxy)ethoxy)ethyl (4-nitrophenyl) carbonate (0.26 g, 0.39 mmol) in dichloromethane (5 mL) at 0° C. and the mixture was stirred at room temperature for 16 h. After completion (monitored by LCMS), the reaction mixture was evaporated to give crude, which was then purified by reverse phase C18 column chromatography using 40% of 0.1% formic acid in water and acetonitrile as a mobile phase. The desired product containing fractions were collected and evaporated to give 2-(2-(((1R,3S,5S)-3-((2-((S)-2-cyanopyrrolidin-1-yl)-2-oxoethyl)amino)adamantan-1-yl)oxy)ethoxy)ethyl (4-((ethyl((2S,3R,4R,5R)-2,3,4,5,6-pentahydroxyhexyl)amino)methyl)benzyl) carbamate (0.3 g, crude) as an yellow semi solid.

Step 6. 2-(2-(((1R,3S,5S)-3-((2-((S)-2-cyanopyrrolidin-1-yl)-2-oxoethyl)amino)adamantan-1-yl)oxy)ethoxy)ethyl (4-((ethyl((2S,3R,4R,5R)-2,3,4,5,6-pentahydroxyhexyl)amino)methyl)benzyl)carbamate (12-formate salt)

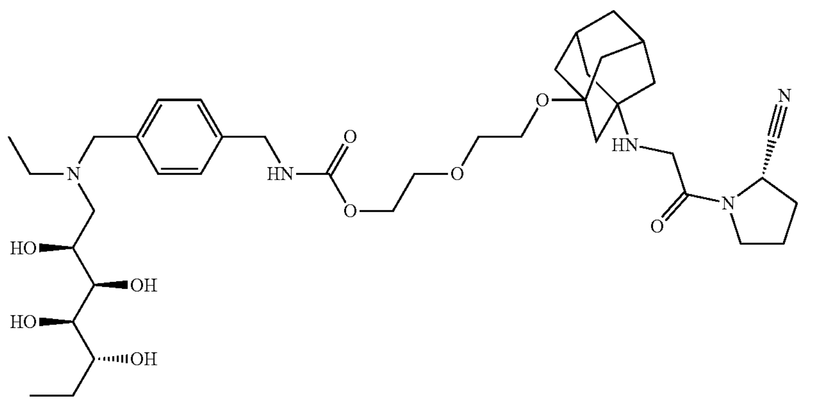 [SMILES: CC[C@@H](O)[C@@H](O)[C@H](O)[C@@H](O)CN(CC)Cc1ccc(CNC(=O)OCCOCCOC23CC4CC(CC(NCC(=O)N5CCC[C@H]5C#N)(C4)C2)C3)cc1]

To a stirred suspension of 2-(2-(((1R,3S,5S)-3-((2-((S)-2-cyanopyrrolidin-1-yl)-2-oxoethyl)amino)adamantan-1-yl)oxy)ethoxy)ethyl (4-((ethyl((2S,3R,4R,5R)-2,3,4,5,6-pentahydroxyhexyl)amino)methyl)benzyl)carbamate (0.29 g, 0.34 mmol) in dichloromethane (4 mL), trifluroacetic acid was added at 0° C. and the reaction mixture was stirred at room temperature for 3 h. After completion (monitored by LCMS), the reaction mixture was concentrated and the residue was washed with diethyl ether (3×10 mL) and dried to give crude product. The crude product was then purified by reverse phase preparative HPLC using following conditions: Column/dimensions: SUNFIREC18 (19*150*5μ), mobile phase A: 0.1% FA in water (aq), mobile phase B: acetonitrile, gradient (time/% B): 0/5, 2/5, 10/20, 10.1/100, 14/100, 14.1/5, 16/5, flow rate: 17 ml/min. The desired fraction was lyophilized to afford 2-(2-(((1R,3S,5S)-3-((2-((S)-2-cyanopyrrolidin-1-yl)-2-oxoethyl)amino)adamantan-1-yl)oxy)ethoxy)ethyl (4-((ethyl((2S,3R,4R,5R)-2,3,4,5,6-pentahydroxyhexyl)amino)methyl)benzyl)carbamate formate (0.038 g) as an off-white solid. LCMS M/Z 746.72 (M+1) $^{1}$H NMR (400 MHz, DMSO-$d_6$): δ 8.17 (s, 2H), 7.73 (s, 1H), 7.27 (d, J=7.6 Hz, 2H), 7.17 (d, J=8.0 Hz, 2H), 4.75-4.74 (m, 3H), 4.16-4.06 (m, 4H), 3.75-3.35 (m, 21H), 2.61-2.50 (m, 1H), 2.46-2.41 (m, 3H), 2.19-1.99 (m, 6H), 1.60-1.52 (m, 12H), 0.94 (t, J=7.2 Hz, 3H).

Example 13. Synthesis of 2-(((1R,3S,5S)-3-((2-((S)-2-cyanopyrrolidin-1-yl)-2-oxoethyl)amino)adamantan-1-yl)oxy)ethyl (2-(4-(2-(hexyl((2S,3R,4R,5R)-2,3,4,5,6-pentahydroxyhexyl)amino)ethyl)phenoxy)ethyl)carbamate (13)

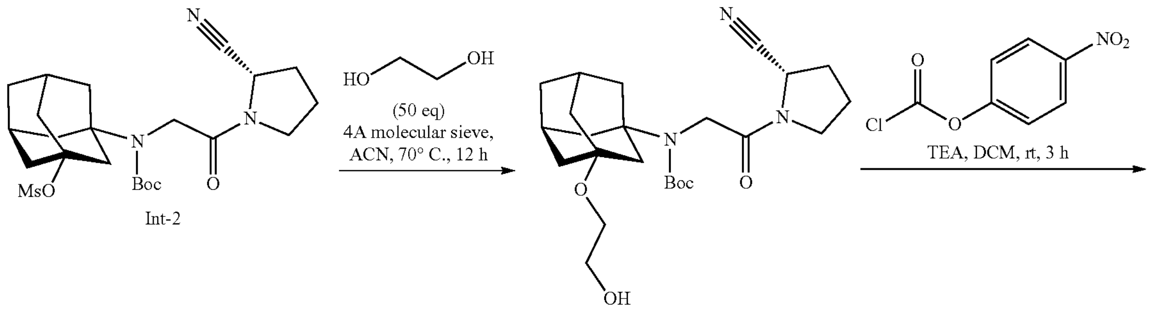

-continued
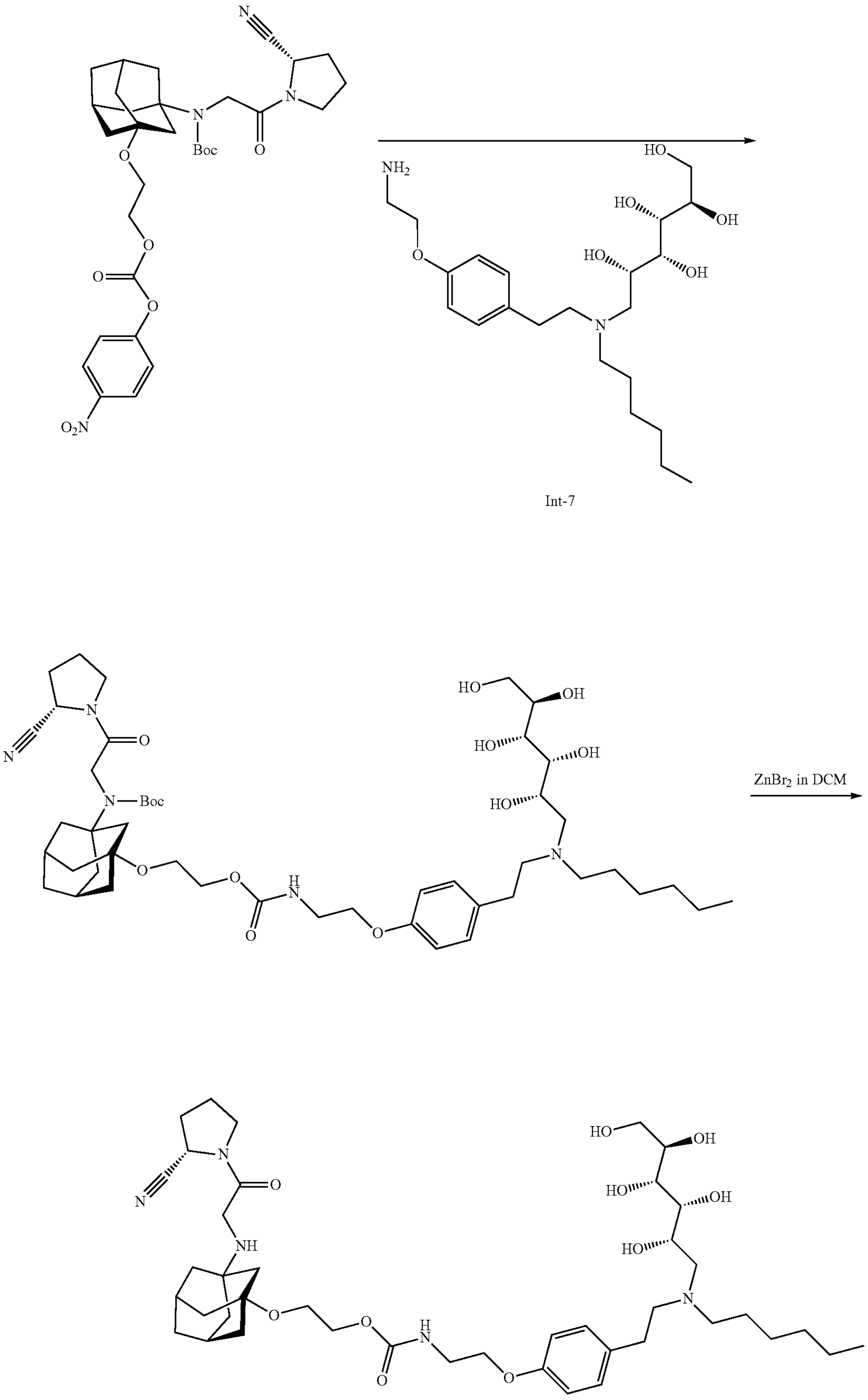
Int-7

Step 1. Tert-butyl (2-((S)-2-cyanopyrrolidin-1-yl)-2-oxoethyl)((1S,3R,5S)-3-(2-hydroxyethoxy)adamantan-1-yl)carbamate

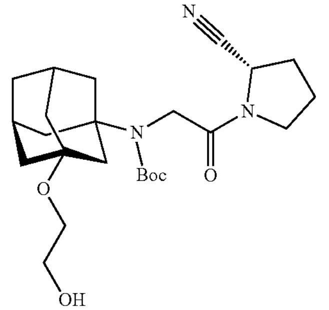

To a solution of (1R,3S,5S)-3-((tert-butoxycarbonyl)(2-((S)-2-cyanopyrrolidin-1-yl)-2-oxoethyl)amino)adamantan-1-yl methanesulfonate (1.25 g, 2.59 mmol) in MeCN (5 mL) was added ethane-1,2-diol (8.04 g, 129.6 mmol). The reaction mixture was stirred at 70° C. for 12 hrs. The reaction mixture was concentrated under pressure at 40° C. The residue was purified via Flash column chromatography and eluted with (MeOH/DCM, from 1% to 10%) to give tert-butyl (2-((S)-2-cyanopyrrolidin-1-yl)-2-oxoethyl)((1S,3R,5S)-3-(2-hydroxyethoxy)adamantan-1-yl)carbamate (860 mg, 74% yield) as a yellow oil. ES MS M/Z=470 (M+23).

Step 2. Tert-butyl (2-((S)-2-cyanopyrrolidin-1-yl)-2-oxoethyl)((1S,3R,5S)-3-(2-(((4-nitrophenoxy)carbonyl)oxy)ethoxy)adamantan-1-yl)carbamate

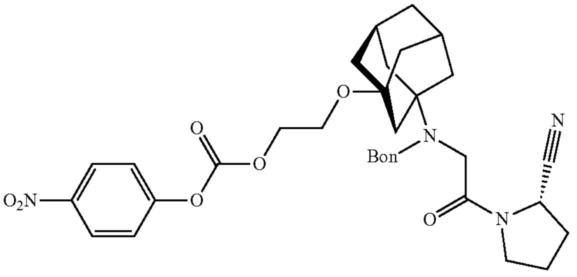

To a solution of tert-butyl (2-((S)-2-cyanopyrrolidin-1-yl)-2-oxoethyl)((1S,3R,5S)-3-(2-hydroxyethoxy)adamantan-1-yl)carbamate (860 mg, 1.92 mmol) and TEA (1000 mg, 10 mmol) in DCM (20 mL) was added 4-nitrophenyl chloroformate (800 mg, 4 mmol). The reaction mixture was stirred at 25° C. for 3 hrs. The mixture was quenched with $H_2O$ (20 mL) and extracted with DCM (30 mL). The organic layer was dried over $Na_2SO_4$ and concentrated under pressure at 30° C. to give tert-butyl (2-((S)-2-cyanopyrrolidin-1-yl)-2-oxoethyl((1S,3R,5S)-3-(2-(((4-nitrophenoxy)carbonyl)oxy)ethoxy) adamantan-1-yl)carbamate (1.2 g, crude) as a yellow oil, which was used to the next step without further purification. ES MS M/Z=635 (M+23).

Step 2. Tert-butyl (2-((S)-2-cyanopyrrolidin-1-yl)-2-oxoethyl)((1S,3R,5S)-3-(2-(((2-(4-(2-(hexyl((2S,3R,4R,5R)-2,3,4,5,6-pentahydroxyhexyl)amino)ethyl)phenoxy)ethyl)carbamoyl)oxy)ethoxy)adamantan-1-yl)carbamate

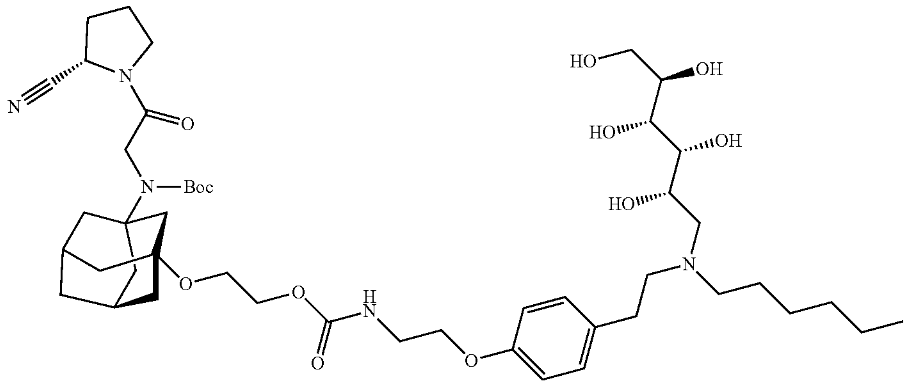

To a solution of (2R,3R,4R,5S)-6-((4-(2-aminoethoxy)phenethyl)(hexyl)amino)hexane-1,2,3,4,5-pentaol in THF (10 mL) was added TEA (210 mg, 2.1 mmol), followed by a solution of tert-butyl (2-((S)-2-cyanopyrrolidin-1-yl)-2-oxoethyl)((1S,3R,5S)-3-(2-(((4-nitrophenoxy)carbonyl)oxy)ethoxy)adamantan-1-yl)carbamate (428 mg, 0.7 mmol) in THF (1 mL). The reaction mixture was stirred at 25° C. for 4 hrs. The reaction mixture was concentrated under pressure at 40° C. The residue was purified via Flash column chromatography and eluted with (MeOH/DCM, from 10% to 50%) to give tert-butyl (2-((S)-2-cyanopyrrolidin-1-yl)-2-oxoethyl)((1 S,3R,5S)-3-(2-(((2-(4-(2-(hexyl((2S,3R,4R,5R)-2,3,4,5,6-pentahydroxyhexyl)amino)ethyl)phenoxy)ethyl)carbamoyl)oxy)ethoxy)adamantan-1-yl)carbamate (436 mg, 69% yield) as a yellow oil. ES MS M/Z=902 (M+1).

Step 3. 2-(((1R,3S,5S)-3-((2-((S)-2-cyanopyrrolidin-1-yl)-2-oxoethyl)amino)adamantan-1-yl)oxy)ethyl (2-(4-(2-(hexyl((2S,3R,4R,5R)-2,3,4,5,6-pentahydroxyhexyl)amino)ethyl)phenoxy)ethyl)carbamate (13)

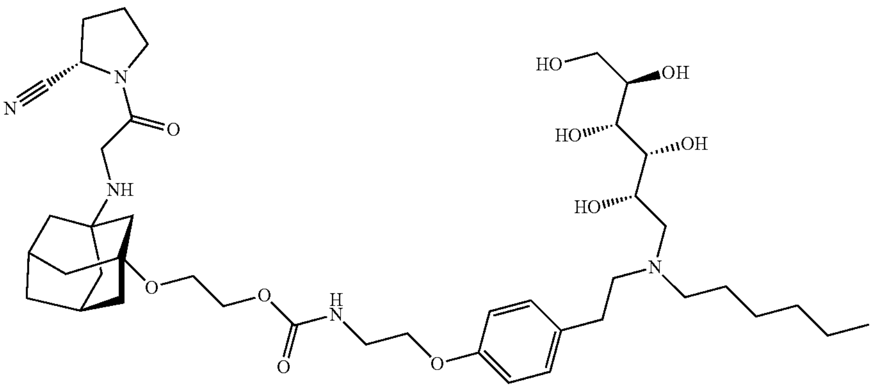

To a solution of tert-butyl (2-((S)-2-cyanopyrrolidin-1-yl)-2-oxoethyl)((1S,3R,5S)-3-(2-(((2-(4-(2-(hexyl((2S,3R,4R,5R)-2,3,4,5,6-pentahydroxyhexyl)amino)ethyl)phenoxy)ethyl)carbamoyl)oxy)ethoxy)adamantan-1-yl) carbamate (436 mg, 0.48 mmol) in DCM (15 mL) was added $ZnBr_2$ (1086 mg, 4.8 mmol). The reaction mixture was stirred at 25° C. for 12 hrs. The mixture was filtered and the filtrate was concentrated under pressure at 35° C. The residue was purified via Prep-TLC ($CH_2Cl_2$/MeOH=5:1) to give impure product, which was purified via Genal-Prep-HPLC (Gemini-C18 150×21.2 mm, 5 um, mobile phase: ACN—$H_2O$, 0.1% FA, gradient: 5~50%) 2-(((1R,3S,5S)-3-((2-((S)-2-cyanopyrrolidin-1-yl)-2-oxoethyl)amino)adamantan-1-yl)oxy)ethyl (2-(4-(2-(hexyl((2S,3R,4R,5R)-2,3,4,5,6-pentahydroxyhexyl)amino)ethyl)phenoxy)ethyl) carbamate (13) (50 mg, 12% yield) as a white solid. ES MS M/Z=802 (M+1). $^1$H NMR (400 MHz, $CD_3OD$) 8.48 (s, 2H), 7.22 (d, J=8.5 Hz, 2H), 6.92 (d, J=8.6 Hz, 2H), 4.83-4.78 (m, 1H), 4.17-4.07 (m, 3H), 4.05-3.95 (m, 2H), 3.91-3.74 (m, 4H), 3.74-3.60 (m, 6H), 3.55-3.50 (m, 1H), 3.50-3.43 (m, 2H), 3.41-3.32 (m, 4H), 3.26-3.16 (m, 2H), 3.05-2.94 (m, 2H), 2.40-2.09 (m, 6H), 1.85-1.65 (m, 12H), 1.58 (s, 2H), 1.42-1.30 (m, 6H), 0.97-0.89 (m, 3H).

Example 14. Synthesis of (2S)-1-(((1S,3R,5S)-3-(2-(2-(4-((((2S,3R,4R,5R)-2,3,4,5,6-pentahydroxyhexyl)amino)methyl)-1H-1,2,3-triazol-1-yl)ethoxy)ethoxy)adamantan-1-yl)glycyl)pyrrolidine-2-carbonitrile (14)

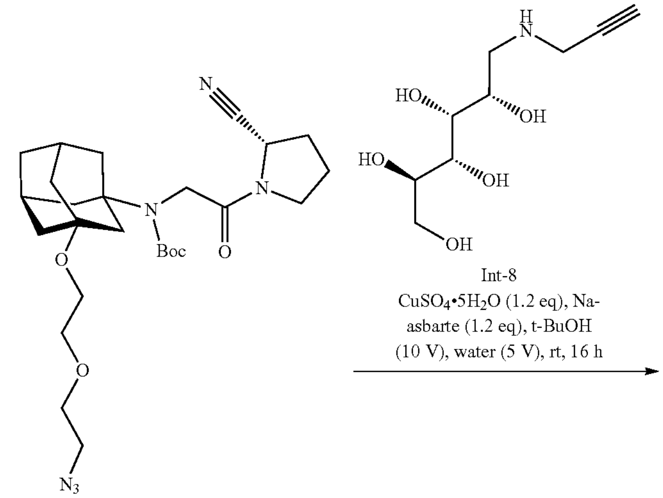

-continued
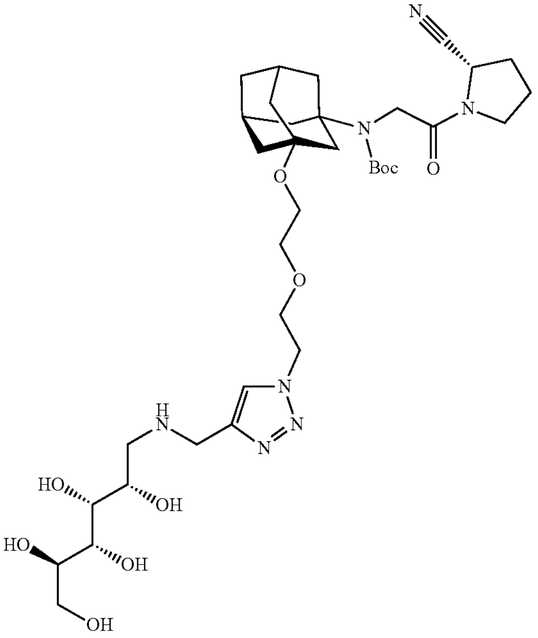
+
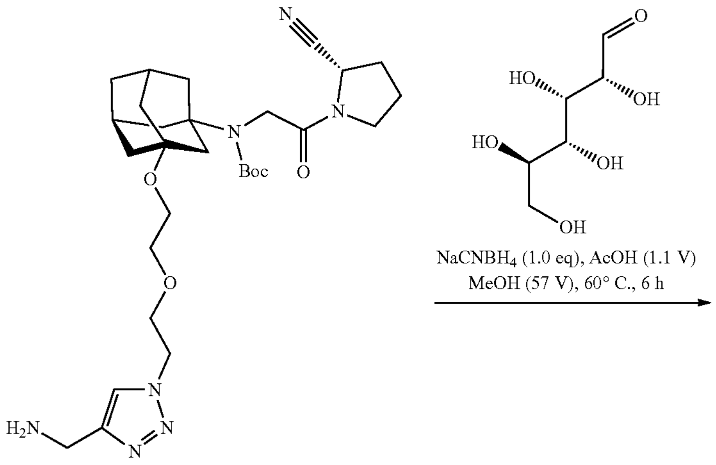

-continued
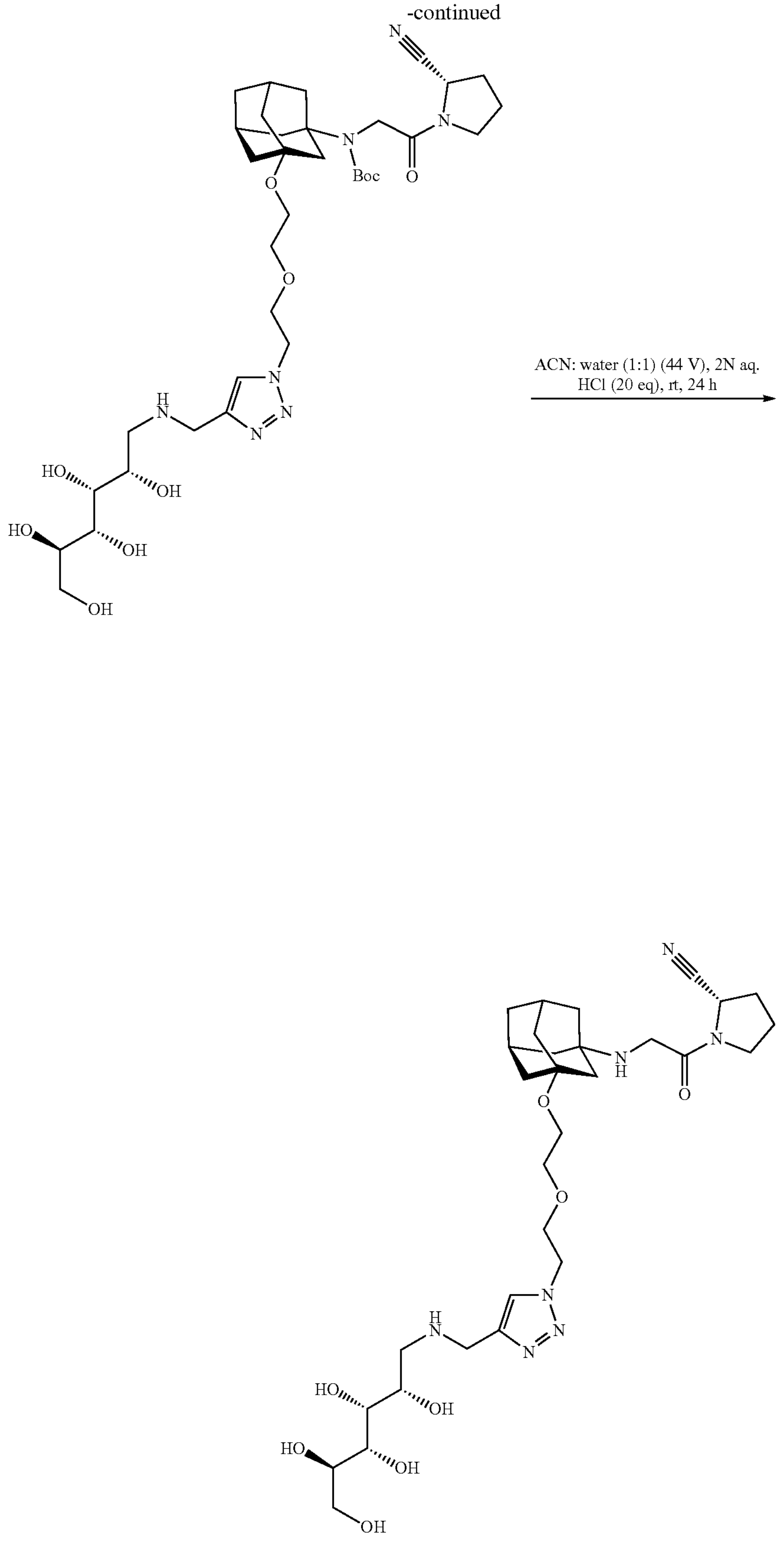

Step 1. Mixture of tert-butyl (2-((S)-2-cyanopyrrolidin-1-yl)-2-oxoethyl)(1S,3R,5S)-3-(2-(2-(4-((((2S,3R,4R,5R)-2,3,4,5,6-pentahydroxyhexyl)amino)methyl)-1H-1,2,3-triazol-1-yl)ethoxy)ethoxy)adamantan-1-yl)carbamate and tert-butyl ((1S,3R,5S)-3-(2-(2-(4-(aminomethyl)-1H-1,2,3-triazol-1-yl)ethoxy)ethoxy)adamantan-1-yl)(2-((S)-2-cyanopyrrolidin-1-yl)-2-oxoethyl)carbamate

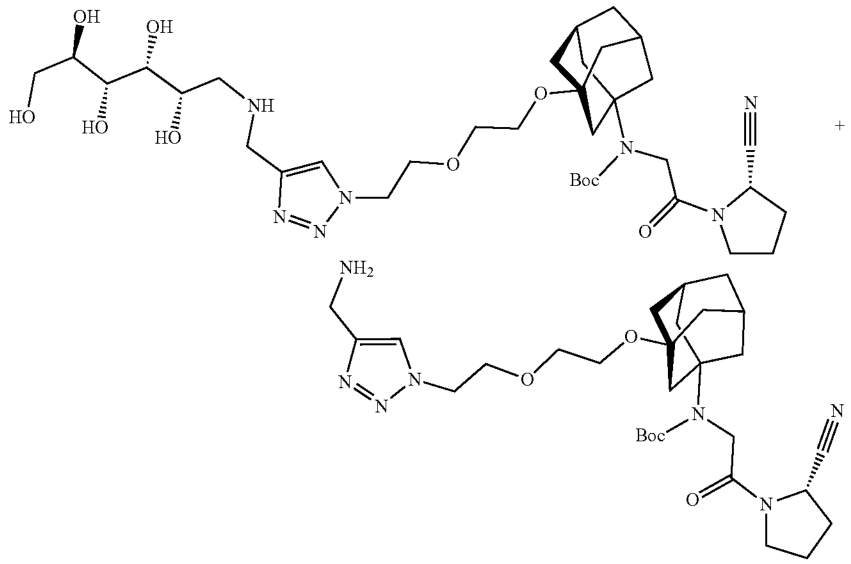

Mixture of tert-butyl ((1S,3R,5S)-3-(2-(2-azidoethoxy)ethoxy)adamantan-1-yl)(2-((S)-2-cyanopyrrolidin-1-yl)-2-oxoethyl)carbamate (1.0 g, 1.94 mmol), (2R,3R,4R,5S)-6-(prop-2-yn-1-ylamino)hexane-1,2,3,4,5-pentaol (0.64 g, 2.90 mmol), copper (11) sulfate pentahydrate (0.58 g, 2.33 mmol) and sodium ascorbate (0.58 g, 2.91 mmol) in tert-butyl alcohol (10 mL) and water (2 mL) mixture was stirred at room temperature for 16 h. After completion, the reaction mixture was filtered through celite and washed with methanol and water (1:1) (100 mL) and the filtrate was evaporated to give crude. The crude was then purified by reverse phase C18 column chromatography using 50% methanol in 0.1% formic acid in water. The desired product containing fractions were collected and evaporated to give mixture of tert-butyl (2-((S)-2-cyanopyrrolidin-1-yl)-2-oxoethyl)((1S,3R,5S)-3-(2-(2-(4-((((2S,3R,4R,5R)-2,3,4,5,6-pentahydroxyhexyl)amino)methyl)-1H-1,2,3-triazol-1-yl)ethoxy)ethoxy)adamantan-1-yl)carbamate and tert-butyl ((1S,3R,5S)-3-(2-(2-(4-(aminomethyl)-1H-1,2,3-triazol-1-yl)ethoxy)ethoxy)adamantan-1-yl)(2-((S)-2-cyanopyrrolidin-1-yl)-2-oxoethyl)carbamate (0.59 g, crude) as a brown solid.

Step 2. Tert-butyl (2-((S)-2-cyanopyrrolidin-1-yl)-2-oxoethyl)((1S,3R,5S)-3-(2-(2-(4-((((2S,3R,4R,5R)-2,3,4,5,6-pentahydroxyhexyl)amino)methyl)-1H-1,2,3-triazol-1-yl)ethoxy)ethoxy)adamantan-1-yl)carbamate

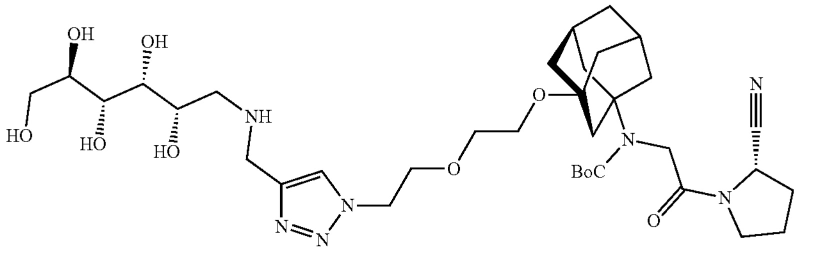

Mixture of tert-butyl ((1S,3R,5S)-3-(2-(2-(4-(aminomethyl)-1H-1,2,3-triazol-1-yl)ethoxy)ethoxy)adamantan-1-yl)(2-((S)-2-cyanopyrrolidin-1-yl)-2-oxoethyl)carbamate (0.44 g, 0.77 mmol), (2R,3S,4R,5R)-2,3,4,5,6-pentahydroxyhexanal (0.11 g, 0.61 mmol) and acetic acid (0.5 mL) in methanol (25 mL) was added sodium cyanoborohydride (0.048 g, 0.77 mmol) and the mixture was stirred at 60° C. for 6 h. After completion, the reaction mixture was evaporated to give crude product which was then purified by RP preparative HPLC using following conditions. Column/dimensions: X-BRIDGE C18 (19*250) Sum, mobile phase A: 10 mM ABC in water (aq), mobile phase B: 100% ACN, gradient (time/% B): 0/20, 3/20, 18/40, 18.1/100, 20/100, 20.1/20, 24/20, flow rate: 17 ml/min. The desired product containing fraction was evaporated to afford tert-butyl (2-((S)-2-cyanopyrrolidin-1-yl)-2-oxoethyl)((1S,3R,5S)-3-(2-(2-(4-((((2S,3R,4R,5R)-2,3,4,5,6-pentahydroxyhexyl)amino)methyl)-1H-1,2,3-triazol-1-yl)ethoxy)ethoxy)adamantan-1-yl)carbamate (0.1 g) as an off-white solid.

Step 3. (2S)-1-(((1S,3R,5S)-3-(2-(2-(4-((((2S,3R,4R,5R)-2,3,4,5,6-pentahydroxyhexyl)amino)methyl)-1H-1,2,3-triazol-1-yl)ethoxy)ethoxy)adamantan-1-yl)glycyl)pyrrolidine-2-carbonitrile (14)

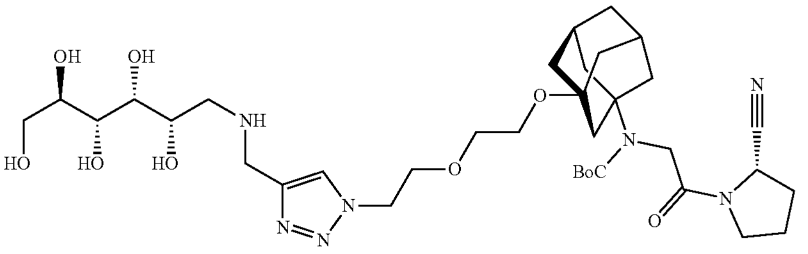

To the stirred solution of tert-butyl (2-((S)-2-cyanopyrrolidin-1-yl)-2-oxoethyl)((1S,3R,5S)-3-(2-(2-(4-((((2S,3R,4R,5R)-2,3,4,5,6-pentahydroxyhexyl)amino)methyl)-1H-1,2,3-triazol-1-yl)ethoxy)ethoxy)adamantan-1-yl)carbamate (0.1 g, 0.122 mmol) in acetonitrile and water (1:1) mixture (4 mL), 2N aqueous hydrochloric acid (1.22 mL, 2.44 mmol) was added and the reaction mixture was stirred at room temperature for 24 h. After completion of reaction (monitored by LCMS). The reaction mixture was evaporated to get crude. Obtained crude was purified by RP preparative HPLC using following conditions. Column/dimensions: X BRIDGE C18 (19×250 mm), 5μ, mobile phase A: 10 mM ABC in water, mobile phase B: acetonitrile, gradient (time/% B): 0/5, 4/5, 12/75, 12.1/5, 15/5. flow rate: 16 ml/min. The desired peak fraction was lyophilized to afford (2S)-1-(((1S,3R,5S)-3-(2-(2-(4-((((2S,3R,4R,5R)-2,3,4,5,6-pentahydroxyhexyl)amino)methyl)-1H-1,2,3-triazol-1-yl)ethoxy)ethoxy)adamantan-1-yl)glycyl)pyrrolidine-2-carbonitrile (0.063 g, 73.3%) as off-white solid. LCMS M/Z 636.49 (M+1) $^1$H NMR (400 MHz, DMSO-$d_6$) δ 7.92 (s, 1H), 5.10 (bs, 1H), 4.73-4.65 (m, 2H), 4.49-4.43 (m, 3H), 4.3 (bs, 2H), 3.80-3.36 (m, 19H), 2.64-2.60 (m, 2H), 2.16-2.01 (m, 6H), 1.56-1.46 (m, 12H).

Example 15. Synthesis of (1S,3S,5S)-2-((2S)-2-amino-2-((1S,3R,5S)-3-(2-hydroxyethoxy) adamantan-1-yl)acetyl)-2-azabicyclo[3.1.0]hexane-3-carbonitrile (16)

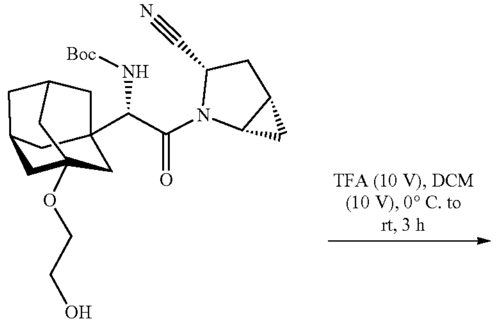

Int-9

-continued

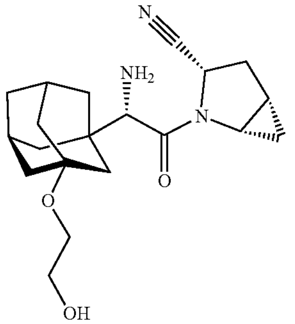

To the stirred solution of tert-butyl ((1S)-2-((1S,3S,5S)-3-cyano-2-azabicyclo[3.1.0]hexan-2-yl)-1-((1S,3R,5S)-3-(2-hydroxyethoxy)adamantan-1-yl)-2-oxoethyl) carbamate (0.30 g, 0.65 mmol), DCM (3 mL), TFA (3 mL) was added drop wise at 0° C. and the reaction mixture was stirred at room temperature for 3 h. After completion of reaction (monitored by LCMS), the reaction mixture was concentrated and wash with diethyl ether (2×50 mL) and evaporated to get crude. The obtained crude was basified with $NaHCO_3$ (20 mL) and extracted with DCM (3-50 mL) dried over anhydrous $Na_2SO_4$ and concentrated. The crude was purified by reverse phase C-18 column chromatography using 27% ACN and 10 mM ABC in water. The desired product containing fractions were collected and lyophilized to afford (1S,3S,5S)-2-((2S)-2-amino-2-((1S,3R,5S)-3-(2-hydroxyethoxy)adamantan-1-yl)acetyl)-2-azabicyclo[3.1.0]hexane-3-carbonitrile (0.053 g) as an off-white solid. LCMS M/Z 360.46 (M+1) $^1$H NMR (400 MHz, DMSO-$d_6$) δ 5.10-5.07 (m, 1H), 4.46-4.43 (m, 1H), 3.89-3.87 (m, 1H), 3.45-3.31 (m, 5H), 2.21-2.14 (m, 3H), 1.77-1.32 (m, 14H), 0.97 (m, 1H), 0.72-0.70 (s, 1H).

Example 16. Synthesis of 2-(((1R,3S,5S)-3-((S)-1-amino-2-((1S,3S,5S)-3-cyano-2-azabicyclo[3.1.0]hexan-2-yl)-2-oxoethyl)adamantan-1-yl)oxy)ethyl (4-((hexyl((2S,3R,4R,5R)-2,3,4,5,6-pentahydroxyhexyl)amino)methyl)phenyl)glycinate (19)

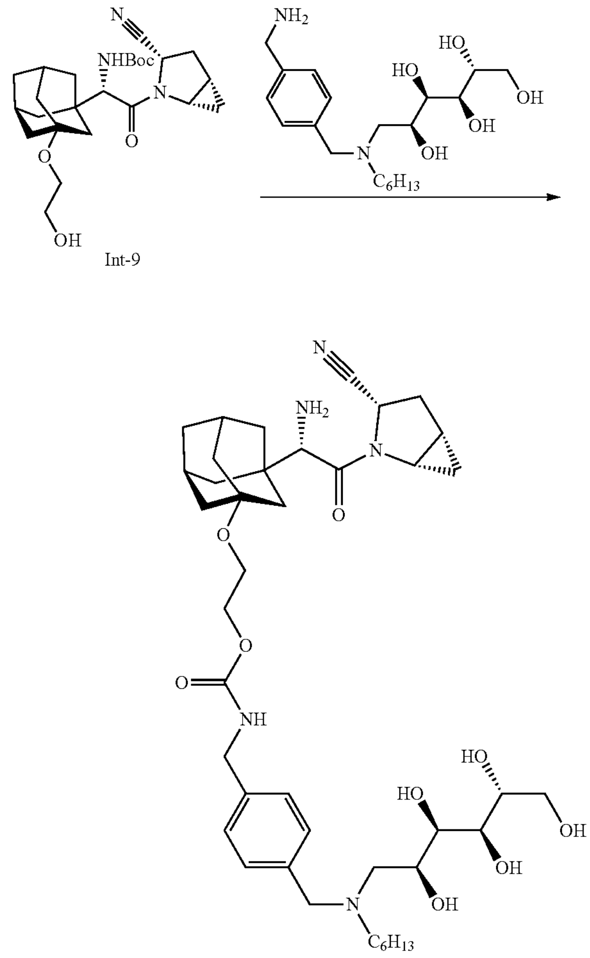

Int-9

To a solution of tert-butyl ((1S)-2-((1S,3S,5S)-3-cyano-2-azabicyclo[3.1.0]hexan-2-yl)-1-((1S,3R,5S)-3-(2-hydroxyethoxy)adamantan-1-yl)-2-oxoethyl)carbamate (36 mg, 1.0 eq) in dichloromethane (0.21 mL), triethylamine (0.04 mL, 4.0 eq) and 4-nitrophenyl chloroformate (17.1 mg in 0.13 mL dichloromethane) were added at 0° C. After stirring for 4 hours at room temperature, the mixture was added to a solution of (2R,3R,4R,5S)-6-((4-(aminomethyl)benzyl)(hexyl)amino)hexane-1,2,3,4,5-pentaol (46 mg, 1.2 eq) and triethylamine (0.08 mL, 6.0 eq) in acetonitrile (0.2 mL+0.05 mL*2 wash) at 0° C. The reaction was stirred for 12 hours before the addition of saturated aqueous $NaHCO_3$. The mixture was then extracted with dichloromethane for three times. The combined organic layer was washed with brine and concentrated in vacuo to provide the crude which was used for the next step without further purification. The above crude was treated with trifluoracetic acid (0.1 mL) and dichloromethane (0.2 mL). After stirring for 4 hours, the volatiles were removed under reduced pressure. The crude was purified by C18 reverse phase prep HPLC to afford the formic salt of 2-(((1R,3S,5S)-3-((S)-1-amino-2-((1S,3S,5S)-3-cyano-2-azabicyclo[3.1.0]hexan-2-yl)-2-oxoethyl)adamantan-1-yl)oxy)ethyl (4-((hexyl((2S,3R,4R,5R)-2,3,4,5,6-pentahydroxyhexyl)amino)methyl)phenyl)glycinate (17.4 mg, 25%) as white powder. ES MS M/Z=501.56 (M+1−adamantane) 1H NMR (500 MHz, MeOD) δ 7.51 (d, J=7.8 Hz, 2H), 7.42 (d, J=7.9 Hz, 2H), 5.21 (dd, J=10.7, 2.3 Hz, 1H), 4.49-4.30 (m, 4H), 4.23-4.12 (m, 4H), 3.94 (td, J=6.2, 2.7 Hz, 1H), 3.83-3.75 (m, 2H), 3.73-3.60 (m, 5H), 3.32-3.27 (m, 2H), 3.11 (qdd, J=13.0, 10.1, 6.1 Hz, 2H), 2.65 (ddd, J=13.7, 10.6, 5.7 Hz, 1H), 2.39-2.26 (m, 3H), 2.03 (dq, J=9.0, 5.7 Hz, 1H), 1.90-1.56 (m, 16H), 1.41-1.23 (m, 11H), 1.14 (dt, J=9.0, 6.4 Hz, 1H), 1.00-0.87 (m, 4H).

Similarly, compounds 17 and 18 were synthesized from Int-9.

Example 17. Synthesis of 2-(((1R,3S,5S)-3-((S)-1-amino-2-((1S,3S,5S)-3-cyano-2-azabicyclo [3.1.0]hexan-2-yl)-2-oxoethyl)adamantan-1-yl)oxy)ethyl (4-((bis((2S,3R,4R,5R)-2,3,4,5,6 pentahydroxyhexy-l)amino)methyl)benzyl)carbamate Trifluoracetate Salt (22)

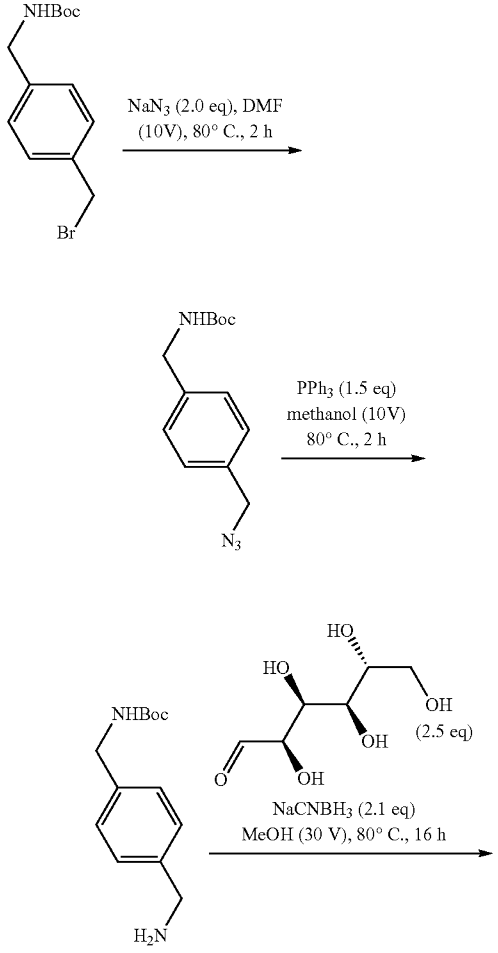

-continued
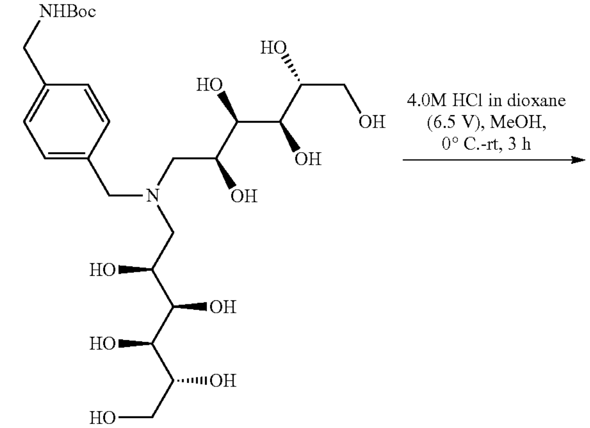
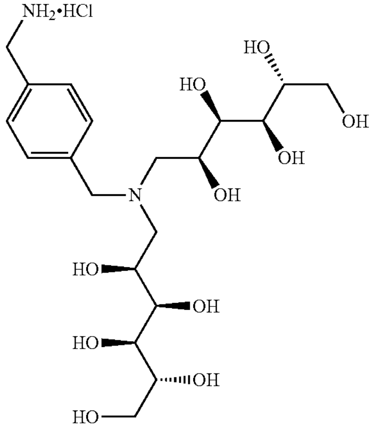
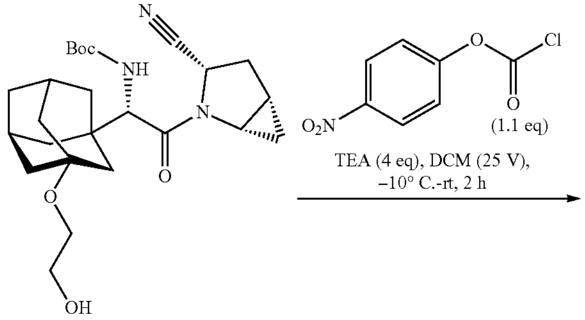
Int-9
-continued
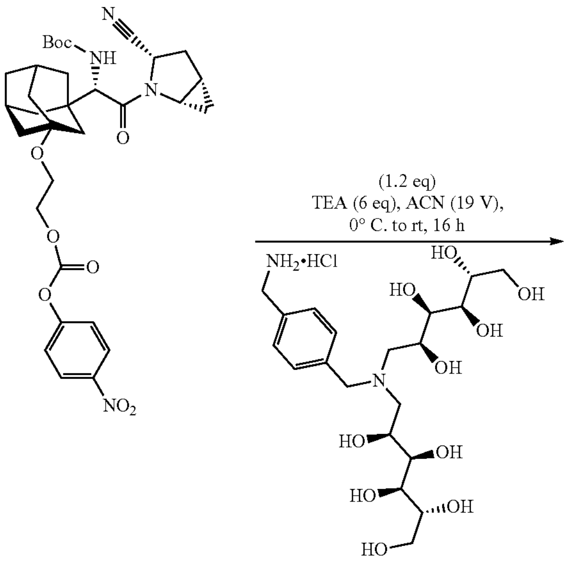
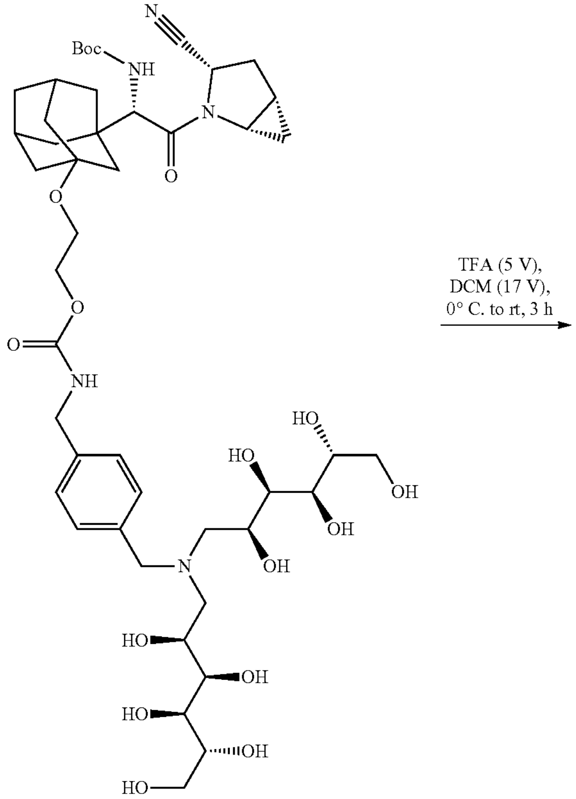

-continued

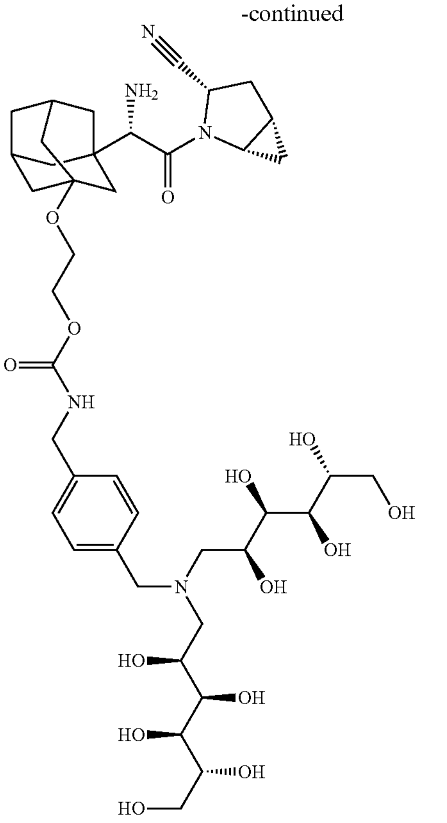

32

Step 1. Tert-butyl (4-(azidomethyl)benzyl)carbamate

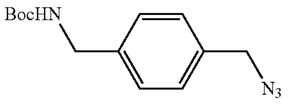

To a stirred solution of tert-butyl (4-(bromomethyl)benzyl)carbamate (2.0 g, 6.66 mmol) in DMF (20 mL), sodium azide (0.86 g, 13.33 mmol) was added at rt and the reaction mixture was stirred at 80° C. for 2 h. After completion, the reaction mixture was quenched with ice cold water solid was filtered through Buchner funnel and dried to afford tert-butyl (4-(azidomethyl)benzyl)carbamate (1.5 g) as an off-white solid. TLC system: EtOAc: pet ether (0.3:0.7); $R_f$, 0.4.

Step 2. Tert-butyl (4-(aminomethyl)benzyl)carbamate

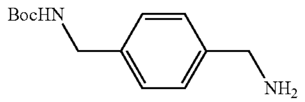

To a stirred solution of tert-butyl (4-(azidomethyl)benzyl) carbamate (1.3 g, 4.95 mmol) in methanol (15 mL), triphenylphosphine (1.9 g, 7.43 mmol) was added and the reaction mixture was stirred at 80° C. for 2 h. After completion, the reaction mixture was evaporated and purified by grace column chromatography using 8-10% MeOH in DCM to afford tert-butyl (4-(aminomethyl)benzyl)carbamate (0.9 g) as a gummy. TLC system: MeOH:DCM (0.1:0.9) $R_f$, 0.2.

Step 3. Tert-butyl (4-((bis((2S,3R,4R,5R)-2,3,4,5,6-pentahydroxyhexyl)amino)methyl)benzyl)carbamate

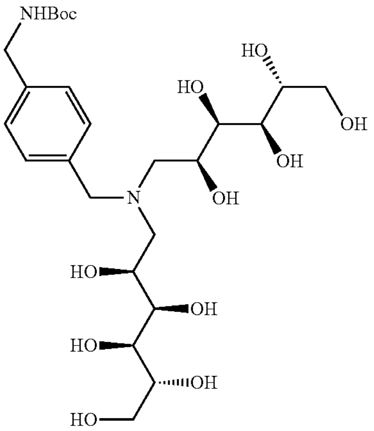 [SMILES: CC(C)(C)OC(=O)NCc1ccc(CN(C[C@H](O)[C@@H](O)[C@H](O)[C@H](O)CO)C[C@H](O)[C@@H](O)[C@H](O)[C@H](O)CO)cc1]

To a stirred solution of tert-butyl (4-(aminomethyl)benzyl)carbamate (0.88 g, 3.72 mmol) and (2R,3S,4R,5R)-2,3,4,5,6-pentahydroxyhexanal (1.6 g, 9.30 mmol) in methanol (26 mL) was acetic acid (0.8 mL) was added at 0° C. and the resultant mixture was stirred at rt for 20 min. Then sodium cyanoborohydride (0.49 g, 7.81 mmol) was added at 0° C. and the reaction mixture was heated at 80° C. for 16 h. After completion, the reaction mixture was concentrated and purified by RP column chromatography using 25% MeOH and 0.1% FA in water. The pure fraction was evaporated to afford tert-butyl (4-((bis((2S,3R,4R,5R)-2,3,4,5,6-pentahydroxyhexyl)amino)methyl)benzyl) carbamate (1.0 g) as a white solid.

Step 4. (2R,2'R,3R,3'R,4R,4'R,5S,5'S)-6,6'-((4-(aminomethyl)benzyl) azanediyl)bis(hexane-1,2,3,4,5-pentaol) hydrochloride

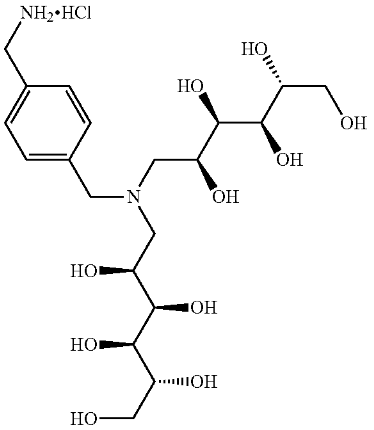

To the stirred solution of tert-butyl (4-((bis((2S,3R,4R,5R)-2,3,4,5,6-pentahydroxyhexyl)amino)methyl)benzyl) carbamate formate (0.8 g, 1.41 mmol) in methanol (4.0 mL), 4 M hydrochloric acid in 1.4 dioxane (8.0 mL) was added at 0° C. and the reaction mixture was stirred at room temperature for 2 h. After completion of reaction (monitored by LCMS), the reaction mixture was evaporated to afford (2R,2'R,3R,3'R,4R,4'R,5S,5'S)-6,6'-((4-(aminomethyl)benzyl)azanediyl)bis(hexane-1,2,3,4,5-pentaol) hydrochloride (0.95 g, crude) as a white gummy solid.

Step 5. Tert-butyl ((1S)-2-((1S,3S,5S)-3-cyano-2-azabicyclo[3.1.0]hexan-2-yl)-1-((1S,3R,5S)-3-(2-(((4-nitrophenoxy)carbonyl)oxy)ethoxy)adamantan-1-yl)-2-oxoethyl)carbamate

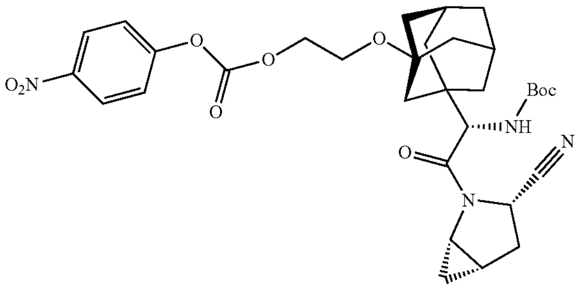

To the stirred solution of tert-butyl ((1S)-2-((1S,3S,5S)-3-cyano-2-azabicyclo[3.1.0]hexan-2-yl)-1-((1S,3R,5S)-3-(2-hydroxyethoxy)adamantan-1-yl)-2-oxoethyl)carbamate (0.8 g, 1.74 mmol) in dichloromethane (10 mL), triethylamine (0.9 mL, 1.91 mmol) was added and then 4-nitrophenyl carbonochloridate (0.38 g, 6.96 mmol) in in dichloromethane (2 mL) was added at −10° C. and the reaction mixture was stirred at room temperature for 2 h. After completion of the reaction, reaction mixture as such taken to next step.

Step 6. 2-(((1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl)oxy)ethyl (4-((bis((2S,3R,4R,5R)-2,3,4,5,6-pentahydroxyhexyl)amino)methyl)benzyl) carbamate

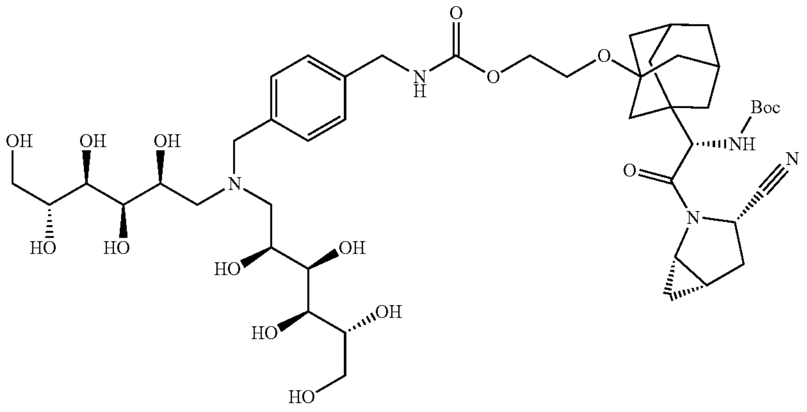 [SMILES: CC(C)(C)OC(=O)N[C@H](C(=O)N1[C@H](C#N)C[C@@H]2C[C@@H]21)C12CC3CC(CC(OCCOC(=O)NCc4ccc(CN(C[C@H](O)[C@@H](O)[C@H](O)[C@H](O)CO)C[C@H](O)[C@@H](O)[C@H](O)[C@H](O)CO)cc4)(C3)C1)C2]

To the stirred solution of (2R,2'R,3R,3'R,4R,4'R,5S,5'S)-6,6'-((4-(aminomethyl)benzyl)azanediyl)bis(hexane-1,2,3,4,5-pentaol) hydrochloride (0.96 g, 1.92 mmol), in ACN (10 mL) TEA (1.3 mL, 9.60 mmol), was added at 0° C. Then tert-butyl ((1S)-2-((1S,3S,5S)-3-cyano-2-azabicyclo[3.1.0]hexan-2-yl)-1-((1S,3R,5S)-3-(2-(((4-nitrophenoxy)carbonyl)oxy)ethoxy)adamantan-1-yl)-2-oxoethyl)carbamate (1.17 g, 1.60 mmol), was added drop wise to the reaction mixture at 0° C. and stirred 80° C. for 16 h. After completion of the reaction the reaction mixture was concentrated and purified by RP C18 column chromatography using 25% MeOH and 0.1 M FA in water. The desired product containing fractions were collected and evaporated to afford 2-(((1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl)oxy)ethyl (4-((bis((2S,3R,4R,5R)-2,3,4,5,6-pentahydroxyhexyl)amino)methyl)benzyl) carbamate (0.8 g) as yellow gum.

Step 7. 2-(((1R,3S,5S)-3-((S)-1-amino-2-((1S,3S,5S)-3-cyano-2-azabicyclo [3.1.0]hexan-2-yl)-2-oxoethyl)adamantan-1-yl)oxy)ethyl (4-((bis((2S,3R,4R,5R)-2,3,4,5,6 pentahydroxyhexyl)amino)methyl) benzyl) carbamate trifluoroacetate salt (22)

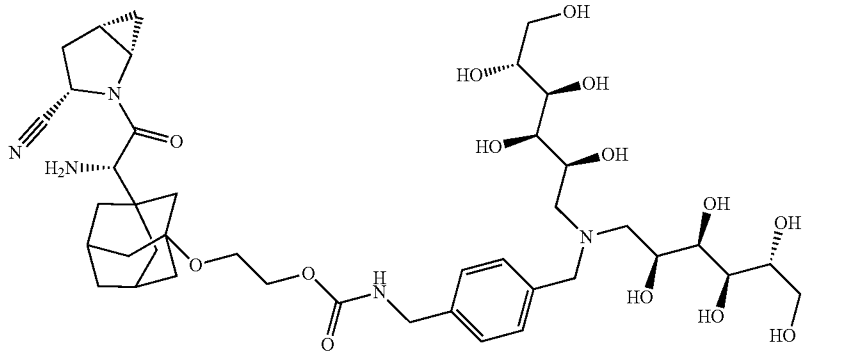 [SMILES: N#C[C@@H]1C[C@@H]2C[C@@H]2N1C(=O)[C@@H](N)C12CC3CC(CC(OCCOC(=O)NCc4ccc(CN(C[C@H](O)[C@@H](O)[C@H](O)[C@H](O)CO)C[C@H](O)[C@@H](O)[C@H](O)[C@H](O)CO)cc4)(C3)C1)C2]

To the stirred solution of 2-(((1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl)oxy)ethyl (4-((bis((2S,3R,4R,5R)-2,3,4,5,6-pentahydroxyhexyl) amino)methyl)benzyl)carbamate (0.80 g, 0.84 mmol), DCM (8 mL), TFA (4 mL) was added drop wise at 0° C. and the reaction mixture was stirred at room temperature for 1 h. After completion of reaction (monitored by LCMS), the reaction mixture was concentrated and wash with diethyl ether (2×100 mL) and evaporated to get crude. The obtained crude was purified by RP SUNFIRE-C18 (150*19*5μ) using 20% ACN and 0.1% TFA in water. The desired product containing fractions were collected and lyophilized to afford of 2-(((1R,3S,5S)-3-((S)-1-amino-2-((1S,3S,5S)-3-cyano-2-azabicyclo[3.1.0]hexan-2-yl)-2-oxoethyl)adamantan-1-yl) oxy)ethyl (4-((bis((2S,3R,4R,5R)-2,3,4,5,6-pentahydroxyhexyl)amino)methyl)benzyl)carbamate trifluoroacetate salt (0.184 g) as an off-white solid. LCMS M/Z 850.68 (M+1) $^1$H NMR (400 MHz, DMSO-$d_6$) δ 8.54 (s, 1H), 8.17 (s, 2H), 7.79 (t, J=6.0 Hz, 1H), 7.48 (d, J 8.0 Hz, 2H), 7.32 (d, J=8.0 Hz, 2H), 5.60 (bs, 1H), 4.95 (bs, 1H), 5.27-5.24 (m, 1H), 4.95 (m, 2H), 4.37-4.02 (m, 16H), 3.72-3.52 (m, 12H), 3.16 (m, 4H), 2.32-2.23 (m, 3H), 2.07 (m, 1H), 1.73-1.46 (m, 12H), 1.04 (m, 1H), 0.75 (s, 1H).

Example 18. Synthesis of 2-(((1R,3S,5S)-3-((S)-1-amino-2-((1S,3S,5S)-3-cyano-2-azabicyclo[3.1.0]hexan-2-yl)-2-oxoethyl)adamantan-1-yl)oxy)ethyl (4-((ethyl((2S,3R,4R,5R)-2,3,4,5,6-pentahydroxyhexyl)amino)methyl)benzyl)carbamate Formate (23)

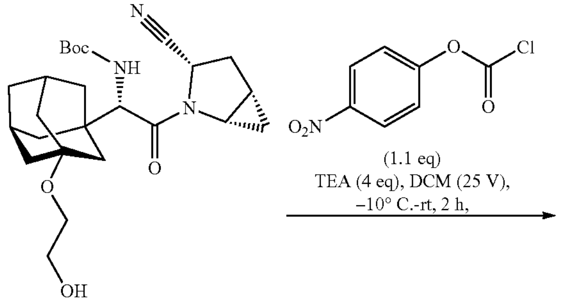

Int-9

-continued

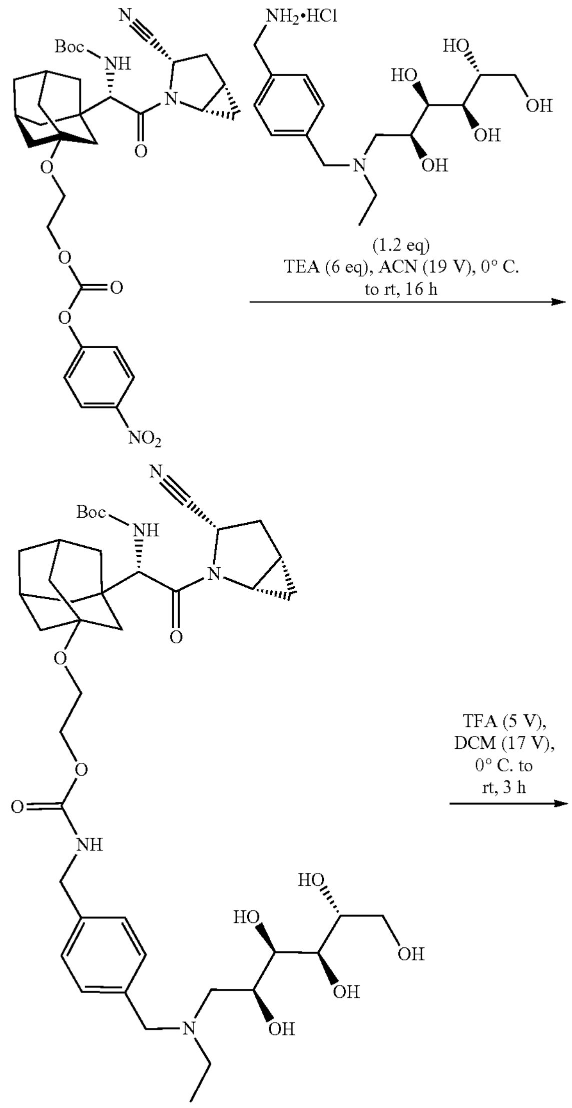

-continued

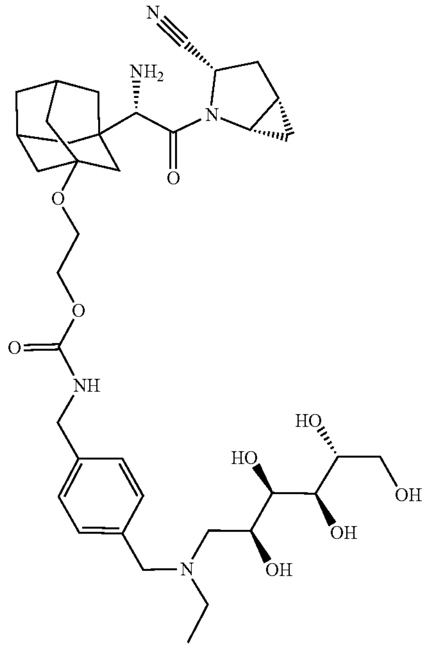 [SMILES: CCN(Cc1ccc(CNC(=O)OCCOC23CC4CC(C2)CC([C@H](N)C(=O)N2[C@H](C#N)C[C@@H]5C[C@@H]52)(C4)C3)cc1)C[C@H](O)[C@@H](O)[C@H](O)[C@H](O)CO]

Step 1. Tert-butyl ((1S)-2-((1S,3S,5S)-3-cyano-2-azabicyclo[3.1.0]hexan-2-yl)-1-((1S,3R,5S)-3-(2-(((4-nitrophenoxy)carbonyl)oxy)ethoxy)adamantan-1-yl)-2-oxoethyl)carbamate

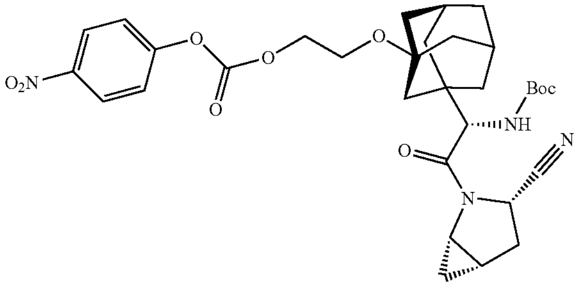

To the stirred solution of tert-butyl ((1S)-2-((1S,3S,5S)-3-cyano-2-azabicyclo[3.1.0]hexan-2-yl)-1-((1S,3R,5S)-3-(2-hydroxyethoxy)adamantan-1-yl)-2-oxoethyl)carbamate (0.8 g, 1.74 mmol) in DCM (10 mL) was added TEA (0.9 mL, 6.96 mmol) followed by 4-nitrophenyl carbonochloridate (0.38 g, 1.91 mmol) in DCM (0.5 mL) dropwise at −10° C. stirred at room temperature for 2 h. After completion, the reaction mixture was taken to next step to give tert-butyl ((1S)-2-((1S,3S,5S)-3-cyano-2-azabicyclo[3.1.0]hexan-2-yl)-1-((1S,3R,5S)-3-(2-(((4-nitrophenoxy)carbonyl)oxy)ethoxy)adamantan-1-yl)-2-oxoethyl)carbamate (1.17 g) as yellow solution. TLC system: 100% EtOAc, $R_f$: 0.4.

Step 2. 2-(((1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl)oxy)ethyl (4-((ethyl((2S,3R,4R,5R)-2,3,4,5,6-pentahydroxyhexyl)amino)methyl)benzyl)carbamate

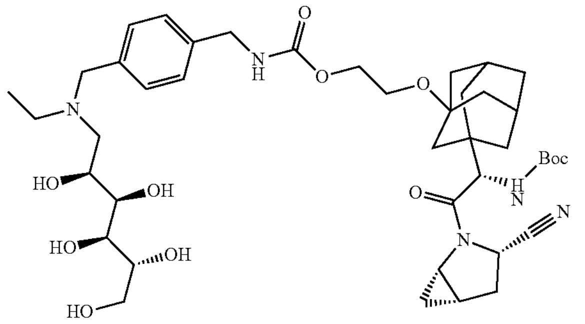 [SMILES: CCN(Cc1ccc(CNC(=O)OCCOC23CC4CC(C2)CC([C@H](NC(=O)OC(C)(C)C)C(=O)N2[C@H](C#N)C[C@@H]5C[C@@H]52)(C4)C3)cc1)C[C@H](O)[C@@H](O)[C@H](O)[C@H](O)CO]

To the stirred solution of tert-butyl (2R,3R,4R,5S)-6-((4-(aminomethyl)benzyl)(ethyl)amino)hexane-1,2,3,4,5-pentaol hydrochloride (0.81 g, 2.24 mmol), in ACN (10 mL) TEA (1.5 mL, 11.22), was added at 0° C. Then tert-butyl ((1S)-2-((1S,3S,5S)-3-cyano-2-azabicyclo[3.1.0]hexan-2-yl)-1-((1S,3R,5S)-3-(2-(((4-nitrophenoxy)carbonyl)oxy)ethoxy)adamantan-1-yl)-2-oxoethyl)carbamate (1.17 g, 1.87 mmol), was added drop wise to the reaction mixture at 0° C. and stirred 80° C. for 16 h. After completion of the reaction the reaction mixture was concentrated and purified by RP C18 column chromatography using 27% ACN and 0.1 M FA in water. The desired product containing fractions were collected and evaporated to afford 2-(((1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl)oxy)ethyl (4-((ethyl((2S,3R,4R,5R)-2,3,4,5,6-pentahydroxyhexyl)amino)methyl)benzyl)carbamate (1.0 g) as a yellow gum.

Step 3. 2-(((1R,3S,5S)-3-((S)-1-amino-2-((1S,3S,5S)-3-cyano-2-azabicyclo[3.1.0]hexan-2-yl)-2-oxoethyl)adamantan-1-yl)oxy)ethyl (4-((ethyl((2S,3R,4R,5R)-2,3,4,5,6-pentahydroxyhexyl)amino)methyl)benzyl)carbamate formate (23)

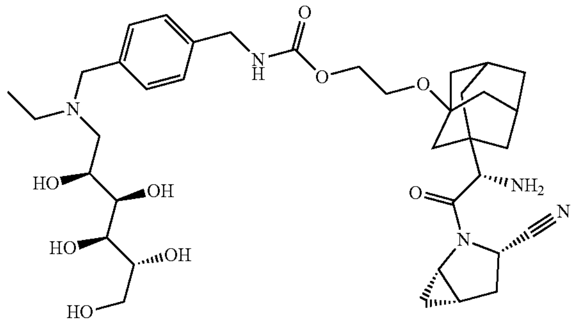 [SMILES: CCN(Cc1ccc(CNC(=O)OCCOC23CC4CC(C2)CC([C@H](N)C(=O)N2[C@H](C#N)C[C@@H]5C[C@@H]52)(C4)C3)cc1)C[C@H](O)[C@@H](O)[C@H](O)[C@H](O)CO]

To the stirred solution of 2-(((1R,3S,5S)-3-((S)-1-((tert-butoxycarbonyl)amino)-2-((1S,3S,5S)-3-cyano-2-azabicyclo[3.1.0]hexan-2-yl)-2-oxoethyl)adamantan-1-yl)oxy)ethyl (4-((ethyl((2S,3R,4R,5R)-2,3,4,5,6-pentahydroxyhexyl)amino)methyl)benzyl)carbamate (1 g, 1.22 mmol) in DCM (10 mL) was added TFA (10 mL) dropwise at 0° C. and the resultant mixture was stirred at room temperature for 1 h. After completion (monitored by LCMS), the reaction mixture was concentrated and washed with diethyl ether (2×100 mL) to give crude product. The obtained crude was then purified by RP chromatography using C-18 column and 20% CAN: 0.1 M FA in water as an eluent. The desired product containing fractions were collected and lyophilized to afford 2-(((1R,3S,5S)-3-((S)-1-amino-2-((1S,3S,5S)-3-cyano-2-azabicyclo[3.1.0]hexan-2-yl)-2-oxoethyl)adamantan-1-yl)oxy)ethyl(4-((ethyl((2S,3R,4R,5R)-2,3,4,5,6-pentahydroxyhexyl)amino)methyl)benzyl)carbamate formate (0.59 g) as an off-white solid. LCMS M/Z 712.50 (M−1) $^1$H NMR (400 MHz, DMSO-$d_6$) δ 8.13 (s, 1H), 7.74 (t, J=6.0 Hz, 1H), 7.38 (d, J=7.6 Hz, 2H), 7.24 (d, J=7.6 Hz, 2H), 5.22 (m, 1H), 4.18-4.02 (m, 10H), 3.89 (s, 1H), 2.17-3.66-3.52 (m, 4H), 3.49-3.47 (m, 4H), 2.92-2.71 (m, 4H), 2.50 (s, 3H), 2.27-2.21 (m, 3H), 1.96 (m, 1H), 1.71-1.43 (m, 12H), 1.09-1.02 (m, 4H), 0.74 (s, 1H).

Example 21. Synthesis of (R)-(2-((8-(3-aminopiperidin-1-yl)-7-(but-2-yn-1-yl)-3-methyl-2,6-dioxo-2,3,6,7-tetrahydro-1H-purin-1-yl)methyl)phenyl)boronic Acid (27)

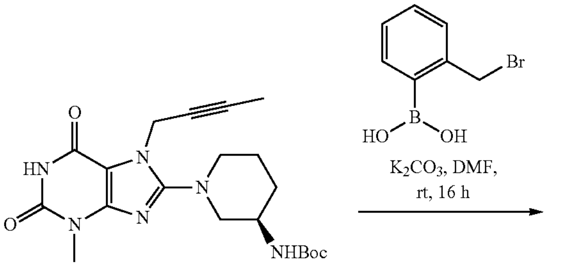

Int-13

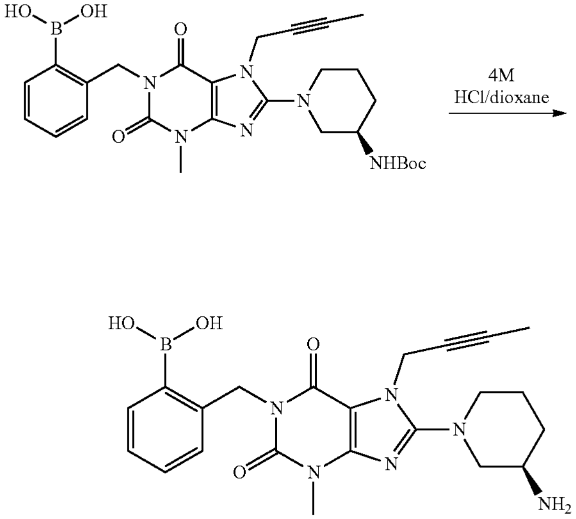

Step 1. (R)-(2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)phenyl)boronic acid

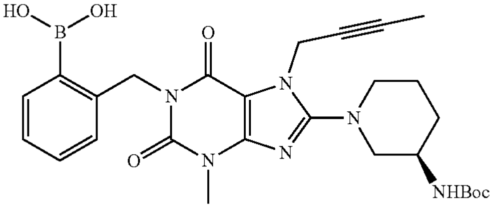 [SMILES: CC#CCn1c(N2CCC[C@@H](NC(=O)OC(C)(C)C)C2)nc2c1c(=O)n(Cc1ccccc1B(O)O)c(=O)n2C]

To a stirred solution of tert-butyl (R)-(1-(7-(but-2-yn-1-yl)-3-methyl-2,6-dioxo-2,3,6,7-tetrahydro-1H-purin-8-yl)piperidin-3-yl)carbamate (0.1 g, 0.24 mmol) and (2-(bromomethyl)phenyl)boronic acid (0.08 g, 0.36 mmol) in DMF (1 mL) was added $K_2CO_3$ (0.03 g, 0.24 mmol) and the reaction mixture was stirred at room temperature for 16 h. After completion of starting material, the reaction mixture was diluted with EtOAc (20 mL), washed with water (20 mL) and brine solution (20 mL), dried over anhydrous sodium sulfate, filtered and concentrated under reduced pressure to get a crude mass. The crude residue was purified by reverse phase preparative-HPLC to afford 0.06 g of (R)-(2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)phenyl)boronic acid as an off-white solid. [TLC system: EtOAc:pet-ether (8:2); Rf value: 0.5].

Step 2. (R)-(2-((8-(3-aminopiperidin-1-yl)-7-(but-2-yn-1-yl)-3-methyl-2,6-dioxo-2,3,6,7-tetrahydro-1H-purin-1-yl)methyl)phenyl)boronic acid (27)

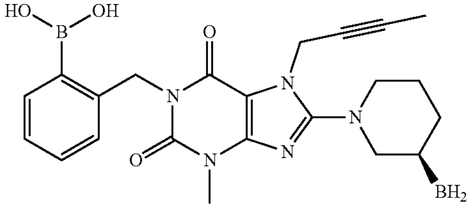

To a stirred solution of (R)-(2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)phenyl)boronic acid (0.06 g, 0.11 mmol) in 1,4-dioxane (0.6 mL) was added 4 M HCl in 1,4-dioxane (0.12 mL) dropwise at 0° C. and the reaction mixture was stirred at room temperature for 3 h. After completion of starting material, the reaction mixture was concentrated under reduced pressure and triturated with diethyl ether to afford 0.025 g of compound 27 (HCl salt) as an off-white solid. [TLC system: MeOH:DCM (1:9); $R_f$-value: 0.2]. LC MS M/Z=451.46 (M+1). $^1$H NMR (400 MHz, DMSO-$d_6$) δ 8.22 (s, 2H), 8.12 (s, 2H), 7.55 (d, J=6.8 Hz, 1H), 7.27-7.14 (m, 2H), 6.91 (d, J=7.6 Hz, 1H), 5.25 (s, 2H), 5.00-4.88 (m, 2H), 3.69 (d, J=2.4 Hz, 1H), 3.49-3.40 (m, 5H), 3.22-3.14 (m, 2H), 2.00-1.90 (m, 2H), 1.79 (s, 3H), 1.71-1.61 (m, 2H).

Example 22. Synthesis of hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-6-fluoronicotinate (30)

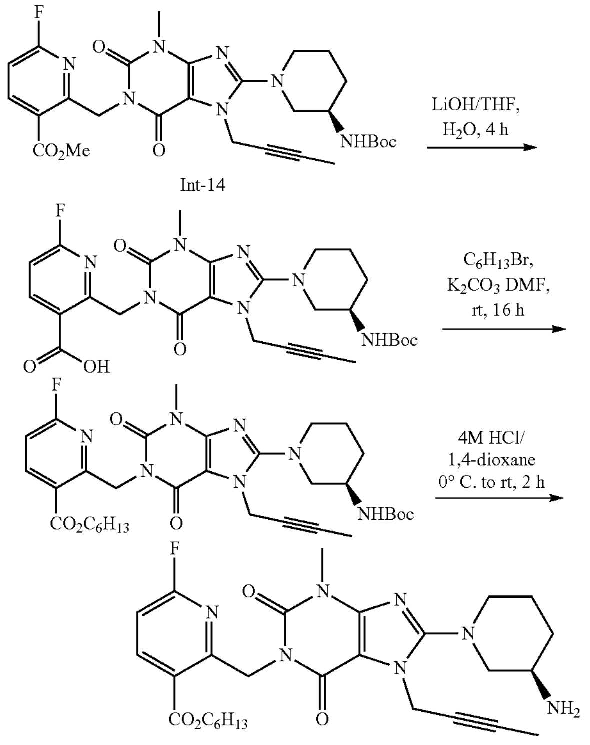

Step 1. (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinic acid

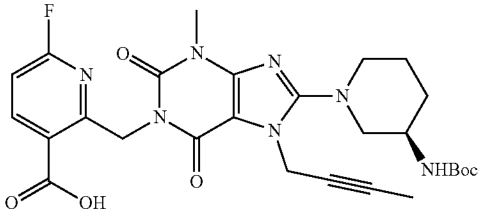 [SMILES: CC#CCn1c(N2CCC[C@@H](NC(=O)OC(C)(C)C)C2)nc2c1c(=O)n(Cc1nc(F)ccc1C(=O)O)c(=O)n2C]

To a stirred solution of methyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinate (0.9 g, 1.56 mmol) in THF (9 mL) and water (2 mL) was added LiOH·$H_2O$ (0.129 g, 3.08 mmol) at 0° C. The reaction mixture was stirred at rt for 4 h. After completion of starting material, the reaction mixture was concentrated under reduced pressure to get crude compound. The crude compound was diluted with water, acidified with 1N HCL. The precipitated solid was filtered off and dried under vacuum to afford 0.72 g of compound (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinic acid as an off-white solid. [TLC system: MeOH:DCM (1:9); $R_f$ value: 0.3].

Step 2. Hexyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinate

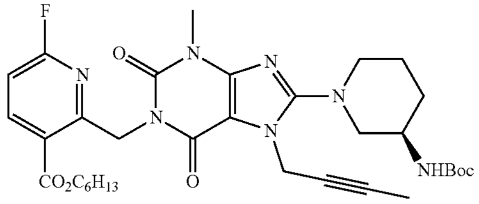

To a stirred solution of compound (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinic acid (0.72 g, 1.26 mmol) in DMF (15 mL) were added $C_6H_{13}Br$ (0.25 g, 1.51 mmol) and $K_2CO_3$ (0.52 g, 3.78 mmol) and the reaction mixture was stirred at rt for 16 h. After completion of starting material, the reaction mixture was quenched with cold water and the precipitated solid was filtered off, dried under vacuum to get 0.3 g of compound hexyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinate as an off-white solid. [TLC system: EtOAc:Pet ether (1:1); $R_f$ value: 0.8].

Step 3. Hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-6-fluoronicotinate (30)

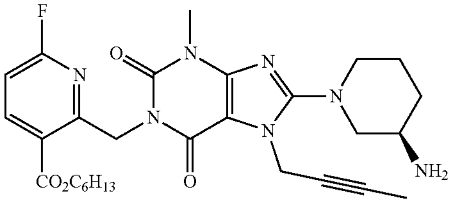

To a stirred solution of compound hexyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-fluoronicotinate (0.30 g, 0.46 mmol) in 1,4-dioxane (3 mL) was added 4 M HCl in 1,4-dioxane (2 mL) at 0° C. and the reaction mixture was stirred at room temperature for 2 h. After completion of starting material, the reaction mixture was concentrated under reduced pressure to get a crude compound. The crude compound was purified by reverse phase preparative-HPLC to afford 0.181 g of compound hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-6-fluoronicotinate as an off white solid. [TLC system: MeOH:DCM (1:9); $R_f$ value: 0.3].

LC MS M/Z=554.87 (M+1) $^1$H NMR (400 MHz, DMSO-$d_6$) δ 8.48 (t, J=8.4 Hz, 1H), 8.12 (d, J=3.6 Hz, 3H), 7.22-7.19 (dd, J=8.4 Hz, 2.4 Hz, 1H), 5.49 (s, 2H), 4.94 (m, 2H), 4.34 (t, J=6.4 Hz, 2H), 3.71 (m, 1H), 3.50-3.40 (m, 5H), 3.21-3.16 (m, 2H), 2.02-1.89 (m, 1H), 1.89-1.77 (m, 1H), 1.76-1.65 (m, 7H), 1.44-1.41 (m, 2H), 1.34-1.31 (m, 4H), 0.89-0.86 (m, 3H).

Example 23. Synthesis of hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-6-(methylamino)nicotinic Acid (31)

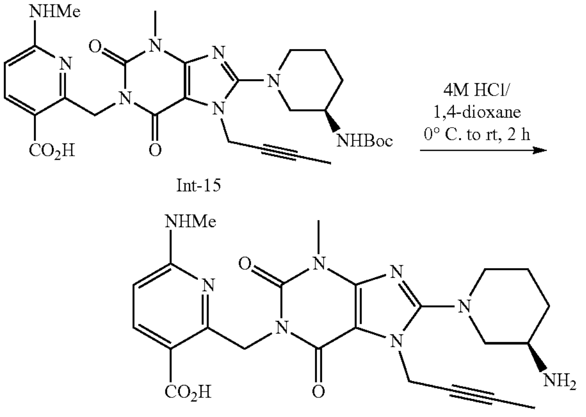

Int-15

To a stirred solution of compound (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl) methyl)-6-(methylamino)nicotinic acid (0.5 g, 0.86 mmol) in 1,4-dioxane (3 mL) was added 4 M HCl in 1,4-dioxane (2 mL) at 0° C. and the reaction mixture was stirred at room temperature for 2 h. After completion of starting material, the reaction mixture was concentrated under reduced pressure to get a crude compound. The crude compound was purified by reverse phase preparative-HPLC to afford 0.157 g of compound hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-6-(methylamino)nicotinic acid as an off white solid. [TLC system: MeOH:DCM (1:9); $R_f$ value: 0.3]. LC MS M/Z=481.28 (M+1) $^1$H NMR (400 MHz, DMSO-$d_6$) δ 8.24 (m, 3H), 7.87 (d, J=7.6 Hz, 1H), 6.33 (d, J=8.4 Hz, 1H), 5.37 (s, 2H), 5.00-4.88 (m, 2H), 3.68-3.38 (m, 6H), 3.18-3.12 (m, 2H), 2.45 (m, 3H), 2.02-1.90 (m, 2H), 1.77 (s, 3H), 1.70-1.62 (m, 2H).

Example 24. Synthesis of hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-6-(methylamino)nicotinate (32)

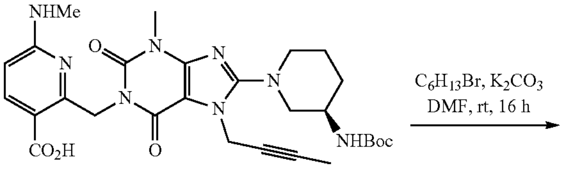

Int-15

-continued

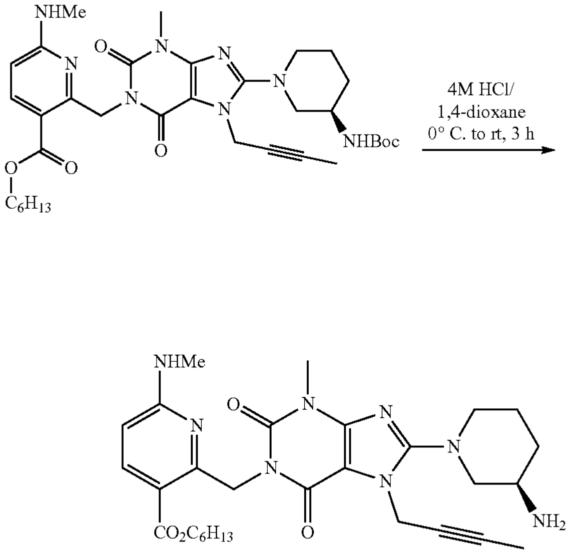

Step 1. (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-(methylamino)nicotinic acid

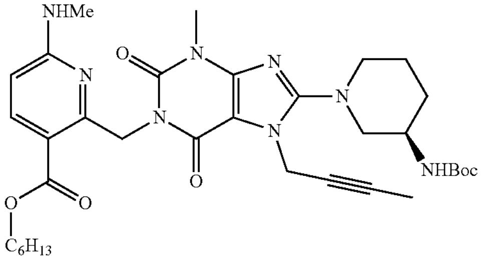

To a stirred solution of compound (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl) methyl)-6-(methylamino)nicotinic acid (1.0 g, 1.72 mmol, sharing same intermediate with mCMT478) in DMF (10 mL) were added $C_6H_{13}Br$ (0.34 g, 2.06 mmol) and $K_2CO_3$ (0.71 g, 5.16 mmol) and the reaction mixture was stirred at rt for 16 h. After completion of starting material, the reaction mixture was quenched with cold water and the precipitated solid was filtered off, dried under vacuum to get 0.7 g of compound (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-6-(methylamino)nicotinic acid as an off-white solid. [TLC system: MeOH:DCM (1:9); $R_f$ value: 0.8].

Step 2. Hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-6-(methylamino)nicotinate (32)

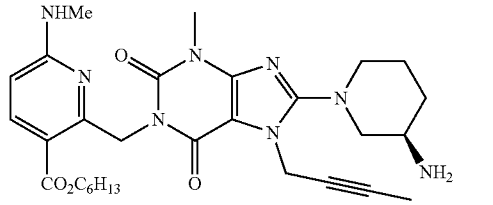

To a stirred solution of compound hexyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl) methyl)-6-(methylamino)nicotinate (0.41 g, 0.62 mmol) in 1,4-dioxane (4 mL) was added 4 M HCl in 1,4-dioxane (3 mL) at 0° C. and the reaction mixture was stirred at room temperature for 2 h. After completion of starting material, the reaction mixture was concentrated under reduced pressure to get a crude compound. The crude compound was purified by reverse phase preparative-HPLC to afford 0.161 g of compound hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-6-(methylamino)nicotinate as an off white solid. [TLC system: MeOH:DCM (1:9); $R_f$ value: 0.3]. LC MS M/Z=565.79 (M+1) $^1$H NMR (400 MHz, DMSO-$d_6$) δ 8.18 (s, 3H), 7.87 (d, J=8.4 Hz, 1H), 7.21 (br s, 1H), 6.34 (d, J=8.8, 1H), 5.36 (s, 2H), 4.99-4.88 (m, 2H), 4.22 (t, J=6.4 Hz, 2H), 3.70-3.59 (m, 1H), 3.49-3.39 (m, 5H), 3.18-3.11 (m, 2H), 2.44 (s, 3H), 2.02-1.99 (m, 2H), 1.90-1.61 (m, 7H), 1.42-1.31 (m, 6H), 0.89 (s, 3H).

Example 25. Synthesis of methyl 2-((8-((R)-3-aminopiperidin-1-yl)-7-(but-2-yn-1-yl)-3-methyl-2,6-dioxo-2,3,6,7-tetrahydro-1H-purin-1-yl)methyl)-6-((7-(4-((bis((2S,3R,4R,5R)-2,3,4,5,6-pentahydroxyhexyl)amino)methyl)-1H-1,2,3-triazol-1-yl)heptyl)amino)nicotinate (34)

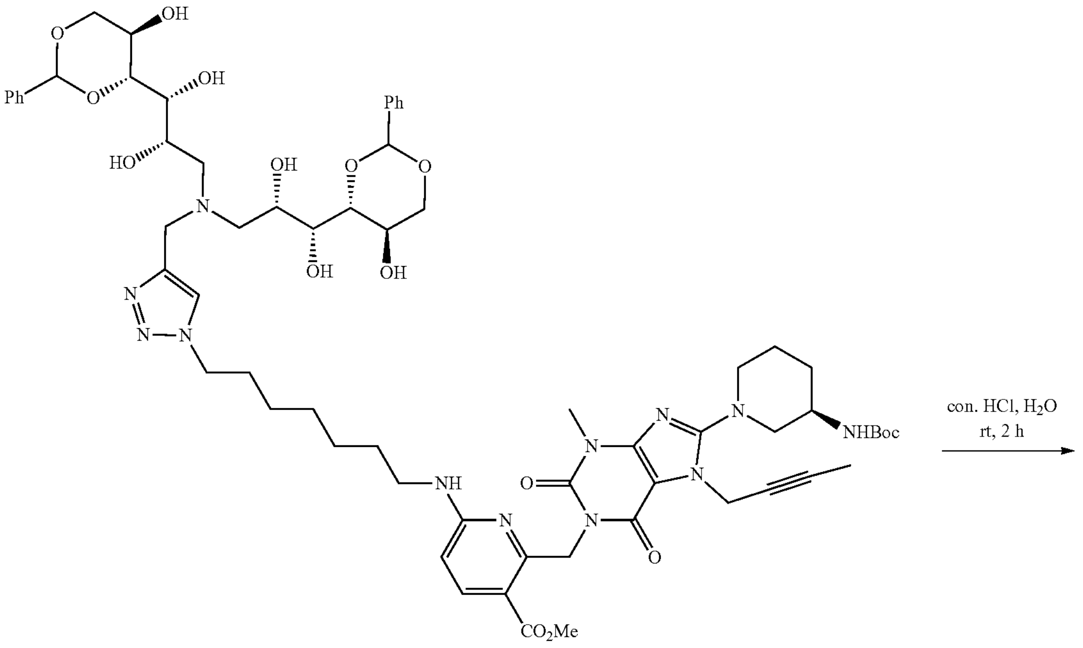

Int-18

-continued

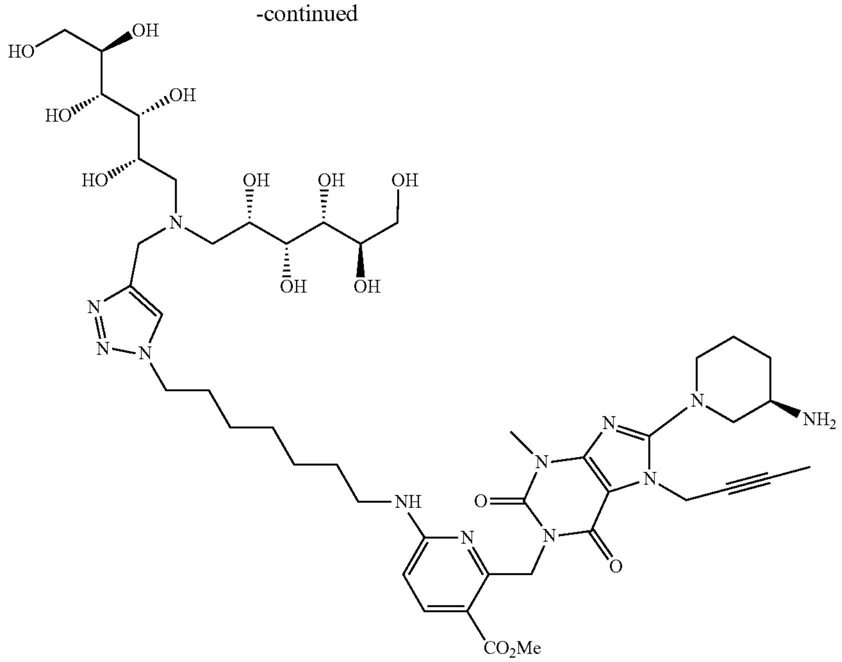

To the solution of compound methyl 6-((7-(4-((bis((2S,3R)-2,3-dihydroxy-3-((4R,5R)-5-hydroxy-2-phenyl-1,3-dioxan-4-yl)propyl)amino)methyl)-1H-1,2,3-triazol-1-yl)heptyl)amino)-2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)nicotinate (0.9 g, 0.70 mmol) in $H_2O$ (10 mL) and then was added conc. HCl (2 mL) at 0° C. and the reaction mixture was stirred at room temperature for 2 h. After completion of the reaction (LCMS monitoring), the reaction mixture was concentrated under reduced pressure to get a crude mass. The crude purified by RP-HPLC to afford compound methyl 2-((8-((R)-3-aminopiperidin-1-yl)-7-(but-2-yn-1-yl)-3-methyl-2,6-dioxo-2,3,6,7-tetrahydro-1H-purin-1-yl)methyl)-6-((7-(4-((bis((2S,3R,4R,5R)-2,3,4,5,6-pentahydroxyhexyl)amino)methyl)-1H-1,2,3-triazol-1-yl)heptyl)amino)nicotinate (0.041 g) as off white solid. LC MS M/Z=1003.62 (M+1) $^1H$ NMR (400 MHz, DMSO $d_6$) δ 8.95 (s, 1H), 8.34 (s, 1H), 8.21 (m, 3H), 7.84 (d, J=8.7 Hz, 1H), 7.39 (brs, 1H), 6.31 (d, J=8.8 Hz, 1H), 5.34 (br m, 4H), 4.93 (m, 2H), 4.56 (m, 2H), 4.39 (t, J=6.9 Hz, 2H), 4.13 (m, 2H), 3.79 (s, 3H), 3.59 (m, 6H), 3.43 (m, 11H), 3.15 (m, 6H), 2.86 (s, 2H), 2.04 (m, 1H), 1.91 (m, 1H), 1.78 (m, 7H), 1.16 (m, 8H), 0.89 (m, 2H).

Example 26. Synthesis of 2-((8-((R)-3-aminopiperidin-1-yl)-7-(but-2-yn-1-yl)-3-methyl-2,6-dioxo-2,3,6,7-tetrahydro-1H-purin-1-yl)methyl)-6-((7-(4-((bis((2S,3R,4R,5R)-2,3,4,5,6-pentahydroxyhexyl)amino)methyl)-1H-1,2,3-triazol-1-yl)heptyl)amino)nicotinic acid (35)

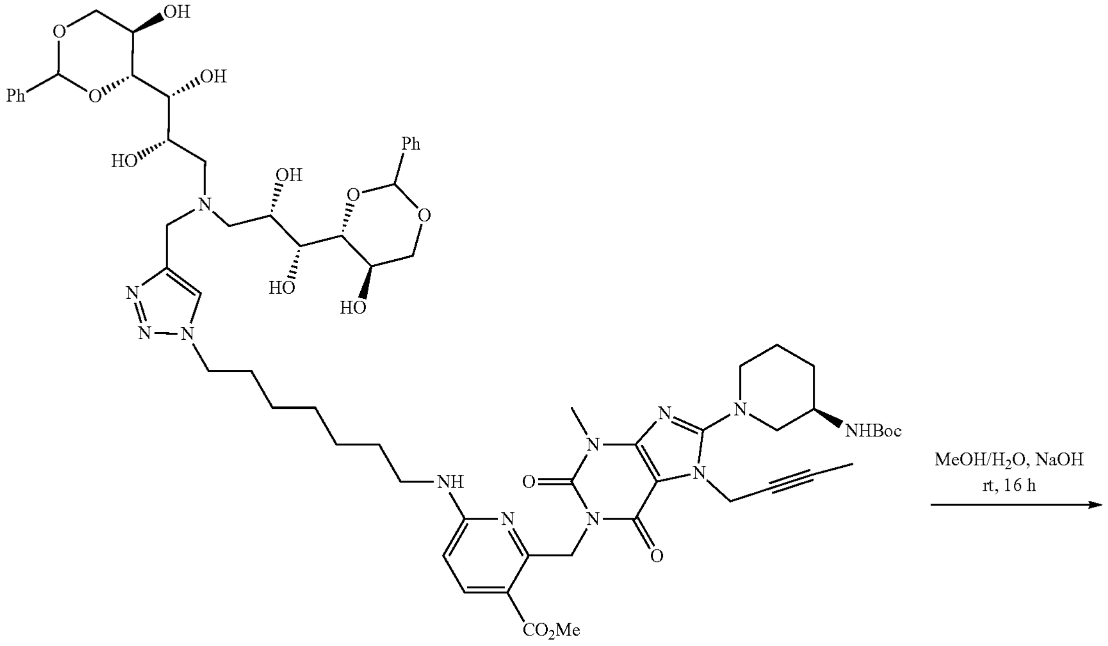

Int-18

-continued
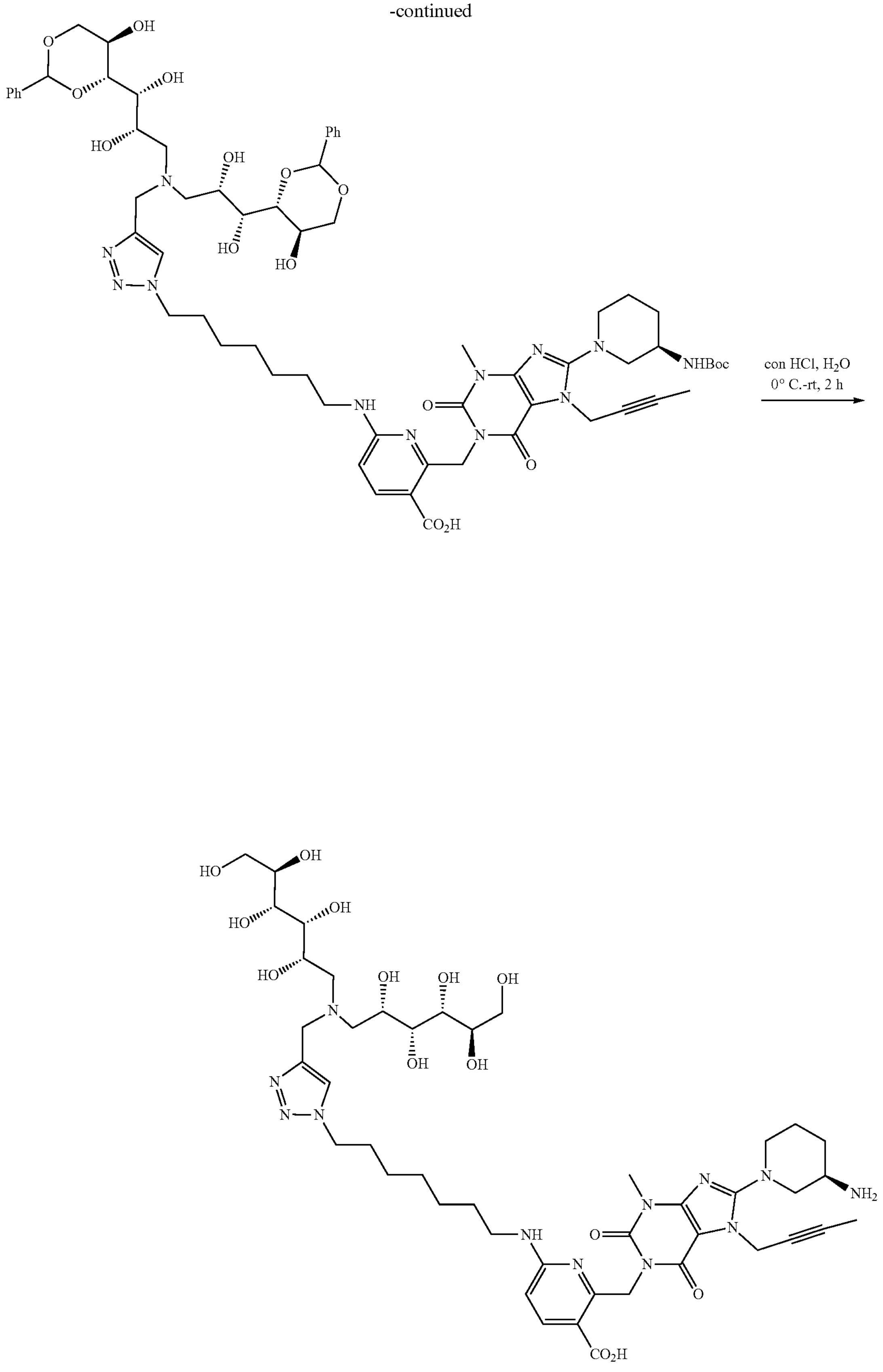

Step 1. 6-((7-(4-((bis((2S,3R)-2,3-dihydroxy-3-((4R,5R)-5-hydroxy-2-phenyl-1,3-dioxan-4-yl)propyl)amino)methyl)-1H-1,2,3-triazol-1-yl)heptyl)amino)-2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)nicotinic acid

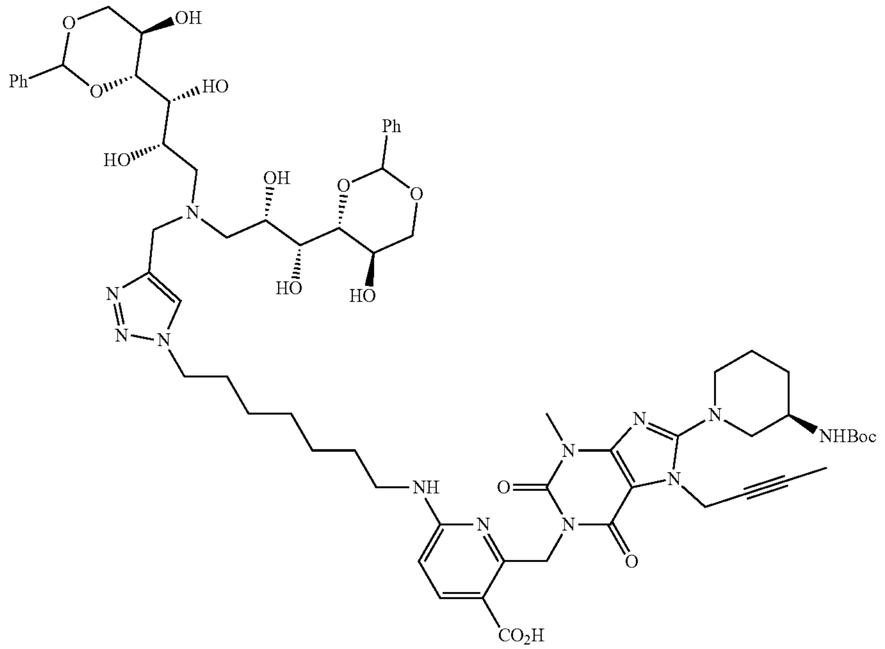

To the solution of compound methyl 6-((7-(4-((bis((2S,3R)-2,3-dihydroxy-3-((4R,5R)-5-hydroxy-2-phenyl-1,3-dioxan-4-yl)propyl)amino)methyl)-1H-1,2,3-triazol-1-yl)heptyl)amino)-2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)nicotinate (0.350 g, 0.27 mmol) in MeOH (5 mL) and $H_2O$ (1 mL) and was added NaOH (0.054 g, 1.35 mmol) and the reaction mixture was stirred at rt for 16 h. After completion of the reaction (LCMS monitoring). The reaction mixture was concentrated under reduced pressure to get a crude mass. The crude compound was washed with $Et_2O$ (50 mL) and dried in vacuo to afford compound 6-((7-(4-((bis((2S,3R)-2,3-dihydroxy-3-((4R,5R)-5-hydroxy-2-phenyl-1,3-dioxan-4-yl)propyl)amino)methyl)-1H-1,2,3-triazol-1-yl)heptyl)amino)-2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)nicotinic acid (0.3 g) as off-white solid. The curded compound take for next step.

Step 2. 2-((8-((R)-3-aminopiperidin-1-yl)-7-(but-2-yn-1-yl)-3-methyl-2,6-dioxo-2,3,6,7-tetrahydro-1H-purin-1-yl)methyl)-6-((7-(4-((bis((2S,3R,4R,5R)-2,3,4,5,6-pentahydroxyhexyl)amino)methyl)-1H-1,2,3-triazol-1-yl)heptyl)amino)nicotinic acid (35)

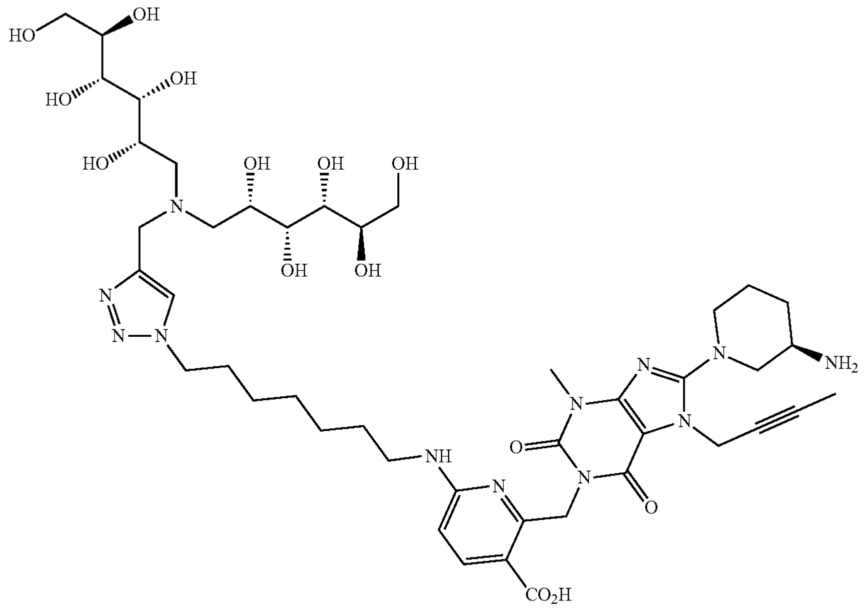 [SMILES: CC#CCn1c(N2CCC[C@@H](N)C2)nc2c1c(=O)n(Cc1nc(NCCCCCCCn3cc(CN(C[C@H](O)[C@@H](O)[C@H](O)[C@H](O)CO)C[C@H](O)[C@@H](O)[C@H](O)[C@H](O)CO)nn3)ccc1C(=O)O)c(=O)n2C]

To the solution of compound 6-((7-(4-((bis((2S,3R)-2,3-dihydroxy-3-((4R,5R)-5-hydroxy-2-phenyl-1,3-dioxan-4-yl)propyl)amino)methyl)-1H-1,2,3-triazol-1-yl)heptyl) amino)-2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)nicotinic acid (0.3 g, 0.24 mmol) in $H_2O$ (10 mL) was added con·HCl (0.6 mL) at 0° C. and the reaction mixture was stirred at room temperature for 2 h. After completion of the reaction (LCMS monitoring), the reaction mixture was concentrated under reduced pressure to get a crude mass. The crude purified by RP prep HPLC to afford compound 2-((8-((R)-3-aminopiperidin-1-yl)-7-(but-2-yn-1-yl)-3-methyl-2,6-dioxo-2,3,6,7-tetrahydro-1H-purin-1-yl)methyl)-6-((7-(4-((bis((2S,3R,4R,5R)-2,3,4,5,6-pentahydroxyhexyl)amino)methyl)-1H-1,2,3-triazol-1-yl)heptyl)amino)nicotinic acid (0.014 g) as off white solid. LC MS M/Z=987.62 (M+1) $^1$H NMR (400 MHz, DMSO) δ 7.93 (s, 1H), 7.79 (d, J=8.6 Hz, 1H), 7.01 (br s, 1H), 6.22 (d, J=8.6 Hz, 1H), 5.31 (s, 2H), 4.59-4.26 (m, 14H), 3.77 (m, 4H), 3.55 (m, 9H), 3.38 (m, 7H), 2.90 (m, 5H), 2.50 (m, 2H), 1.74 (m, 9H), 1.27 (m, 1H), 1.12 (m, 6H), 0.91 (m, 2H).

Example 27. Synthesis of Nonyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate (37)

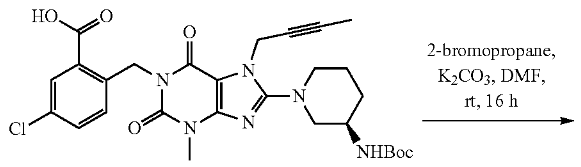

Int-20

-continued

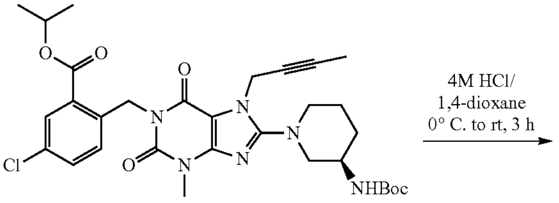

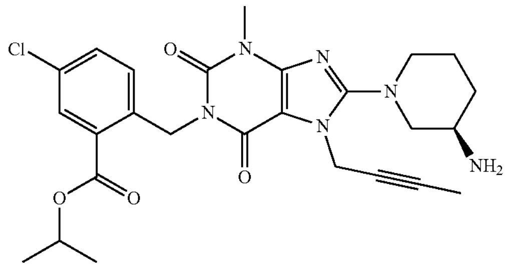

Step 1. Isopropyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl) methyl)-5-chlorobenzoate

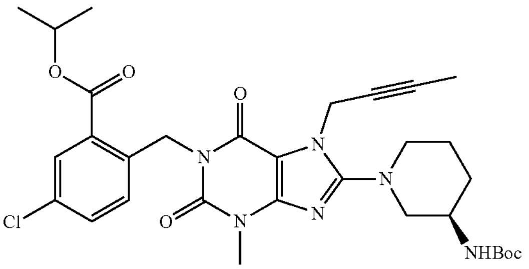 [SMILES: CC#CCn1c(N2CCC[C@@H](NC(=O)OC(C)(C)C)C2)nc2c1c(=O)n(Cc1ccc(Cl)cc1C(=O)OC(C)C)c(=O)n2C]

To a stirred solution of compound (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl) methyl)-5-chlorobenzoic acid (0.5 g, 0.85 mmol) in DMF (5 mL) were added 2-bromopropane (0.15 g, 1.28 mmol) and $K_2CO_3$ (0.35 g, 2.56 mmol) and the reaction mixture was stirred at room temperature for 16 h. After completion of starting material, the reaction mixture was quenched with cold water. The precipitated solid was filtered off, dried under vacuum and washed with diethyl ether to afford 0.4 g of compound isopropyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate as an off-white solid. [TLC system: EtOAc:pet-ether (3:7); $R_f$ value: 0.7].

Step 2. Isopropyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate (37)

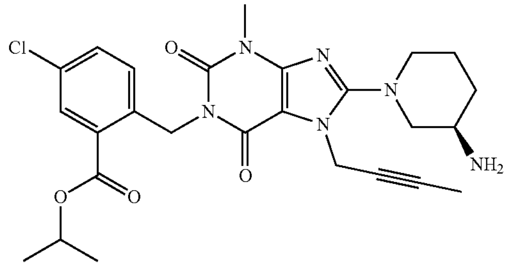 [SMILES: CC#CCn1c(N2CCC[C@@H](N)C2)nc2c1c(=O)n(Cc1ccc(Cl)cc1C(=O)OC(C)C)c(=O)n2C]

To a stirred solution of compound isopropyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate (0.4 g, 0.64 mmol) in 1,4-dioxane (4 mL) was added 4 M HCl in 1,4-dioxane (4 mL) at 0° C. and the reaction mixture was stirred at room temperature for 3 h. After completion of starting material, the reaction mixture was concentrated under reduced pressure to get a crude mass. The crude compound was purified by reverse phase preparative-HPLC to afford 0.19 g of compound isopropyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate as off-white solid. [TLC system: MeOH:DCM (1:9); $R_f$ value: 0.2]. LC MS M/Z=527.49 (M+1) $^1$H NMR (400 MHz, DMSO-$d_6$) δ 7.83 (d, J=2.0 Hz, 1H), 7.54 (dd, J=8.4, 2.0 Hz, 1H), 7.08 (d, J=8.4 Hz, 1H), 5.32 (s, 2H), 5.22-5.16 (m, 1H), 4.88 (s, 2H), 3.66-3.58 (m, 2H), 3.38 (s, 3H), 2.99 (t, J=10.4 Hz, 1H), 2.84-2.72 (m, 2H), 1.87-1.57 (m, 8H), 1.37 (d, J=6.0 Hz, 6H), 1.27-1.26 (m, 1H).

Similarly, hexyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate (38) was synthesized.

Example 28. Synthesis of nonyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate (39)

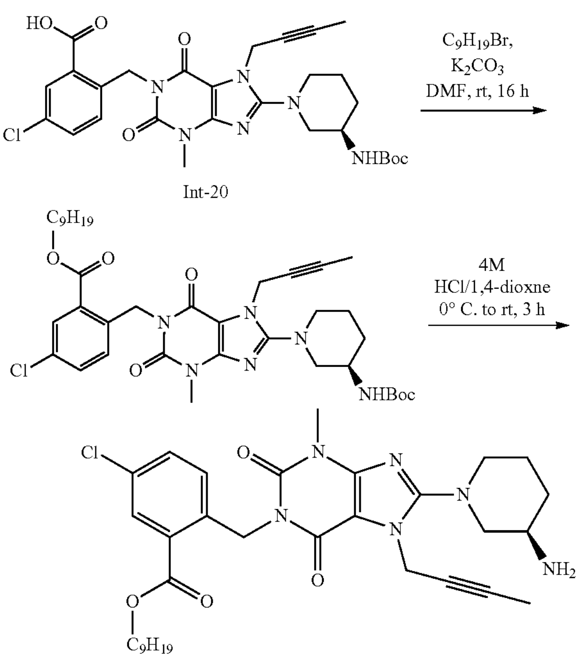

52

Step 1. Nonyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate

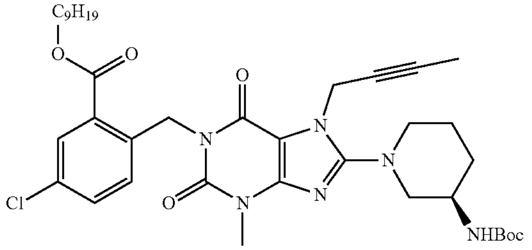

To a stirred solution of (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoic acid (0.35 g, 0.6 mmol) in DMF (3.5 mL) were added 1-bromononane (0.15 g, 0.72 mmol) and K2CO3

(0.25 g, 1.8 mmol) and the reaction mixture was stirred at room temperature for 16 h. After completion of starting material, the reaction mixture was quenched with cold water. The precipitated solid was filtered off, dried under vacuum and washed with diethyl ether to afford 0.25 g of nonyl (R)-2-((7-(but-2-yn-1-yl)-8-(3-((tert-butoxycarbonyl) amino)piperidin-1-yl)-3-methyl-2,6-dioxo-2,3,6,7-tetra-hydro-1H-purin-1-yl)methyl)-5-chlorobenzoate as an off-white solid. [TLC system: EtOAc:pet-ether (1:1); Rf value: 0.7].

Step 2. Nonyl (R)-2-((8-(3-aminopiperidin-1-yl)-7-(but-2-yn-1-yl)-3-methyl-2,6-dioxo-2,3,6,7-tetra-hydro-1H-purin-1-yl)methyl)-5-chlorobenzoate (39)

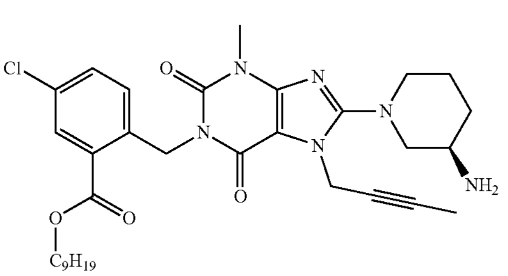

To a stirred solution of nonyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate (0.35 g, 0.49 mmol) in 1,4-dioxane (2 mL) was added 4 M HCl in 1,4-dioxane (2 mL) at 0° C. and the reaction mixture was stirred at room temperature for 3 h. After completion of starting material, the reaction mixture was concentrated under reduced pressure to get a crude mass. The crude compound was purified by reverse phase preparative-HPLC to afford 0.13 g of nonyl (R)-2-((8-(3-aminopiperidin-1-yl)-7-(but-2-yn-1-yl)-3-methyl-2,6-dioxo-2,3,6,7-tetrahydro-1H-purin-1-yl)methyl)-5-chlorobenzoate (39) as a brown solid. [TLC system: MeOH:DCM (1:9); $R_f$ value: 0.3]. LC MS M/Z=611.64 (M+1). $^1$H NMR (400 MHz, DMSO-$d_6$) δ 7.85 (d, J=2.4 Hz, 1H), 7.55 (dd, J=8.4, 2.0 Hz, 1H), 7.08 (d, J=8.4 Hz, 1H), 5.32 (s, 2H), 4.88 (s, 2H), 4.32 (t, J=6.4 Hz, 2H), 3.66-3.58 (m, 2H), 3.37 (s, 3H), 3.01-2.96 (m, 1H), 2.82-2.72 (m, 2H), 1.87-1.60 (m, 10H), 1.41-1.24 (m, 13H), 0.84 (t, J=6.4 Hz, 3H).

Similarly, (R)-2-((8-(3-aminopiperidin-1-yl)-7-(but-2-yn-1-yl)-3-methyl-2,6-dioxo-2,3,6,7-tetrahydro-1H-purin-1-yl) methyl)-5-chloro-N-pentylbenzamide (40) was synthesized.

Example 29. Synthesis of 2-(2-(4-((hexyl(2,3,4,5,6-pentahydroxyhexyl)amino)methyl)-1H-1,2,3-triazol-1-yl)ethoxy)ethyl 2-((8-((R)-3-aminopiperidin-1-yl)-7-(but-2-yn-1-yl)-3-methyl-2,6-dioxo-2,3,6,7-tetrahydro-1H-purin-1-yl)methyl)-5-chlorobenzoate (41)

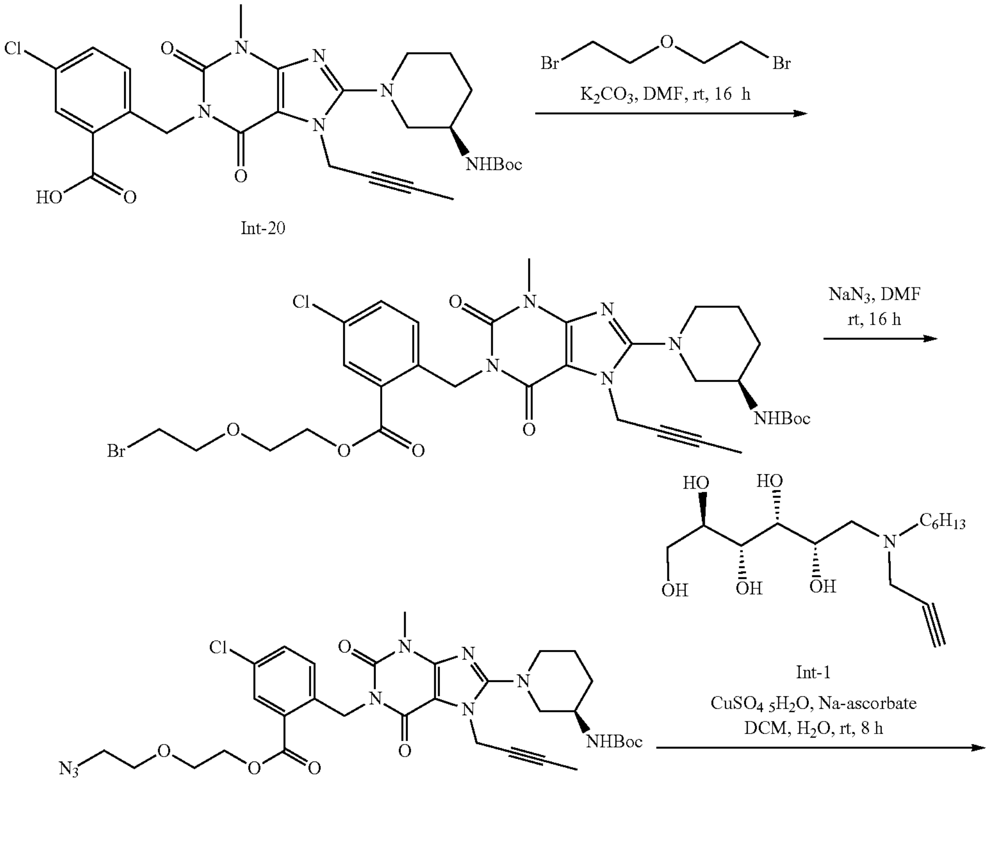

-continued

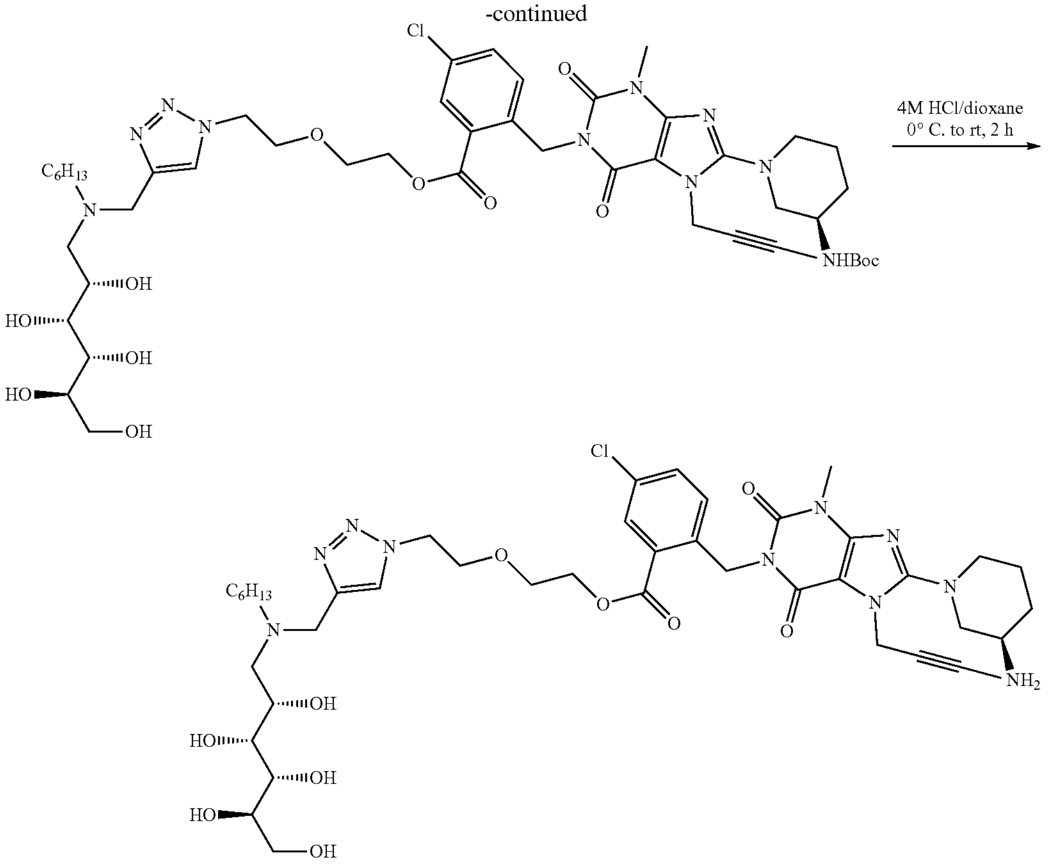

Step 1. 2-(2-bromoethoxy)ethyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate

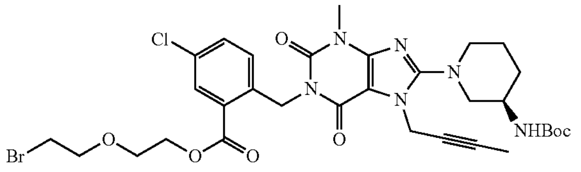 [SMILES: CC#CCn1c(N2CCC[C@@H](NC(=O)OC(C)(C)C)C2)nc2c1c(=O)n(Cc1ccc(Cl)cc1C(=O)OCCOCCBr)c(=O)n2C]

To a stirred solution of (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoic acid (1.0 g, 1.71 mmol) and 1-bromo-2-(2-bromoethoxy)ethane (1.98 g, 8.55 mmol) in DMF (10 mL) was added $K_2CO_3$ (0.71 g, 5.13 mmol) and the reaction mixture was stirred at room temperature for 16 h. After completion of starting material, the reaction mixture was quenched with cold water and the precipitated solid was filtered off, dried under vacuum to get 1.0 g of 2-(2-bromoethoxy)ethyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate as an off-white solid. [TLC system: EtOAc:pet ether (3:7); $R_f$ value: 0.6].

Step 2. 2-(2-azidoethoxy)ethyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate

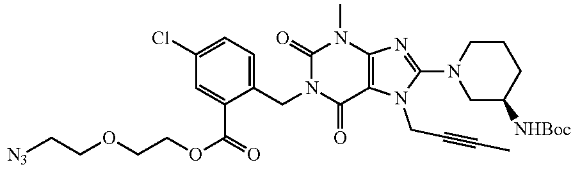 [SMILES: CC#CCn1c(N2CCC[C@@H](NC(=O)OC(C)(C)C)C2)nc2c1c(=O)n(Cc1ccc(Cl)cc1C(=O)OCCOCCN=[N+]=[N-])c(=O)n2C]

To a stirred solution of 2-(2-bromoethoxy)ethyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate (3) (1.0 g, 1.36 mmol) in DMF (10 mL) was added $NaN_3$ (0.44 g, 6.79 mmol) and the reaction mixture was stirred at room temperature for 16 h. After completion of starting material, the reaction mixture was quenched with water and extracted with ethyl acetate (3×25 mL). The combined organic layer was washed with brine solution (100 mL), dried over anhydrous sodium sulfate, filtered and concentrated under reduced pressure to get crude compound. The crude compound was purified by column chromatography (using silica gel 100-200 mesh, 30% ethyl acetate in pet-ether as an eluent) to afford 0.7 g of 2-(2-azidoethoxy)ethyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate as an off-white solid. [TLC system: EtOAc:pet ether (1:1); $R_f$ value: 0.4].

Step 3. 2-(2-(4-((hexyl((2S,3R,4R,5R)-2,3,4,5,6-pentahydroxyhexyl)amino)methyl)-1H-1,2,3-triazol-1-yl)ethoxy)ethyl 2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)-5-chlorobenzoate

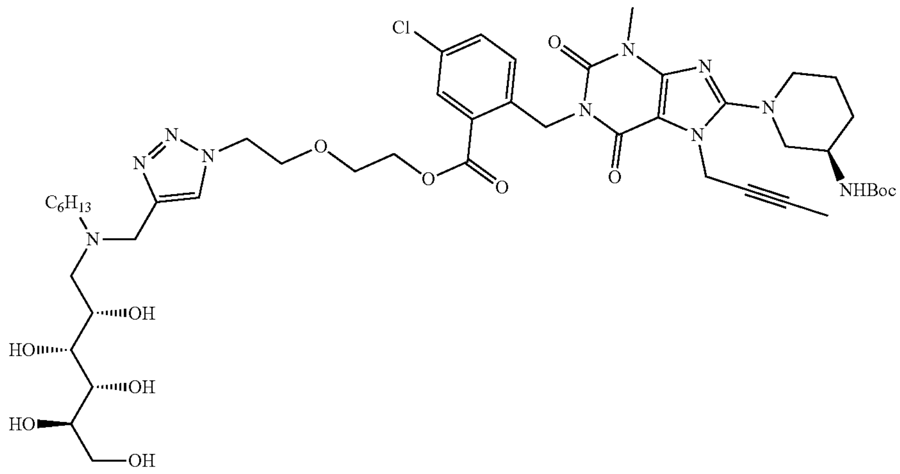

To a stirred solution of 2-(2-azidoethoxy)ethyl (R)-2-((7-(but-2-yn-1-yl)-8-(3-((tert-butoxycarbonyl)amino)piperidin-1-yl)-3-methyl-2,6-dioxo-2,3,6,7-tetrahydro-1H-purin-1-yl)methyl)-5-chlorobenzoate (0.3 g, 0.43 mmol) and (2R,3R,4R,5S)-6-(hexyl(prop-2-yn-1-yl)amino)hexane-1,2,3,4,5-pentaol 5 (0.26 g, 0.86 mmol) in a mixture of DCM and water (6 mL, 1:1) were added CuSO4·5$H_2$O (0.13 g, 0.52 mmol) and Sodium ascorbate (0.13 g, 0.65 mmol). The reaction mixture was stirred at room temperature for 8 h. After completion of starting material, the reaction mixture was quenched with water and extracted with DCM (3×20 mL). The combined organic layer was dried over anhydrous sodium sulfate, filtered and concentrated under reduced pressure to furnish 0.45 g of crude 2-(2-(4-((hexyl((2S,3R,4R,5R)-2,3,4,5,6-pentahydroxyhexyl)amino)methyl)-1H-1,2,3-triazol-1-yl)ethoxy)ethyl 2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)-5-chlorobenzoate as yellow color solid. [TLC system: MeOH: DCM (1:9); Rf value: 0.5]. This crude compound was used in the next step without any further purification.

Step 4. 2-(2-(4-((hexyl(2,3,4,5,6-pentahydroxyhexyl)amino)methyl)-1H-1,2,3-triazol-1-yl)ethoxy)ethyl 2-((8-((R)-3-aminopiperidin-1-yl)-7-(but-2-yn-1-yl)-3-methyl-2,6-dioxo-2,3,6,7-tetrahydro-1H-purin-1-yl)methyl)-5-chlorobenzoate (41)

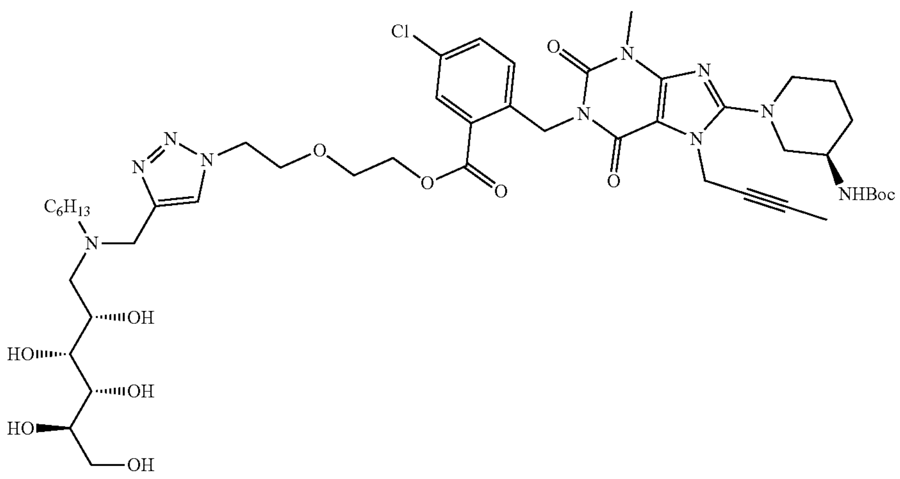

To a stirred solution of 2-(2-(4-((hexyl((2S,3R,4R,5R)-2,3,4,5,6-pentahydroxyhexyl)amino)methyl)-1H-1,2,3-triazol-1-yl)ethoxy)ethyl 2-((7-(but-2-yn-1-yl)-8-((R)-3-((tert-butoxycarbonyl)amino)piperidin-1-yl)-3-methyl-2,6-dioxo-2,3,6,7-tetrahydro-1H-purin-1-yl)methyl)-5-chlorobenzoate (0.45 g, 0.45 mmol) in 1,4-dioxane (4.5 mL) was added 4 M HCl in 1,4-dioxane (1 mL) dropwise at 0° C. and the reaction mixture was stirred at room temperature for 2 h. After completion of starting material, the reaction mixture was concentrated under reduced pressure to get crude compound. The crude compound was purified by reverse phase preparative-HPLC to afford 0.1 g of compound 41 (HCl salt) as an off-white solid. [TLC system: MeOH:DCM (1:9); $R_f$ value: 0.2]. LC MS M/Z=901.25 (M+H). $^1$H NMR (400 MHz, DMSO-$d_6$) δ 9.5 (s, 1H), 8.31 (d, J=7.6 Hz, 1H), 8.23 (s, 3H), 7.84 (s, 1H), 7.57 (dd, J=8.4, 2.0 Hz, 1H), 7.08 (d, J=8.4 Hz, 1H), 5.33 (s, 3H), 5.01-4.87 (m, 2H), 4.63 (s, 2H), 4.41 (s, 4H), 4.12-4.03 (m, 1H), 3.93-3.91 (m, 2H), 3.79 (m, 2H), 3.74-3.60 (m, 3H), 3.39 (m, 8H), 3.20-3.17 (m, 4H), 2.99-2.98 (m, 2H), 2.02-1.91 (m, 2H), 1.78-1.63 (m, 7H), 1.25 (s, 6H), 0.86 (s, 3H).

Example 30. Synthesis of 2-(2-(2-azidoethoxy)ethoxy)ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (42)

To a solution of compound 2-(2-(2-azidoethoxy)ethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.4 g, 0.565 mmol) in DCM (10 mL) was added 4 M HCl in 1,4-dioxane at 0° C. Then reaction was stirred at RT for 3 h. After completion of reaction, reaction mixture was concentrated and residue was basified with saturated $NaHCO_3$ solution and extracted with EtOAc (20 mL×2) and dried over anhydrous sodium sulfate and evaporated to get crude which was purified by column chromatography over silica gel (Davisil) (using 0-8% MeOH in DCM as an eluent) to afford 30 mg of 2-(2-(2-azidoethoxy)ethoxy)ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate as pale brown gum. [TLC system: MeOH:DCM (1:9); $R_f$ value: 0.5]. LC MS M/Z=608.64 (M+1). $^1$H NMR (400 MHz, DMSO-$d_6$) δ 7.45-7.43 (m, 2H), 4.96-4.93 (m, 2H), 4.37-4.36 (m, 2H), 4.25-4.11 (m, 2H), 3.94-3.93 (m, 2H), 3.75-3.71 (m, 2H), 3.60-3.58 (m, 6H), 3.37-3.34 (m, 2H), 3.31 (m, 1H), 2.73-2.58 (m, 2H), 2.51-2.49 (m, 2H), 1.80 (bs, 2H).

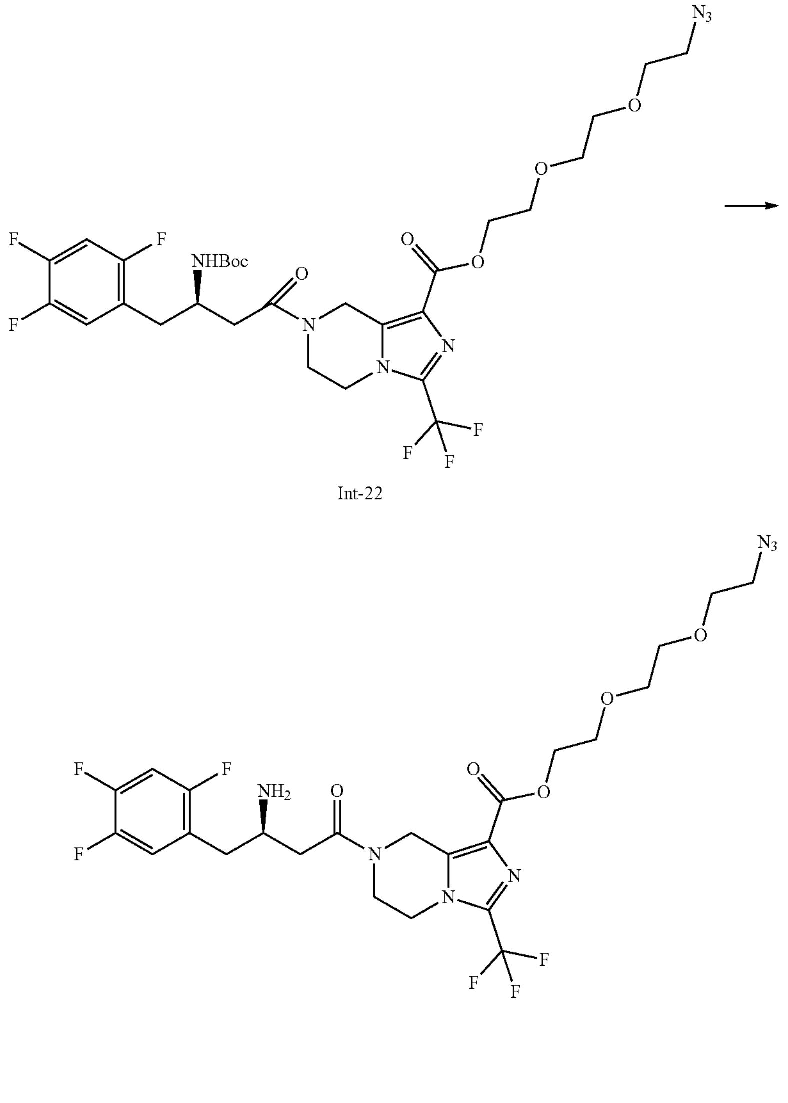

Int-22

Example 31. Synthesis of 2-(2-(2-(4-((((2S,3R,4R,5R)-2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate(44)
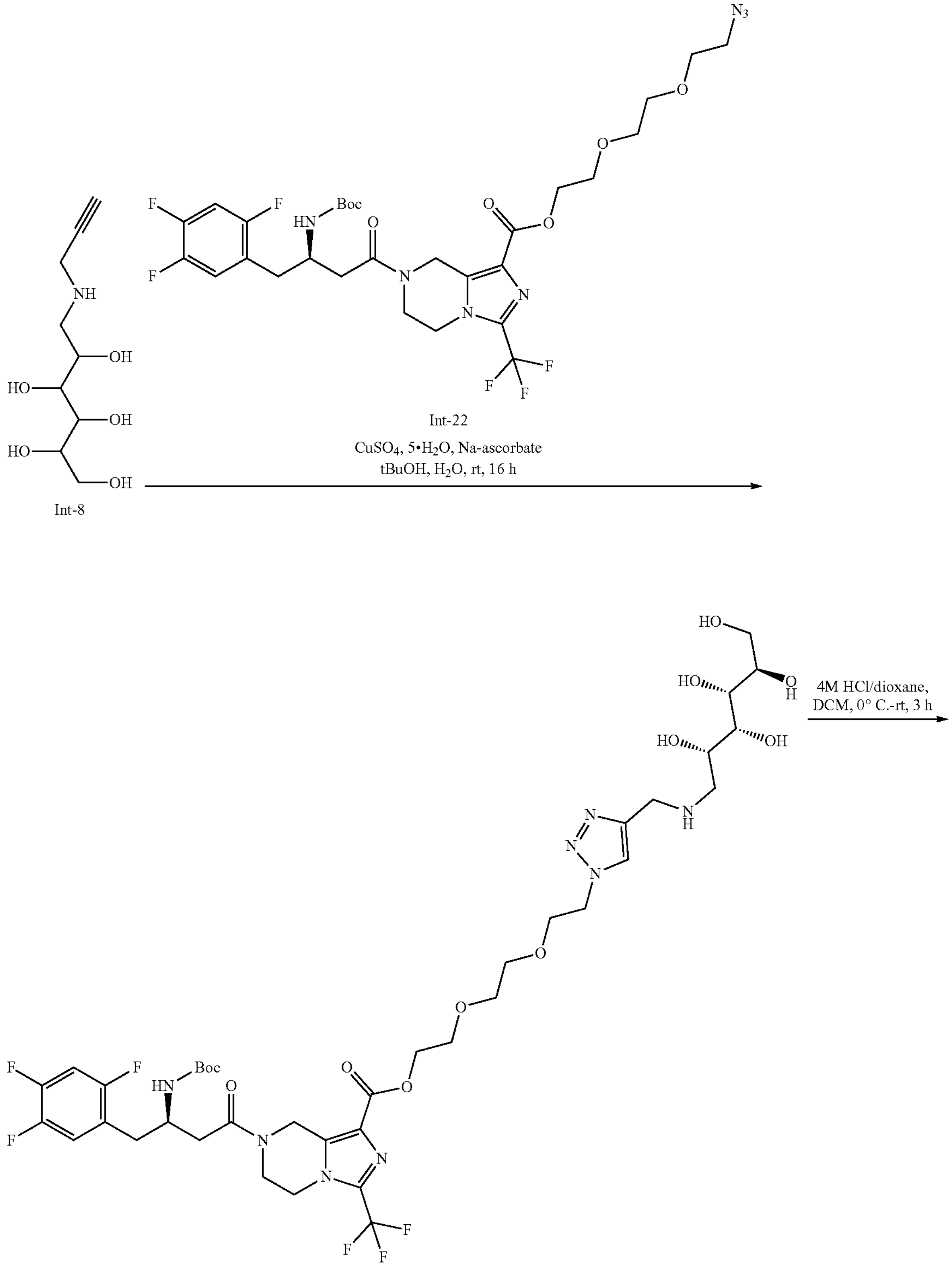 [SMILES: C#CCNCC(O)C(O)C(O)C(O)CO ; CC(C)(C)OC(=O)N[C@@H](CC(=O)N1CCn2c(C(F)(F)F)nc(C(=O)OCCOCCOCCN=[N+]=[N-])c2C1)Cc1cc(F)c(F)cc1F ; CC(C)(C)OC(=O)N[C@@H](CC(=O)N1CCn2c(C(F)(F)F)nc(C(=O)OCCOCCOCCn3cc(CNC[C@H](O)[C@@H](O)[C@H](O)[C@H](O)CO)nn3)c2C1)Cc1cc(F)c(F)cc1F]

-continued
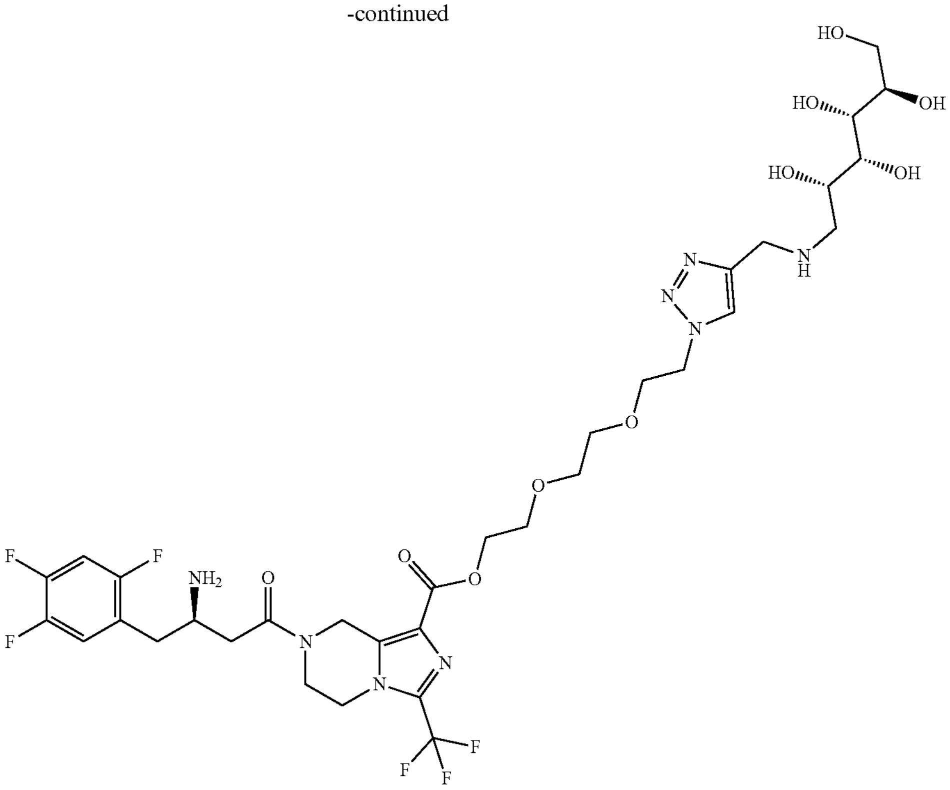
Step 1. 2-(2-(2-(4-((((2S,3R,4R,5R)-2,3,4,5,6-pentahydroxyhexyl)amino)methyl)-1H-1,2,3-triazol-1-yl)ethoxy)ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate
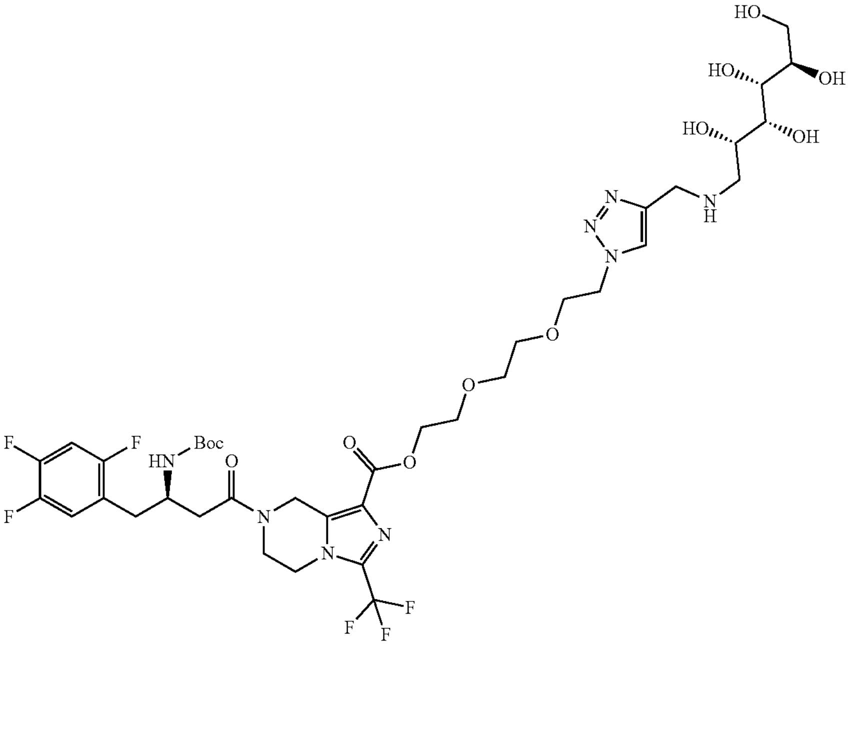 [SMILES: CC(C)(C)OC(=O)N[C@@H](CC(=O)N1CCn2c(C(F)(F)F)nc(C(=O)OCCOCCOCCn3cc(CNC[C@H](O)[C@@H](O)[C@H](O)[C@H](O)CO)nn3)c2C1)Cc1cc(F)c(F)cc1F]

To a stirred solution of compound 2-(2-(2-azidoethoxy)ethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.6 g, 0.847 mmol) and compound 6-(prop-2-yn-1-ylamino)hexane-1,2,3,4,5-pentaol (0.371 g, 1.695 mmol) in t-BuOH (5 mL) and water (1 mL) was added $CuSO_4$, $5{\cdot}H_2O$ (0.254 g, 1.017 mmol) and Na-ascorbate (0.251 g, 1.271 mmol). The resulting mixture was stirred at RT for 16 h. After completion of reaction, reaction mixture was filtered. The filtrate was concentrated under reduced pressure to get crude compound. The crude compound was purified by RP-Prep-HPLC to afford 60 mg of compound 2-(2-(2-(4-((((2S,3R,4R,5R)-2,3,4,5,6-pentahydroxyhexyl)amino)methyl)-1H-1,2,3-triazol-1-yl)ethoxy)ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate as brown sticky solid.

Prep-HPLC Method of Purification

Column/dimensions: X-bridge phenyl (19*250*5μ)
Mobile phase A: 10 Mm Ammonium Bicarbonate in water
Mobile phase B: Acetonitrile
Gradient (Time/% B): 0/10, 1/10, 27/75, 27.10/95, 29.10/95, 31.20/10, 35/10
Flow rate: 18 ml/min. Solubility: ACN+WATER Step 2. 2-(2-(2-(4-((((2S,3R,4R,5R)-2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (44)

To a solution of compound 2-(2-(2-(4-((((2S,3R,4R,5R)-2,3,4,5,6-pentahydroxyhexyl)amino)methyl)-1H-1,2,3-triazol-1-yl)ethoxy)ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.060 g, 0.064 mmol) in DCM (1 mL) was added 4 M HCl in 1,4-dioxane (0.6 mL). The reaction mixture was stirred at RT for 3 h. After completion of reaction, reaction mixture was filtered and concentrated to get crude compound. The crude compound was purified by RP-Prep-HPLC to afford 0.0157 g of 2-(2-(2-(4-((((2S,3R,4R,5R)-2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate as an off white solid. LC MS M/Z=827.41 (M+1) $^1H$ NMR (400 MHz, DMSO-$d_6$) δ 7.89 (s, 1H), 7.45-7.41 (m, 2H), 5.10-4.85 (m, 3H), 4.60-4.10 (m, 10H), 4.00-3.30 (m, 20H), 3.10-3.05 (m, 1H), 2.71-2.50 (m, 5H), 2.10-1.40 (m, 2H).

Prep-HPLC Method of Purification

Column/dimensions: X BRIDGE C18 (19 mm*250 mm*5μ)
Mobile phase A: 10 mM ABC IN WATER
Mobile phase B: Acetonitrile
Gradient (Time/% B): 0/10, 1/10, 18/44, 18.10/95, 20.10/95, 20.20/10, 22/10

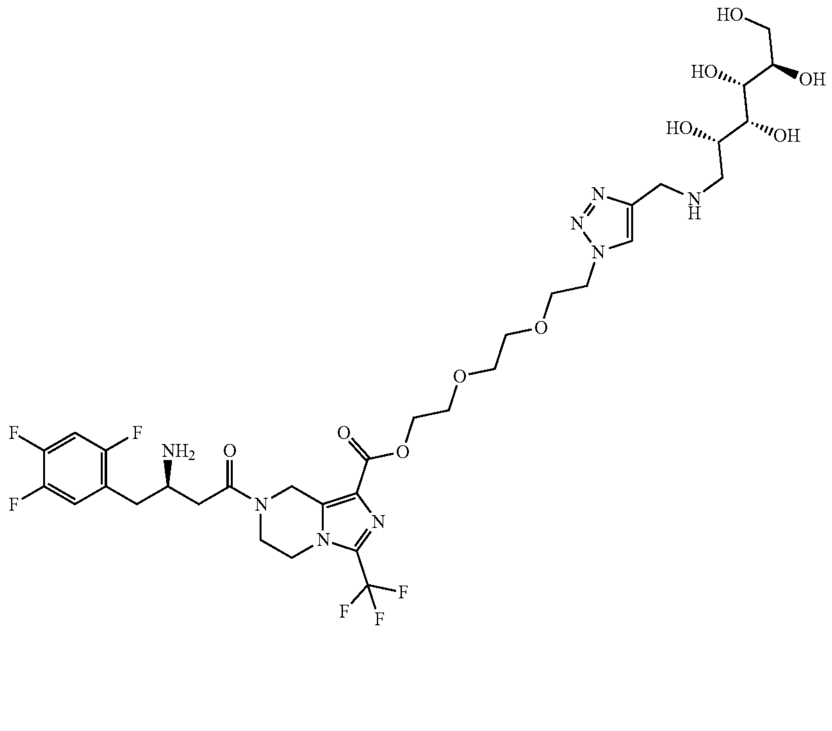

Example 32. Synthesis of 2-(2-(2-(4-((ethyl((2S,3R,4R,5R)-2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (45)
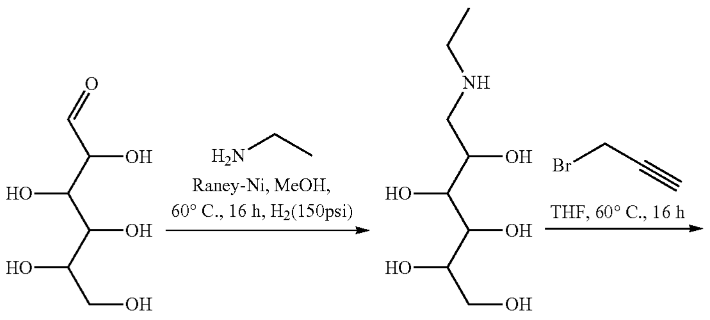
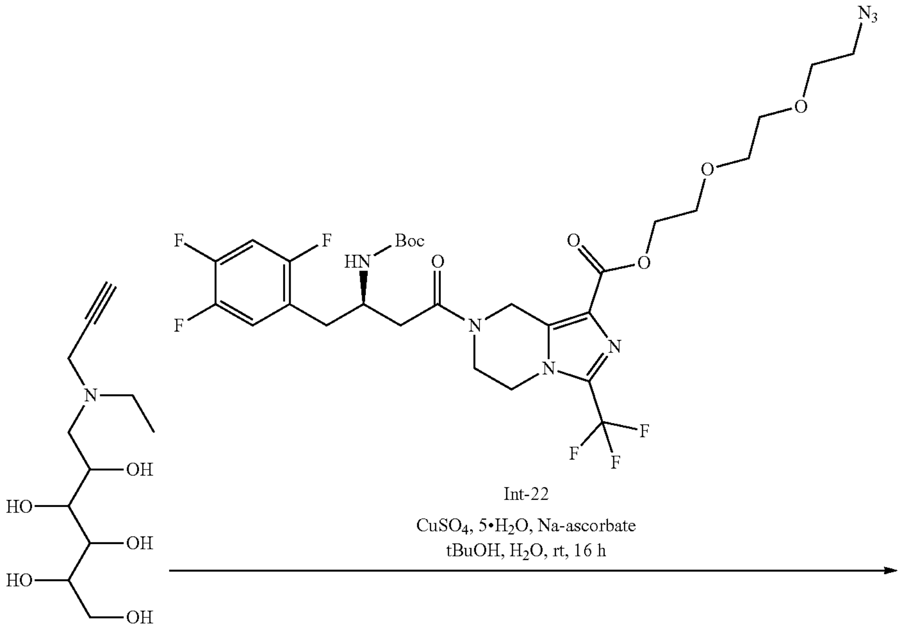

-continued
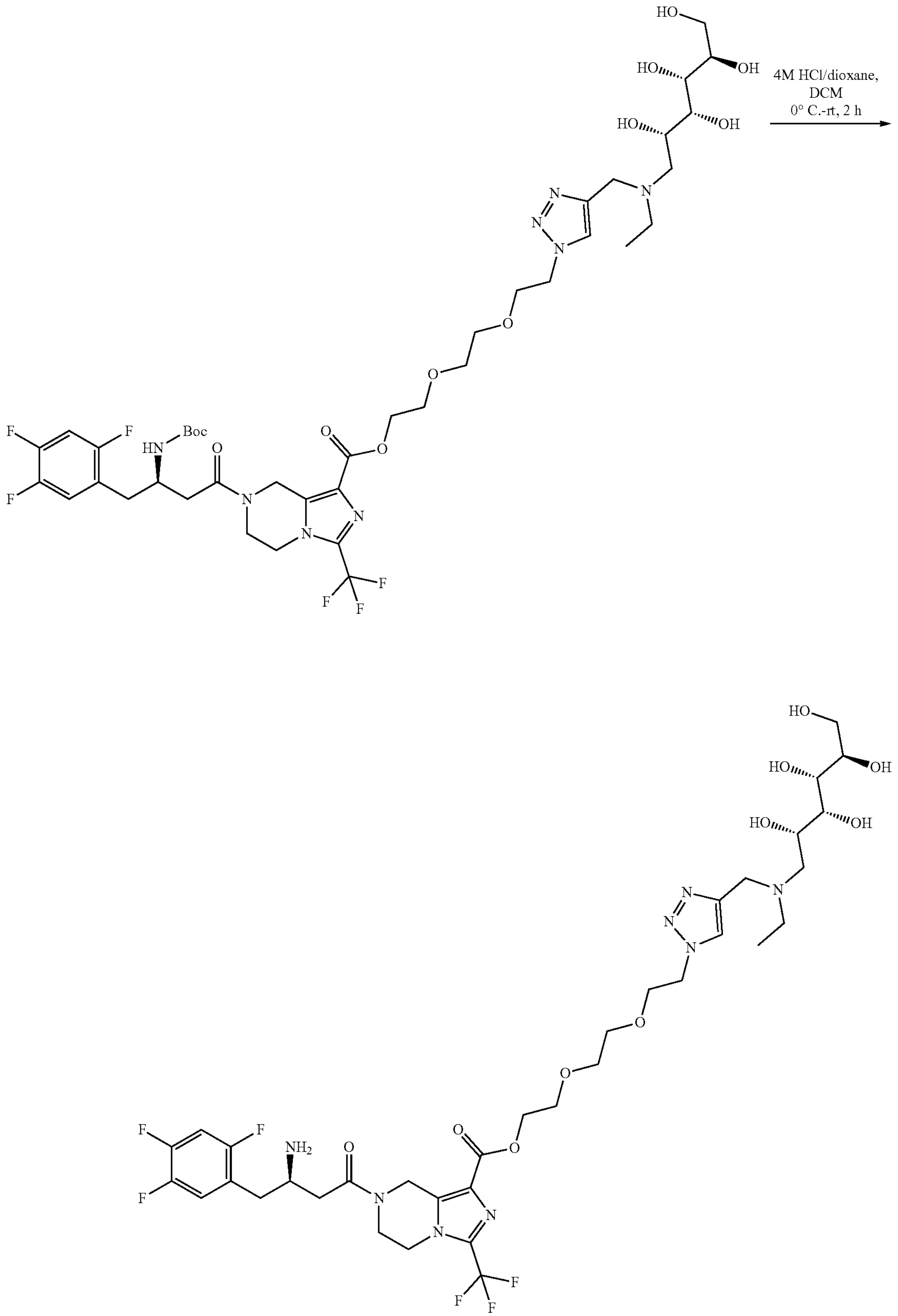

Step 1. 6-(ethylamino)hexane-1,2,3,4,5-pentaol

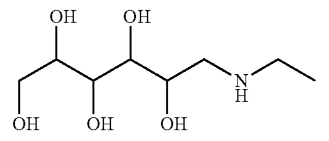

To a solution of compound 2,3,4,5,6-pentahydroxyhexanal (5.0 g, 27.75 mmol) and compound ethanamine (20.8 mL, 41.62 mmol) in MeOH (30 mL) was added Raney-Ni (5.0 g). The reaction mixture was stirred at 60° C. under $H_2$ atmosphere (150 psi) for 16 h. After completion of reaction, reaction mixture was filtered through celite-bed and filtrate was concentrated to get 5.0 g compound 6-(ethylamino)hexane-1,2,3,4,5-pentaol (crude) as off white solid which was used for next step without purification.

Step 2. 6-(ethyl(prop-2-yn-1-yl)amino)hexane-1,2,3,4,5-pentaol

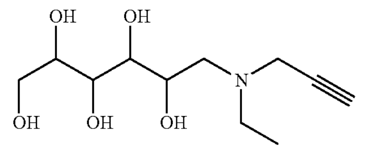 [SMILES: C#CCN(CC)CC(O)C(O)C(O)C(O)CO]

To a solution of compound 6-(ethylamino)hexane-1,2,3,4,5-pentaol (2.0 g, 9.563 mmol), compound 3-bromoprop-1-yne (0.85 mL, 11.47 mmol) in THF (30 mL) was added and the reaction mixture was heated at 60° C. for 16 h. After completion of reaction, reaction mixture was filtered and filtrate was concentrated to get 0.450 g compound 6-(ethyl(prop-2-yn-1-yl)amino)hexane-1,2,3,4,5-pentaol as brown sticky compound which was used for next step without purification.

Step 3. 2-(2-(2-(4-((ethyl((2S,3R,4R,5R)-2,3,4,5,6-pentahydroxyhexyl)amino)methyl)-1H-1,2,3-triazol-1-yl)ethoxy)ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate

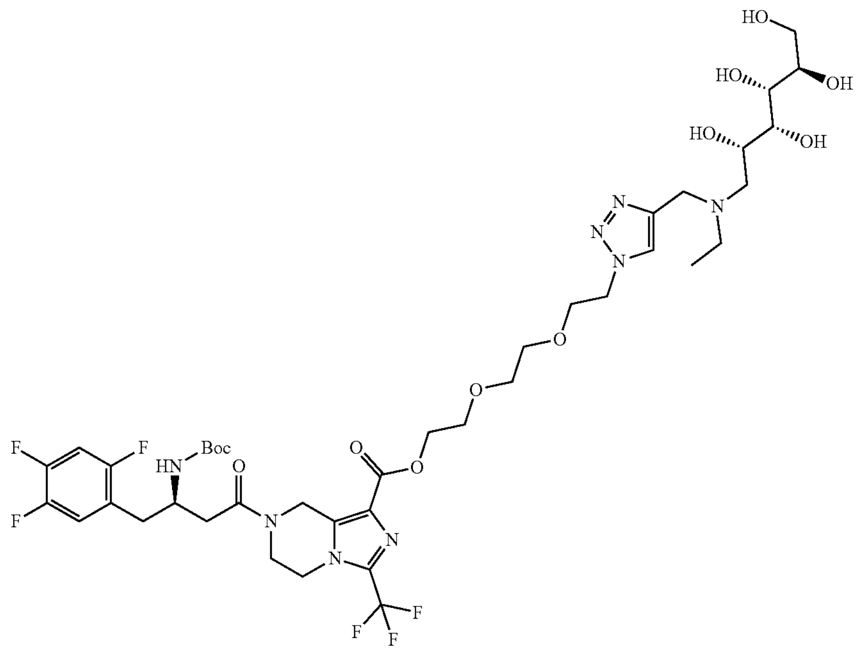 [SMILES: CCN(Cc1cn(CCOCCOCCOC(=O)c2nc(C(F)(F)F)n3c2CN(C(=O)C[C@@H](Cc2cc(F)c(F)cc2F)NC(=O)OC(C)(C)C)CC3)nn1)C[C@H](O)[C@@H](O)[C@H](O)[C@H](O)CO]

To a solution of compound 2-(2-(2-azidoethoxy)ethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.6 g, 0.847 mmol) and compound 6-(ethyl(prop-2-yn-1-yl)amino)hexane-1,2,3,4,5-pentaol (0.420 g, 169 mmol) in t-BuOH (10 mL) and water (2 mL) was added $CuSO_4$, $5{\cdot}H_2O$ (0.254 g, 1.017 mmol) and Na-ascorbate (0.251 g, 1.271 mmol). The resultant reaction mixture was stirred at RT for 16 h. After completion of reaction, reaction mixture was filtered and concentrated to get crude compound. The crude compound was purified by Prep-HPLC to afford 0.240 g of compound 2-(2-(2-(4-((ethyl((2S,3R,4R,5R)-2,3,4,5,6-pentahydroxyhexyl)amino)methyl)-1H-1,2,3-triazol-1-yl)ethoxy)ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate as brown sticky compound.

Prep-HPLC Method

Column/dimensions: X BRIDGE C8 (19*250*5 um)
Mobile phase A: 10 MM ABC IN WATER
Mobile phase B: Acetonitrile (org)
Gradient (Time/% B): 0/20, 1/20, 9/50, 14/50, 14.1/98, 18/98, 18.1/20, 21/20
Flow rate: 17 ml/min, Solubility: Acetonitrile+THF+WATER Step 4. 2-(2-(2-(4-((ethyl((2S,3R,4R,5R)-2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (45)

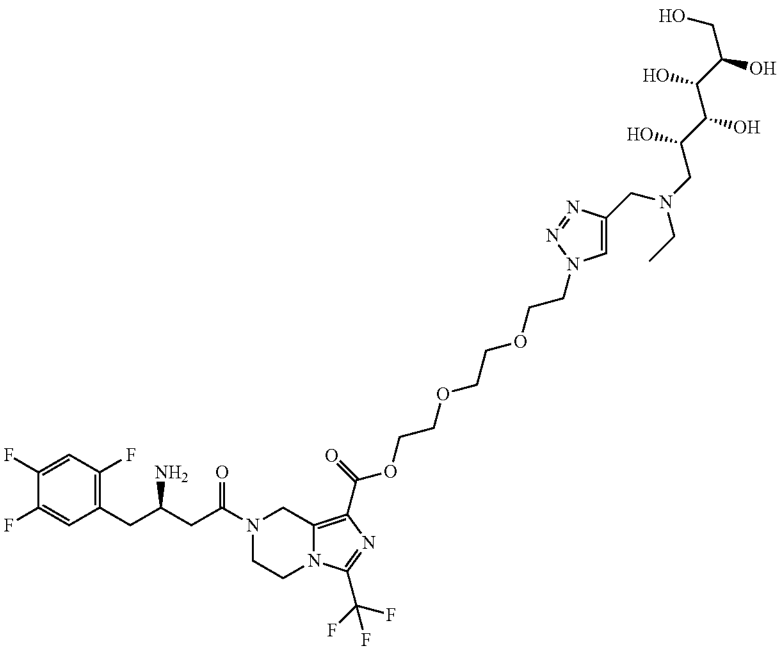 [SMILES: CCN(Cc1cn(CCOCCOCCOC(=O)c2nc(C(F)(F)F)n3c2CN(C(=O)C[C@H](N)Cc2cc(F)c(F)cc2F)CC3)nn1)C[C@H](O)[C@@H](O)[C@H](O)[C@H](O)CO]

To a solution of compound 2-(2-(2-(4-((ethyl((2S,3R,4R,5R)-2,3,4,5,6-pentahydroxyhexyl)amino)methyl)-1H-1,2,3-triazol-1-yl)ethoxy)ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.240 g, 0.280 mmol) in DCM (3 mL) was added 4 M HCl in 1,4-dioxane (2.4 mL). The reaction mixture was stirred at RT for 2 h. After completion of reaction, reaction mixture was filtered and concentrated under reduced pressure to afford crude compound. The crude compound was purified by trituration using diethyl ether to afford 175 mg of 2-(2-(2-(4-((ethyl((2S,3R,4R,5R)-2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate as off white solid. LC MS M/Z=855.65 (M+1) $^{1}$H NMR (400 MHz, DMSO-$d_6$) δ 9.55 (s, 1H), 8.29 (d, J=5.8 Hz, 1H), 8.10-8.00 (m, 3H), 7.58 (q, J=9.0 Hz, 2H), 5.49 (s, 1H), 4.95-4.93 (m, 3H), 4.57-3.38 (m, 28H), 3.18-2.66 (m, 8H), 1.31-1.26 (m, 3H).

Example 33. Synthesis of 2-(2-(2-(4-((hexyl(2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (46)

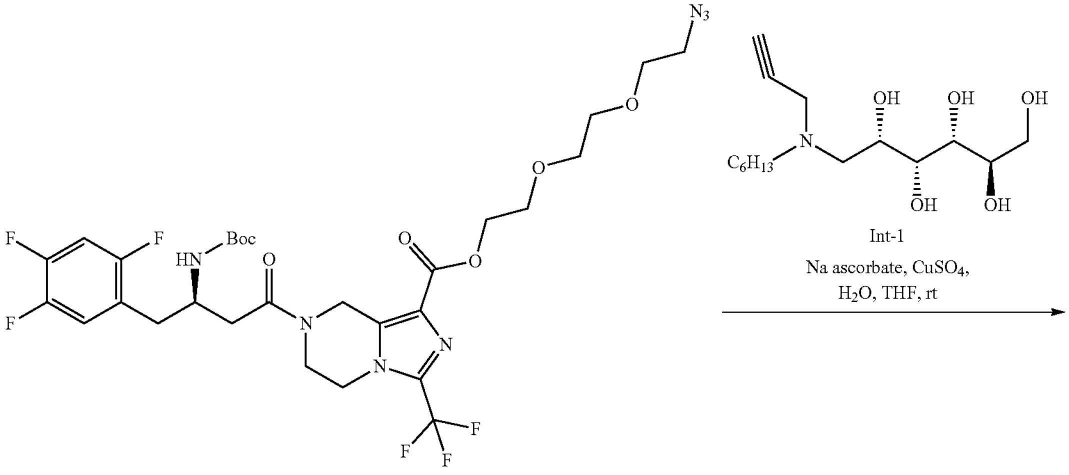

Int-22

-continued
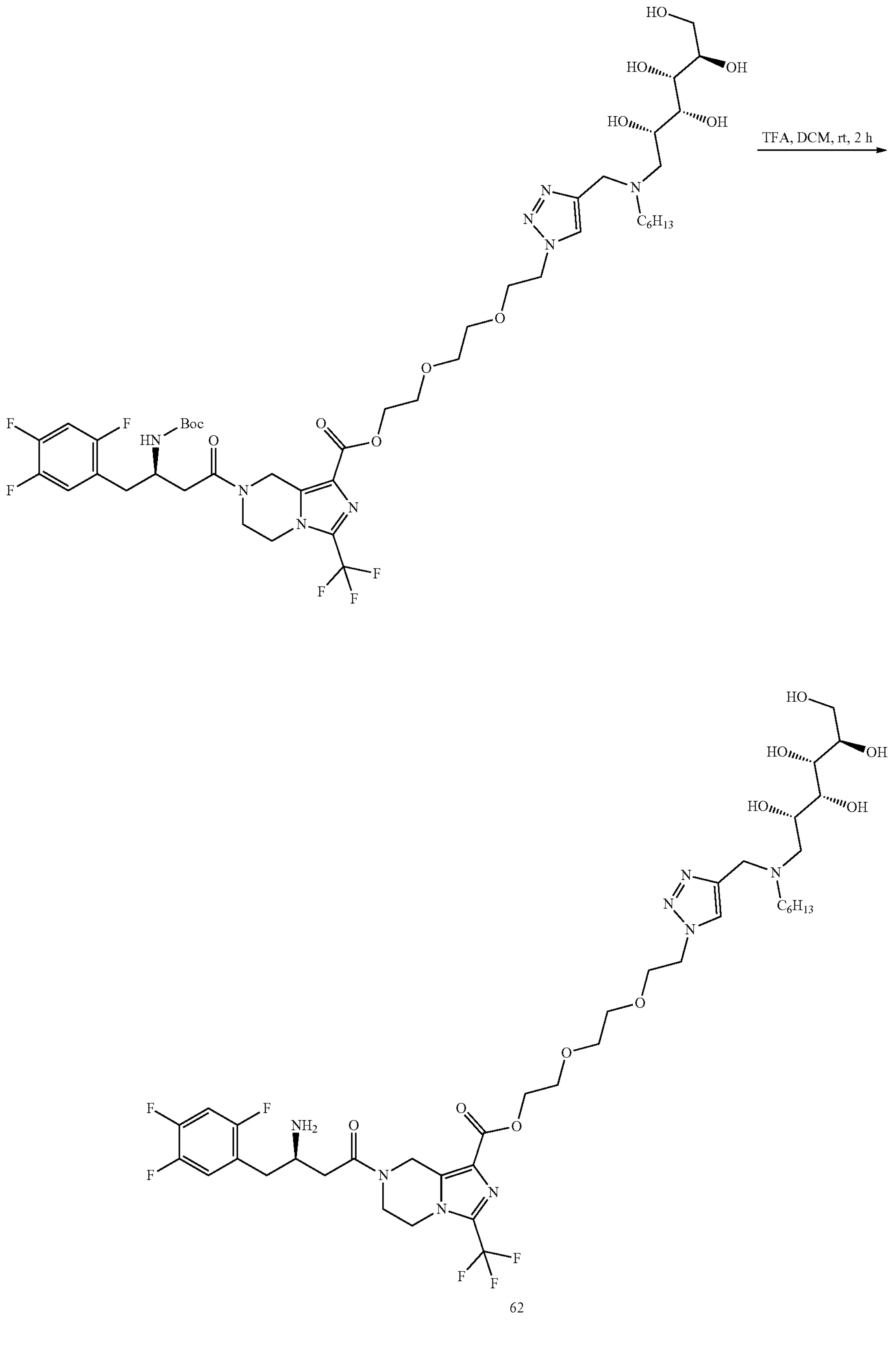
62

Step 1. 2-(2-(2-(4-((hexyl(2,3,4,5,6-pentahydroxy-hexyl)amino)methyl)-1H-1,2,3-triazol-1-yl)ethoxy) ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a] pyrazine-1-carboxylate

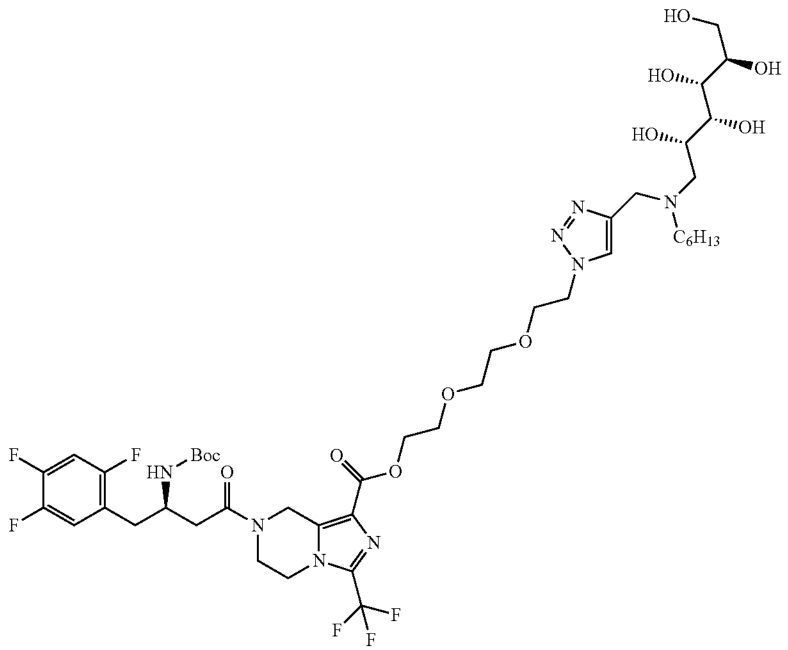

To a solution of 2-(2-(2-azidoethoxy)ethoxy)ethyl (R)-7-(3-((tert-butoxycarbonyl)amino)-4-(2,4,5-trifluorophenyl) butanoyl)-3-(trifluoromethyl)-5,6,7,8-tetrahydroimidazo[1,5-a]pyrazine-1-carboxylate (460 mg, 0.65 mmol) in THF (3 mL) was added 2R,3R,4R,5S)-6-(hexyl(prop-2-yn-1-yl) amino)hexane-1,2,3,4,5-pentaol (prepared in Example 9 step 4) (295 mg, 0.97 mmol), Na ascorbate (193 mg, 0.97 mmol), CuSO4·5$H_2O$ (242.5 mg, 0.97 mmol) and $H_2O$ (2 mL). The mixture was stirred at room temperature for 19 h. The reaction mixture was filtered and the filtrate was purified by Prep-HPLC (Gemini-C18 150×21.2 mm, 5 um, mobile phase: ACN (0.1% FA)-$H_2O$ (0.1% FA), gradient: 20~70%) to give 2-(2-(2-(4-((hexyl(2,3,4,5,6-pentahydroxyhexyl)amino)methyl)-1H-1,2,3-triazol-1-yl)ethoxy) ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (140 mg, 21.2%) as a yellow solid. MS (ESI): mass calcd. for $C_{44}H_{64}F_6N_8O_{12}$ 1010.45, m/z found 1011 [M+1].

Step 2. 2-(2-(2-(4-((hexyl(2,3,4,5,6-pentahydroxy-hexyl)amino)methyl)-1H-1,2,3-triazol-1-yl)ethoxy) ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (46)

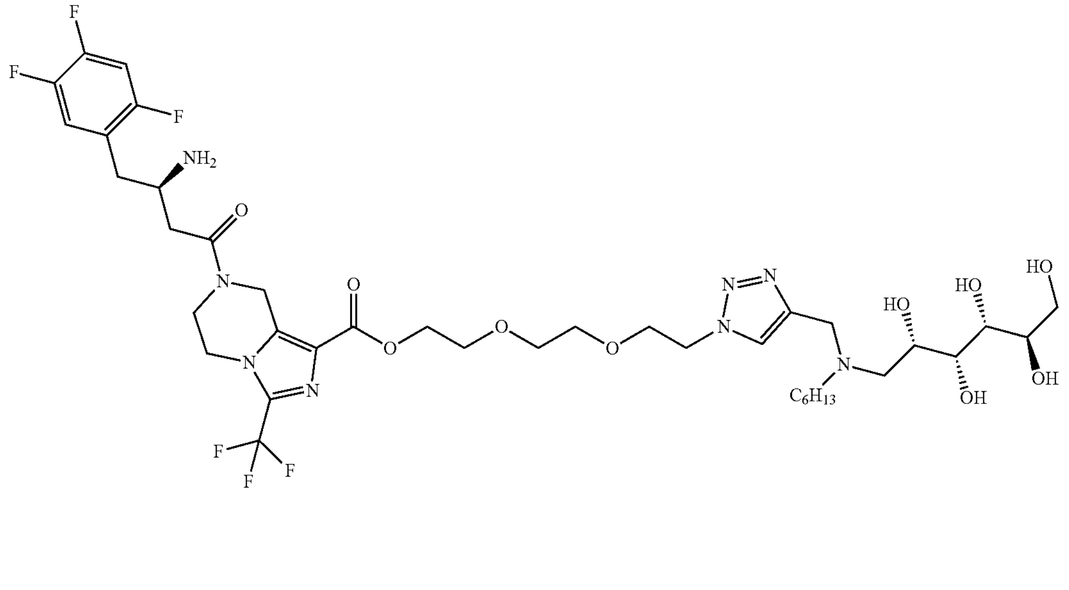

To a 2-(2-(2-(4-((hexyl(2,3,4,5,6-pentahydroxyhexyl)amino)methyl)-1H-1,2,3-triazol-1-yl)ethoxy)ethoxy)ethyl 7-((R)-3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate in DCM (5 mL) was added TFA (0.5 mL). The mixture was stirred at room temperature for 2 h. The reaction mixture was concentrated under pressure at 40° C. and the residue was purified by Prep-HPLC (Gemini-C18 150×21.2 mm, 5 um, mobile phase: ACN (0.1% TFA)-$H_2O$ (0.1% TFA), gradient: 20-70%) to give 2-(2-(2-(4-((hexyl(2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (65.4 mg, 51.8%) as a yellow solid. MS (ESI): mass calcd. for Chemical Formula: $C_{39}H_{56}F_6N_8O_{10}$ 910.40, m/z found 911.4 [M+1]. $^1$H NMR (400 MHz, MeOD) δ 8.28 (s, 1H), 7.36 (m, 1H), 7.27-7.17 (m, 1H), 5.07 (m, 1H), 4.99 (m, 1H), 4.58 (m, 4H), 4.45 (m, 2H), 4.29 (m, 4H), 4.11-3.94 (m, 2H), 3.92-3.87 (m, 3H), 3.77 (m, 4H), 3.64 (m, 7H), 3.27-3.03 (m, 5H), 3.00-2.92 (m, 1H), 2.84 (m, 1H), 1.83 (s, 2H), 1.36 (s, 6H), 0.91 (t, J=6.5 Hz, 3H).

An alternative synthesis of compound (46) is described below.

Synthesis of 2-(2-(2-(4-((hexyl(2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate Tartrate Salt (46 salt)

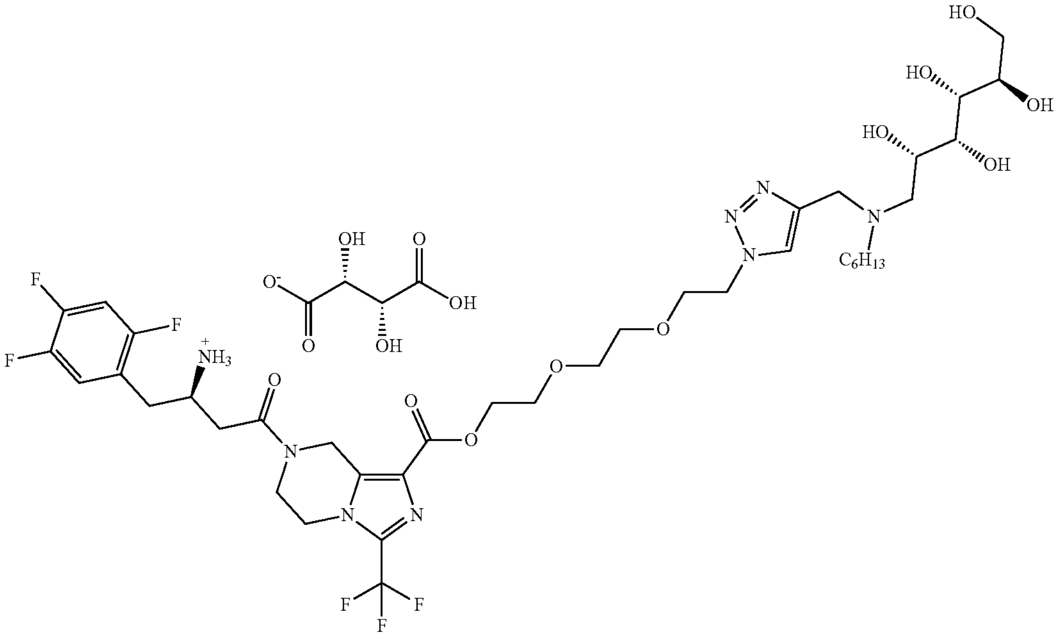

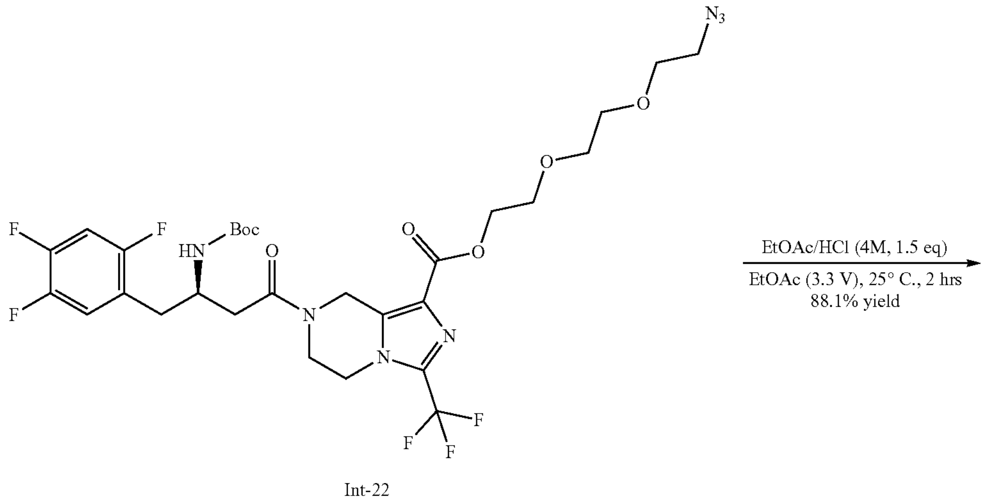

Int-22

-continued
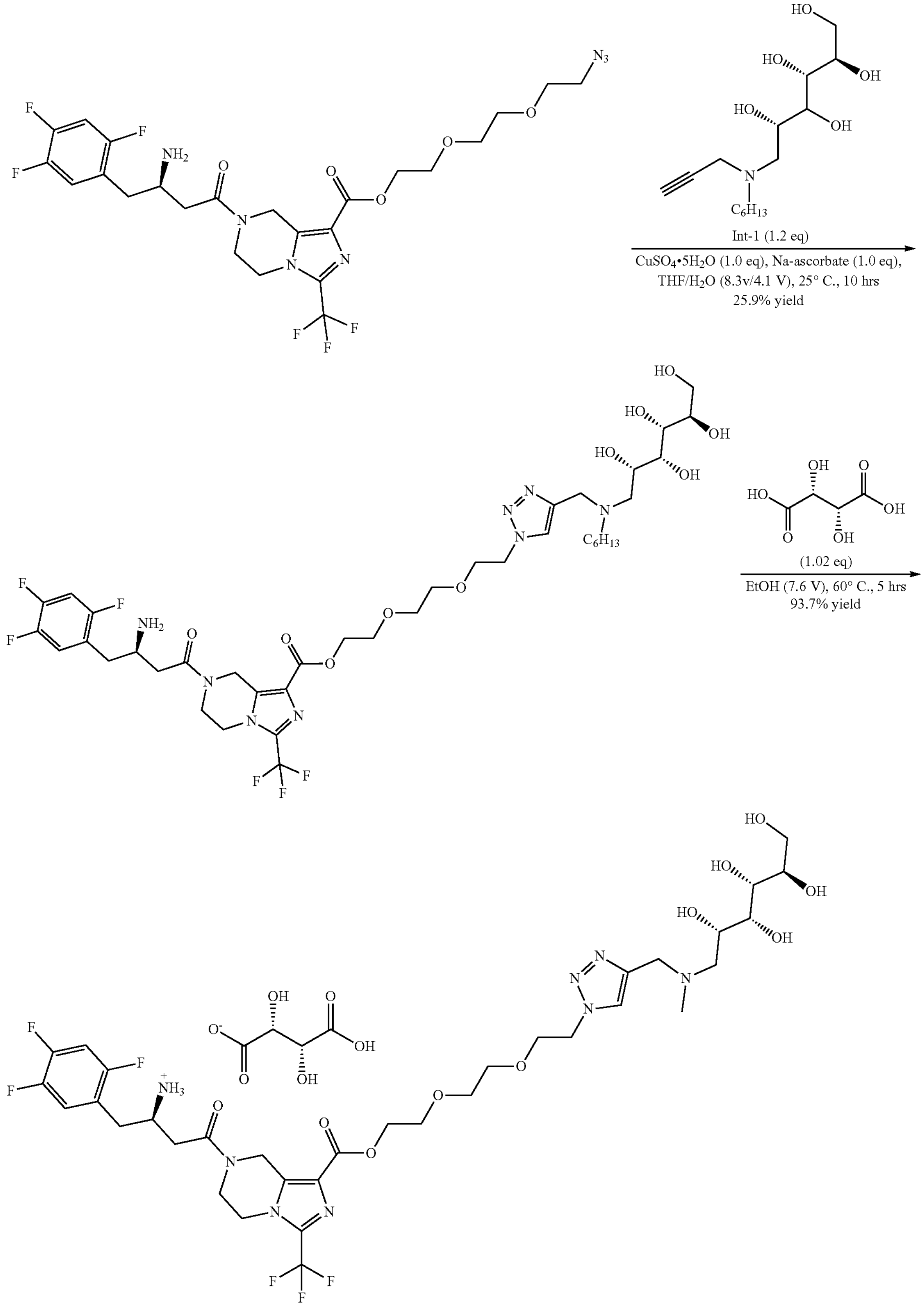

Step 1. 2-(2-(2-azidoethoxy)ethoxy)ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate To a solution of 2-(2-(2-azidoethoxy)ethoxy)ethyl (R)-7-(3-((tert-butoxycarbonyl)amino)-4-(2,4,5-trifluorophenyl) butanoyl)-3-(trifluoromethyl)-5,6,7,8-tetrahydroimidazo[1,5-a]pyrazine-1-carboxylate (Int-22, 300 g, 424 mmol) in ethyl acetate (1 L) was added HCl in ethyl acetate (4 M, 1 L) at room temperature. The mixture was stirred for 2 hours and concentrated to give a crude reside. It was redissolved in EA (1.00 L), quenched with aq. $NaHCO_3$ to adjust pH=8, the organic layer was separated, dried over with $Na_2SO_4$, filtered and the filtrate was concentrated to give compound 2-(2-(2-azidoethoxy)ethoxy)ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (720 g, 1.12 mol, 88.1% yield, 94.5% purity) as yellow oil. $^1$H NMR: DMSO-d6 7.92 (s, 1H), 7.52-7.33 (m, 2H), 5.00-4.95 (m, 2H), 4.48-4.25 (m, 10H), 3.94-3.81 (m, 2H), 3.81-3.78 (m, 2H), 3.71-3.54 (m, 14H), 3.39-3.35 (m, 2H), 2.57-2.56 (m, 3H), 2.38-2.33 (m, 4H), 1.40-1.39 (m, 4H), 1.24-1.17 (m, 6H), 0.83 (t, J=6.8 Hz, 3H).

Step 2. 2-(2-(2-(4-((hexyl(2,3,4,5,6-pentahydroxyhexyl)amino)methyl)-1H-1,2,3-triazol-1-yl)ethoxy) ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (46)

A solution of Compound 2-(2-(2-azidoethoxy)ethoxy) ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (240 g, 395 mmol, 1.00 eq) and (2R,3R,4R,5S)-6-(hexyl(prop-2-yn-1-yl)amino)hexane-1,2,3,4,5-pentaol (Int-1, 144 g, 474.63 mmol, 1.20 eq) in THF (2.00 L) and $H_2O$ (1.00 L) was prepared. $CuSO4{\cdot}5H_2O$ (99.0 g, 396 mmol, 1.00 eq) and Na-ascorbate (78.9 g, 398 mmol, 1.01 eq) was added to the mixture at 10-25° C. and the mixture was stirred at 25° C. for 10 hrs. The mixture of three batches was diluted with $NH_3{\cdot}H_2O$/aq·NaCl=1V/2V (1.50 L), extracted with EA (1.50 L×2), washed with $NH_3{\cdot}H_2O$/aq·NaCl=1V/2V (1.50 L×3), until the aqueous phase color turned colorless form blue. The organic layer was dried over with $Na_2SO_4$, filtered and the filtrate was concentrated under reduced pressure to give a residue. The crude product was purified by reversed-phase HPLC (0.1% FA condition), the mixture was concentrated to remove MeCN, and then quenched with $NaHCO_3$ to adjust pH=9, extracted with EA (10.0 L×2), dried over with $Na_2SO_4$, filtered. The filtrate was concentrated under reduced pressure to give 2-(2-(2-(4-((hexyl(2,3,4,5,6-pentahydroxyhexyl)amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (46) (290 g, 306 mmol, 25.9% yield, 96.3% purity) as yellow solid. MS (ESI): mass calcd. for Chemical Formula: $C_{39}H_{56}F_6N_8O_{10}$ 910.40, m/z found 911.5 [M+1]. 1H NMR (DMSO-$d_6$) 7.92 (s, 1H), 7.52-7.33 (m, 2H), 5.00-4.95 (m, 2H), 4.48-4.25 (m, 10H), 3.94-3.93 (m, 2H), 3.81-3.79 (m, 2H), 3.71-3.39 (m, 14H), 3.35-3.27 (m, 2H), 2.72-2.54 (m, 3H), 2.38-2.33 (m, 4H), 1.55-1.33 (m, 4H), 1.24-1.15 (m, 6H), 0.83 (t, J=8.0 Hz, 3H).

Step 3. 2-(2-(2-(4-((hexyl(2,3,4,5,6-pentahydroxyhexyl)amino)methyl)-1H-1,2,3-triazol-1-yl)ethoxy) ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate tartrate salt To a solution of 2-(2-(2-(4-((hexyl(2,3,4,5,6-pentahydroxyhexyl)amino)methyl)-1H-1,2,3-triazol-1-yl)ethoxy) ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate (260 g, 285 mmol) in ethanol (1 L) was added tartaric acid (43.7 g, 291 mmol, 1.02 eq.) in ethanol (1 L). The mixture was stirred at 60° C. for 5 hrs. The mixture was concentrated under reduced pressure to give 2-(2-(2-(4-((hexyl(2,3,4,5,6-pentahydroxyhexyl) amino)methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate tartrate salt as yellow solid (293.3 g, 93.7% yield, 96.8% pure). 1H NMR DMSO-d6 8.01-7.95 (m, 1H), 7.55-7.47 (m, 2H), 5.02-4.90 (m, 2H), 4.48 (t, J=8.0 Hz, 2H), 4.34-3.7 (m, 9H), 3.81-3.48 (m, 15H), 3.40-3.35 (m, 2H), 2.97-2.58 (m, 5H), 2.46-2.33 (m, 4H), 1.43-1.42 (m, 2H), 1.27-1.20 (m, 6H), 0.83 (t, J=6.0 Hz, 3H).

Example 34. Synthesis of 7-((R)-3-amino-4-(2,4,5-trifluorophenyl)butanoyl)-N-(2-(2-(2-(4-((hexyl(2,3,4,5,6-pentahydroxyhexyl)amino)methyl)-1H-1,2,3-triazol-1-yl)ethoxy)ethoxy)ethyl)-3-(trifluoromethyl)-5,6,7,8-tetrahydroimidazo[1,5-a] pyrazine-1-carboxamide (47)

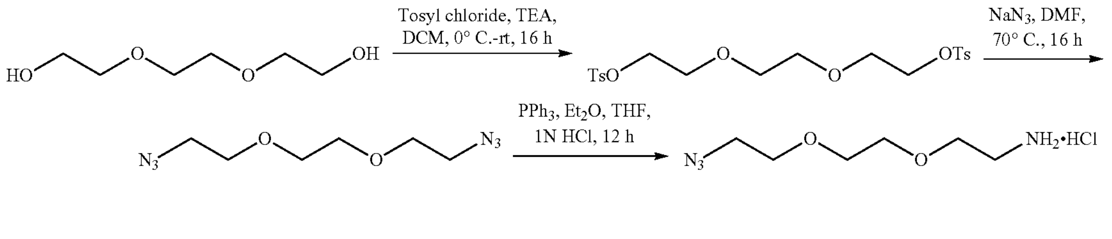

-continued
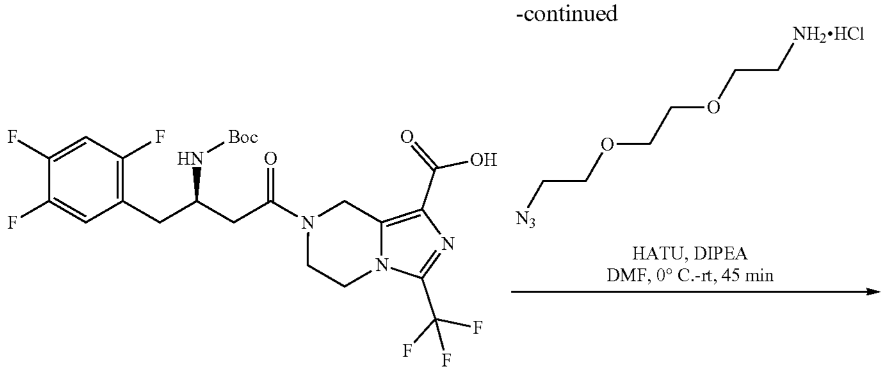
Int-21
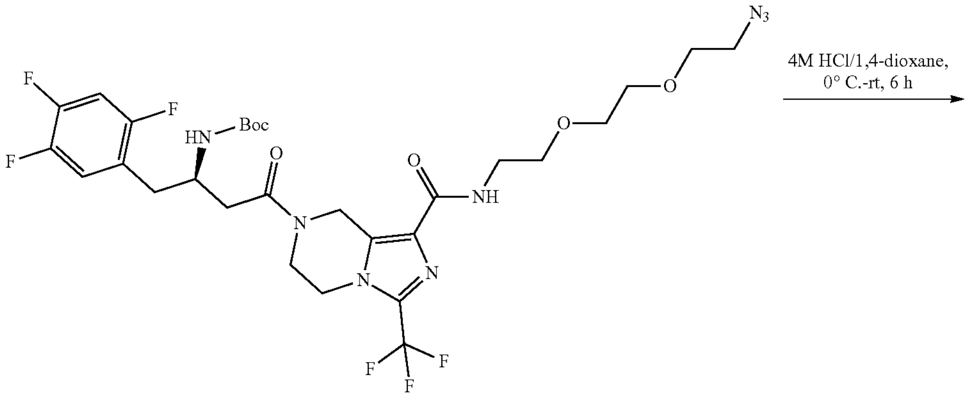
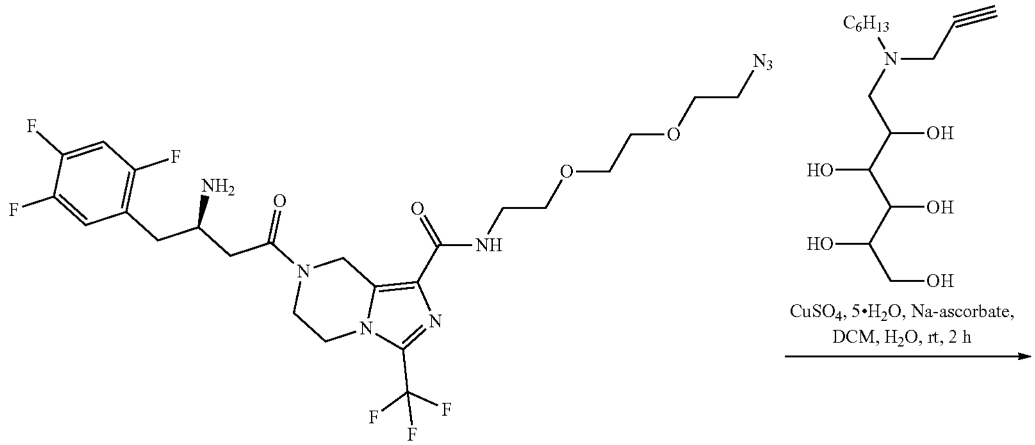

-continued

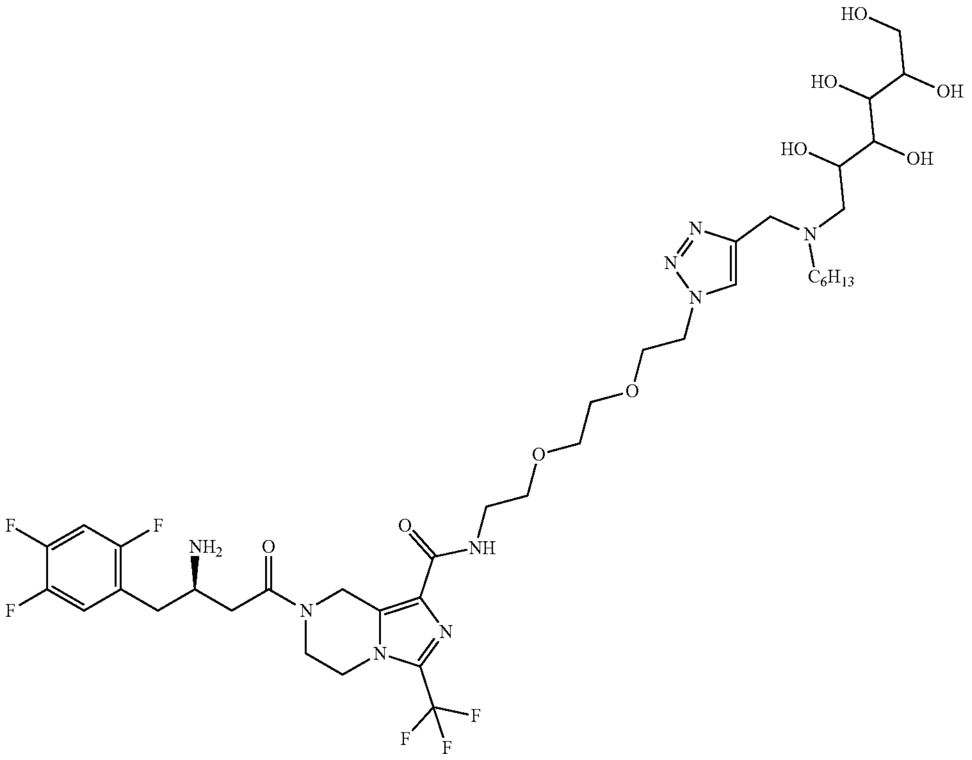

Step 1. Synthesis of (ethane-1,2-diylbis(oxy))bis(ethane-2,1-diyl)bis(4-methyl benzene sulfonate)

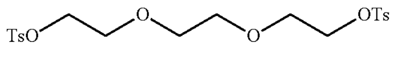 [SMILES: Cc1ccc(S(=O)(=O)OCCOCCOCCOS(=O)(=O)c2ccc(C)cc2)cc1]

To the stirred solution of 2,2'-(ethane-1,2-diylbis(oxy))bis(ethan-1-ol) (15.0 g, 99.88 mmol) in DCM (300 mL), Et3N (55.58 mL, 399.54 mmol) was added at 0° C. followed by tosyl Chloride (76.16 g, 399.54 mmol). The reaction mixture was stirred at room temperature for 16 h. After completion of reaction, reaction mixture was quenched with cold water (500 mL) and extracted with CH2Cl2 (2×500 mL). Combined organic layer was washed with cold water (500 mL), brine (500 mL), dried over anhydrous $Na_2SO_4$, concentrated under reduced pressure to get crude compound. The crude compound was purified by column chromatography over silica gel (100-200 mesh) (using 0-50% EtOAc in Pet Ether as an eluent) to afford 37.0 g of (ethane-1,2-diylbis(oxy))bis(ethane-2,1-diyl)bis(4-methylbenzenesulfonate) as off white solid. [TLC system: EtOAc: Pet Ether (4:6); $R_f$-value: 0.6].

Step 2. Synthesis of 1,2-bis(2-azidoethoxy)ethane

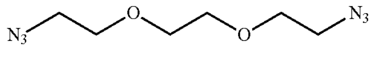

To a stirred solution of (ethane-1,2-diylbis(oxy))bis(ethane-1,2-diylbis(4-methylbenzenesulfonate) (5.0 g, 10.90 mmol) in DMF (50 mL), sodium azide (2.83 g, 43.61 mmol) was added. Then reaction mixture was heated at 70° C. for 16 h. After completion of reaction, reaction mixture was concentrated, and the residue was stirred in diethyl ether and filtered. Filtrate was concentrated to get 2.0 g of 1,2-bis(2-azidoethoxy)ethane as colorless oil. [TLC system: EtOAc: Pet Ether (2:8); $R_f$-value: 0.6].

Step 3. 2-(2-(2-azidoethoxy)ethoxy)ethan-1-amine hydrochloride

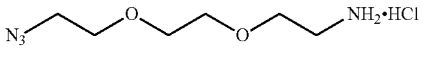

To a vigorously stirred solution of 1,2-bis(2-azidoethoxy)ethane (3.0 g, 14.98 mmol) in $Et_2O$ (22 mL) and THF (4.4 mL) was added 1N HCl (17.6 mL) solution followed by $PPh_3$ (3.9 g, 14.98 mmol) in $Et_2O$ (22 mL). The reaction mixture was stirred at room temperature for 12 h. After completion of reaction, aqueous layer was separated and washed with diethyl ether (2×100 mL). The aqueous layer was concentrated and residue was co-evaporated with acetonitrile (2-3 times) to get 2.0 g of 2-(2-(2-azidoethoxy)ethoxy)ethan-1-amine hydrochloride as colorless oil. [TLC system: MeOH:DCM (0.5:9.5); $R_f$-value: 0.4].

Step 4. tert-butyl (R)-(4-(1-((2-(2-(2-azidoethoxy) ethoxy)ethyl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate

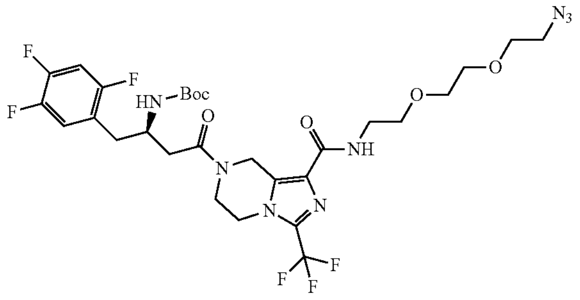 [SMILES: CC(C)(C)OC(=O)N[C@@H](CC(=O)N1CCn2c(C(F)(F)F)nc(C(=O)NCCOCCOCCN=[N+]=[N-])c2C1)Cc1cc(F)c(F)cc1F]

To a stirred solution of (R)-7-(3-((tert-butoxycarbonyl) amino)-4-(2,4,5-trifluorophenyl)butanoyl)-3-(trifluoromethyl)-5,6,7,8-tetrahydroimidazo[1,5-a]pyrazine-1-carboxylic acid (2.9 g, 5.27 mmol) and 2-(2-(2-azidoethoxy) ethoxy)ethan-1-amine hydrochloride (1.66 g, 7.90 mmol) in DMF (30 mL) was added HATU (3.0 g, 7.90 mmol) followed by DIPEA (3.39 mL, 26.35 mmol) at 0° C. The reaction mixture was stirred at room temperature for 45 min. The progress of the reaction was monitored by TLC. After completion of reaction, reaction mixture was quenched with cold water (2×50 mL) and extracted with EtOAc (2×100 mL). The combined organic layer was washed with cold water (100 mL), brine (100 mL), dried over anhydrous Na2SO4 and concentrated to get crude compound. The crude compound was purified by column chromatography over silica gel (Davisil) (using 0-70% EtOAc in Pet Ether as an eluent) to afford 3.0 g of. tert-butyl (R)-(4-(1-((2-(2-(2-azidoethoxy)ethoxy)ethyl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate as an off white solid. [TLC system: EtOAc: Pet Ether (7:3); $R_f$ value: 0.5].

Step 5. (R)-7-(3-amino-4-(2,4,5-trifluorophenyl) butanoyl)-N-(2-(2-(2-azidoethoxy) ethoxy)ethyl)-3-(trifluoromethyl)-5,6,7,8-tetrahydroimidazo[1,5-a] pyrazine-1-carboxamide

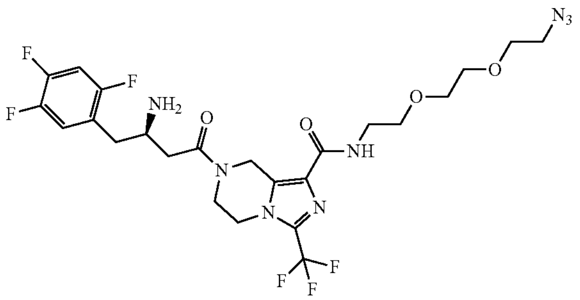 [SMILES: [N-]=[N+]=NCCOCCOCCNC(=O)c1nc(C(F)(F)F)n2c1CN(C(=O)C[C@H](N)Cc1cc(F)c(F)cc1F)CC2]

To a solution of tert-butyl (R)-(4-(1-((2-(2-(2-azidoethoxy)ethoxy)ethyl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate (2.4 g, 3.339 mmol) in $CH_2Cl_2$ (24 mL) was added 4 M HCl in 1,4-dioxane (24.0 mL) at 0° C. The reaction mixture was stirred at room temperature for 6 h. After completion of reaction, reaction mixture was concentrated and residue was basified with saturated $NaHCO_3$ solution and extracted with 10% MeOH in DCM (2×200 mL). The combined organic layer was dried over anhydrous $Na_2SO_4$ and concentrated to get 2.2 g (R)-7-(3-amino-4-(2,4,5-trifluorophenyl)butanoyl)-N-(2-(2-(2-azidoethoxy) ethoxy)ethyl)-3-(trifluoromethyl)-5,6,7,8-tetrahydroimidazo[1,5-a]pyrazine-1-carboxamide as an oil. [TLC system: MeOH:DCM (0.5:9.5); $R_f$ value: 0.4].

Step 6. 7-((R)-3-amino-4-(2,4,5-trifluorophenyl) butanoyl)-N-(2-(2-(2-(4-((hexyl(2,3,4,5,6-pentahydroxyhexyl)amino)methyl)-1H-1,2,3-triazol-1-yl) ethoxy)ethoxy)ethyl)-3-(trifluoromethyl)-5,6,7,8-tetrahydroimidazo[1,5-a]pyrazine-1-carboxamide

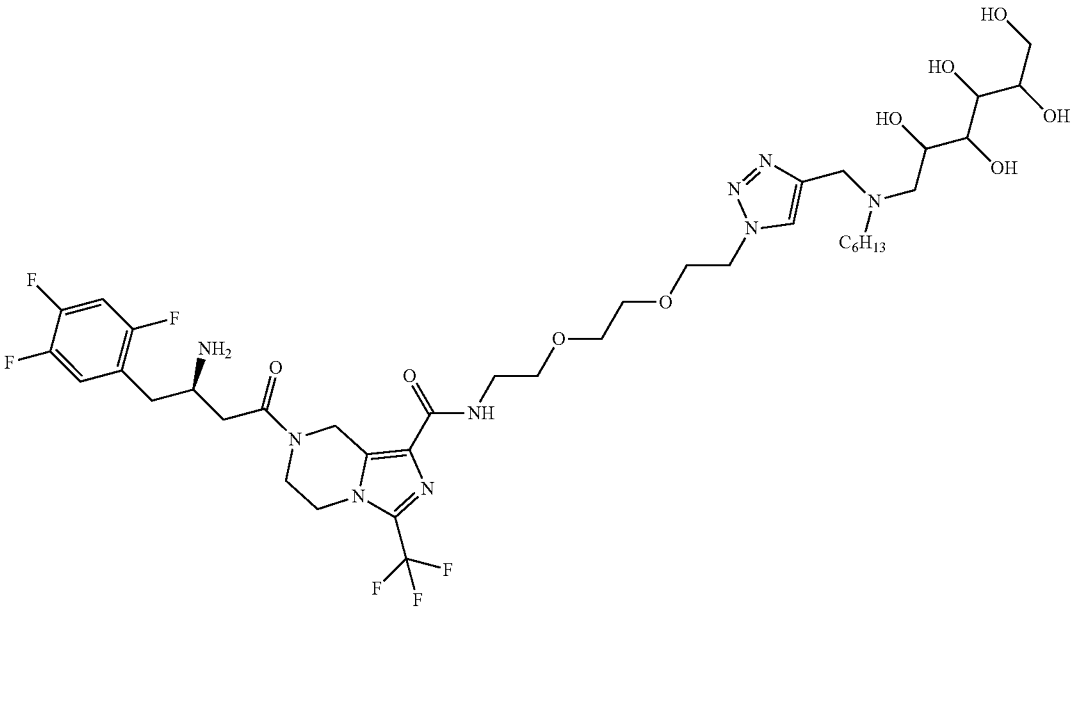

To a solution of (R)-7-(3-amino-4-(2,4,5-trifluorophenyl) butanoyl)-N-(2-(2-(2-azidoethoxy) ethoxy)ethyl)-3-(trifluoromethyl)-5,6,7,8-tetrahydroimidazo[1,5-a]pyrazine-1-carboxamide (2.2 g, 3.627 mmol) and compound 8 (1.65 g, 5.440 mmol) in t-BuOH (66 mL) and water (22 mL) was added CuSO4, 5·H2O (1.08 g, 4.352 mmol) and Na-ascorbate (1.07 g, 5.440 mmol). The reaction mixture was stirred at room temperature for 2 h. After completion of reaction, reaction mixture was filtered and concentrated to get crude compound. The crude compound was purified by RP-Prep-HPLC afford 0.573 g of 7-((R)-3-amino-4-(2,4,5-trifluorophenyl)butanoyl)-N-(2-(2-(2-(4-((hexyl(2,3,4,5,6-pentahydroxyhexyl)amino)methyl)-1H-1,2,3-triazol-1-yl)ethoxy) ethoxy)ethyl)-3-(trifluoromethyl)-5,6,7,8-tetrahydroimidazo[1,5-a]pyrazine-1-carboxamide as an off white solid.

RP-Prep-HPLC Purification Method

COLUMN: X BRIDGE C18 (19×250 mm)
Mobile phase A: 10 MM ABC IN WATER
Mobile phase B: Acetonitrile Solubility: ACN+WATER+THF Gradient % B: 0/10, 1/30, 18.5/45.4, 18.6/95, 20.5/95, 20.6/10, 22/10.

LC MS M/Z=910.51 (M+1) 1H NMR (400 MHz, DMSO-$d_6$) δ 8.02-7.98 (m, 1H), 7.91 (s, 1H), 7.45-7.41 (m, 2H), 4.98-4.87 (m, 2H), 4.47-4.46 (m, 4H), 4.42-4.13 (m, 4H), 3.92 (s, 2H), 3.80 (s, 2H), 3.72 (s, 3H), 3.62-3.56 (m, 2H), 3.59-3.32 (m, 12H), 2.67-2.56 (m, 4H), 2.40-2.33 (m, 4H), 1.40 (bs, 2H), 1.23-1.15 (m, 6H), 0.83 (t, J=7.2 Hz, 3H).

Example 35. Synthesis of 2-(2-(2-(4-((bis((2S,3R, 4R,5R)-2,3,4,5,6-pentahydroxyhexyl)amino) methyl)-1H-1,2,3-triazol-1-yl)ethoxy)ethoxy)ethyl 7-((R)-3-amino-4-(2,4,5-trifluorophenyl)butanoyl)-3-(trifluoromethyl)-5,6,7,8-tetrahydroimidazo[1,5-a] pyrazine-1-carboxylate (48)

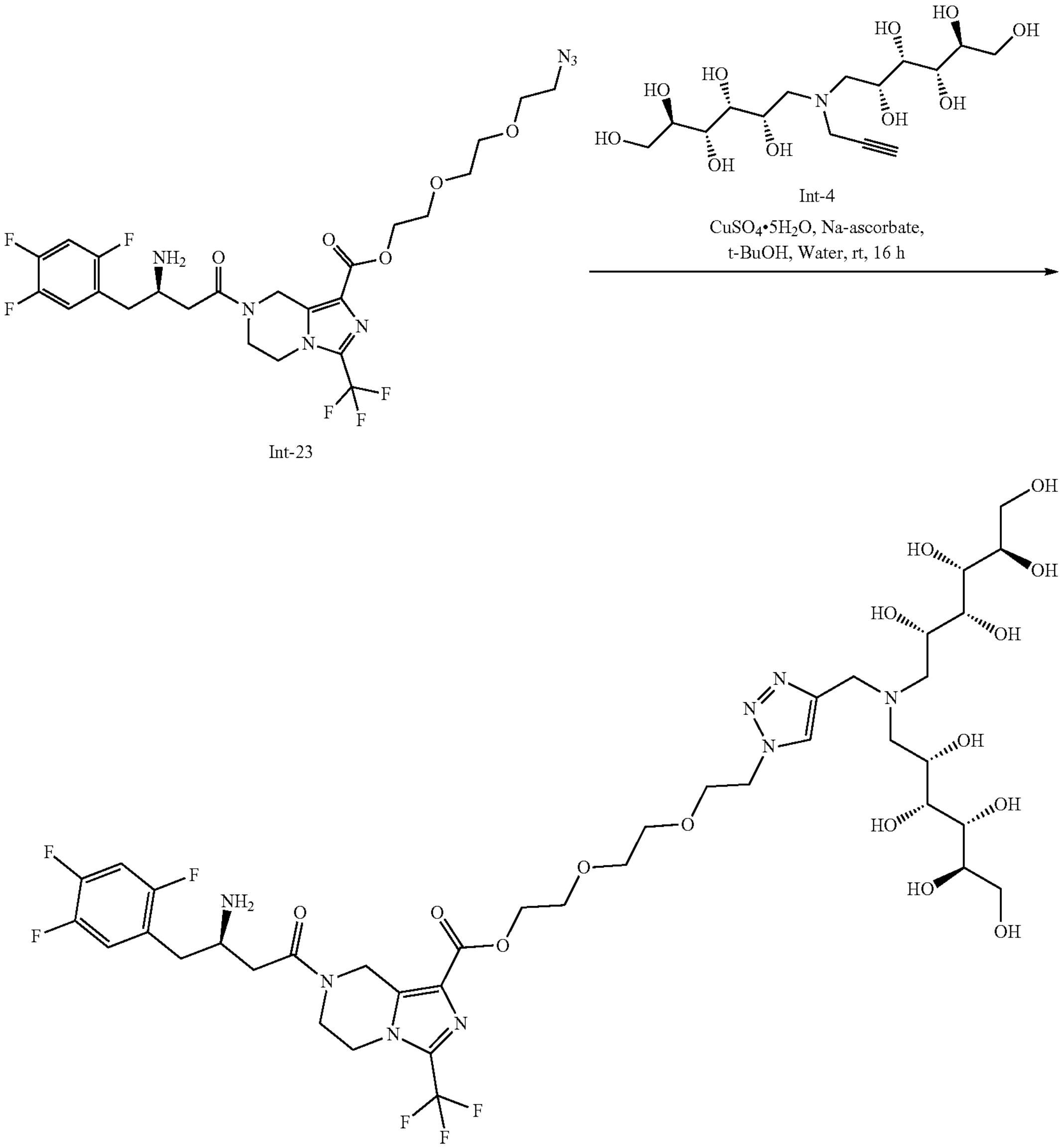

To a solution of compound 2-(2-(2-azidoethoxy)ethoxy) ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.1 g, 0.164 mmol) and compound (2R,3R,4R,5S)-6-(((2R,3S,4S,5S)-2,3,4,5,6-pentahydroxyhexyl)(prop-2-yn-1-yl)amino)hexane-1,2,3,4,5-pentaol (0.126 g, 0.329 mmol) in t-BuOH (3.0 mL) and water (0.6 mL) was added $CuSO_4$,5·$H_2O$ (0.05 g, 0.197 mmol) and Na-ascorbate (0.048 g, 0.246 mmol). Then reaction was stirred at RT for 16 h. After completion of reaction, reaction mixture was filtered and concentrated to get crude compound. The crude compound was purified by RP-Prep-H-PLC to afford 20 mg of 2-(2-(2-(4-((bis((2S,3R,4R,5R)-2,3,4,5,6-pentahydroxyhexyl)amino)methyl)-1H-1,2,3-triazol-1-yl)ethoxy)ethoxy) ethyl 7-((R)-3-amino-4-(2,4,5-trifluorophenyl)butanoyl)-3-(trifluoromethyl)-5,6,7,8-tetrahydroimidazo[1,5-a]pyrazine-1-carboxylate as off white solid compound. LC MS M/Z=991.57 (M+1) $^1$H NMR (400 MHz, DMSO-$d_6$) δ 7.94 (s, 1H), 7.45-7.43 (m, 2H), 5.00-4.95 (m, 2H), 4.87-4.14 (m, 18H), 3.93-3.47 (m, 23H), 3.39-3.16 (m, 8H), 2.61-2.58 (m, 2H).

RP-Prep-HPLC Purification Condition

Column/dimensions: X BRIDGE C18 (19×250 mm), 5μ Mobile phase A: 10 MM ABC (pH) IN WATER Mobile phase B: Acetonitrile.

Gradient (Time/% B): 0/10, 1/10, 11/50, 12.6/50, 12.7/98, 16/98, 16.1/10, 19/10.

Flow rate: 16 ml/min.

Example 36. Synthesis of (R)-4-(1-((2-morpholinoethoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3S)-3-carboxy-2,3-dihydroxypropanoate (Tartrate Salt) (49)

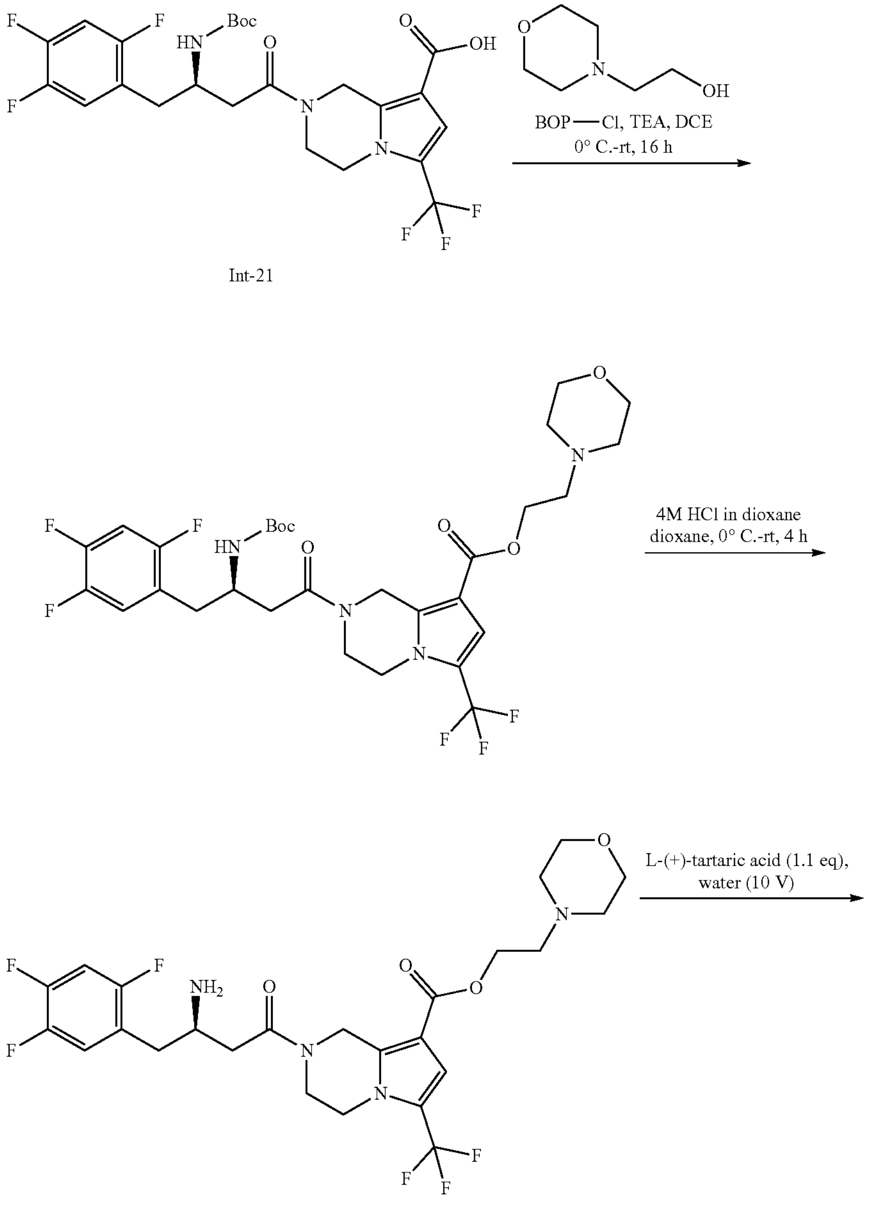

Int-21

-continued

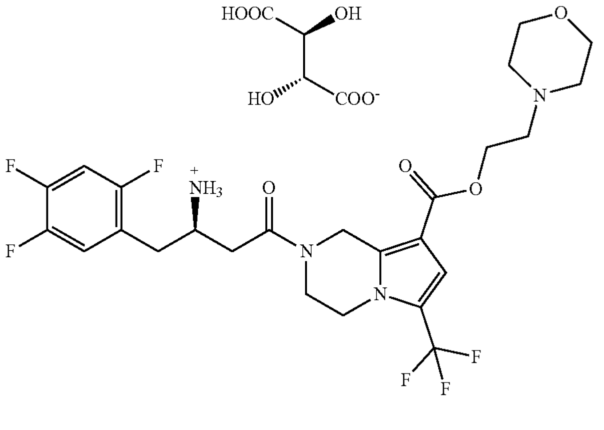

Step 1. 2-morpholinoethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate

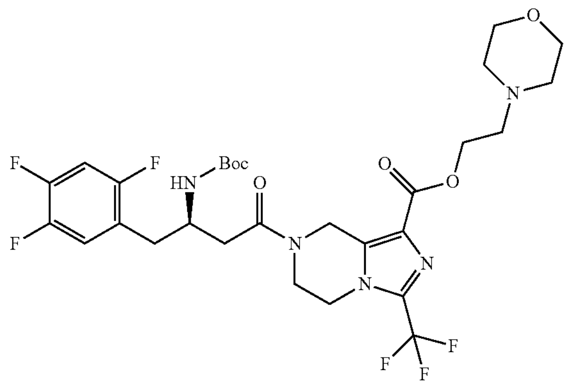 [SMILES: CC(C)(C)OC(=O)N[C@@H](CC(=O)N1CCn2c(C(F)(F)F)nc(C(=O)OCCN3CCOCC3)c2C1)Cc1cc(F)c(F)cc1F]

To a stirred solution of (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid (0.5 g, 0.91 mmol) in 1.2 dichloroethane (10 mL) and triethylamine (0.37 g, 3.64 mmol) was added bis(2-oxo-3-oxazolidinyl)phosphinic chloride (0.46 g, 1.82 mmol) at 0° C. and the resulting mixture was stirred at 0° C. for 1 h. Then 2-morpholinoethan-1-ol (0.24 g, 1.82 mmol) was added at 0° C. and the reaction mixture was stirred at room temperature for 16 h. After completion, the reaction mixture was diluted with water (10 mL) and extracted with dichloromethane (2×50 mL). The combined organic layer was dried over anhydrous sodium sulphate and concentrated under reduced pressure to give crude product. The obtained crude residue was then purified by column chromatography over silica gel (230-400 mesh) using 4% methanol in dichloromethane as a gradient to afford 2-morpholinoethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.51 g, 84.7%) as an off-white solid. TLC system. MeOH:DCM (1:9); $R_f$: 0.3.

Step 2. 2-morpholinoethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate

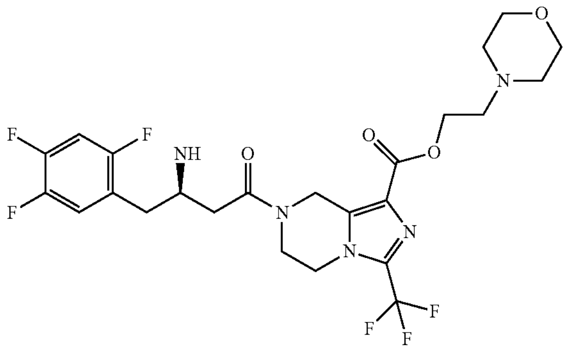 [SMILES: N[C@@H](CC(=O)N1CCn2c(C(F)(F)F)nc(C(=O)OCCN3CCOCC3)c2C1)Cc1cc(F)c(F)cc1F]

To a stirred solution of 2-morpholinoethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.51 g, 0.77 mmol) in 1.4 dioxane (5.1 mL), hydrogen chloride solution 4.0 M in dioxane (5.1 mL) was added at 0° C. and the reaction mixture was stirred at room temperature for 4 h. After completion, the reaction mixture was concentrated under reduced pressure to give crude product. The obtained crude product was then purified by RP preparative HPLC using following conditions. Column/dimensions: X-BRIDGE-C18 (19*250) 5 um, mobile phase A; 10 mM ammonium bicarbonate in water, mobile phase B: acetonitrile, gradient (time/% B): 0/5, 1/5, 8/40, 13.5/40, 13.51/100, 18/100, 18.1/5, 20.5/5, flow rate: 18 ml/min. The desired fraction was lyophilized to afford 2-morpholinoethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.25 g, 57.7%) as an off-white semi solid. TLC system. MeOH:DCM (1:9); $R_f$: 0.05.

Step 3. (R)-4-(1-((2-morpholinoethoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3S)-3-carboxy-2,3-dihydroxypropanoate-Tartrate salt (49)

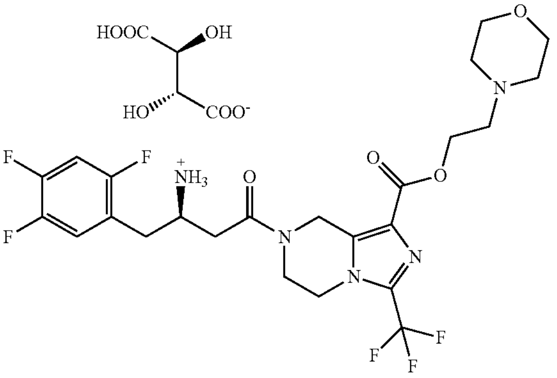

Mixture of 2-morpholinoethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.25 g, 0.44 mmol) and L(+)-tartaric acid (0.73 g, 0.49 mmol) in demineralized water (2.5 mL) was sonicated to get clear solution. The resulting solution was lyophilized to afford (R)-4-(1-((2-morpholinoethoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3S)-3-carboxy-2,3-dihydroxypropanoate (0.32 g) as an off-white solid. LCMS M/Z 564.46. $^{1}$H NMR (400 MHz, DMSO) δ 7.52 (dd, J=9.5, 4.0 Hz, 2H), 5.03-4.87 (m, 2H), 4.35-4.08 (m, 5H), 3.95-3.88 (m, 4H), 3.67 (s, 2H), 3.56 (t, J=4.6 Hz, 4H), 2.89 (s, 3H), 2.82-2.58 (m, 4H), 2.44 (t, J=4.7 Hz, 4H).

Example 37. Synthesis of (R)-4-(1-((2-(2-morpholinoethoxy)ethyl)carbamoyl)-3-(trifluoromethyl)-5,6-dihydroimidazol[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate Salt) (50)

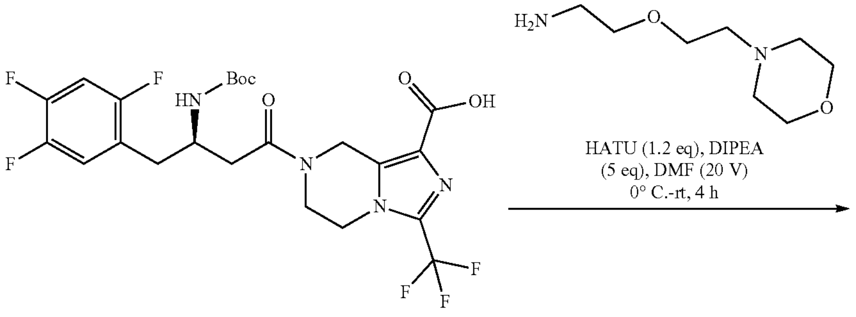

Int-21

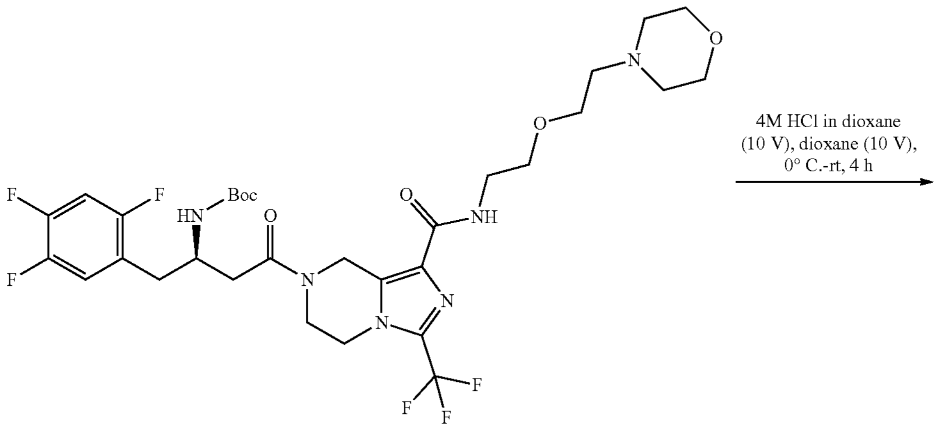

-continued

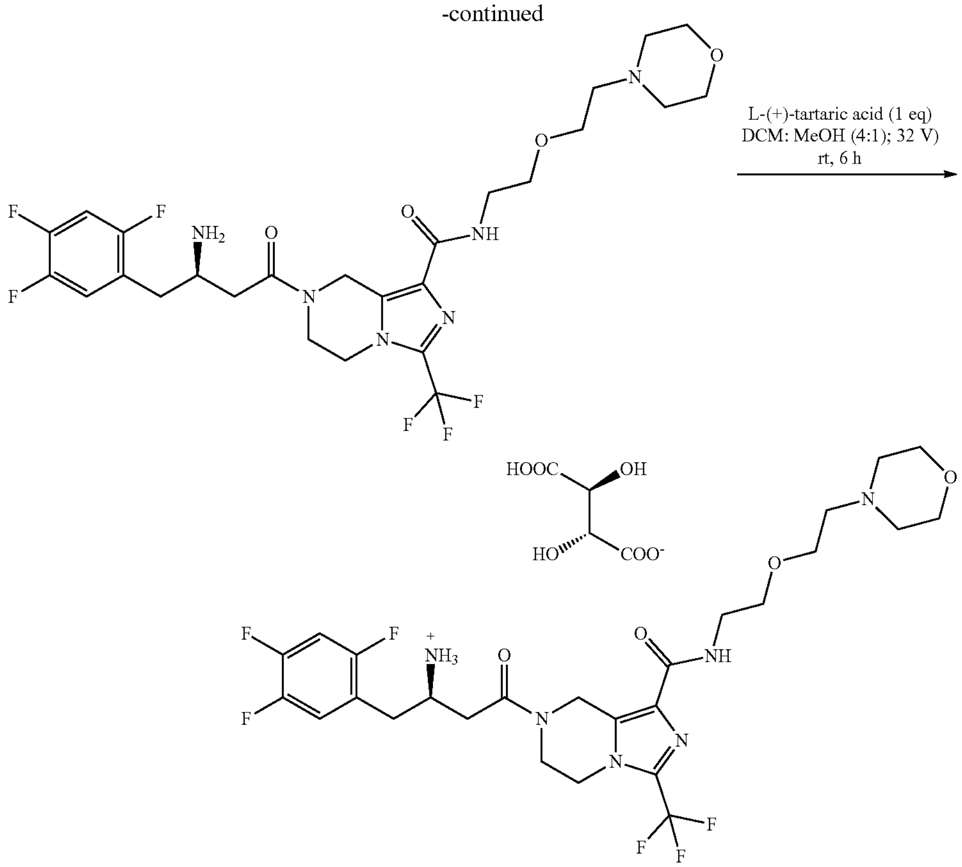

Step 1. tert-butyl (R)-(4-(1-((2-(2-morpholinoethoxy)ethyl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate

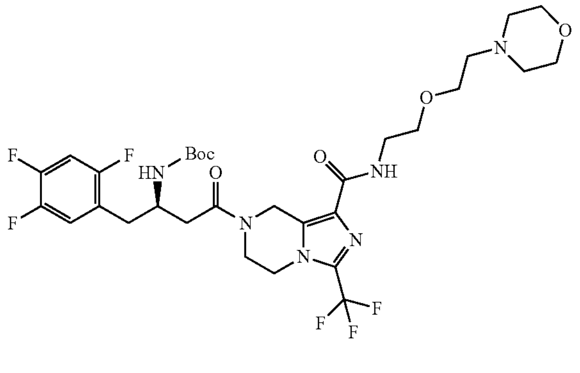 [SMILES: CC(C)(C)OC(=O)N[C@@H](CC(=O)N1CCn2c(C(F)(F)F)nc(C(=O)NCCOCCN3CCOCC3)c2C1)Cc1cc(F)c(F)cc1F]

To a stirred solution of (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid (0.4 g, 0.73 mmol), 2-(2-morpholinoethoxy)ethan-1-amine (0.127 g, (1-[Bis(dimethylamino)methylene]-1H-1,2,3-triazolo[4,5-b]pyridinium 3-oxide hexafluorophosphate (0.334 g, 0.88 mmol) in N,N-dimethylformamide (4 mL) was slowly added N,N-diisopropylethylamine (0.47 g, 3.65 mmol) at 0° C. and the reaction mixture was stirred at at room temperature for 4 h. After completion, the reaction mixture was diluted with water (30 mL) and extracted with ethyl acetate (3×100 mL). The combined organic layer was dried over anhydrous sodium sulphate and concentrated under reduced pressure to give crude product. The obtained crude residue was then purified by column chromatography over silica gel (230-400 mesh) using 4% methanol in dichloromethane as a gradient to afford tert-butyl (R)-(4-(1-((2-(2-morpholinoethoxy)ethyl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate (0.4 g, 78%) as a brown solid. TLC system. MeOH:DCM (1:9); $R_f$: 0.3.

Step 2. (R)-7-(3-amino-4-(2,4,5-trifluorophenyl)butanoyl)-N-(2-(2-morpholinoethoxy)ethyl)-3-(trifluoromethyl)-5,6,7,8-tetrahydroimidazo[1,5-a]pyrazine-1-carboxamide

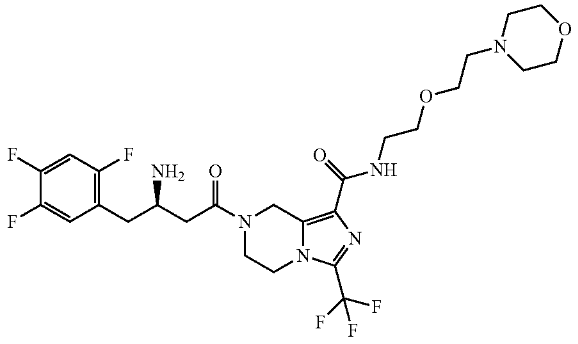 [SMILES: N[C@@H](CC(=O)N1CCn2c(C(F)(F)F)nc(C(=O)NCCOCCN3CCOCC3)c2C1)Cc1cc(F)c(F)cc1F]

To a stirred solution of tert-butyl (R)-(4-(1-((2-(2-morpholinoethoxy)ethyl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate (0.4 g, 0.566 mmol) in 1.4 dioxane (4 mL), 4.0 M HCl in dioxane (4 mL) was added at 0° C. and the mixture was stirred at room temperature for 4 h. After completion, the reaction mixture was concentrated under reduced pressure to give crude product. Obtained crude was then purified by RP preparative HPLC using following conditions. Column/dimensions: Column/dimensions: X-select C18 (19*250 mm), 5 um, mobile phase A: 10 MM ammonium bicarbonate in water, mobile phase B: acetonitrile, gradient (time?% B): 0/10, 1/10, 10/40, 15.51/61.5, 15.6/100, 18/100, 18.1/10, 20/10, flow rate: 17 ml/min. The desired fraction was lyophilized to afford (R)-7-(3-amino-4-(2,4,5-trifluorophenyl)butanoyl)-N-(2-(2-morpholinoethoxy)ethyl)-3-(trifluoromethyl)-5,6,7,8-tetrahydroimidazo[1,5-a]pyrazine-1-carboxamide (0.16 g, 46.6%) as a colorless gum. TLC system. MeOH:DCM (1:9); $R_f$: 0.05.

Step 3. (R)-4-(1-((2-(2-morpholinoethoxy)ethyl)carbamoyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (tartrate salt) (50)

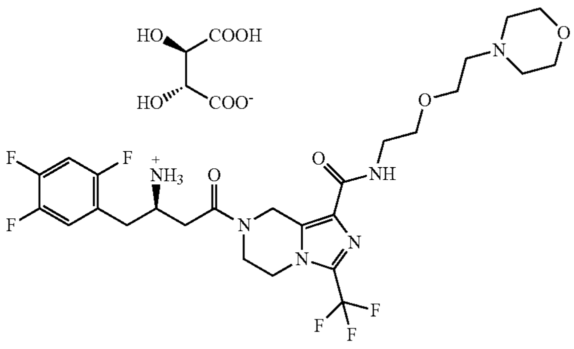

To a stirred solution of (R)-7-(3-amino-4-(2,4,5-trifluorophenyl)butanoyl)-N-(2-(2-morpholinoethoxy)ethyl)-3-(trifluoromethyl)-5,6,7,8-tetrahydroimidazo[1,5-a]pyrazine-1-carboxamide (0.16 g, 0.26 mmol) in dichloromethane (4 mL) and methanol (1 mL) mixture was added L(+) tartaric acid (0.039 g, 0.26 mmol), the mixture was stirred at room temperature for 6 h. The solvent was evaporated under reduced pressure, the residue was then washed with n-pentane (2×5 mL) and re-dissolved demineralized water (1.4 mL). The resulting solution was lyophilized to afford (R)-4-(1-((2-(2-morpholinoethoxy)ethyl)carbamoyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (0.175 g) as an off-white solid. LCMS M/Z 607.51. $^1$H NMR (400 MHz, DMSO) δ 8.08-7.95 (m, 1H), 7.56-7.44 (m, 2H), 5.03-4.87 (m, 2H), 4.26-4.07 (m, 3H), 3.88 (s, 4H), 3.37 (t, J=6.1 Hz, 13H), 2.87 (d, J=6.7 Hz, 2H), 2.72-2.65 (m, 2H), 2.46-2.36 (m, 7H).

Example 38. Synthesis of (R)-4-(1-((3-morpholinopropoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate Salt) (51)

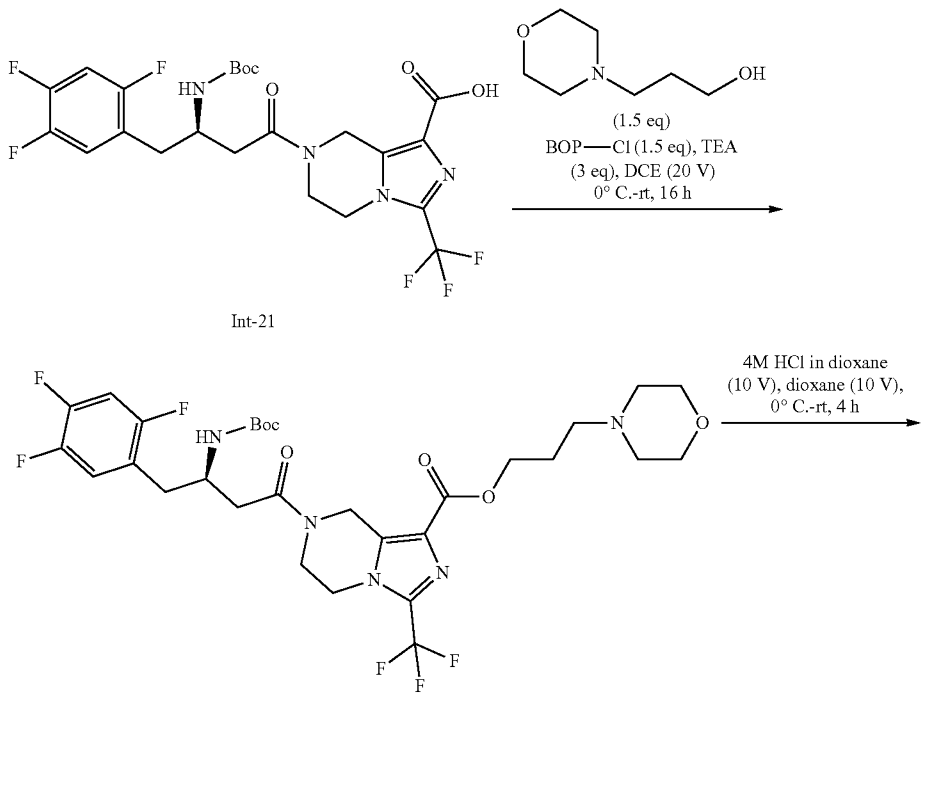

Int-21

-continued

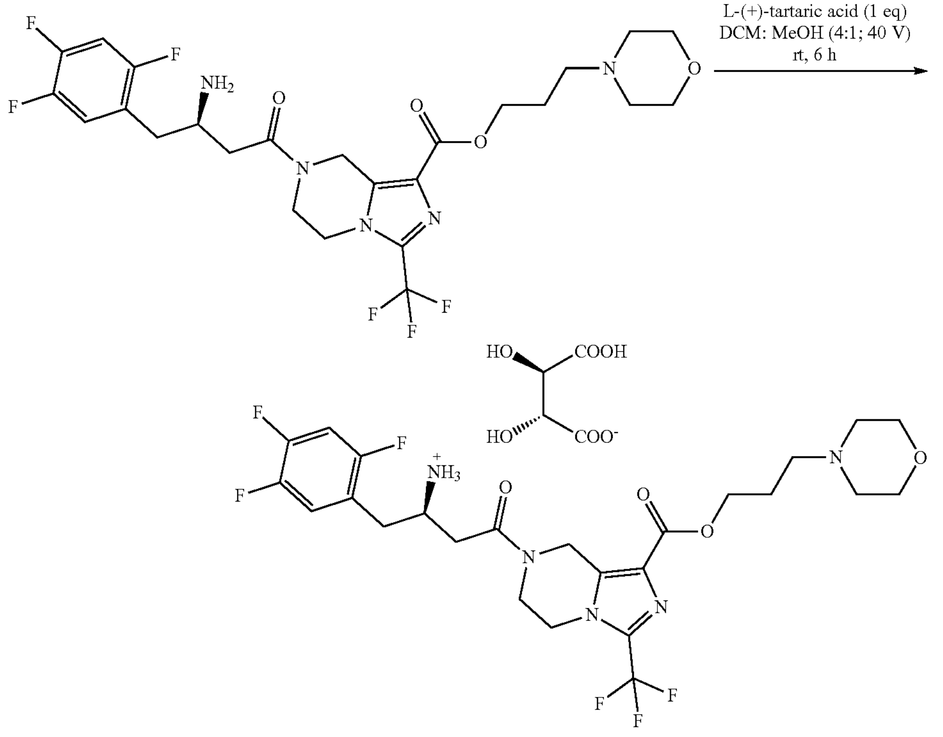

Step 1. 3-morpholinopropyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate

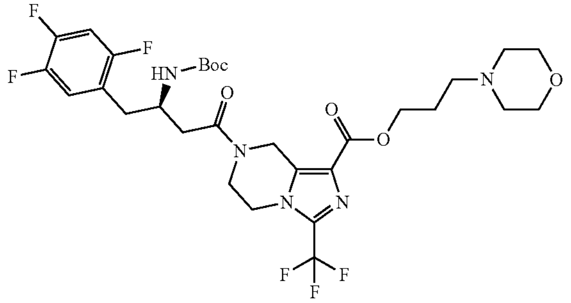 [SMILES: CC(C)(C)OC(=O)N[C@@H](CC(=O)N1CCn2c(C(F)(F)F)nc(C(=O)OCCCN3CCOCC3)c2C1)Cc1cc(F)c(F)cc1F]

To a stirred solution of (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid (0.3 g, 0.545 mmol) in 1.2 dichloroethane (6 mL) and triethylamine (0.165 g, 1.63 mmol), was added bis(2-oxo-3-oxazolidinyl)phosphinic chloride (0.207 g, 0.817 mmol) at 0° C. and the resulting mixture was stirred at 0° C. for 1 h. Then 3-morpholinopropan-1-ol (0.119 g, 0.817 mmol) was added at 0° C. and the reaction mixture was stirred at room temperature for 16 h. After completion, the reaction mixture was diluted with water (10 mL) and extracted with dichloromethane (2×30 mL). The combined organic layer was dried over anhydrous sodium sulphate and concentrated under reduced pressure to give crude product. The obtained crude residue was then purified by column chromatography over silica gel (230-400 mesh) using 4% methanol in dichloromethane as a gradient to afford 3-morpholinopropyl (R)-7-(3-((tert-butoxycarbonyl)amino)-4(2,4,5-trifluorophenyl)butanoyl)-3-(trifluoromethyl)-5,6,7,8-tetrahydroimidazo[1,5-a]pyrazine-1-carboxylate (0.21 g, 57.2%) as an off-white solid. TLC system. MeOH:DCM (1:9); $R_f$: 0.3.

Step 2. 3-morpholinopropyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate

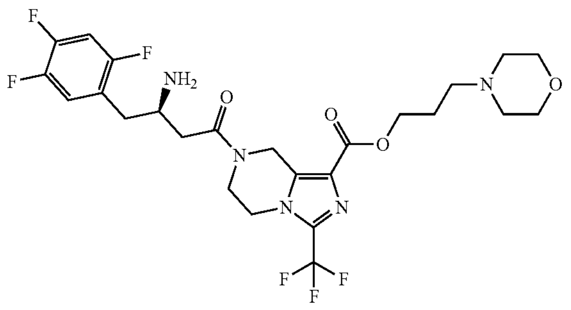 [SMILES: N[C@@H](CC(=O)N1CCn2c(C(F)(F)F)nc(C(=O)OCCCN3CCOCC3)c2C1)Cc1cc(F)c(F)cc1F]

To a stirred solution of 3-morpholinopropyl (R)-7-(3-((tert-butoxycarbonyl)amino)-4(2,4,5-trifluorophenyl)butanoyl)-3-(trifluoromethyl)-5,6,7,8-tetrahydroimidazo[1,5-a]pyrazine-1-carboxylate (0.21 g, 0.31 mmol) in 1.4 dioxane (2 mL) was added 4.0 M in dioxane (2 mL) at 0° C. and the reaction mixture was stirred at room temperature for 4 h. After completion, the reaction mixture was concentrated under reduced pressure to give crude product. Obtained crude was purified by RP preparative HPLC using following conditions. Column/dimensions: X select C18 (19*250 mm)

5μ, mobile phase A: 10 mM ammonium bicarbonate in water, mobile phase B: acetonitrile, gradient (time/% B): 0.01/25, 1/25, 9/40, 13/40, 13.1/100, 18/100, 18.1/25, 20/25 flow rate: 18 ml/min. The desired fraction was lyophilized to afford 3-morpholinopropyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.125 g, 69.8%) as a colorless gum. TLC system. MeOH:DCM (1:9); $R_f$: 0.05.

Step 3. (R)-4-(1-((3-morpholinopropoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (51)

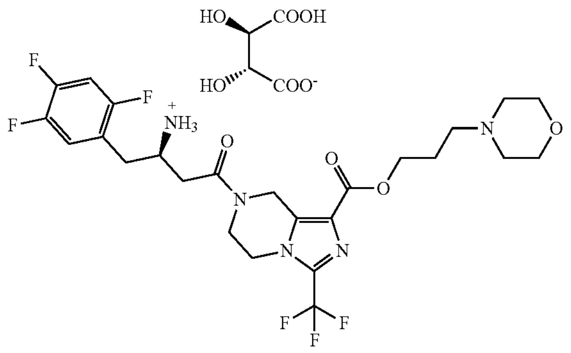

To a stirred solution of 3-morpholinopropyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.125 g, 0.216 mmol) in mixture of dichloromethane (4 mL) and methanol (1.0 mL) was added L(+)-tartaric acid (0.032 g, 0.216 mmol) and the mixture was stirred at room temperature for 6 h. The reaction mixture was concentrated, washed with n-pentane (2×5 mL). The resulting residue was dissolved in water and lyophilized to afford (R)-4-(1-((3-morpholinopropoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (0.077 g) as off-white solid. LCMS M/Z 578.22. $^1$H NMR (400 MHz, DMSO) δ 7.56-7.46 (m, 2H), 4.94 (d, J=11.9 Hz, 2H), 4.28 (t, J=6.6 Hz, 5H), 3.90 (s, 6H), 3.56 (s, 4H), 2.86 (s, 3H), 2.72-2.66 (m, 2H), 2.38 (dd, J=13.7, 6.5 Hz, 6H), 1.89-1.80 (m, 2H).

Example 39. Synthesis of (R)-4-(1-((2-(2-morpholinoethoxy)ethoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate Salt) (52)

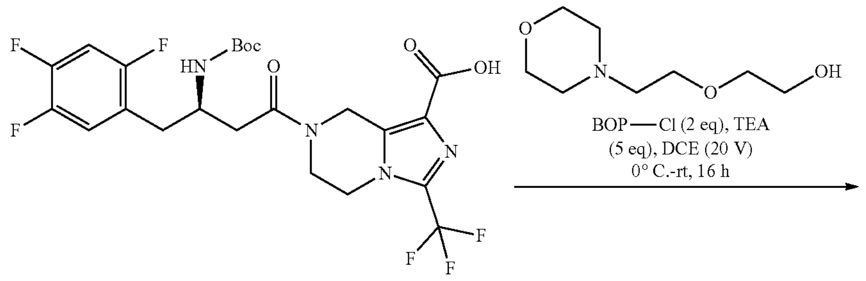

Int-21

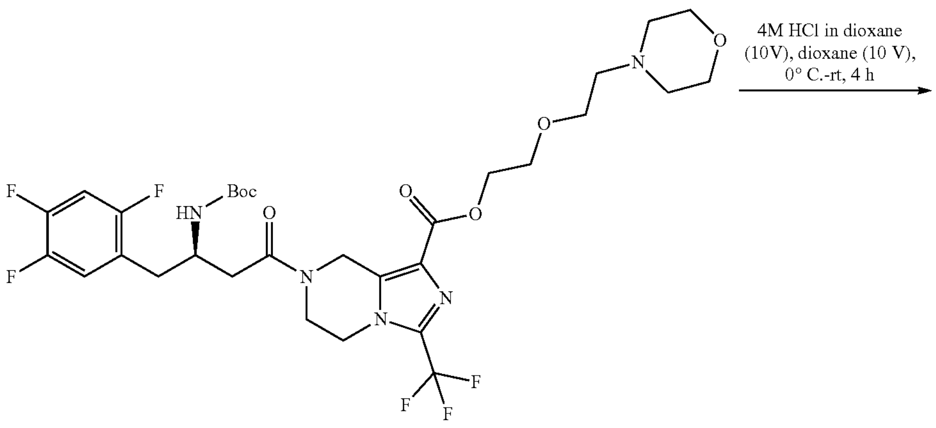

-continued

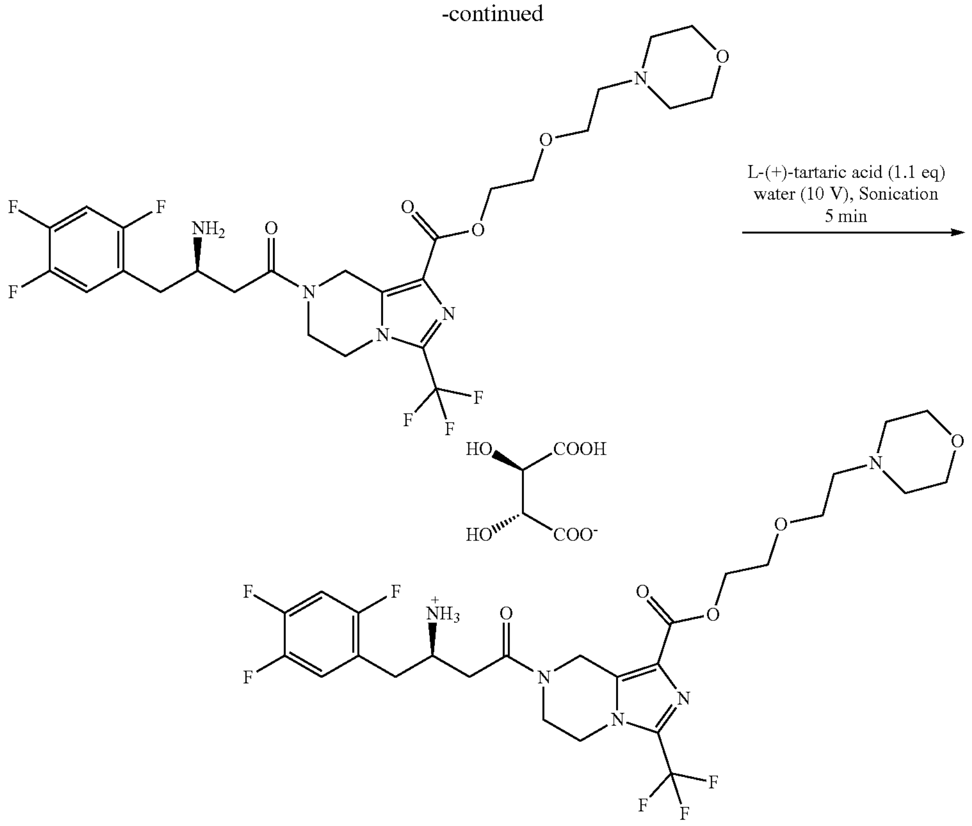

Step 1. 2-(2-morpholinoethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate

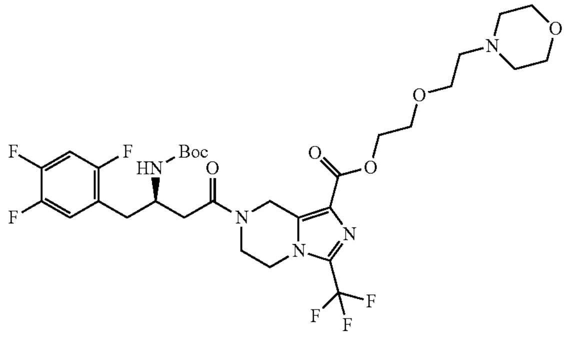 [SMILES: CC(C)(C)OC(=O)N[C@@H](CC(=O)N1CCn2c(C(F)(F)F)nc(C(=O)OCCOCCN3CCOCC3)c2C1)Cc1cc(F)c(F)cc1F]

To a stirred solution of (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine—To a mixture of 1-carboxylic acid (0.3 g, 0.54 mmol) in 1.2 dichloroethane (6 mL) and triethylamine (0.27 g, 2.7 mmol) was added bis(2-oxo-3-oxazolidinyl)phosphinic chloride (0.28 g, 1.09 mmol) at 0° C. and the resulting mixture was stirred at 0° C. for 1 h. Then 2-(2-morpholinoethoxy)ethan-1-ol (0.191 g, 1.09 mmol) was added at 0° C. and the reaction mixture was stirred at room temperature for 16 h. After completion, the reaction mixture was diluted with water (10 mL) and extracted with dichloromethane (2×30 mL). The combined organic layer was dried over anhydrous sodium sulphate and concentrated under reduced pressure to give crude product. The obtained crude residue was then purified by column chromatography over silica gel (230-400 mesh) using 4% methanol in dichloromethane as a gradient to afford 22-(2-morpholinoethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.32 g, 83.1%) as an off-white solid. TLC system. MeOH:DCM (1:9); $R_f$: 0.3.

Step 2. 2-(2-morpholinoethoxy)ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate

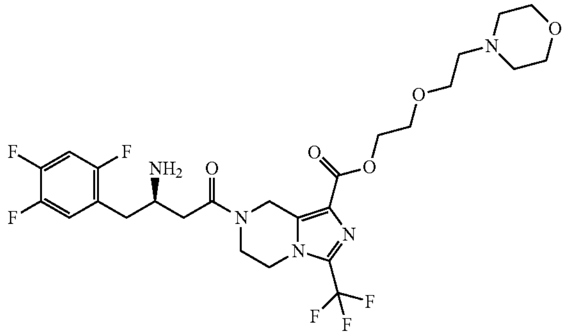 [SMILES: N[C@@H](CC(=O)N1CCn2c(C(F)(F)F)nc(C(=O)OCCOCCN3CCOCC3)c2C1)Cc1cc(F)c(F)cc1F]

To a stirred solution of 2-(2-morpholinoethoxy)ethyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.32 g, 0.45 mmol) in 1.4 dioxane (3.2 mL) was added 4.0 M HCl in dioxane (3.2 mL) at 0° C. and the mixture was stirred at room temperature for 4 h. After completion, the reaction mixture was concentrated under reduced pressure to give crude product. The crude product was then purified by reverse phase preparative HPLC using following conditions. Column/dimensions: X-bridge-C18 (19*250 mm) 5 um, mobile phase A: 10 mM ammonium bicarbonate in water, mobile phase B: acetonitrile, gradient (time/% B): 0/5, 1/5, 12/75, 14/75, 14.05/98, 16.50/98, 16.51/5, 19/5, flow rate: 18 ml/min. The desired fraction was lyophilized to afford 2-(2-morpholinoethoxy) ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.14 g, 51.1%) as a colorless gum. TLC system. MeOH:DCM (1:9); $R_f$: 0.05.

Step 3. (R)-4-(1-((2-(2-morpholinoethoxy)ethoxy) carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate salt) (52)

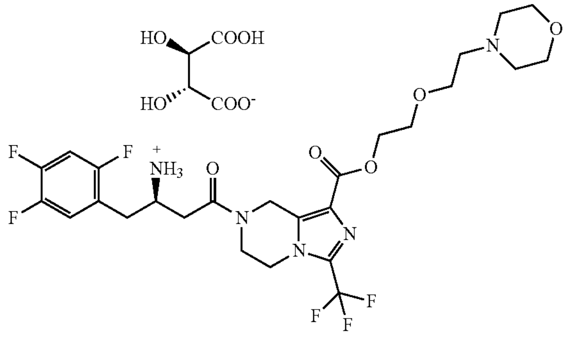

Mixture of 2-(2-morpholinoethoxy)ethyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.14 g, 0.23 mmol) and L(+)-tartaric acid (0.038 g, 0.25 mmol) in demineralized water (1.4 mL) was sonicated to get clear solution. The resulting solution was lyophilized to afford (R)-4-(1-((2-(2-morpholinoethoxy)ethoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (0.172 g) as an off-white solid. LCMS M/Z 608.46. $^1$H NMR (400 MHz, DMSO) δ 7.53 (q, J=9.6 Hz, 2H), 4.95 (q, J=18.0 Hz, 2H), 4.40-4.05 (m, 6H), 3.92 (d, J=12.6 Hz, 5H), 3.68 (t, J=4.8 Hz, 5H), 3.50 (t, J=4.6 Hz, 4H), 2.73 (s, 2H), 2.46 (d, J=5.7 Hz, 3H), 2.38 (s, 4H).

Example 40. Synthesis of (R)-4-(1-(((5-morpholinopentyl)oxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate Salt) (53)

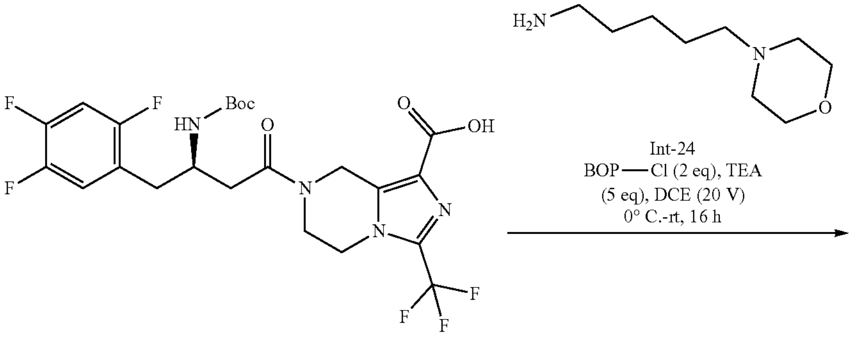

Int-21

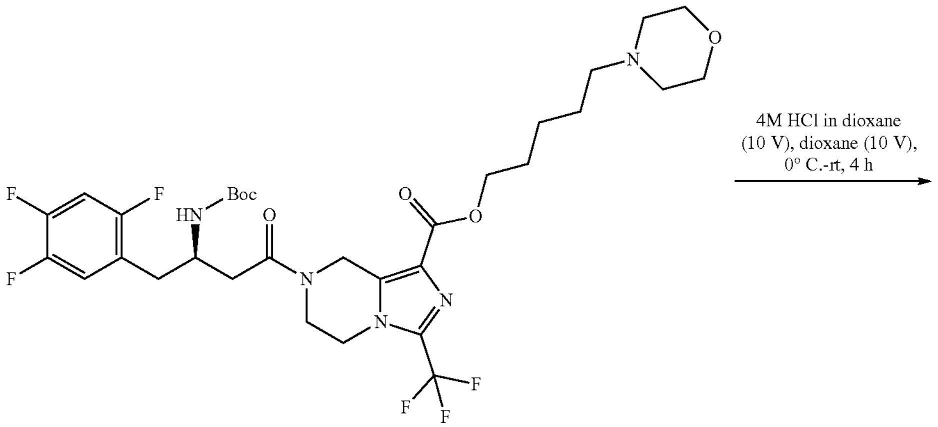

-continued

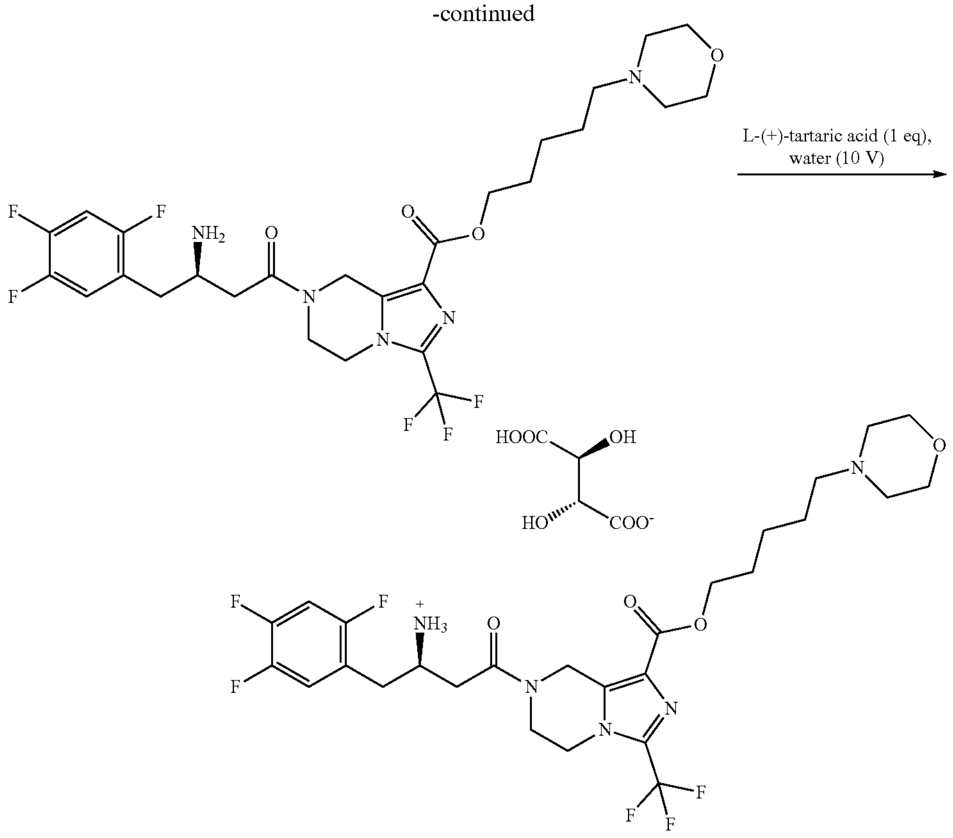

Step 1. 5-morpholinopentyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate

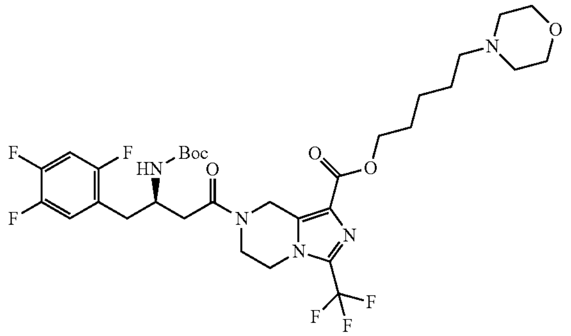 [SMILES: CC(C)(C)OC(=O)N[C@@H](CC(=O)N1CCn2c(C(F)(F)F)nc(C(=O)OCCCCCN3CCOCC3)c2C1)Cc1cc(F)c(F)cc1F]

To a stirred solution of (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid (1.0 g, 1.82 mmol) in 1.2 dichloroethane (20 mL) and triethylamine (1.27 g, 9.1 mmol), was added bis(2-oxo-3-oxazolidinyl)phosphinic chloride (0.93 g, 3.64 mmol) at 0° C. and the resulting mixture was stirred at 0° C. for 1 h. Then 5-morpholinopentan-1-ol (0.94 g, 5.45 mmol) was added at 0° C. and the mixture was stirred at room temperature for 16 h. After completion, the reaction mixture was diluted with water (10 mL) and extracted with dichloromethane (2x30 mL). The combined organic layer was dried over anhydrous sodium sulphate and concentrated under reduced pressure to give crude product. The obtained crude residue was then purified by column chromatography over silica gel (230-400 mesh) using 4% methanol in dichloromethane as a gradient to afford 5-morpholinopentyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.6 g, 46.9%) as a colorless gum. TLC system. MeOH:DCM (1:9); $R_f$: 0.3.

Sep 2. 5-morpholinopentyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate

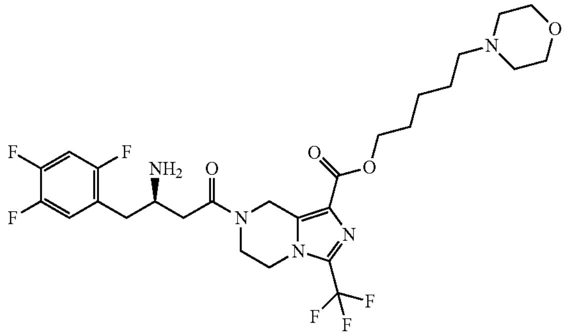 [SMILES: N[C@@H](CC(=O)N1CCn2c(C(F)(F)F)nc(C(=O)OCCCCCN3CCOCC3)c2C1)Cc1cc(F)c(F)cc1F]

To a stirred solution of 5-morpholinopentyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.6 g, 0.85 mmol) in 1.4 dioxane (6 mL) was added 4.0 M HCl in dioxane (6 mL) at 0° C. and the mixture was stirred at room temperature for 4 h. After completion, the reaction mixture was concentrated under reduced pressure to give crude product. The crude product was then purified by RP preparative HPLC using following conditions. Column/dimensions: X select C18 (19*250 mm) 5 um, mobile phase A: 10 mM ammonium bicarbonate in water, mobile phase B: acetonitrile, gradient (time/% B): 0/20, 1/20, 12/50, 16.5/50, 16.6/100, 19/100, 19.1/20, 21/20, flow rate: 18 ml/min. The desired fraction was lyophilized to afford 5-morpholinopentyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.29 g, 56.3%) as a colorless gum. TLC system. MeOH:DCM (1:9); $R_f$: 0.05.

Step 3. (R)-4-(1-(((5-morpholinopentyl)oxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate salt) (53)

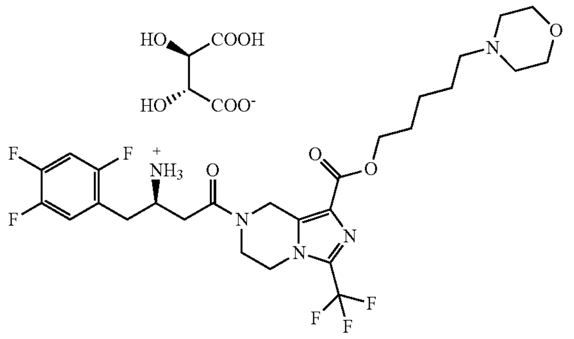

Mixture of 5-morpholinopentyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.19 g, 0.31 mmol) and L(+)-tartaric acid (0.052 g, 0.34 mmol) in demineralized water (1.9 mL) was sonicated for 2 min to get clear solution. The resulting solution was lyophilized to afford (R)-4-(1-(((5-morpholinopentyl)oxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (0.23 g) as an off-white solid. LCMS M/Z 606.48. $^1H$ NMR (400 MHz, DMSO) δ 7.51 (td, J=10.2, 6.9 Hz, 2H), 5.00-4.88 (m, 2H), 4.24 (td, J=7.2, 3.4 Hz, 5H), 3.99-3.87 (m, 5H), 3.68 (s, 2H), 3.54 (t, J=4.5 Hz, 5H), 2.90 (s, 2H), 2.80-2.64 (m, 2H), 2.38-2.26 (m, 6H), 1.68 (p, J=7.3 Hz, 2H), 1.55-1.34 (m, 4H).

Example 41. Synthesis of (R)-4-(1-((4-morpholinobutoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate Salt) (54)

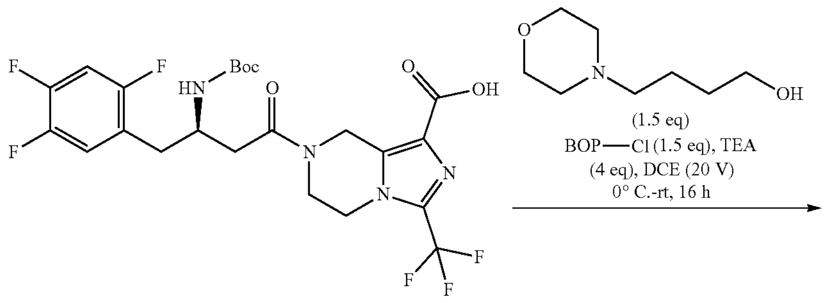

Int-21

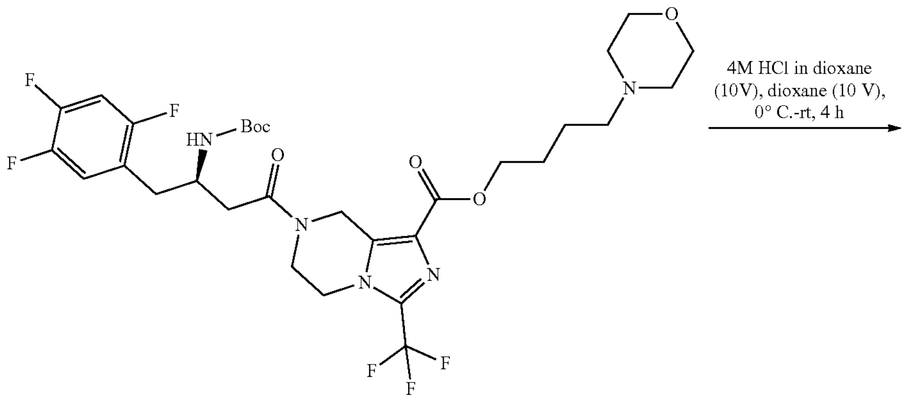

-continued

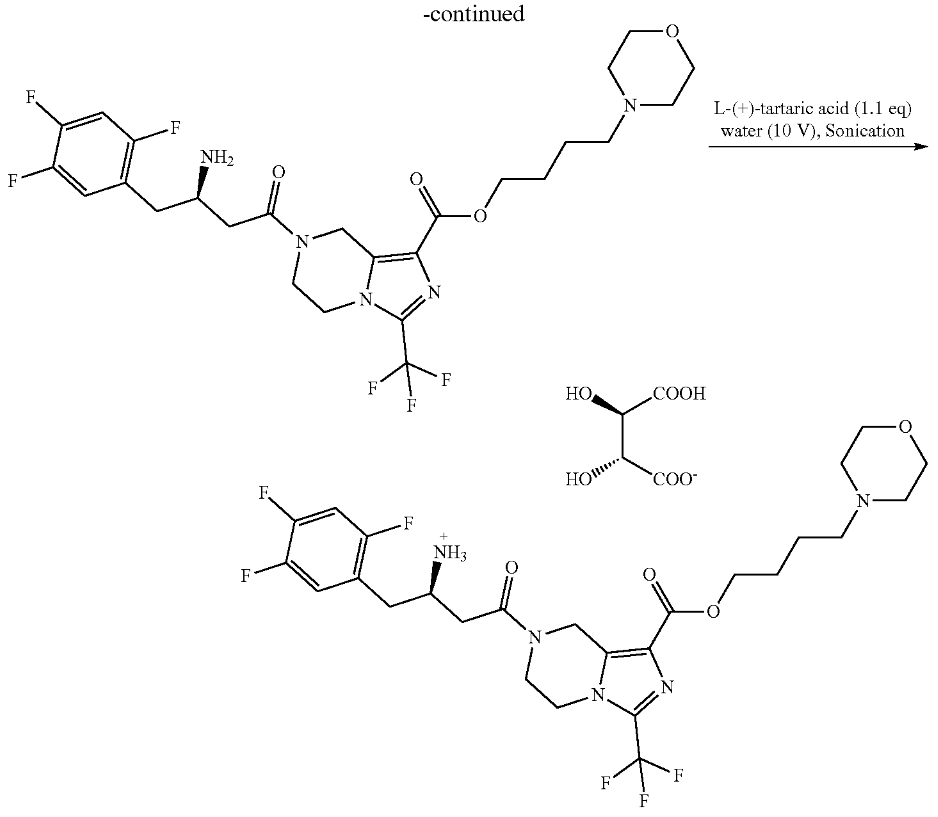

Step 1. 4-morpholinobutyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate

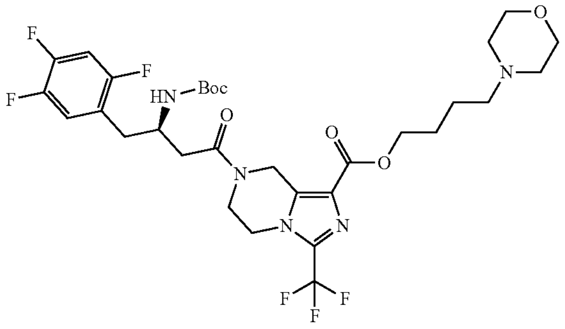 [SMILES: CC(C)(C)OC(=O)N[C@@H](CC(=O)N1CCn2c(C(F)(F)F)nc(C(=O)OCCCCN3CCOCC3)c2C1)Cc1cc(F)c(F)cc1F]

To a stirred solution of (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid (0.5 g, 0.91 mmol) in 1.2 dichloroethane (10 mL) and triethylamine (0.37 g, 3.64 mmol) was added bis(2-oxo-3-oxazolidinyl)phosphinic chloride (0.35 g, 1.36 mmol) at 0° C. and the mixture was stirred at 0° C. for 1 h. Then 4-morpholinobutan-1-ol (0.22 g, 1.36 mmol) was added at 0° C. and the reaction mixture was stirred at room temperature for 16 h. After completion, the reaction mixture was diluted with water (10 mL) and extracted with dichloromethane (2×30 mL). The combined organic layer was dried over anhydrous sodium sulphate and concentrated under reduced pressure to give crude product. The crude residue was then purified by column chromatography over silica gel (230-400 mesh) using 4% methanol in dichloromethane as an eluent to afford 4-morpholinobutyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.45 g, 71.6%) as an off-white solid. TLC system. MeOH:DCM (1:9); $R_f$: 0.3.

Step 2. 4-morpholinobutyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate

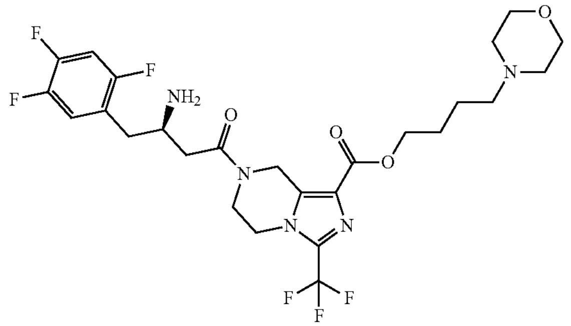 [SMILES: N[C@@H](CC(=O)N1CCn2c(C(F)(F)F)nc(C(=O)OCCCCN3CCOCC3)c2C1)Cc1cc(F)c(F)cc1F]

To a stirred solution of 4-morpholinobutyl (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylate (0.45 g, 0.65 mmol) in 1.4 dioxane (4.5 mL) was added 4.0 M HCl in dioxane (4.5 mL) at 0° C. and the mixture was stirred at room temperature for 4 h. After completion, the reaction mixture was concentrated under reduced pressure to give crude product. The crude product was then purified by RP preparative HPLC using following conditions. Column/dimensions: X-bridge C 18 (19*250 mm) 5μ, mobile phase A: 10 MM ammonium bicarbonate in water, mobile phase B: acetonitrile (org), gradient (time/%

B): 0/20, 2/20, 10/45, 14/45, 14.10/100, 16/100, 16.10/20, 18/20, flow rate: 17 ml/min. The desired fraction was lyophilized to afford 4-morpholinobutyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.16 g, 41.7%) as colorless gum. TLC system. MeOH:DCM (1:9); $R_f$: 0.05.

Step 3. (R)-4-(1-((4-morpholinobutoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate salt) (54)

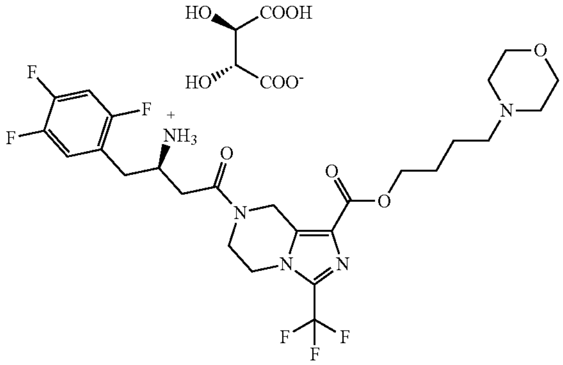

Mixture of 5-morpholinopentyl 4-morpholinobutyl (R)-7-(3-amino-4-(2,4,5-trifluorophenyl)butanoyl)-3-(trifluoromethyl)-5,6,7,8-tetrahydroimidazo[1,5-a]pyrazine-1-carboxylate (0.09 g, 0.15 mmol) and L(+)-tartaric acid (0.025 g, 0.167 mmol) in demineralized water (1 mL) was sonicated to get clear solution. The resulting solution was lyophilized to afford (R)-4-(1-((4-morpholinobutoxy)carbonyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (0.115 g) as an off-white solid. LCMS M/Z 592.49. $^1$H NMR (400 MHz, DMSO) δ 7.53 (q, J=8.2 Hz, 2H), 4.94 (d, J=11.9 Hz, 2H), 4.25 (dd, J=7.7, 5.3 Hz, 5H), 3.93 (s, 5H), 3.64 (d, J=6.5 Hz, 5H), 2.87 (d, J=7.4 Hz, 2H), 2.78-2.64 (m, 2H), 2.45-2.13 (m, 6H), 1.68 (d, J=8.2 Hz, 2H), 1.54 (q, J=7.4 Hz, 2H).

Example 42. Synthesis of (R)-4-(1-((2-methyl-2-azaspiro[3.3]heptan-6-yl)carbamoyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate Salt) (55)

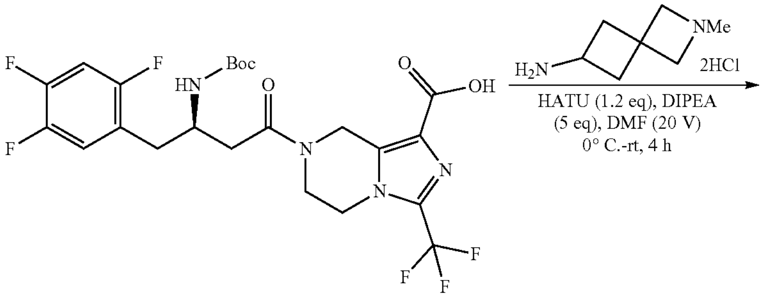

Int-21

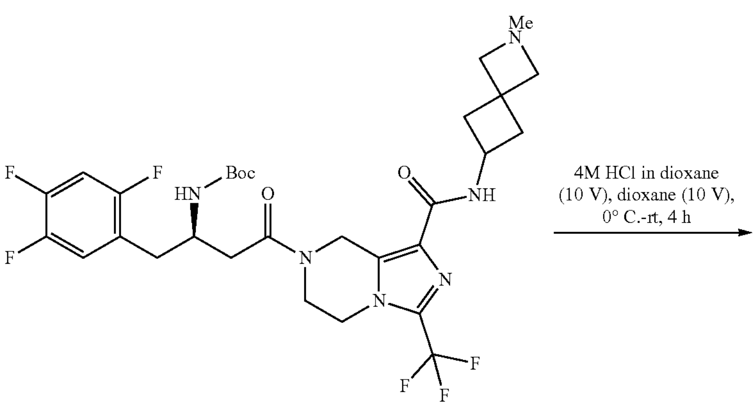

-continued

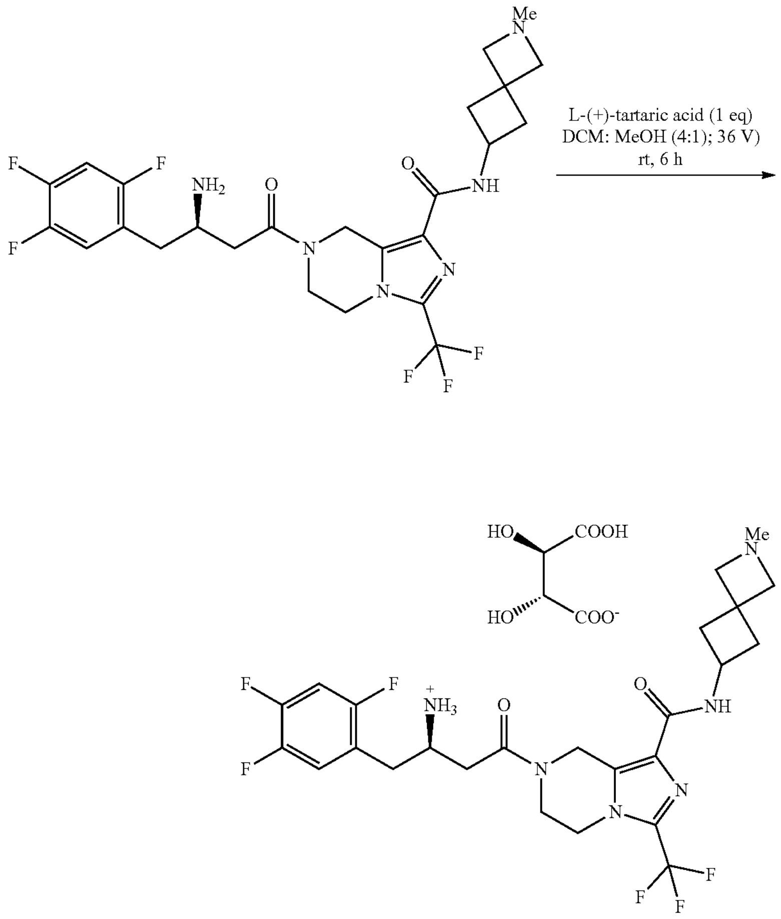

Step 1. Tert-butyl (R)-(4-(1-((2-methyl-2-azaspiro[3.3]heptan-6-yl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate

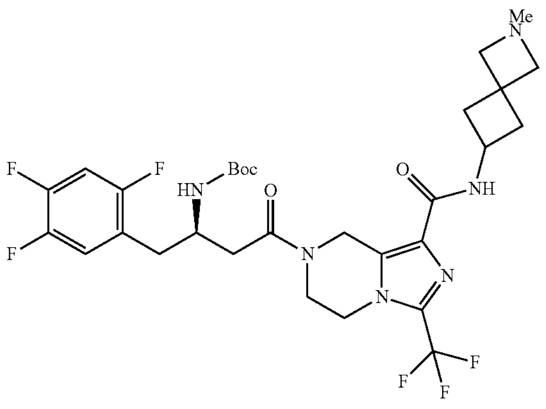 [SMILES: CN1CC2(CC(NC(=O)c3nc(C(F)(F)F)n4c3CN(C(=O)C[C@@H](Cc3cc(F)c(F)cc3F)NC(=O)OC(C)(C)C)CC4)C2)C1]

To a stirred solution of (R)-7-(3-((tert-butoxycarbonyl)amino)-4-(2,4,5-trifluorophenyl)butanoyl)-3-(trifluoromethyl)-5,6,7,8-tetrahydroimidazo[1,5-a]pyrazine-1-carboxylic acid (0.5 g, 0.91 mmol), 2-methyl-2-azaspiro[3.3]heptan-6-amine hydrochloride (0.18 g, 0.91), (1-[Bis(dimethylamino)methylene]-1H-1,2,3-triazolo[4,5-b]pyridinium 3-oxide hexafluorophosphate (0.415 g, 0.1.09 mmol) in N,N-dimethylformamide (5 mL) was slowly added N,N-diisopropylethylamine (0.59 g, 4.55 mmol) at 0° C. and the reaction mixture was stirred at at room temperature for 4 h. After completion, the reaction mixture was diluted with water (30 mL) and extracted with ethyl acetate (3-100 mL). The combined organic layer was dried over anhydrous sodium sulphate and concentrated under reduced pressure to give crude product. The obtained crude residue was then purified by column chromatography over silica gel (230-400 mesh) using 4% methanol in dichloromethane as an eluent to afford tert-butyl (R)-(4-(1-((2-methyl-2-azaspiro[3.3]heptan-6-yl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate (0.3 g, 50.2%) as an off-white solid. TLC system. MeOH:DCM (1:9); $R_f$: 0.3.

Step 2. (R)-7-(3-amino-4-(2,4,5-trifluorophenyl) butanoyl)-N-(2-methyl-2-azaspiro[3.3]heptan-6-yl)-3-(trifluoromethyl)-5,6,7,8-tetrahydroimidazo[1,5-a] pyrazine-1-carboxamide

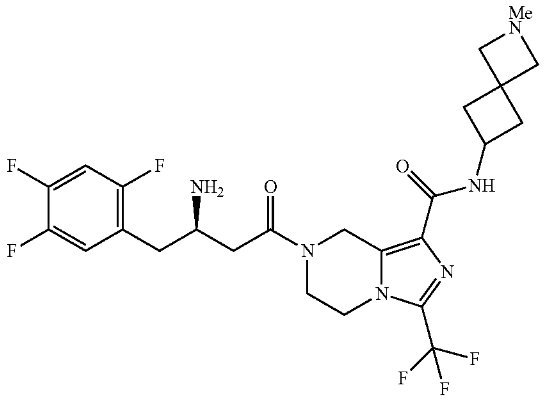 [SMILES: CN1CC2(CC(NC(=O)c3nc(C(F)(F)F)n4c3CN(C(=O)C[C@H](N)Cc3cc(F)c(F)cc3F)CC4)C2)C1]

To a stirred solution of tert-butyl (R)-(4-(1-((2-methyl-2-azaspiro[3.3]heptan-6-yl)carbamoyl)-3-(trifluoromethyl)-5,6-dihydroimidazo[1,5-a]pyrazin-7(8H)-yl)-4-oxo-1-(2,4,5-trifluorophenyl)butan-2-yl)carbamate (0.3 g, 0.45 mmol) in 1.4 dioxane (3 mL), was added 4.0 M HCl in dioxane (3 mL) at 0° C. and the mixture was stirred at room temperature for 4 h. After completion, the reaction mixture was concentrated under reduced pressure to give crude product. The obtained crude was then purified by RP preparative HPLC using following conditions. Column/dimensions: X-select C 18 (19*250 mm) 5μ, mobile phase A: 10 MM ammonium bicarbonate in water, mobile phase B: acetonitrile (org), gradient (time/% B): 0/10, 1/10, 10/40, 16/63.2, 16.1/100, 19/100, 19.1/10, 22/10, flow rate: 17 ml/min. The desired fraction was lyophilized to afford (R)-7-(3-amino-4-(2,4,5-trifluorophenyl)butanoyl)-N-(2-methyl-2-azaspiro[3.3]heptan-6-yl)-3-(trifluoromethyl)-5,6,7,8-tetrahydroimidazo[1,5-a]pyrazine-1-carboxamide (0.09 g, 35.4%) as an off-white solid. TLC system. MeOH:DCM (1:9); $R_f$: 0.05.

Step 3. (R)-4-(1-((2-methyl-2-azaspiro[3.3]heptan-6-yl)carbamoyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (Tartrate salt) (55)

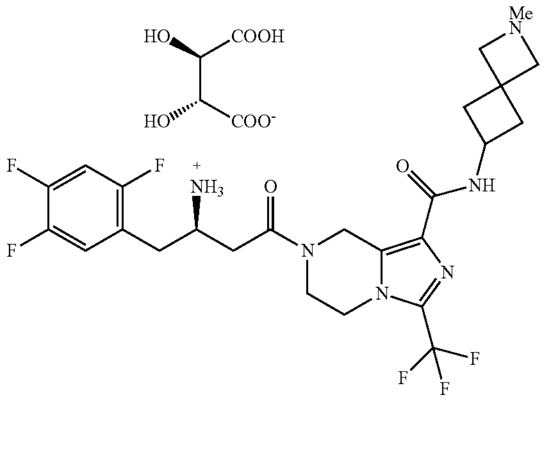

Mixture of (R)-7-(3-amino-4-(2,4,5-trifluorophenyl)butanoyl)-N-(2-methyl-2-azaspiro[3.3]heptan-6-yl)-3-(trifluoromethyl)-5,6,7,8-tetrahydroimidazo[1,5-a]pyrazine-1-carboxamide (0.14 g, 0.25 mmol), in dichloromethane (4 mL) and methanol (I mL) mixture L(+) tartaric acid (0.038 g, 0.25 mmol) was added and the reaction mixture was stirred at room temperature for 6 h. The reaction mixture was concentrated, residue was washed with n-pentane (2×5 mL) and residue was dissolved demineralized water (3 mL). The resulting solution was lyophilized to afford (R)-4-(1-((2-methyl-2-azaspiro[3.3]heptan-6-yl)carbamoyl)-3-(trifluoromethyl)-5,6-dihydroimidazo[1,5-a]pyrazin-7(8H)-yl)-4-oxo-1-(2,4,5-trifluorophenyl)butan-2-aminium (2R,3R)-3-carboxy-2,3-dihydroxypropanoate (0.155 g) as an off-white solid. LCMS M/Z 559.46. $^1H$ NMR (400 MHz, DMSO) δ 8.40-8.22 (m, 1H), 7.48 (q, J=9.2 Hz, 2H), 4.91 (d, J=14.9 Hz, 2H), 4.26 (dd, J=16.4, 8.0 Hz, 3H), 4.11 (s, 1H), 3.89 (s, 3H), 3.83 (s, 3H), 2.78 (d, J=7.1 Hz, 2H), 2.70-2.56 (m, 3H), 2.45-2.28 (m, 7H).

Example 45: In Vitro and Additional Characterizing Data

DPP4 activity assay. Human DPP4 activity assay data were obtained using a DPP4 Activity Assay Kit (Sigma-Aldrich, MAK088) according to the manufacturer's instructions. Briefly, 10 μL of DPP4 Assay Buffer were transferred per well in low volume 384-well plates before transferring 10 μL of test compound dissolved in DPP4 assay buffer. To each well was added 5 μL of Master Reaction Mix containing a fluorescent substrate that becomes fluorescent upon cleavage by the enzyme. Fluorescence intensity measurements were recorded at 1-minute time intervals over the course of 20 minutes using an Envision Multimode Plate Reader (PerkinElmer). Results are presented in Table 4 below.

AEC2 proliferation assay. Primary human AEC2s were plated at a density of 1,500 cells per well in black 384-well plates (Greiner) coated with 10 ug/mL Laminin (Life Technologies) in 50 μL of Small Airway Epithelial Cell Growth Medium (Lonza) without EGF, retinoic acid and with 5% BPE. 100 nL of test compound dissolved in DMSO was then delivered using a Biomek FX instrument (Beckman Coulter) fitted with a pintool head (V & P Scientific). After 96 hours of growth at 37° C., cells were fixed with 4% paraformaldehyde, washed three times with PBS, and then immunostained for KI-67 positivity (1:1000, Abcam, ab15580) overnight at 4° C. After three additional washes, the cells were incubated with secondary AlexaFluor conjugated secondary antibody for 1 hour at room temperature and then exposed to 10 μg/mL Hoechst 33342 (Life Technologies). Plates were sealed, and then quantitative high content imaging carried out on CellInsight CX5 HCS instrument (ThermoFisher). The ACE2 proliferation concentration curve for compound 46 is depicted in FIG. 1.

TABLE 4

Compound characterization and Inhibition of DPP4 data ($IC_{50}$)

| | Structure | DPP4 inhibition $IC_{50}$ [nM]) | $[M + 1]^+$/ $[M - H]^-$ | $^1H$ NMR |
|---|---|---|---|---|
| 1 | 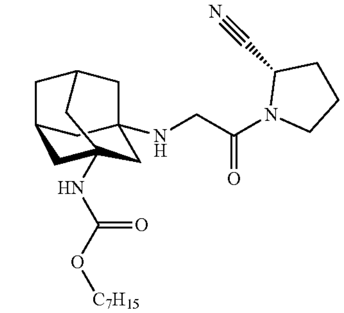 | 31 | 445.31 | $^1H$ NMR (400 MHz, DMSO-$d_6$) 6.79 (s, 1H), 4.73 (dd, J = 7.3, 3.8 Hz, 1H), 3.85 (t, J = 6.4 Hz, 2H), 3.65-3.55 (m, 1H), 3.51-3.38 (m, 2H), 3.36 (d, J = 7.3 Hz, 1H), 3.29 (s, 1H), 2.17-2.06 (m, 4H), 2.05-1.95 (m, 2H), 1.72 (d, J = 17.5 Hz, 6H), 1.49 (d, J = 12.8 Hz, 8H), 1.26 (s, 8H), 0.86 (t, J = 6.9 Hz, 3H). |
| 2 | 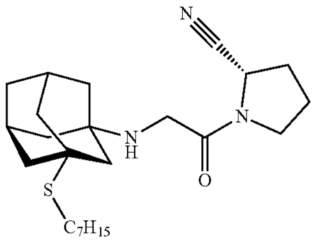 | 26 | 418.281 | $^1H$ NMR (400 MHz, $CD_3OD$) 8.40 (s, 1H), 4.81 (t, J = 5.2 Hz, 1H), 3.99-3.87 (m, 2H), 3.74-3.68 (m, 1H), 3.56-3.49 (m, 1H), 2.56 (t, J = 7.2 Hz, 2H), 2.35-2.24 (m, 4H), 2.23-2.14 (m, 2H), 2.01-1.94 (m, 2H), 1.92-1.78 (m, 8H), 1.73-1.65 (m, 2H), 1.57-1.50 (m, 2H), 1.43-1.36 (m, 2H), 1.35-1.24 (m, 6H), 0.90 (t, J = 6.8 Hz, 3H). |
| 3 | 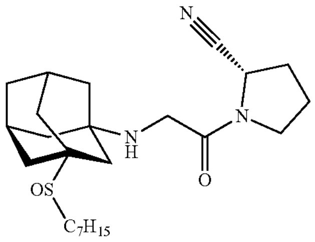 | 9 | 434.276 | 1H NMR (400 MHz, CD3OD) 8.38 (s, 1H), 4.82-4.79 (m, 1H), 3.95-3.84 (m, 2H), 3.75-3.70 (m, 1H), 3.56-3.50 (m, 1H), 2.72-2.66 (m, 2H), 2.43 (s, 2H), 2.31-2.25 (m, 2H), 2.22-2.14 (m, 2H), 2.01-1.72 (m, 14H), 1.57-1.45 (m, 2H), 1.42-1.35 (m, 2H), 1.33-1.31 (m, 4H), 0.92-0.89 (m, 3H). |
| 4 | 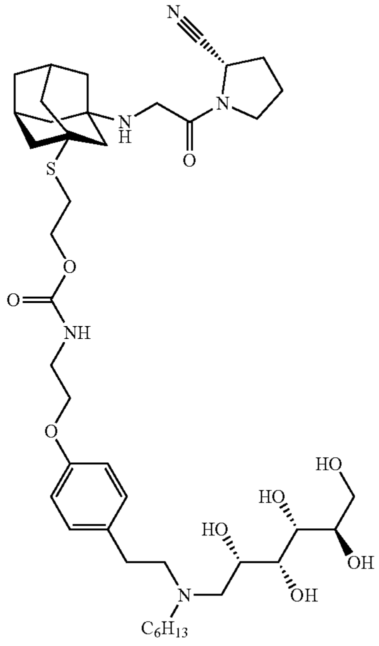 | 11 | 818.466 | 1H NMR (400 MHz, MeOD) δ 8.53 (s, 2H), 7.24 (d, J = 8.1 Hz, 2H), 6.94 (d, J = 8.2 Hz, 2H), 4.77-4.86 (m, 1H), 4.24-3.97 (m, 5H), 3.94-3.78 (m, 4H), 3.77-3.63 (m, 4H), 3.61-3.45 (m, 3H), 3.44-3.33 (m, 5H), 3.22-3.15 (m, 2H), 3.10-2.95 (m, 2H), 2.88-2.73 (m, 2H), 2.40-2.10 (m, 6H), 2.02-1.92 (m, 2H), 1.88-1.66 (m, 11H), 1.45-1.30 (m, 6H), 1.00-0.90 (m, 3H). |

TABLE 4-continued

| | Compound characterization and Inhibition of DPP4 data ($IC_{50}$) | | | |
|---|---|---|---|---|
| | Structure | DPP4 inhibition $IC_{50}$ [nM]) | $[M + 1]^+$/ $[M - H]^-$ | $^1H$ NMR |
| 5 | 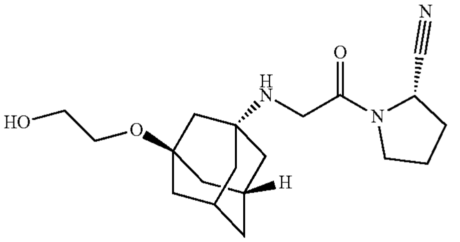 [SMILES: N#C[C@@H]1CCCN1C(=O)CN[C@@]12CC3C[C@@H](C1)C[C@](OCCO)(C3)C2] | 2.3 | 348.65 | $^1H$ NMR (400 MHz, DMSO-$d_6$) δ 4.74-4.72 (m, 1H), 4.46 (bs, 1H), 3.63-3.32 (m, 8H), 2.17-2.11 (m, 4H), 2.03-1.99 (m, 2H), 1.68 (t, J = 6.0 Hz, 1H), 1.60-1.40 (m, 12H). |
| 6 | 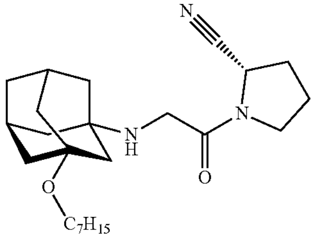 | 31 | 402.304 | $^1H$ NMR (400 MHz, $CDCl_3$) 4.73 (d, 1H), 3.91 (d, 1H), 3.71-3.52 (m, 4H), 3.38 (t, 2H), 2.38 (s, 2H), 2.27-2.10 (m, 4H), 1.83-1.73 (m, 10H), 1.58 (s, 2H), 1.50 (t, 2H), 1.28 (s, 8H), 0.88 (t, J = 7.2 Hz, 3H). |
| 7 | 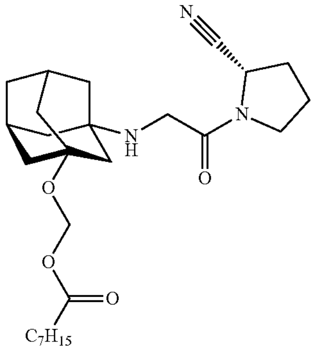 | 32 | 460.31 | $^1H$ NMR (400 MHz, $CDCl_3$) 5.39 (s, 2H), 4.87-4.73 (m, 1H), 3.66-3.39 (m, 4H), 2.36-2.25 (m, 6H), 2.24-2.13 (m, 2H), 1.83 (s, 3H), 1.80-1.68 (m, 6H), 1.66-1.56 (m, 6H), 1.33-1.24 (m, 8H), 0.88 (t, J = 7.2 Hz, 3H). |
| 8 | 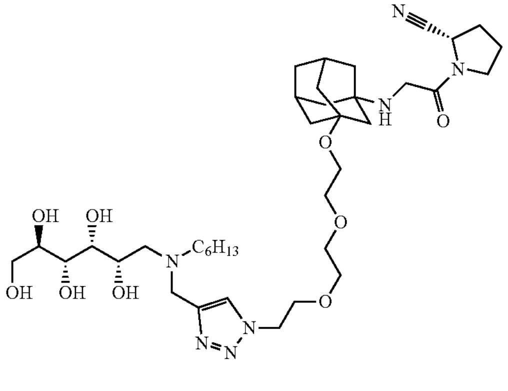 | 14.2 | 764.484 | $^1H$-NMR (400 MHz, $CDCl_3$) δ 7.73 (s, 1H), 4.92-4.70 (m, 1H), 4.52 (br t, J = 4.5 Hz, 2H), 3.94-3.82 (m, 5H), 3.81-3.71 (m, 4H), 3.71-3.63 (m, 3H), 3.56 (br d, J = 19.3 Hz, 9H), 3.47-3.33 (m, 3H), 2.77-2.58 (m, 2H), 2.53 (td, J = 7.7, 12.7 Hz, 1H), 2.47-2.37 (m, 1H), 2.36-2.01 (m, 6H), 1.99 (s, 1H), 1.75-1.40 (m, 14H), 1.23 (br s, 6H), 0.84 (br t, J = 6.7 Hz, 3H). |

TABLE 4-continued
Compound characterization and Inhibition of DPP4 data ($IC_{50}$)
| | Structure | DPP4 inhibition $IC_{50}$ [nM]) | $[M + 1]^+$/ $[M - H]^-$ | $^1H$ NMR |
|---|---|---|---|---|
| 9 | 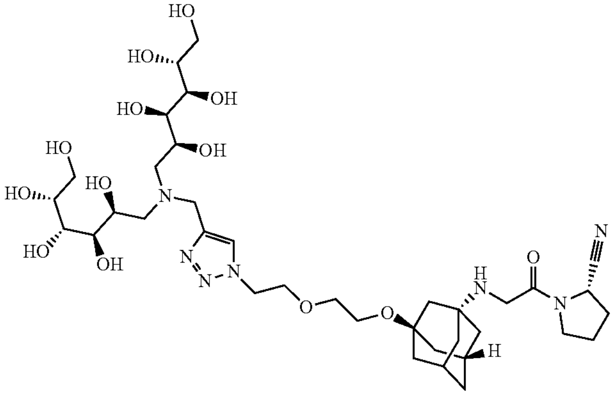 [SMILES: N#C[C@@H]1CCCN1C(=O)CN[C@@]12CC3C[C@@H](C1)C[C@](OCCOCCn1cc(CN(C[C@H](O)[C@@H](O)[C@H](O)[C@H](O)CO)C[C@H](O)[C@@H](O)[C@H](O)[C@H](O)CO)nn1)(C3)C2] | 10.8 | 800.59 | $^1H$ NMR (400 MHz, DMSO-$d_6$) δ 7.95 (s, 1H), 4.75-4.72 (m, 1H), 4.70-4.10 (m, 12H), 3.81-3.72 (m, 6H), 3.63-3.39 (m, 22H), 2.17-1.91 (m, 6H), 1.56-1.44 (m, 12H). |
| 10 | 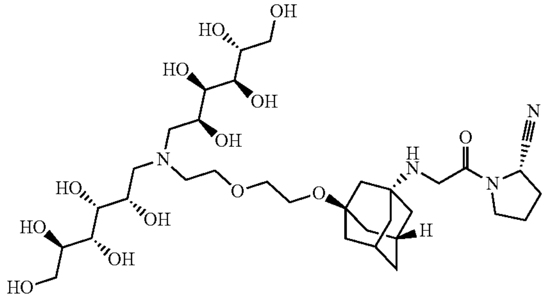 [SMILES: N#C[C@@H]1CCCN1C(=O)CN[C@@]12CC3C[C@@H](C1)C[C@](OCCOCCN(C[C@H](O)[C@@H](O)[C@H](O)[C@H](O)CO)C[C@H](O)[C@@H](O)[C@H](O)[C@H](O)CO)(C3)C2] | 20.8 | 717.52 | $^1H$ NMR (400 MHz, DMSO-$d_6$): δ 4.74-4.70 (m, 1H), 4.51-4.46 (m, 4H), 4.35-4.29 (m, 4H), 4.19 (d, J = 6.4 Hz, 2H), 3.65-3.55 (m, 7H), 3.49-3.33 (m, 16H), 2.75-2.50 (m, 5H), 2.17-1.95 (m, 6H), 1.70 (bs, 1H), 1.59-1.45 (m, 12H). |
| 11 | 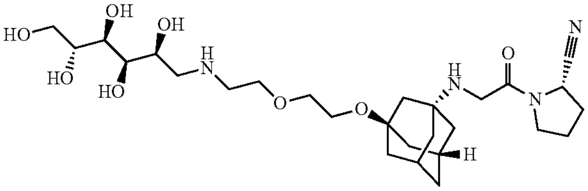 [SMILES: N#C[C@@H]1CCCN1C(=O)CN[C@@]12CC3C[C@@H](C1)C[C@](OCCOCCNC[C@H](O)[C@@H](O)[C@H](O)[C@H](O)CO)(C3)C2] | 31.6 | 555.29 | $^1H$ NMR (400 MHz, DMSO-$d_6$) δ 4.73-4.29 (m, 6H), 3.63-3.13 (m, 17H), 2.67-2.60 (m, 4H), 2.16-1.99 (m, 6H), 1.59-1.45 (m, 12H). |
| 12 | 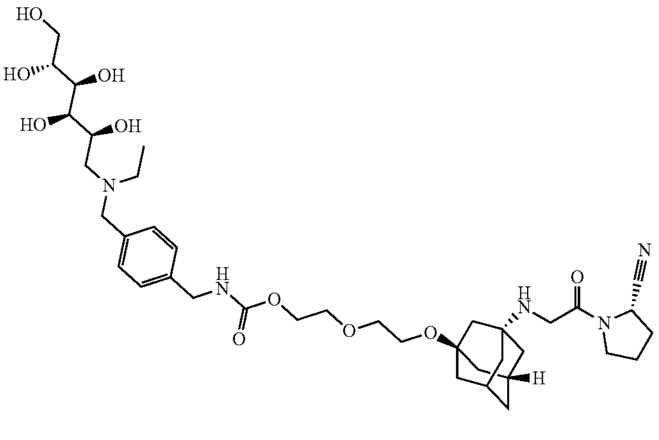 [SMILES: CCN(Cc1ccc(CNC(=O)OCCOCCO[C@@]23CC4C[C@@H](C[C@@](NCC(=O)N5CCC[C@H]5C#N)(C4)C2)C3)cc1)C[C@H](O)[C@@H](O)[C@H](O)[C@H](O)CO] | 7.9 | 746.72 | $^1H$ NMR (400 MHz, DMSO-$d_6$): δ 8.17 (s, 2H), 7.73 (s, 1H), 7.27 (d, J = 7.6 Hz, 2H), 7.17 (d, J = 8.0 Hz, 2H), 4.75-4.74 (m, 3H), 4.16-4.06 (m, 4H), 3.75-3.35 (m, 21H), 2.61-2.50 (m, 1H), 2.46-2.41 (m, 3H), 2.19-1.99 (m, 6H), 1.60-1.52 (m, 12H), 0.94 (t, J = 7.2 Hz, 3H). |

TABLE 4-continued

Compound characterization and Inhibition of DPP4 data ($IC_{50}$)

| | Structure | DPP4 inhibition $IC_{50}$ [nM]) | $[M + 1]^+$/ $[M - H]^-$ | $^1$H NMR |
|---|---|---|---|---|
| 13 | 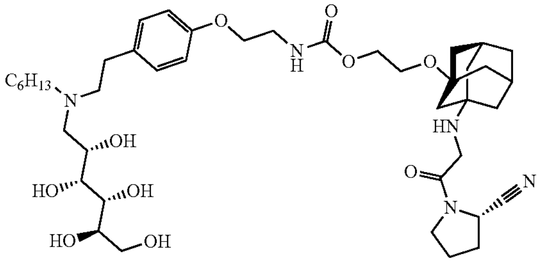 | 23 | 802.489 | $^1$H NMR (400 MHz, $CD_3OD$) 8.48 (s, 2H), 7.22 (d, J = 8.5 Hz, 2H), 6.92 (d, J = 8.6 Hz, 2H), 4.83-4.78 (m, 1H), 4.17-4.07 (m, 3H), 4.05-3.95 (m, 2H), 3.91-3.74 (m, 4H), 3.74-3.60 (m, 6H), 3.55-3.50 (m, 1H), 3.50-3.43 (m, 2H), 3.41-3.32 (m, 4H), 3.26-3.16 (m, 2H), 3.05-2.94 (m, 2H), 2.40-2.09 (m, 6H), 1.85-1.65 (m, 12H), 1.58 (s, 2H), 1.42-1.30 (m, 6H), 0.97-0.89 (m, 3H). |
| 14 | 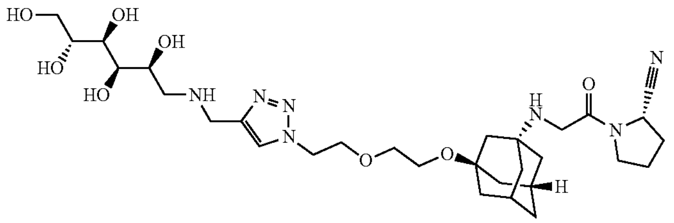 [SMILES: N#C[C@@H]1CCCN1C(=O)CN[C@@]12CC3C[C@@H](C1)C[C@](OCCOCCn1cc(CNC[C@H](O)[C@@H](O)[C@H](O)[C@H](O)CO)nn1)(C3)C2] | 8.2 | 636.49 | $^1$H NMR (400 MHz, DMSO-$d_6$) δ 7.92 (s, 1H), 5.10 (bs, 1H), 4.73-4.65 (m, 2H), 4.49-4.43 (m, 3H), 4.3 (bs, 2H), 3.80-3.36 (m, 19H), 2.64-2.60 (m, 2H), 2.16-2.01 (m, 6H), 1.56-1.46 (m, 12H). |
| 15 | 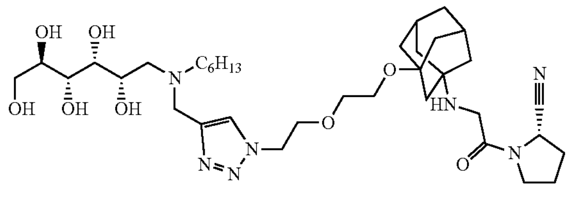 | 17.4 | 720.458 | $^1$H NMR (400 MHz, MeOD) δ 8.44 (br, 2H), 8.13 (s, 1H), 4.82 (t, 1H), 4.60 (t, 2H), 4.24 (d, 2H), 4.08 (dd, 1H), 3.97 (d, 1H), 3.91-3.87 (m, 2H), 3.74-3.56 (m, 12H), 3.01 (d, 2H), 2.89-2.82 (m, 2H), 2.37 (br, 2H), 2.27 (t, 2H), 2.20-2.07 (m, 2H), 1.84-1.68 (m, 12H), 1.61 (s, 2H), 1.31 (s, 6H), 0.91 (t, 3H). |
| 16 | 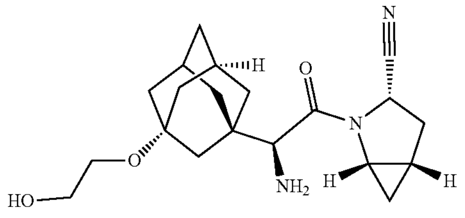 [SMILES: N#C[C@@H]1C[C@@H]2C[C@@H]2N1C(=O)[C@@H](N)[C@]12CC3C[C@H](C[C@](OCCO)(C3)C1)C2] | 7.9 | 360.46 | $^1$H NMR (400 MHz, DMSO-$d_6$) δ 5.10-5.07 (m, 1H), 4.46-4.43 (m, 1H), 3.89-3.87 (m, 1H), 3.45-3.31 (m, 5H), 2.21-2.14 (m, 3H), 1.77-1.32 (m, 14H), 0.97 (m, 1H), 0.72-0.70 (s, 1H). |
| 17 | 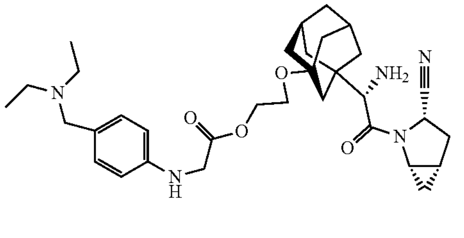 | 28 | 798.494 | $^1$H NMR (500 MHz, MeOD) δ 7.55-7.37 (m, 4H), 5.23 (dd, J = 10.7, 2.3 Hz, 1H), 4.39-4.26 (m, 5H), 4.15 (t, J = 5.0 Hz, 2H), 3.94 (td, J = 6.2, 2.7 Hz, 1H), 3.68 (t, J = 5.1 Hz, 2H), 3.28-3.12 (m, 4H), 2.65 (ddd, J = 14.1, 10.8, 5.7 Hz, 1H), 2.43-2.27 (m, 3H), 2.05 (dq, J = 9.0, 5.6 Hz, 1H), 1.91-1.56 (m, 12H), 1.36 (t, J = 7.3 Hz, 7H), 1.15 (q, J = 6.9 Hz, 1H), 1.02-0.94 (m, 1H). |

TABLE 4-continued

Compound characterization and Inhibition of DPP4 data ($IC_{50}$)

| | Structure | DPP4 inhibition $IC_{50}$ [nM]) | $[M + 1]^+$/ $[M - H]^-$ | $^1H$ NMR |
|---|---|---|---|---|
| 18 | 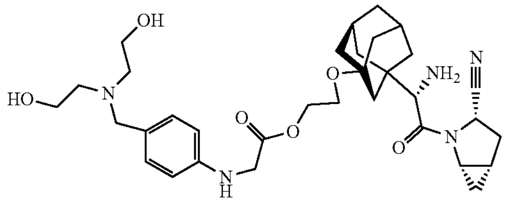 | 12 | 610.353 | $^1H$ NMR (500 MHz, MeOD) δ 7.53 (d, J = 8.1 Hz, 2H), 7.44 (d, J = 7.9 Hz, 2H), 5.23 (dd, J = 10.7, 2.3 Hz, 1H), 4.52 (s, 2H), 4.33 (d, J = 20.1 Hz, 3H), 4.15 (t, J = 5.0 Hz, 2H), 3.98-3.88 (m, 5H), 3.68 (t, J = 5.1 Hz, 2H), 3.37 (m, 4H), 2.65 (ddd, J = 13.8, 10.8, 5.7 Hz, 1H), 2.42-2.29 (m, 3H), 2.05 (dq, J = 8.9, 5.7 Hz, 1H), 1.90-1.58 (m, 13H), 1.36-1.29 (m, 1H), 1.15 (q, J = 6.8 Hz, 1H), 0.98 (ddd, J = 7.1, 5.2, 2.7 Hz, 1H). |
| 19 | 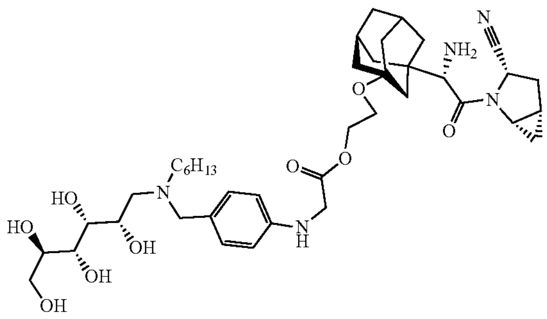 | 25 | 798.494 | $^1H$ NMR (500 MHz, MeOD) δ 7.51 (d, J = 7.8 Hz, 2H), 7.42 (d, J = 7.9 Hz, 2H), 5.21 (dd, J = 10.7, 2.3 Hz, 1H), 4.49-4.30 (m, 4H), 4.23-4.12 (m, 4H), 3.94 (td, J = 6.2, 2.7 Hz, 1H), 3.83-3.75 (m, 2H), 3.73-3.60 (m, 5H), 3.32-3.27 (m, 2H), 3.11 (qdd, J = 13.0, 10.1, 6.1 Hz, 2H), 2.65 (ddd, J = 13.7, 10.6, 5.7 Hz, 1H), 2.39-2.26 (m, 3H), 2.03 (dq, J = 9.0, 5.7 Hz, 1H), 1.90-1.56 (m, 16H), 1.41-1.23 (m, 11H), 1.14 (dt, J = 9.0, 6.4 Hz, 1H), 1.00-0.87 (m, 4H). |
| 20 | 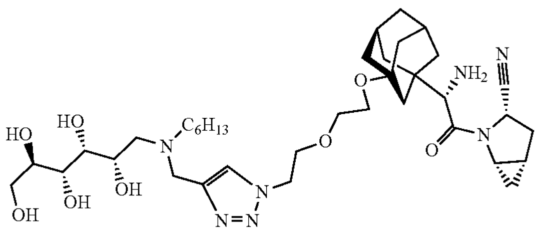 | 47.8 | 732.458 | $^1H$ NMR (400 MHz, MeOD) δ 8.41 (br, 2H), 8.20 (s, 1H), 5.20 (dd, 1H), 4.61 (t, 2H), 4.36 (d, 2H), 4.13 (t, 2H), 3.97 (t, 3H), 3.71-3.64 (m, 5H), 3.49 (s, 4H), 3.91-3.12 (m, 2H), 3.01-2.91 (m, 2H), 2.63-2.59 (m, 1H), 2.31-2.33 (m, 3H), 2.03-1.98 (m, 1H), 1.80-1.57 (m, 14H), 1.32 (s, 6H), 1.10 (dd, 1H), 0.95-0.90 (m, 4H). |
| 21 | 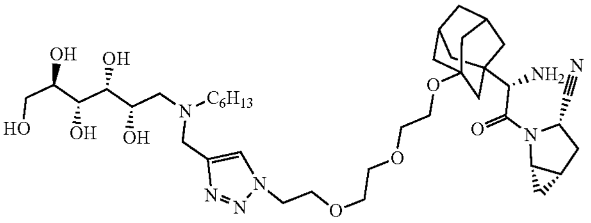 | 7.7 | 776.484 | $^1H$ NMR (400 MHz, MeOD) δ 8.38 (br, 2H), 8.21 (s, 1H), 5.19 (dd, 1H), 4.63 (t, 2H), 4.42 (s, 2H), 4.18-4.15 (m, 2H), 3.98 (t, 3H), 3.70-3.56 (m, 13H), 3.18-3.16 (m, 2H), 3.03-2.93 (m, 2H), 2.63-2.59 (m, 1H), 2.37-2.31 (m, 3H), 2.01-1.98 (m, 1H), 1.76-1.61 (m, 14H), 1.35 (s, 6H), 1.11 (dd, 1H), 0.94-0.91 (m, 4H). |
| 22 | 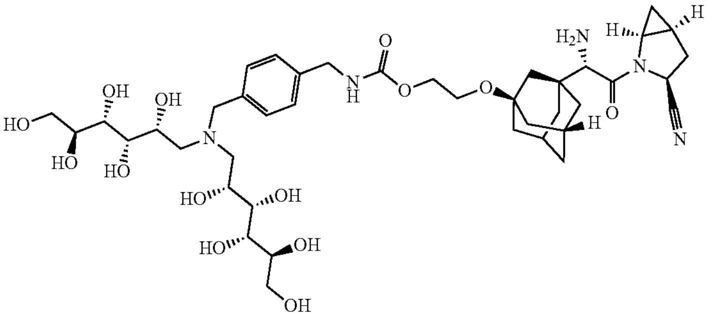 [SMILES: N#C[C@@H]1C[C@@H]2C[C@@H]2N1C(=O)[C@@H](N)[C@]12CC3C[C@H](C[C@](OCCOC(=O)NCc4ccc(CN(C[C@@H](O)[C@H](O)[C@@H](O)[C@@H](O)CO)C[C@@H](O)[C@H](O)[C@@H](O)[C@@H](O)CO)cc4)(C3)C1)C2] | 6.6 | 850.68 | $^1H$ NMR (400 MHz, DMSO-$d_6$) δ 8.54 (s, 1H), 8.17 (s, 2H), 7.79 (t, J = 6.0 Hz, 1H), 7.48 (d, J = 8.0 Hz, 2H), 7.32 (d, J = 8.0 Hz, 2H), 5.60 (bs, 1H), 4.95 (bs, 1H), 5.27-5.24 (m, 1H), 4.95 (m, 2H), 4.37-4.02 (m, 16H), 3.72-3.52 (m, 12H), 3.16 (m, 4H), 2.32-2.23 (m, 3H), 2.07 (m, 1H), 1.73-1.46 (m, 12H), 1.04 (m, 1H), 0.75 (s, 1H). |

TABLE 4-continued

Compound characterization and Inhibition of DPP4 data ($IC_{50}$)

| | Structure | DPP4 inhibition $IC_{50}$ [nM]) | $[M + 1]^+$/ $[M - H]^-$ | $^1H$ NMR |
|---|---|---|---|---|
| 23 | 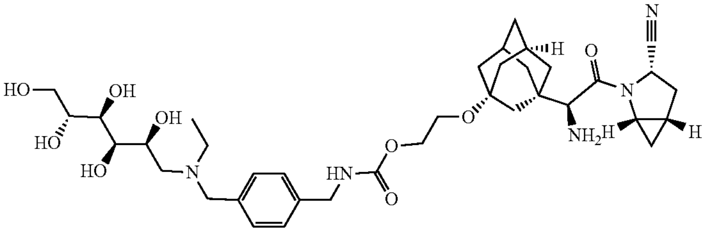 [SMILES: CCN(Cc1ccc(CNC(=O)OCCO[C@]23CC4C[C@H](C2)C[C@@]([C@H](N)C(=O)N2[C@H](C#N)C[C@@H]5C[C@@H]52)(C4)C3)cc1)C[C@H](O)[C@@H](O)[C@H](O)[C@H](O)CO] | 4.2 | 714.6 | $^1H$ NMR (400 MHz, DMSO-$d_6$) δ 8.13 (s, 1H), 7.74 (t, J = 6.0 Hz, 1H), 7.38 (d, J = 7.6 Hz, 2H), 7.24 (d, J = 7.6 Hz, 2H), 5.22 (m, 1H), 4.18-4.02 (m, 10H), 3.89 (s, 1H), 2.17-3.66-3.52 (m, 4H), 3.49-3.47 (m, 4H), 2.92-2.71 (m, 4H), 2.50 (s, 3H), 2.27-2.21 (m, 3H), 1.96 (m, 1H), 1.71-1.43 (m, 12H), 1.09-1.02 (m, 4H), 0.74 (s, 1H). |
| 24 | 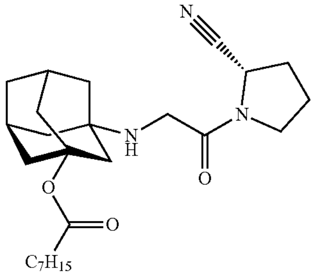 | 238 | 430.299 | $^1H$ NMR (400 MHz, $CDCl_3$) 4.73 (d, 1H), 3.97 (d, 1H), 3.71-3.52 (m, 4H), 3.38 (t, 2H), 2.38 (s, 2H), 2.27-2.10 (m, 4H), 1.83-1.70 (m, 10H), 1.58 (s, 2H), 1.53-1.57 (m, 2H), 1.33-1.22 (m, 8H), 0.90-0.86 (m, 3H). |
| 27 | 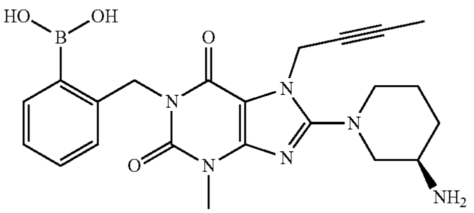 [SMILES: CC#CCn1c(N2CCC[C@@H](N)C2)nc2c1c(=O)n(Cc1ccccc1B(O)O)c(=O)n2C] | 5.3 | 451.219 | $^1H$ NMR (400 MHz, DMSO-d6) δ 8.22 (s, 2H), 8.12 (s, 2H), 7.55 (d, J = 6.8 Hz, 1H), 7.27-7.14 (m, 2H), 6.91 (d, J = 7.6 Hz, 1H), 5.25 (s, 2H), 5.00-4.88 (m, 2H), 3.69 (d, J = 2.4 Hz, 1H), 3.49-3.40 (m, 5H), 3.22-3.14 (m, 2H), 2.00-1.90 (m, 2H), 1.79 (s, 3H), 1.71-1.61 (m, 2H). |
| 28 | 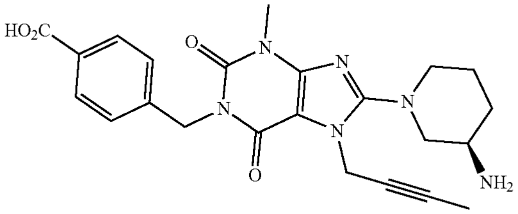 [SMILES: CC#CCn1c(N2CCC[C@@H](N)C2)nc2c1c(=O)n(Cc1ccc(C(=O)O)cc1)c(=O)n2C] | 10.5 | 451.202 | $^1H$ NMR (400 MHz, DMSO-$d_6$) δ 8.13 (br, 3H), 7.87 (d, 2H), 7.38 (d, 2H), 5.10 (s, 2H), 4.93 (dd, 2H), 3.67 (d, 1H), 3.49-3.33 (m, 5H), 3.21-3.08 (m, 2H), 2.01-1.90 (m, 2H), 1.79 (s, 3H), 1.70-1.66 (m, 2H). |
| 29 | 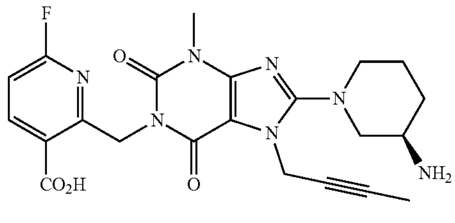 [SMILES: CC#CCn1c(N2CCC[C@@H](N)C2)nc2c1c(=O)n(Cc1nc(F)ccc1C(=O)O)c(=O)n2C] | 7.1 | 470.187 | $^1H$ NMR (400 MHz, DMSO-d6) δ 13.7 (br. s, 1H), 8.46 (t, J = 8.4 Hz, 1H), 8.12 (br. s, 3H), 7.16-7.14 (m, 1H), 5.45 (s, 2H), 4.98-4.86 (m, 2H), 3.71-3.69 (m, 1H), 3.51-3.48 (m, 1H), 3.39 (s, 3H), 3.37 (s, 1H), 3.22-3.16 (m, 2H), 2.00-1.99 (m, 1H), 1.95-1.91 (m, 1H), 1.78 (s, 3H), 1.75-1.62 (m, 2H). |

TABLE 4-continued

Compound characterization and Inhibition of DPP4 data ($IC_{50}$)

| | Structure | DPP4 inhibition $IC_{50}$ [nM]) | $[M + 1]^+$/ $[M - H]^-$ | $^1H$ NMR |
|---|---|---|---|---|
| 30 | 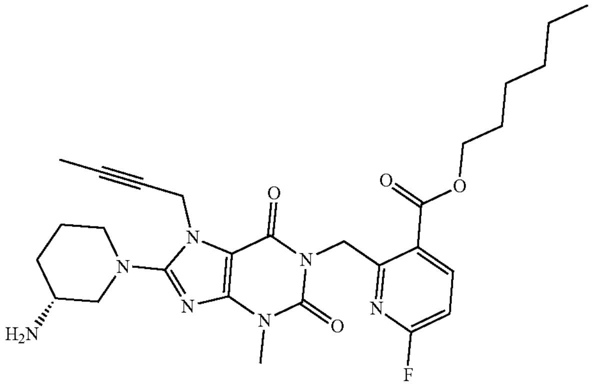 [SMILES: CC#CCn1c(N2CCC[C@@H](N)C2)nc2c1c(=O)n(Cc1nc(F)ccc1C(=O)OCCCCCC)c(=O)n2C] | >1000 | 554.78 | $^1H$ NMR (400 MHz, DMSO-$d_6$) δ 8.48 (t, J = 8.4 Hz, 1H), 8.12 (d, J = 3.6 Hz, 3H), 7.22-7.19 (dd, J = 8.4 Hz, 2.4 Hz, 1H), 5.49 (s, 2H), 4.94 (m, 2H), 4.34 (t, J = 6.4 Hz, 2H), 3.71 (m, 1H), 3.50-3.40 (m, 5H), 3.21-3.16 (m, 2H), 2.02-1.89 (m, 1H), 1.89-1.77 (m, 1H), 1.76-1.65 (m, 7H), 1.44-1.41 (m, 2H), 1.34-1.31 (m, 4H), 0.89-0.86 (m, 3H). |
| 31 | 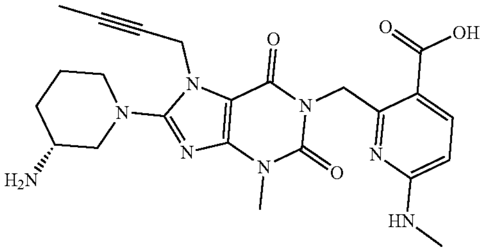 [SMILES: CC#CCn1c(N2CCC[C@@H](N)C2)nc2c1c(=O)n(Cc1nc(NC)ccc1C(=O)O)c(=O)n2C] | 11.4 | 481.28 | $^1H$ NMR (400 MHz, DMSO-$d_6$) δ 8.24 (m, 3H), 7.87 (d, J = 7.6 Hz, 1H), 6.33 (d, J = 8.4 Hz, 1H), 5.37 (s, 2H), 5.00-4.88 (m, 2H), 3.68-3.38 (m, 6H), 3.18-3.12 (m, 2H), 2.45 (m, 3H), 2.02-1.90 (m, 2H), 1.77 (s, 3H), 1.70-1.62 (m, 2H). |
| 32 | 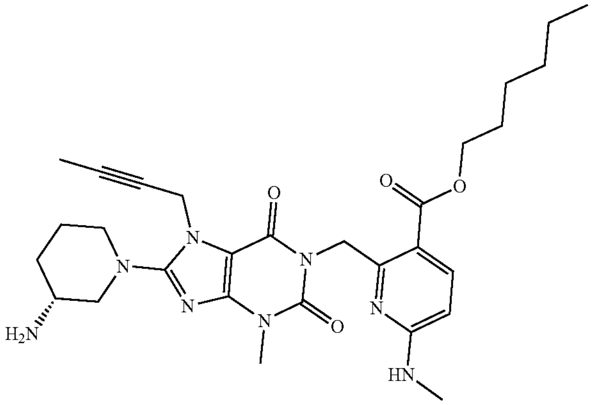 [SMILES: CC#CCn1c(N2CCC[C@@H](N)C2)nc2c1c(=O)n(Cc1nc(NC)ccc1C(=O)OCCCCCC)c(=O)n2C] | >1000 | 565.79 | $^1H$ NMR (400 MHz, DMSO-$d_6$) δ 8.18 (s, 3H), 7.87 (d, J = 8.4 Hz, 1H), 7.21 (br s, 1H), 6.34 (d, J = 8.8, 1H), 5.36 (s, 2H), 4.99-4.88 (m, 2H), 4.22 (t, J = 6.4 Hz, 2H), 3.70-3.59 (m, 1H), 3.49-3.39 (m, 5H), 3.18-3.11 (m, 2H), 2.44 (s, 3H), 2.02-1.99 (m, 2H), 1.90-1.61 (m, 7H), 1.42-1.31 (m, 6H), 0.89 (s, 3H). |
| 33 | 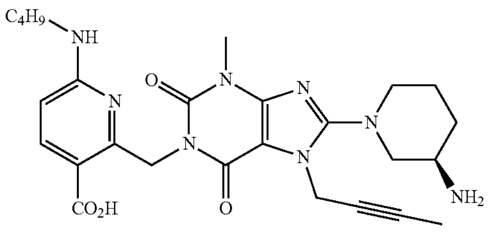 | 11.4 | 523.27 | $^1H$ NMR (400 MHz, DMSO-$d_6$) δ 12.26 (br. s, 1H), 8.19 (s, 3H), 7.82 (d, J = 8.8 Hz, 1H), 7.30 (br. s, 1H), 6.29 (d, J = 8.8 Hz, 1H), 5.35 (s, 2H), 5.00-4.86 (m, 2H), 3.68-3.65 (m, 2H), 3.38 (s, 4H), 3.14-3.09 (m, 2H), 2.87 (br. s, 2H), 2.03-2.01 (m, 1H), 1.90 (m, 1H), 1.76-1.61 (m, 5H), 1.14-1.11 (m, 2H), 0.93-0.91 (m, 2H), 0.68 (t, J = 7.2 Hz, 3H). |

TABLE 4-continued

Compound characterization and Inhibition of DPP4 data ($IC_{50}$)

| | Structure | DPP4 inhibition $IC_{50}$ [nM]) | $[M + 1]^+$/ $[M - H]^-$ | $^1H$ NMR |
|---|---|---|---|---|
| 34 | 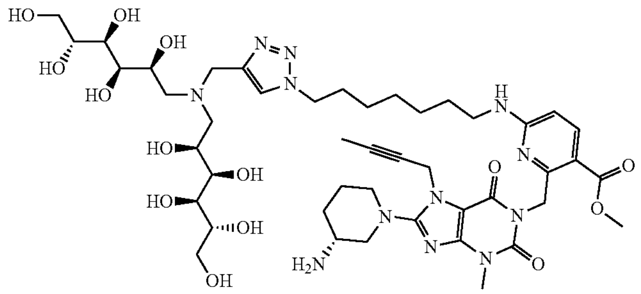 [SMILES: CC#CCn1c(N2CCC[C@@H](N)C2)nc2c1c(=O)n(Cc1nc(NCCCCCCCn3cc(CN(C[C@H](O)[C@@H](O)[C@H](O)[C@H](O)CO)C[C@H](O)[C@@H](O)[C@H](O)[C@H](O)CO)nn3)ccc1C(=O)OC)c(=O)n2C] | 41.0 | 1003.62 | $^1H$ NMR (400 MHz, DMSO $d_6$) δ 8.95 (s, 1H), 8.34 (s, 1H), 8.21 (m, 3H), 7.84 (d, J = 8.7 Hz, 1H), 7.39 (brs, 1H), 6.31 (d, J = 8.8 Hz, 1H), 5.34 (br m, 4H), 4.93 (m, 2H), 4.56 (m, 2H), 4.39 (t, J = 6.9 Hz, 2H), 4.13 (m, 2H), 3.79 (s, 3H), 3.59 (m, 6H), 3.43 (m, 11H), 3.15 (m, 6H), 2.86 (s, 2H), 2.04 (m, 1H), 1.91 (m, 1H), 1.78 (m, 7H), 1.16 (m, 8H), 0.89 (m, 2H). |
| 35 | 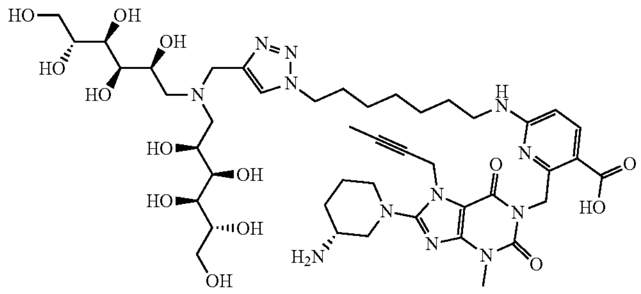 [SMILES: CC#CCn1c(N2CCC[C@@H](N)C2)nc2c1c(=O)n(Cc1nc(NCCCCCCCn3cc(CN(C[C@H](O)[C@@H](O)[C@H](O)[C@H](O)CO)C[C@H](O)[C@@H](O)[C@H](O)[C@H](O)CO)nn3)ccc1C(=O)O)c(=O)n2C] | 34.3 | 987.62 | $^1H$ NMR (400 MHz, DMSO) δ 7.93 (s, 1H), 7.79 (d, J = 8.6 Hz, 1H), 7.01 (br s, 1H), 6.22 (d, J = 8.6 Hz, 1H), 5.31 (s, 2H), 4.59-4.26 (m, 14H), 3.77 (m, 4H), 3.55 (m, 9H), 3.38 (m, 7H), 2.90 (m, 5H), 2.50 (m, 2H), 1.74 (m, 9H), 1.27 (m, 1H), 1.12 (m, 6H), 0.91 (m, 2H). |
| 36 | 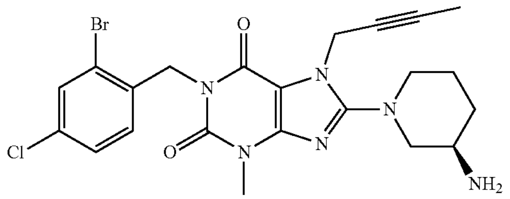 [SMILES: CC#CCn1c(N2CCC[C@@H](N)C2)nc2c1c(=O)n(Cc1ccc(Cl)cc1Br)c(=O)n2C] | 27 | 519.083 | $^1H$ NMR (400 MHz, DMSO-$d_6$) δ 7.79 (d, J = 2.0 Hz, 1H), 7.35 (dd, J = 8.4, 2.4 Hz, 1H), 6.95 (d, J = 8.4 Hz, 1H), 5.00 (s, 2H), 4.88 (s, 2H), 3.66-3.58 (m, 2H), 3.39 (s, 3H), 3.00 (t, J = 10.0 Hz, 1H), 2.84-2.72 (m, 2H), 1.87-1.61 (m, 8H), 1.24-1.21 (m, 1H). |
| 37 | 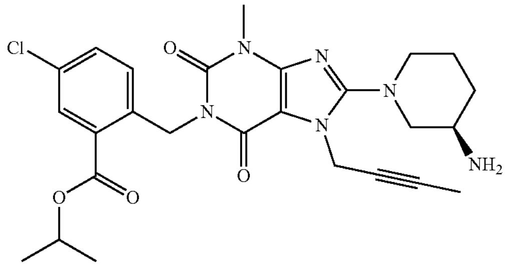 [SMILES: CC#CCn1c(N2CCC[C@@H](N)C2)nc2c1c(=O)n(Cc1ccc(Cl)cc1C(=O)OC(C)C)c(=O)n2C] | 700 | 527.21 | $^1H$ NMR (400 MHz, DMSO-$d_6$) δ 7.83 (d, J = 2.0 Hz, 1H), 7.54 (dd, J = 8.4, 2.0 Hz, 1H), 7.08 (d, J = 8.4 Hz, 1H), 5.32 (s, 2H), 5.22-5.16 (m, 1H), 4.88 (s, 2H), 3.66-3.58 (m, 2H), 3.38 (s, 3H), 2.99 (t, J = 10.4 Hz, 1H), 2.84-2.72 (m, 2H), 1.87-1.57 (m, 8H), 1.37 (d, J = 6.0 Hz, 6H), 1.27-1.26 (m, 1H). |
| 38 | 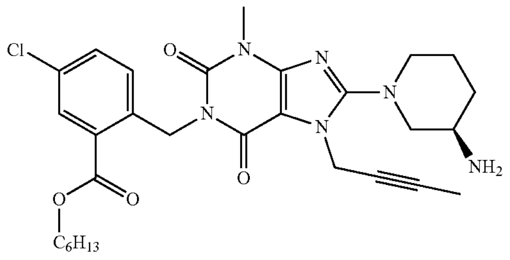 | >10000 | 569.256 | $^1H$ NMR (400 MHz, DMSO-d6) δ 7.84 (d, 1H), 7.54 (dd, 1H), 7.07 (d, 1H), 5.32 (s, 2H), 4.88 (s, 2H), 4.31 (t, 2H), 3.65-3.57 (m, 2H), 3.37 (s, 3H), 3.01-2.96 (m, 1H), 2.82-2.68 (m, 2H), 1.87-1.59 (m, 9H), 1.42-1.20 (m, 7H), 0.88 (t, 3H). |

TABLE 4-continued

| | Compound characterization and Inhibition of DPP4 data ($IC_{50}$) | | | |
|---|---|---|---|---|
| | Structure | DPP4 inhibition $IC_{50}$ [nM]) | $[M + 1]^+$/ $[M - H]^-$ | $^1H$ NMR |
| 39 | 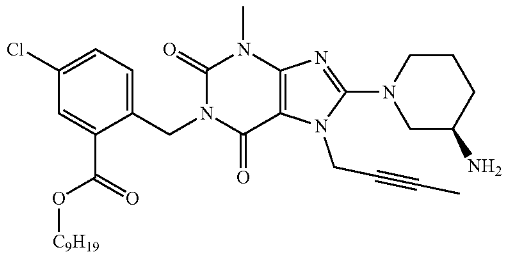 | 1000 | 611.303 | $^1H$ NMR (400 MHz, DMSO-d6) δ 7.85 (d, J = 2.4 Hz, 1H), 7.55 (dd, J = 8.4, 2.0 Hz, 1H), 7.08 (d, J = 8.4 Hz, 1H), 5.32 (s, 2H), 4.88 (s, 2H), 4.32 (t, J = 6.4 Hz, 2H), 3.66-3.58 (m, 2H), 3.37 (s, 3H), 3.01-2.96 (m, 1H), 2.82-2.72 (m, 2H), 1.87-1.60 (m, 10H), 1.41-1.24 (m, 13H), 0.84 (t, J = 6.4 Hz, 3H). |
| 40 | 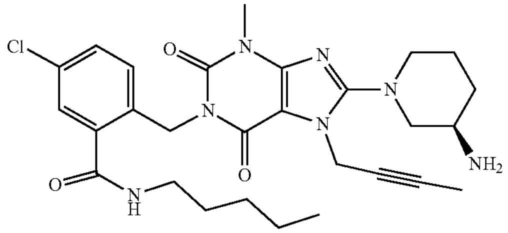 [SMILES: CC#CCn1c(N2CCC[C@@H](N)C2)nc2c1c(=O)n(Cc1ccc(Cl)cc1C(=O)NCCCCC)c(=O)n2C] | 700 | 554.257 | $^1H$ NMR (400 MHz, DMSO-$d_6$) δ 8.56 (t, J = 5.2 Hz, 1H), 7.44 (d, J = 2.0 Hz, 1H), 7.37 (dd, J = 8.4, 2.4 Hz, 1H), 6.97 (d, J = 8.4 Hz, 1H), 5.14 (s, 2H), 4.88 (s, 2H), 3.65-3.57 (m, 2H), 3.37 (s, 3H), 3.27-3.23 (m, 2H), 2.98 (t, J = 10.4 Hz, 1H), 2.88-2.71 (m, 2H), 1.87-1.52 (m, 9H), 1.39-1.27 (m, 5H), 0.89 (t, J = 6.8 Hz, 3H). |
| 41 | 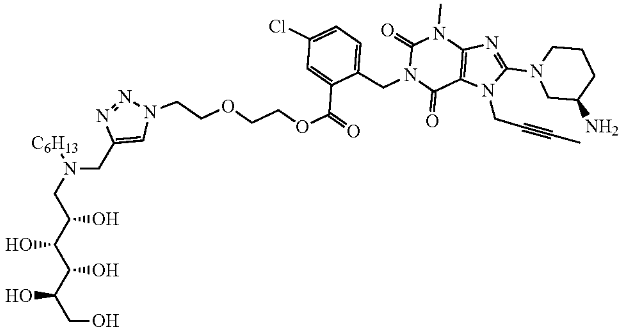 | >10000 | 901.426 | $^1H$ NMR (400 MHz, DMSO-d6) δ 9.5 (s, 1H), 8.31 (d, J = 7.6 Hz, 1H), 8.23 (s, 3H), 7.84 (s, 1H), 7.57 (dd, J = 8.4, 2.0 Hz, 1H), 7.08 (d, J = 8.4 Hz, 1H), 5.33 (s, 3H), 5.01-4.87 (m, 2H), 4.63 (s, 2H), 4.41 (s, 4H), 4.12-4.03 (m, 1H), 3.93-3.91 (m, 2H), 3.79 (m, 2H), 3.74-3.60 (m, 3H), 3.39 (m, 8H), 3.20-3.17 (m, 4H), 2.99-2.98 (m, 2H), 2.02-1.91 (m, 2H), 1.78-1.63 (m, 7H), 1.25 (s, 6H), 0.86 (s, 3H). |
| 42 | 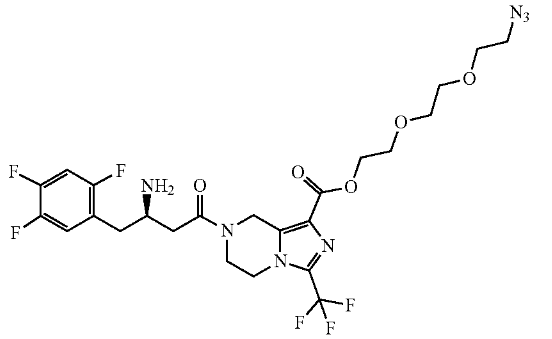 [SMILES: [N-]=[N+]=NCCOCCOCCOC(=O)c1nc(C(F)(F)F)n2c1CN(C(=O)C[C@H](N)Cc1cc(F)c(F)cc1F)CC2] | 0.4 | 608.198 | $^1H$ NMR (400 MHz, DMSO-d6) δ 7.45-7.43 (m, 2H), 4.96-4.93 (m, 2H), 4.37-4.36 (m, 2H), 4.25-4.11 (m, 2H), 3.94-3.93 (m, 2H), 3.75-3.71 (m, 2H), 3.60-3.58 (m, 6H), 3.37-3.34 (m, 2H), 3.31 (m, 1H), 2.73-2.58 (m, 2H), 2.51-2.49 (m, 2H), 1.80 (bs, 2H). |

TABLE 4-continued
| Compound characterization and Inhibition of DPP4 data ($IC_{50}$) | | | | |
|---|---|---|---|---|
| | Structure | DPP4 inhibition $IC_{50}$ [nM]) | $[M + 1]^+$/ $[M - H]^-$ | $^1H$ NMR |
| 43 | 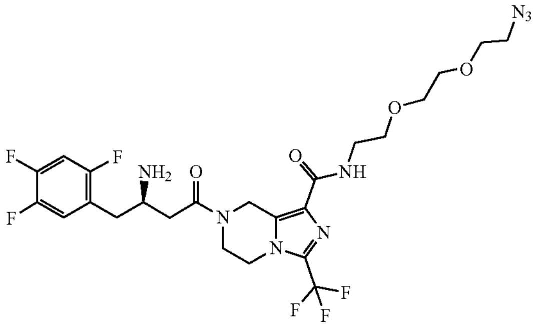 [SMILES: [N-]=[N+]=NCCOCCOCCNC(=O)c1nc(C(F)(F)F)n2c1CN(C(=O)C[C@H](N)Cc1cc(F)c(F)cc1F)CC2] | 1 | 607.214 | $^1H$ NMR (400 MHz, DMSO-d6) δ 7.45-7.43 (m, 2H), 4.96-4.93 (m, 2H), 4.37-4.36 (m, 2H), 4.25-4.11 (m, 2H), 3.94-3.93 (m, 2H), 3.75-3.71 (m, 2H), 3.60-3.58 (m, 6H), 3.37-3.34 (m, 2H), 3.31 (m, 1H), 2.73-2.58 (m, 2H), 2.51-2.49 (m, 2H), 1.80 (bs, 2H). |
| 44 | 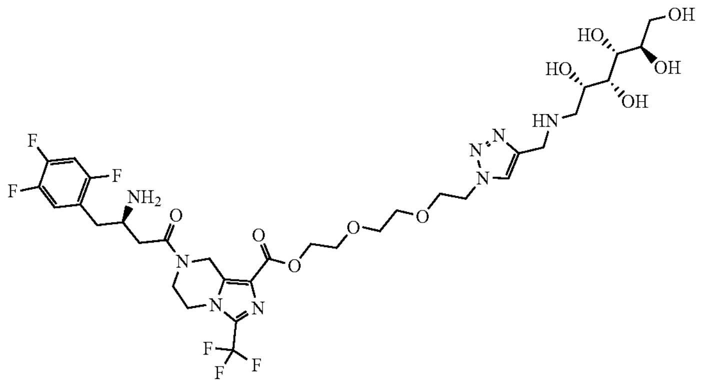 [SMILES: N[C@@H](CC(=O)N1CCn2c(C(F)(F)F)nc(C(=O)OCCOCCOCCn3cc(CNC[C@H](O)[C@@H](O)[C@H](O)[C@H](O)CO)nn3)c2C1)Cc1cc(F)c(F)cc1F] | 0.11 | 827.4 | $^1H$ NMR (400 MHz, DMSO-$d_6$) δ 7.89 (s, 1H), 7.45-7.41 (m, 2H), 5.10-4.85 (m, 3H), 4.60-4.10 (m, 10H), 4.00-3.30 (m, 20H), 3.10-3.05 (m, 1H), 2.71-2.50 (m, 5H), 2.10-1.40 (m, 2H). |
| 45 | 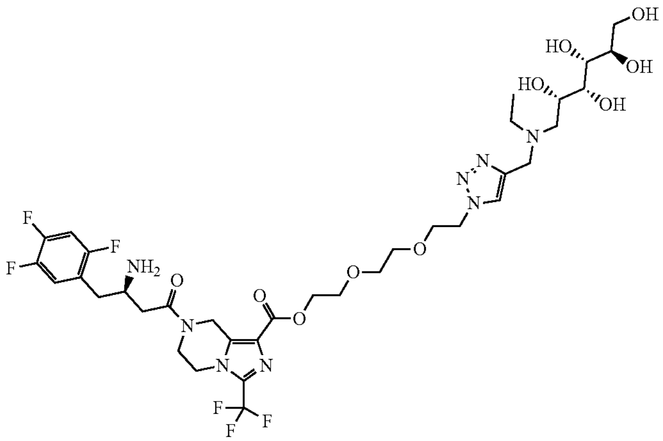 [SMILES: CCN(Cc1cn(CCOCCOCCOC(=O)c2nc(C(F)(F)F)n3c2CN(C(=O)C[C@H](N)Cc2cc(F)c(F)cc2F)CC3)nn1)C[C@H](O)[C@@H](O)[C@H](O)[C@H](O)CO] | 0.55 | 855.65 | $^1H$ NMR (400 MHz, DMSO-$d_6$) δ 9.55 (s, 1H), 8.29 (d, J = 5.8 Hz, 1H), 8.10-8.00 (m, 3H), 7.58 (q, J = 9.0 Hz, 2H), 5.49 (s, 1H), 4.95-4.93 (m, 3H), 4.57-3.38 (m, 28H), 3.18-2.66 (m, 8H), 1.31-1.26 (m, 3H). |

TABLE 4-continued
Compound characterization and Inhibition of DPP4 data ($IC_{50}$)
| | Structure | DPP4 inhibition $IC_{50}$ [nM]) | $[M + 1]^+$/ $[M - H]^-$ | $^1H$ NMR |
|---|---|---|---|---|
| 46 | 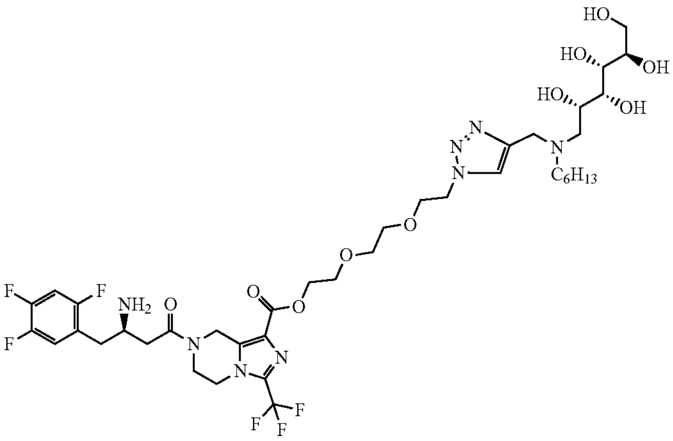 | 0.15 | 911.404 | $^1H$ NMR (400 MHz, MeOD) δ 8.28 (s, 1H), 7.36 (m, 1H), 7.27-7.17 (m, 1H), 5.07 (m, 1H), 4.99 (m, 1H), 4.58 (m, 4H), 4.45 (m, 2H), 4.29 (m, 4H), 4.11-3.94 (m, 2H), 3.92-3.87 (m, 3H), 3.77 (m, 4H), 3.64 (m, 7H), 3.27-3.03 (m, 5H), 3.00-2.92 (m, 1H), 2.84 (m, 1H), 1.83 (s, 2H), 1.36 (s, 6H), 0.91 (t, J = 6.5 Hz, 3H). |
| 47 | 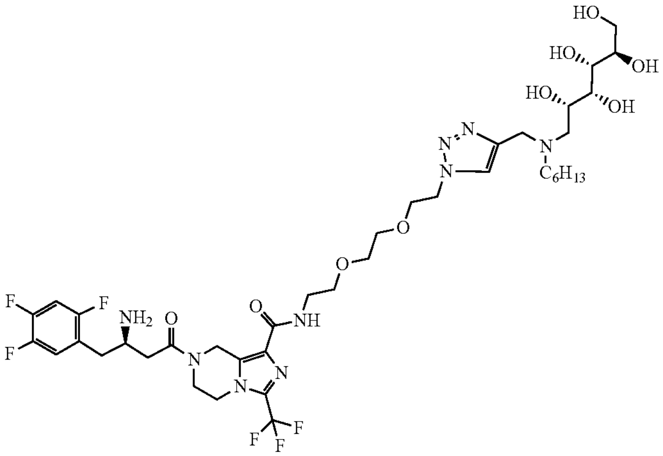 | 2.2 | 910.418 | $^1H$ NMR (400 MHz, DMSO-$d_6$) δ 8.02-7.98 (m, 1H), 7.91 (s, 1H), 7.45-7.41 (m, 2H), 4.98-4.87 (m, 2H), 4.47-4.46 (m, 4H), 4.42-4.13 (m, 4H), 3.92 (s, 2H), 3.80 (s, 2H), 3.72 (s, 3H), 3.62-3.56 (m, 2H), 3.59-3.32 (m, 12H), 2.67-2.56 (m, 4H), 2.40-2.33 (m, 4H), 1.40 (bs, 2H), 1.23-1.15 (m, 6H), 0.83 (t, J = 7.2 Hz, 3H). |
| 48 | 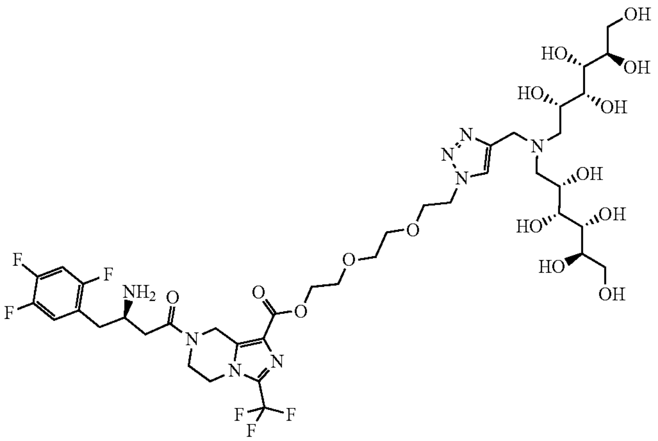 [SMILES: N[C@@H](CC(=O)N1CCn2c(C(F)(F)F)nc(C(=O)OCCOCCOCCn3cc(CN(C[C@H](O)[C@@H](O)[C@H](O)[C@H](O)CO)C[C@H](O)[C@@H](O)[C@H](O)[C@H](O)CO)nn3)c2C1)Cc1cc(F)c(F)cc1F] | 0.55 | 991.57 | $^1H$ NMR (400 MHz, DMSO-$d_6$) δ 7.94 (s, 1H), 7.45-7.43 (m, 2H), 5.00-4.95 (m, 2H), 4.87-4.14 (m, 18H), 3.93-3.47 (m, 23H), 3.39-3.16 (m, 8H), 2.61-2.58 (m, 2H). |

TABLE 4-continued

Compound characterization and Inhibition of DPP4 data ($IC_{50}$)

| | Structure | DPP4 inhibition $IC_{50}$ [nM]) | $[M+1]^+$/ $[M-H]^-$ | $^1H$ NMR |
|---|---|---|---|---|
| 49 | 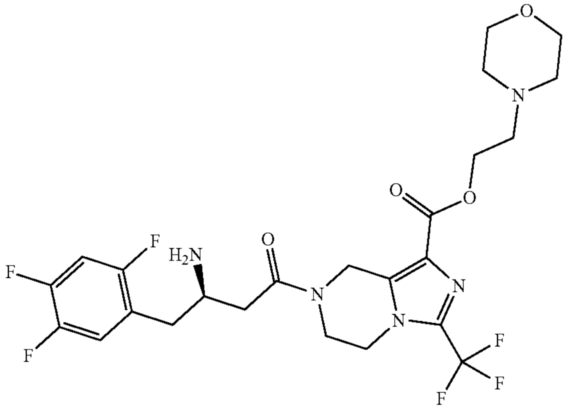 [SMILES: N[C@@H](CC(=O)N1CCn2c(C(F)(F)F)nc(C(=O)OCCN3CCOCC3)c2C1)Cc1cc(F)c(F)cc1F] | 0.82 | 564.46 | $^1H$ NMR (400 MHz, DMSO) δ 7.52 (dd, J = 9.5, 4.0 Hz, 2H), 5.03-4.87 (m, 2H), 4.35-4.08 (m, 5H), 3.95-3.88 (m, 4H), 3.67 (s, 2H), 3.56 (t, J = 4.6 Hz, 4H), 2.89 (s, 3H), 2.82-2.58 (m, 4H), 2.44 (t, J = 4.7 Hz, 4H). |
| 50 | 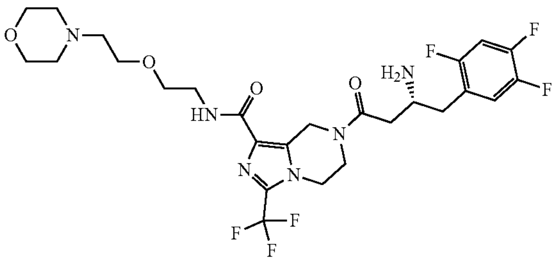 [SMILES: N[C@@H](CC(=O)N1CCn2c(C(F)(F)F)nc(C(=O)NCCOCCN3CCOCC3)c2C1)Cc1cc(F)c(F)cc1F] | 0.54 | 607.51 | $^1H$ NMR (400 MHz, DMSO) δ 8.08-7.95 (m, 1H), 7.56-7.44 (m, 2H), 5.03-4.87 (m, 2H), 4.26-4.07 (m, 3H), 3.88 (s, 4H), 3.37 (t, J = 6.1 Hz, 13H), 2.87 (d, J = 6.7 Hz, 2H), 2.72-2.65 (m, 2H), 2.46-2.36 (m, 7H). |
| 51 | 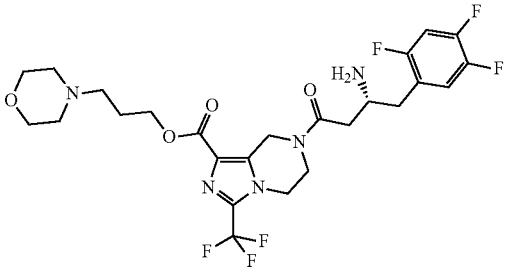 [SMILES: N[C@@H](CC(=O)N1CCn2c(C(F)(F)F)nc(C(=O)OCCCN3CCOCC3)c2C1)Cc1cc(F)c(F)cc1F] | 0.18 | 578.22 | $^1H$ NMR (400 MHz, DMSO) δ 7.56-7.46 (m, 2H), 4.94 (d, J = 11.9 Hz, 2H), 4.28 (t, J = 6.6 Hz, 5H), 3.90 (s, 6H), 3.56 (s, 4H), 2.86 (s, 3H), 2.72-2.66 (m, 2H), 2.38 (dd, J = 13.7, 6.5 Hz, 6H), 1.89-1.80 (m, 2H). |
| 52 | 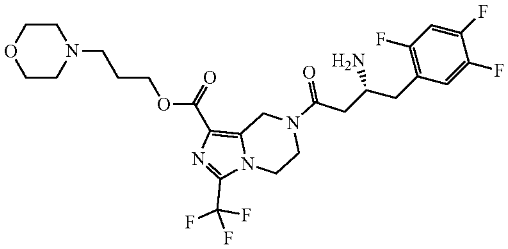 [SMILES: N[C@@H](CC(=O)N1CCn2c(C(F)(F)F)nc(C(=O)OCCCN3CCOCC3)c2C1)Cc1cc(F)c(F)cc1F] | 0.54 | 607.22 | $^1H$ NMR (400 MHz, DMSO) δ 7.53 (q, J = 9.6 Hz, 2H), 4.95 (q, J = 18.0 Hz, 2H), 4.40-4.05 (m, 6H), 3.92 (d, J = 12.6 Hz, 5H), 3.68 (t, J = 4.8 Hz, 5H), 3.50 (t, J = 4.6 Hz, 4H), 2.73 (s, 2H), 2.46 (d, J = 5.7 Hz, 3H), 2.38 (s, 4H). |
| 53 | 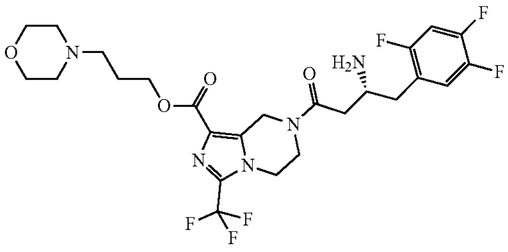 [SMILES: N[C@@H](CC(=O)N1CCn2c(C(F)(F)F)nc(C(=O)OCCCN3CCOCC3)c2C1)Cc1cc(F)c(F)cc1F] | 1.0 | 605.24 | $^1H$ NMR (400 MHz, DMSO) δ 7.51 (td, J = 10.2, 6.9 Hz, 2H), 5.00-4.88 (m, 2H), 4.24 (td, J = 7.2, 3.4 Hz, 5H), 3.99-3.87 (m, 5H), 3.68 (s, 2H), 3.54 (t, J = 4.5 Hz, 5H), 2.90 (s, 2H), 2.80-2.64 (m, 2H), 2.38-2.26 (m, 6H), 1.68 (p, J = 7.3 Hz, 2H), 1.55-1.34 (m, 4H). |

TABLE 4-continued

| Compound characterization and Inhibition of DPP4 data ($IC_{50}$) | | | | |
|---|---|---|---|---|
| | Structure | DPP4 inhibition $IC_{50}$ [nM]) | $[M + 1]^+$/ $[M - H]^-$ | $^1H$ NMR |
| 54 | 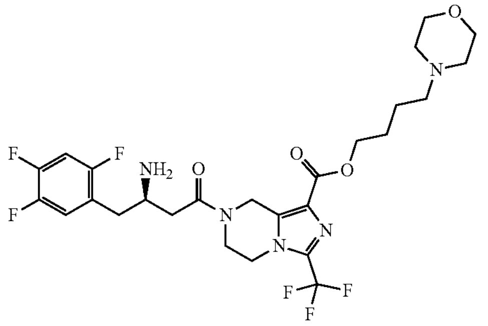 [SMILES: N[C@@H](CC(=O)N1CCn2c(C(F)(F)F)nc(C(=O)OCCCCN3CCOCC3)c2C1)Cc1cc(F)c(F)cc1F] | 0.5 | 591.23 | $^1H$ NMR (400 MHz, DMSO) δ 7.53 (q, J = 8.2 Hz, 2H), 4.94 (d, J = 11.9 Hz, 2H), 4.25 (dd, J = 7.7, 5.3 Hz, 5H), 3.93 (s, 5H), 3.64 (d, J = 6.5 Hz, 5H), 2.87 (d, J = 7.4 Hz, 2H), 2.78-2.64 (m, 2H), 2.45-2.13 (m, 6H), 1.68 (d, J = 8.2 Hz, 2H), 1.54 (q, J = 7.4 Hz, 2H). |
| 55 | 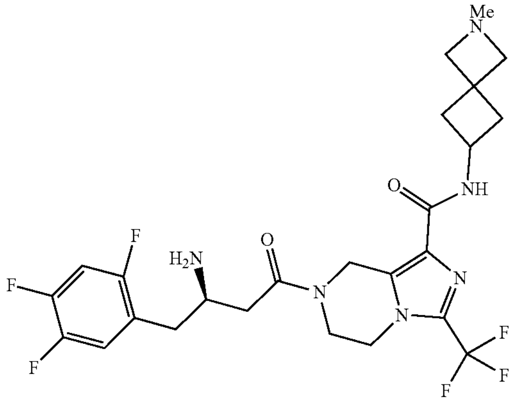 [SMILES: CN1CC2(CC(NC(=O)c3nc(C(F)(F)F)n4c3CN(C(=O)C[C@H](N)Cc3cc(F)c(F)cc3F)CC4)C2)C1] | 17.8 | 559.46 | $^1H$ NMR (400 MHz, DMSO) δ 8.40-8.22 (m, 1H), 7.48 (q, J = 9.2 Hz, 2H), 4.91 (d, J = 14.9 Hz, 2H), 4.26 (dd, J = 16.4, 8.0 Hz, 3H), 4.11 (s, 1H), 3.89 (s, 3H), 3.83 (s, 3H), 2.78 (d, J = 7.1 Hz, 2H), 2.70-2.56 (m, 3H), 2.45-2.28 (m, 7H). |

Example 46. Pharmacokinetic Profiling

To assess the time course of the plasma and lung exposure of compounds disclosed herein, rodents were dosed IT with an exemplary compound of the present disclosure. The plasma and lung samples were taken at different time points. The drug levels were measured by LCMS.

Figure 2:
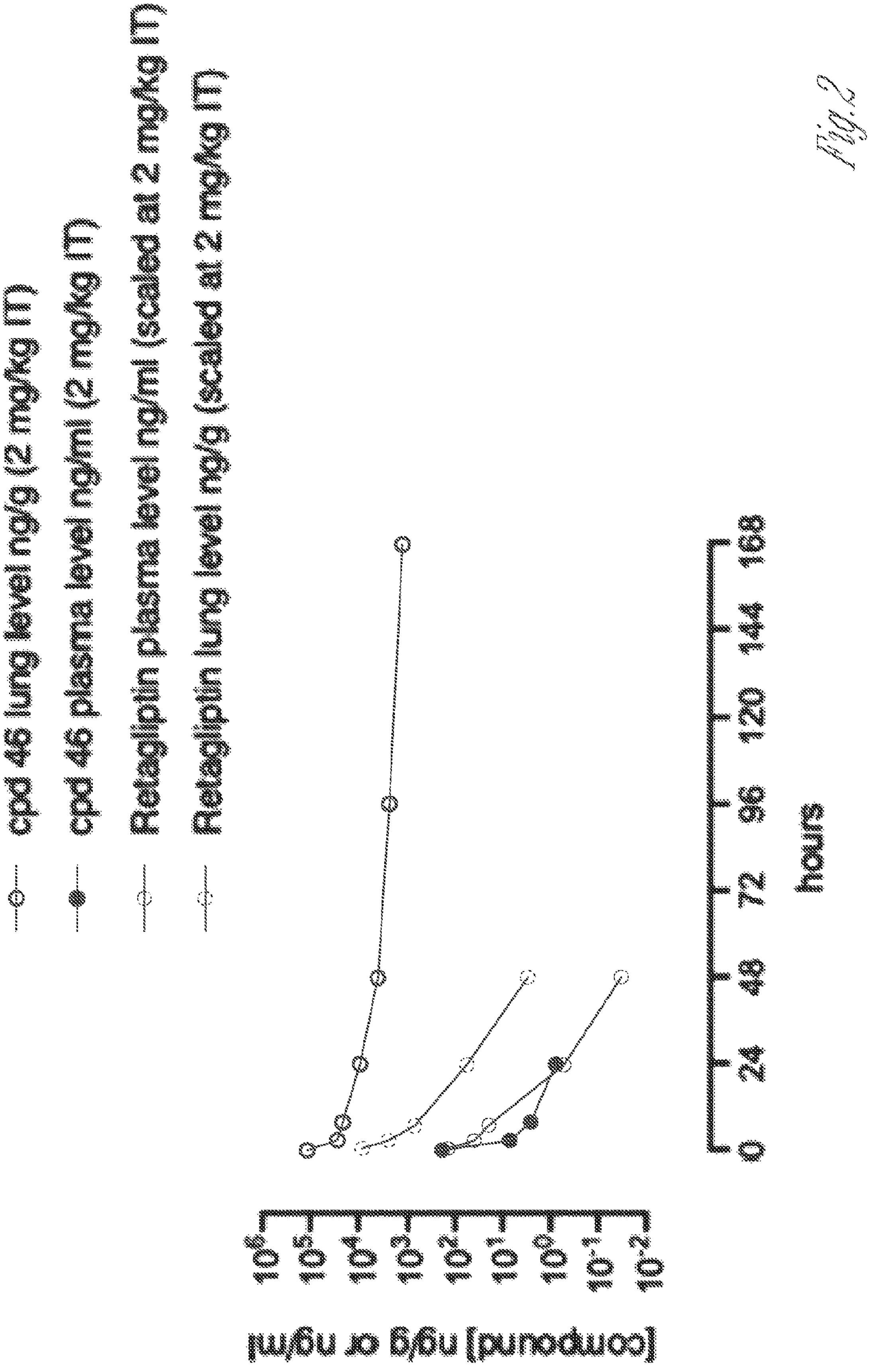
FIG. 2. Comparison of mouse pharmacokinetics of retagliptin and compound 46 with IT (Intratracheal) dosing at 2 mg/kg FIG. 3A-FIG. 3E. Compound 46 displayed efficacy in a bleomycin induced lung fibrosis model in the mouse. (A) Body weight measurements and the dosing schedule used to administer compound 46 intratracheally (0.5 mg/kg every four days). BALF (B), fibrotic area measurements (C), modified Ashcroft scores (D), and representative Masson's Trichrome stained histological slides (E) at study end; , $P<0.005$; *, $P<0.0005$.
Figure 3A:
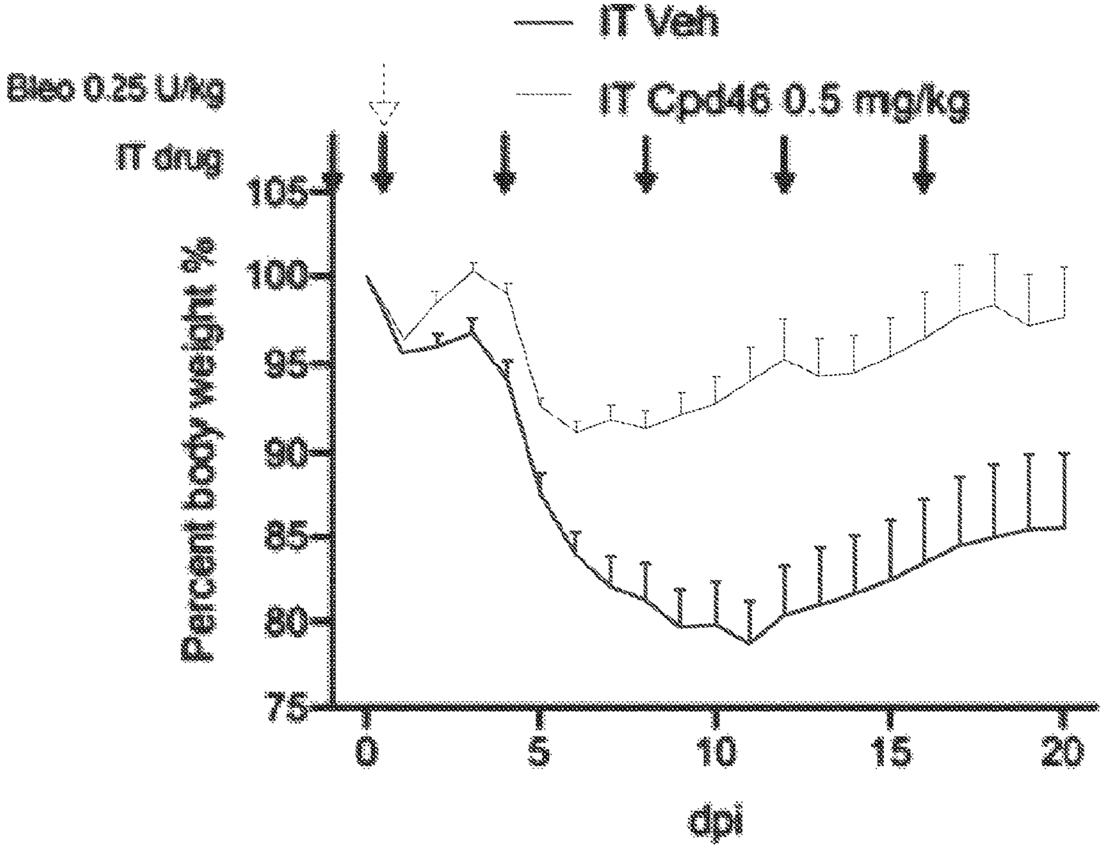
Figure 3B:
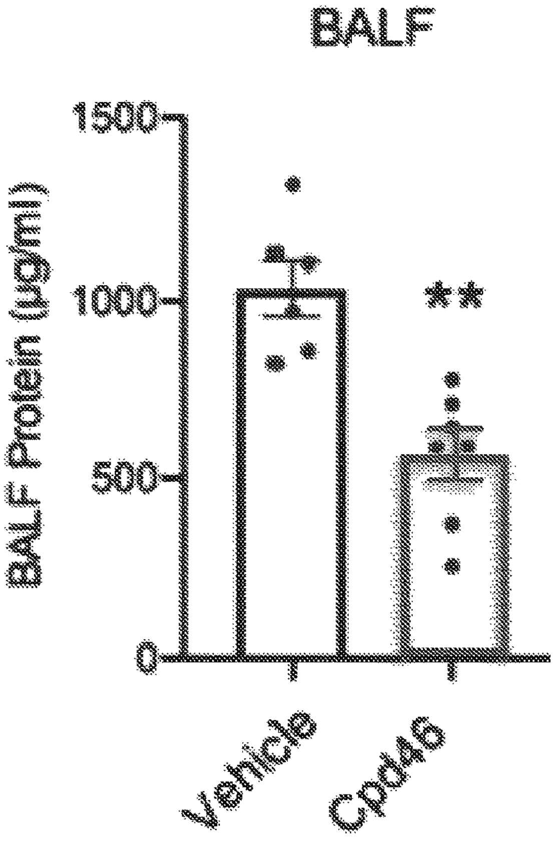
Figure 3C:
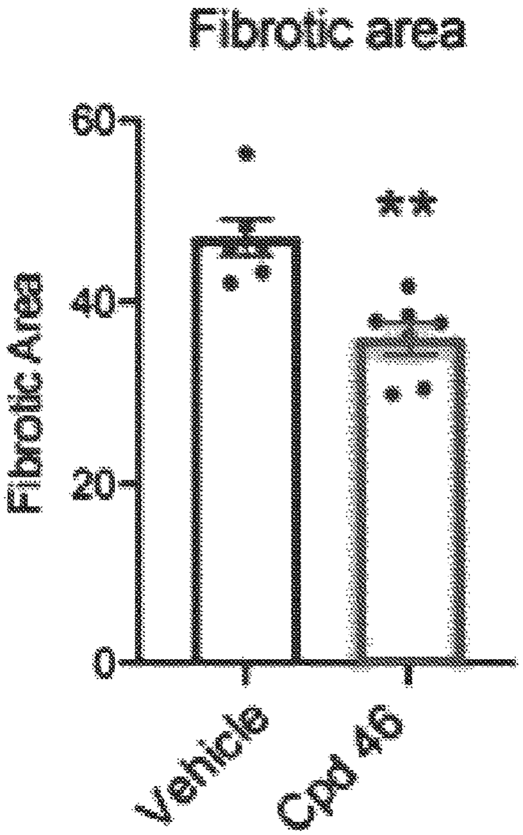
Figure 3D:
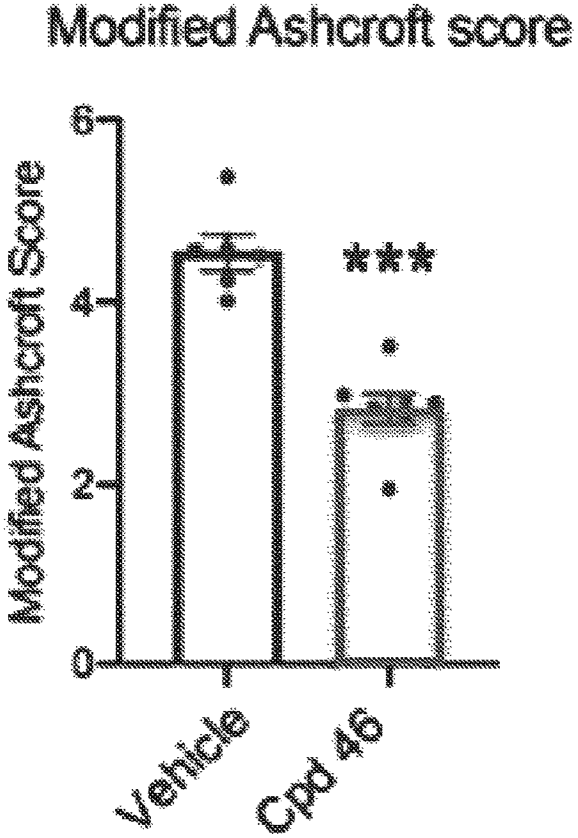
Figure 3E:
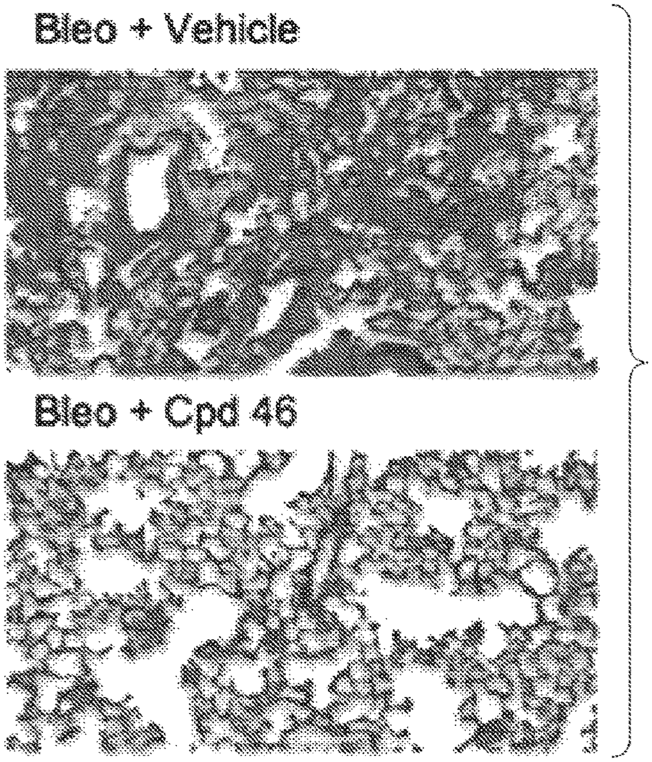
Figure 4A:
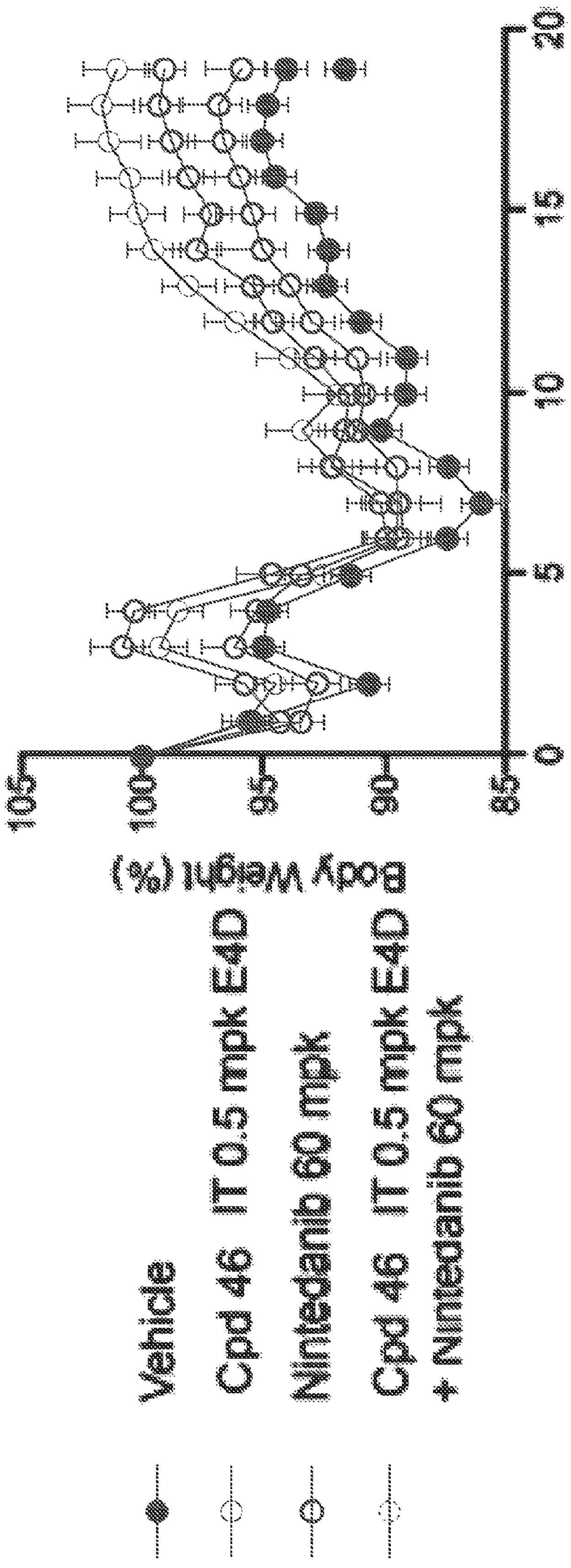
FIG. 4A-FIG. 4D. Compound 46 displays synergistic efficacy in combination with standard of care IPF drug Nintedanib in the bleomycin induced fibrosis model in mice. (A) Legend of treatments and body weight measurements from the bleomycin induced lung fibrosis model in the mouse. Compound 46, 0.5 mg/kg IT, E4D; BALF protein levels (B), modified Ashcroft scores (C), and representative Masson's Trichrome stained histological slides (D) at study end. *, $P<0.05$; ; $P<0.005$; *, $P<0.0005$; NS=not statistically significant.
Figure 4C:
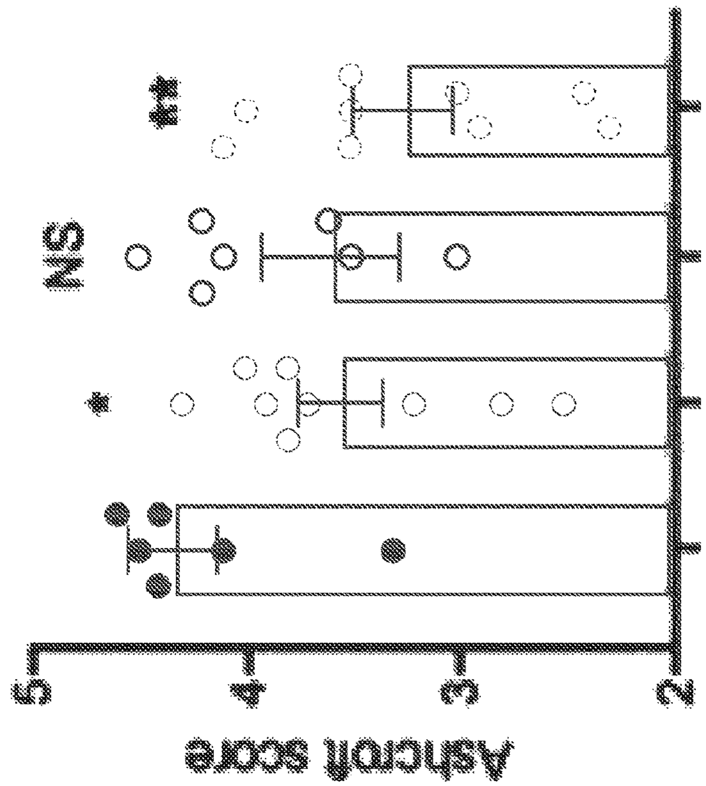
Figure 4B:
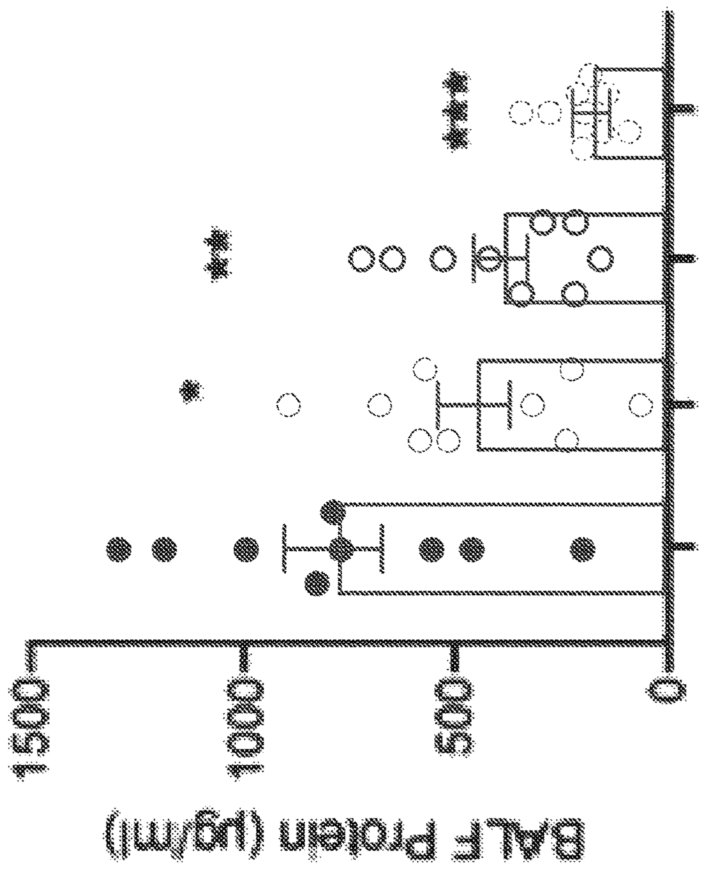
Figure 4D:
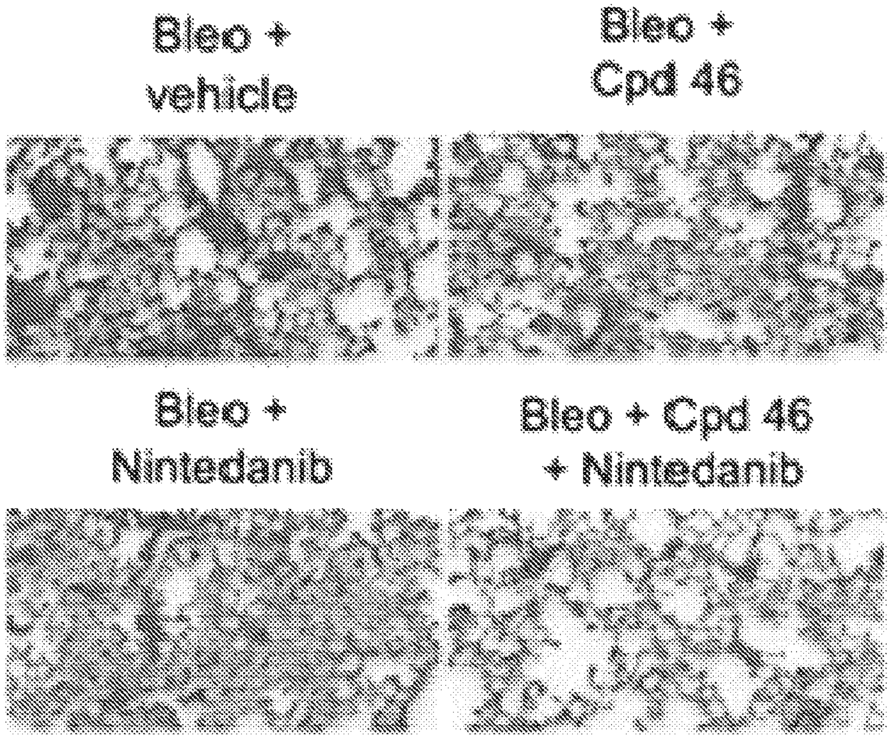

When dosed IT to mouse, compound 46 exhibited significantly higher plasma and lung exposure profiles compared to retagliptin (FIG. 2). Furthermore, the compound was retained in the lung for 7 days while retagliptin level in the lung was very low after 48 h.

Table 5 presents the pharmacokinetic parameters of compound 46 in mouse and rat.

TABLE 5

| PK data from intratracheal or inhalation delivery in the mouse and rat for compound 46 | | | | | | |
|---|---|---|---|---|---|---|
| | Species and strain | | | | | |
| | Mouse; Male; CD-1 strain | | Mouse; Male; CD-1 strain | | Rat; Male; Sprague Dawley strain | |
| | Route of administration | | | | | |
| | Intratracheal | | Inhalation | | Intratracheal | |
| | Dose | | | | | |
| | 2 mg/kg; 1 mg/ml in PBS | | 10 mg/ml in PBS for 15 mins | | 2 mg/kg; 1 mg/ml in PBS | |
| Measurement | Plasma | Lung | Plasma | Lung | Plasma | Lung |
| $C_{max}$ (ng/mL or ng/g) | 435 | 24,623 | 35.9 | 20,939 | 14746 | 41392 |
| $t_{1/2}$ (hr) | 1.28 | 54.1 | 1.5 | | 68.8 | 119 |
| $T_{max}$ (hr) | 0.25 | 0.25 | 0.5 | 0.25 | 0.25 | 0.25 |
| $AUC_{0-24}$ (ng · h/mL or ng · h/g) | 728 | 258,902 | 53.4 | | 18038 | 658004 |

TABLE 5-continued

PK data from intratracheal or inhalation delivery in the mouse and rat for compound 46

| Measurement | Species and strain | | | | | |
|---|---|---|---|---|---|---|
| | Mouse; Male; CD-1 strain | | Mouse; Male; CD-1 strain | | Rat; Male; Sprague Dawley strain | |
| | Route of administration | | | | | |
| | Intratracheal | | Inhalation | | Intratracheal | |
| | Dose | | | | | |
| | 2 mg/kg; 1 mg/ml in PBS | | 10 mg/ml in PBS for 15 mins | | 2 mg/kg; 1 mg/ml in PBS | |
| | Plasma | Lung | Plasma | Lung | Plasma | Lung |
| $AUC_{0\text{-}inf}$ (ng · h/mL or ng · h/g) | 729 | 1,082,408 | 55.2 | 509,951 | 18575 | 4738852 |
| $MRT_{0\text{-}inf}$ (hr) | 1.88 | 80.6 | 1.69 | | 6 | 186 |
| AUC ratio | 1 | 1,349 | 1 | 9238 | 1 | 145 |

Example 47. In Vivo Efficacy Studies

Experimental Methods of ALI Model

LPS from *E. coli* I111:B4 (Sigma) was used to induce acute lung injury in mice. Body weight matched (19 gram-22 gram) female C57BL/6J mice at 9-11 weeks of age were selected to use in ALI model.

For oral delivery, DPP4 inhibitors were dissolved in PBS resulting in clear solution. Vehicle control or DPP4 inhibitors were dosed at 10 ml/kg through oral gavage once or twice a day selected based on PK profile. For intratracheally delivered DPP4 inhibitors, compounds were dissolved in PBS resulting in clear solution. Vehicle control or DPP4 inhibitors were dosed at 2 ml/kg through a 22 g flexible catheter every other day.

LPS (1.5 mg/kg for testing orally delivered DPP4 inhibitors and 1.2 mg/kg for testing intratracheally delivered DPP4 inhibitors) or PBS in sham group was intratracheally injection into mice lung at day 0. DPP4 inhibitors or vehicle control were given to mice starting from one day before LPS injection (day −1).

All animals were sacrificed at day 3.5 after LPS injection. Bronchoalveolar lavage fluid (BALF) was retrieved using standard method. 1 ml 4% formalin was used to inflate the lung, which was subsequently fixed in 4% formalin for 24 hours and preserved in 70% EtOH until histological process.

For readouts, total protein content in BALF was quantified using BCA assay; pulmonary inflammation and damage were assessed using H & E staining.

Experimental Methods of Bleomycin Model

Bleomycin (Hospira) was used to induce lung fibrosis in mice. Body weight matched (24 gram~28 gram) male C57BL/6J mice at 10-12 weeks of age were selected to use in bleomycin model.

For oral delivery, DPP4 inhibitors were dissolved in PBS resulting in clear solution. Vehicle control or DPP4 inhibitors were dosed at 10 ml/kg through oral gavage once or twice a day selected based on PK profile. For intratracheally delivered DPP4 inhibitors, compounds were dissolved in PBS resulting in clear solution. Vehicle control or DPP4 inhibitors were dosed at 2 ml/kg through a 22 g flexible catheter every four days.

0.5 U/kg Bleomycin or PBS in sham group was intratracheally injected into mice lung at day 0. DPP4 inhibitors or vehicle control were given to mice starting from one day before bleomycin injection (day −1).

All animals were sacrificed at day 20 after bleomycin injection. Bronchoalveolar lavage fluid (BALF) was retrieved using standard method. 1 ml 4% formalin was used to inflate the lung, which was subsequently fixed in 4% formalin for 24 hours and preserved in 709% EtOH until histological process.

For readouts, body weight was measured every day; total protein content in BALF was quantified using BCA assay; pulmonary fibrosis was assessed using Masson's trichrome staining.

In a mouse ALI model, Compound 46 showed a minimal efficacious dose of 0.02 mg/kg every other day via intratracheal administration. Compound 46 was also efficacious in the bleomycin induced pulmonary fibrosis model, displaying rescue of key metrics including body weight, BALF protein content, fibrotic area, and histological scoring (FIG. 3). The minimal efficacious dose in every four-day intratracheal dosing regime was 0.5 mg/kg.

Additional assessment of the efficacy of compound 46 was determined in combination with the standard of care drug Nintedanib in the rodent bleomycin model (FIG. 4). The combination of compound 46 and Nintedanib displayed impressive and synergistic efficacy as determined by Bliss independence calculations in metrics of BALF protein content and Ashcroft scoring for fibrotic severity.

Figure 5A:
FIG. 5A-FIG. 5C. Compound 46 selectively expanded AEC2s in the mouse. (A) UMAP plot depicting the multiple populations of cells identified in the mouse lung with key populations of interest highlighted. (B) UMAP plot depicting which cells are expressing a transcriptional profile consistent with a proliferative state. Other populations besides AEC2s proliferating are immune cells. (C) Quantification of total proliferating cells at the indicated time points after treatment with compound 46.
Figure 5B:
Figure 5C:
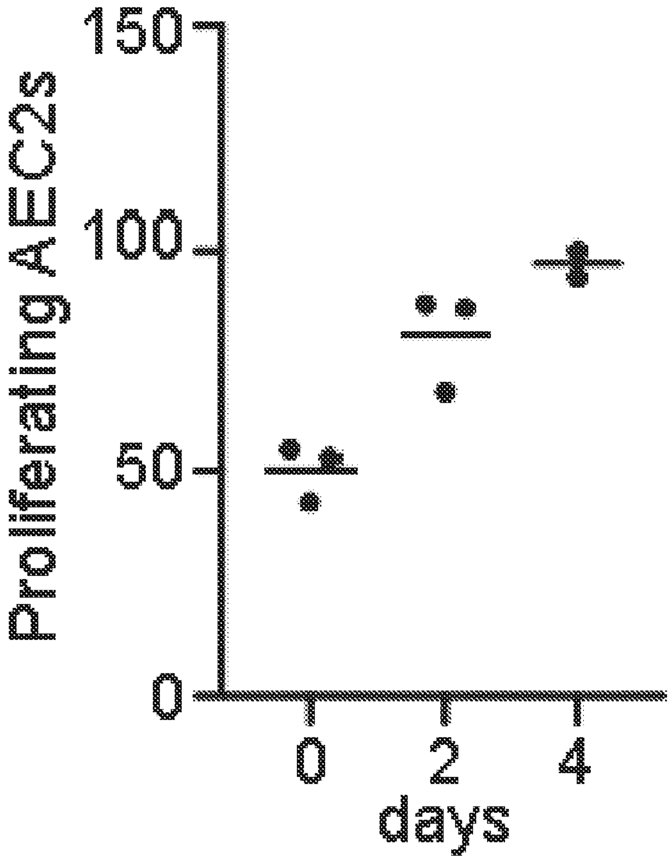

Single cell RNA-sequencing from the lungs of mice was performed to understand which cell types are proliferative in response to compound 46 treatment. After treatment with compound (0.5 mg/kg IT, animals sacrificed 2 and 4 days after dosing), only cycling and transitional AEC2s were induced to proliferate among other cellular populations, including other epithelial cell types but excluding actively expanding immune cells (FIG. 5A, B). The data moreover demonstrates a time-dependent accumulation of AEC2s after treatment with the compound.

We claim:

1. A compound, which compound is of formula (III):

(III)

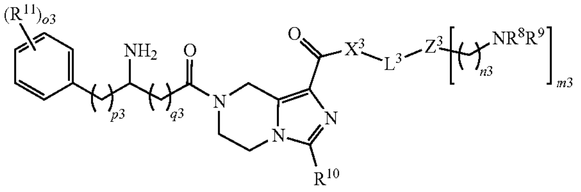

or a pharmaceutically acceptable salt thereof, wherein $X^3$ is —O— or —NH—;

$L^3$ is a bond or $C_2$-$C_{12}$-alkyl wherein one or more —$CH_2$— moieties are optionally and independently replaced with —O—, —C(O)—, or —NH—;

$Z^3$ is —$N_3$, $C_6$-$C_{10}$-aryl, or 5- to 10-membered heteroaryl;

m3 is 0 when $Z^3$ is —$N_3$;

m3 is 1 when $Z^3$ is other than —$N_3$;

n3 is 0, 1, 2, or 3;

$R^8$ is H or optionally substituted $C_1$-$C_{10}$-alkyl or —$C_1$-$C_{10}$-alkyl-($C_6$-$C_{10}$-aryl), which optional substitution is with one to six —OH;

$R^9$ is $C_1$-$C_{10}$-alkyl substituted with one to six —OH;

$R^{10}$ is $C_1$-$C_6$-haloalkyl;

each $R^{11}$ is independently H, halo, or $C_1$-$C_6$-alkyl;

o3 is 0, 1, 2, or 3;

p3 is 0, 1, 2, or 3; and q3 is 0, 1, 2, or 3.

2. The compound of claim 1, wherein $X^3$ is O.

3. The compound of claim 1, wherein $X^3$ is —NH—.

4. The compound of claim 1, wherein each of p3 and q3 is 1.

5. The compound of any one of claims 1 to 3, wherein $Z^3$ is phenyl or triazolyl.

6. The compound of any one of claims 1 to 3, wherein $Z^3$ is triazolyl.

7. The compound of any one of claims 1 to 3, wherein n3 is 1 or 2.

8. The compound of any one of claims 1 to 3, wherein $R^8$ is $C_1$-$C_{10}$-alkyl optionally substituted with one to six —OH.

9. The compound of claim 8, wherein $R^8$ is $C_1$-$C_6$-alkyl.

10. The compound of claim 8, wherein $R^9$ is $C_2$-$C_6$-alkyl substituted with one to five —OH.

11. The compound of claim 8, wherein $R^9$ is $C_2$-$C_6$-alkyl substituted with three to five —OH.

12. The compound of any one of claims 1 to 3, wherein $R^9$ is:

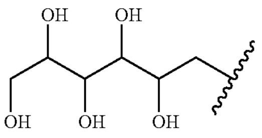

.

13. The compound of claim 1, wherein:

$Z^3$ is $C_6$-$C_{10}$-aryl or 5- to 10-membered heteroaryl;

n3 is 1 or 2;

$R^8$ is $C_1$-$C_{10}$-alkyl; and $R^9$ is $C_2$-$C_6$-alkyl substituted with one to five —OH.

14. A compound, which compound is selected from:

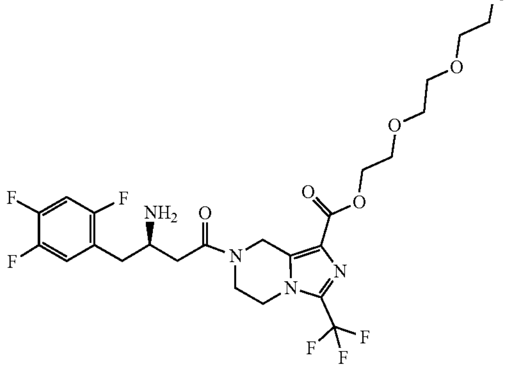

42

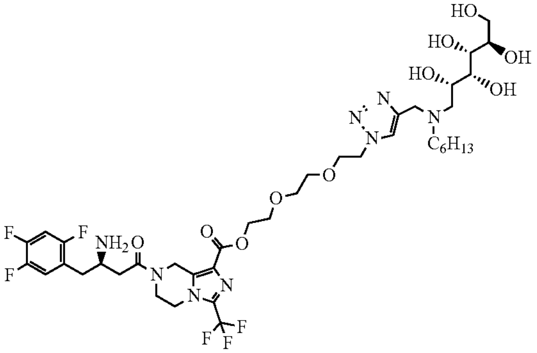

46

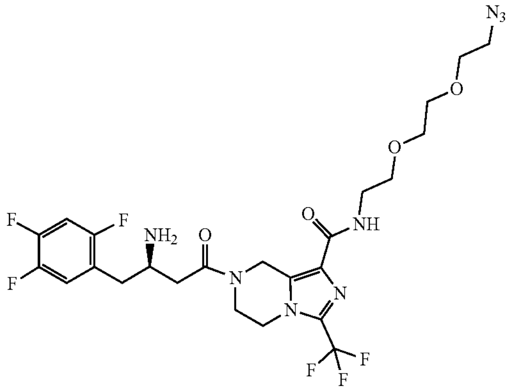 [SMILES: [N-]=[N+]=NCCOCCOCCNC(=O)c1nc(C(F)(F)F)n2c1CN(C(=O)C[C@H](N)Cc1cc(F)c(F)cc1F)CC2]

43

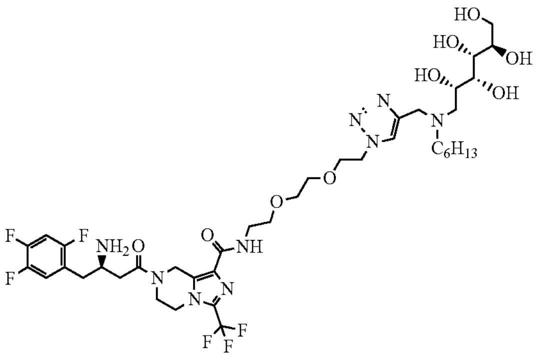

47

-continued
44
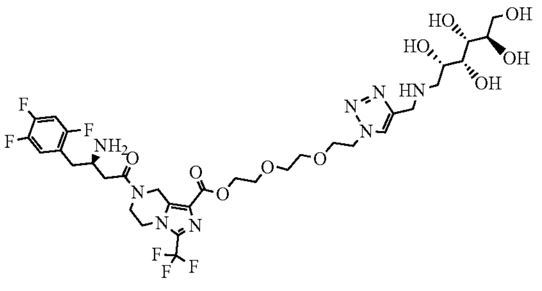 [SMILES: N[C@@H](CC(=O)N1CCn2c(C(F)(F)F)nc(C(=O)OCCOCCOCCn3cc(CNC[C@H](O)[C@@H](O)[C@H](O)[C@H](O)CO)nn3)c2C1)Cc1cc(F)c(F)cc1F]
45
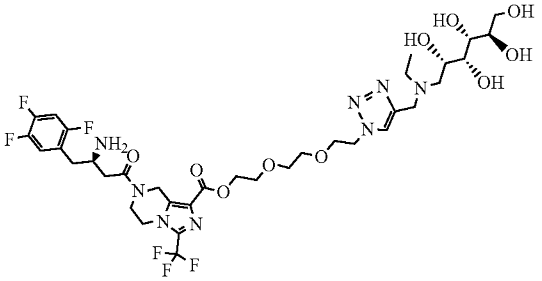 [SMILES: CCN(Cc1cn(CCOCCOCCOC(=O)c2nc(C(F)(F)F)n3c2CN(C(=O)C[C@H](N)Cc2cc(F)c(F)cc2F)CC3)nn1)C[C@H](O)[C@@H](O)[C@H](O)[C@H](O)CO]
48
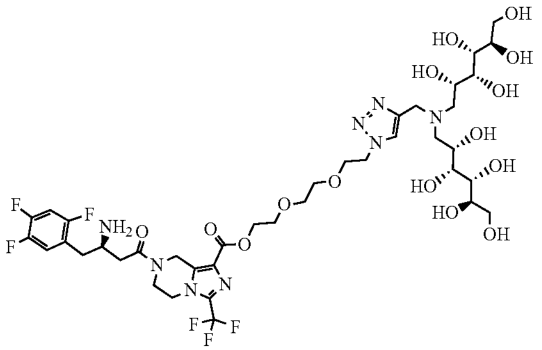 [SMILES: N[C@@H](CC(=O)N1CCn2c(C(F)(F)F)nc(C(=O)OCCOCCOCCn3cc(CN(C[C@H](O)[C@@H](O)[C@H](O)[C@H](O)CO)C[C@H](O)[C@@H](O)[C@H](O)[C@H](O)CO)nn3)c2C1)Cc1cc(F)c(F)cc1F]
49
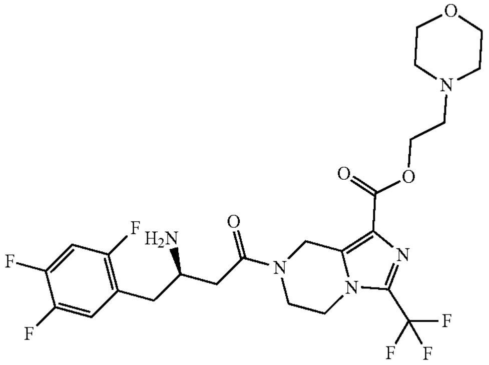 [SMILES: N[C@@H](CC(=O)N1CCn2c(C(F)(F)F)nc(C(=O)OCCN3CCOCC3)c2C1)Cc1cc(F)c(F)cc1F]
50
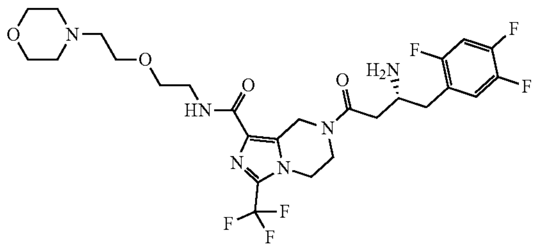 [SMILES: N[C@@H](CC(=O)N1CCn2c(C(F)(F)F)nc(C(=O)NCCOCCN3CCOCC3)c2C1)Cc1cc(F)c(F)cc1F]
-continued
51
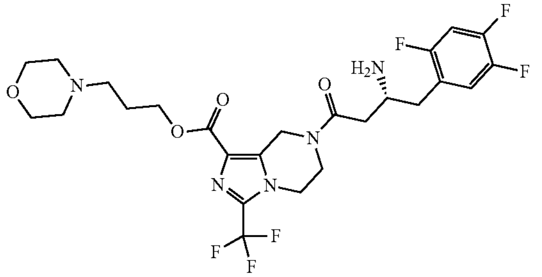 [SMILES: N[C@@H](CC(=O)N1CCn2c(C(F)(F)F)nc(C(=O)OCCCN3CCOCC3)c2C1)Cc1cc(F)c(F)cc1F]
52
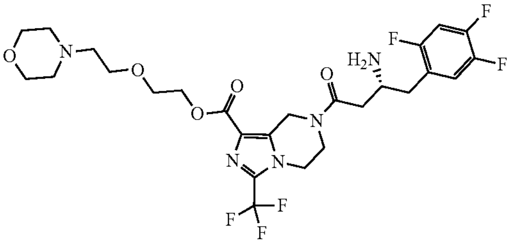 [SMILES: N[C@@H](CC(=O)N1CCn2c(C(F)(F)F)nc(C(=O)OCCOCCN3CCOCC3)c2C1)Cc1cc(F)c(F)cc1F]
53
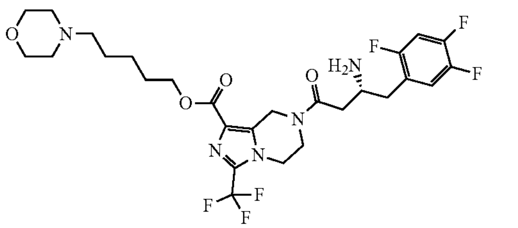 [SMILES: N[C@@H](CC(=O)N1CCn2c(C(F)(F)F)nc(C(=O)OCCCCCN3CCOCC3)c2C1)Cc1cc(F)c(F)cc1F]
54
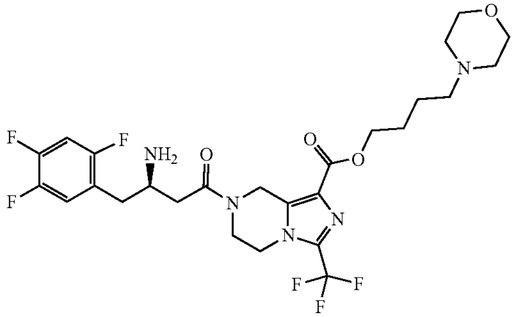 [SMILES: N[C@@H](CC(=O)N1CCn2c(C(F)(F)F)nc(C(=O)OCCCCN3CCOCC3)c2C1)Cc1cc(F)c(F)cc1F]
55
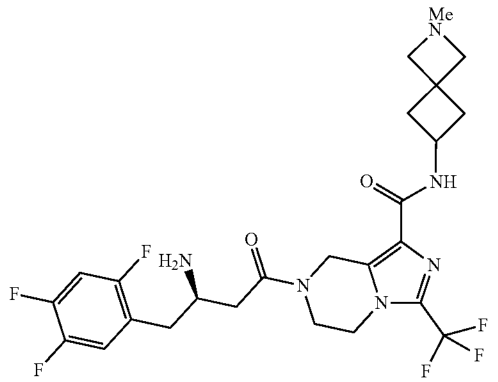 [SMILES: CN1CC2(CC(NC(=O)c3nc(C(F)(F)F)n4c3CN(C(=O)C[C@H](N)Cc3cc(F)c(F)cc3F)CC4)C2)C1]
and pharmaceutically acceptable salts thereof.
15. A pharmaceutical composition comprising a compound of claim 1 and a pharmaceutically acceptable excipient.
16. A method of selectively increasing proliferation of cuboidal alveolar type 2 (AEC2) cells or restoring diminished proliferation of AEC2 cells, which comprises administering to a subject in need thereof an effective amount of a compound of claim 1.

17. A method of inhibiting dipeptidyl peptidase IV (DPP4), which comprises administering to a subject in need thereof an effective amount of a compound of claim 1.

18. A method of treating a pulmonary disease, which comprises administering to a subject in need thereof an effective amount of a compound of claim 1.

19. A pharmaceutical composition comprising a compound of claim 14 and a pharmaceutically acceptable excipient.

20. A method of selectively increasing proliferation of AEC2 cells or restoring diminished proliferation of AEC2 cells, which comprises administering to a patient in need thereof an effective amount of a compound of claim 14.

21. A method of inhibiting DPP4, which comprises administering to a patient in need thereof an effective amount of a compound of claim 14.

* * * * *